United States Patent
Jaïs

(10) Patent No.: US 11,760,982 B2
(45) Date of Patent: Sep. 19, 2023

(54) CHIMERIC ENZYMES AND THEIR APPLICATIONS

(71) Applicant: EUKARYS, Evry (FR)

(72) Inventor: Philippe Jaïs, Issy-les-Moulineaux (FR)

(73) Assignee: EUKARYS, Evry (FR)

( * ) Notice: Subject to any disclaimer, the term of this patent is extended or adjusted under 35 U.S.C. 154(b) by 553 days.

(21) Appl. No.: 16/634,429

(22) PCT Filed: Jul. 27, 2018

(86) PCT No.: PCT/EP2018/070479
§ 371 (c)(1),
(2) Date: Jan. 27, 2020

(87) PCT Pub. No.: WO2019/020811
PCT Pub. Date: Jan. 31, 2019

(65) Prior Publication Data
US 2020/0165585 A1  May 28, 2020

(30) Foreign Application Priority Data

Jul. 27, 2017  (EP) .................................. 17306006

(51) Int. Cl.
| | | |
|---|---|---|
| *C12N 15/73* | (2006.01) | |
| *C12N 9/12* | (2006.01) | |
| *C12N 9/10* | (2006.01) | |
| *C12N 9/14* | (2006.01) | |
| *A61K 38/00* | (2006.01) | |
| *C07K 14/44* | (2006.01) | |

(52) U.S. Cl.
CPC ............ *C12N 9/1241* (2013.01); *C07K 14/44* (2013.01); *C12N 9/1007* (2013.01); *C12N 9/14* (2013.01); *C07K 2319/85* (2013.01); *C12N 2795/00022* (2013.01); *C12Y 201/01056* (2013.01); *C12Y 207/0705* (2013.01); *C12Y 306/01* (2013.01)

(58) Field of Classification Search
CPC .............. C12Q 2521/119; C12N 15/73; C12N 9/1241; C12N 9/1007; C12N 9/1247; C12N 9/14; A61K 38/00
See application file for complete search history.

(56) References Cited

U.S. PATENT DOCUMENTS 5,866,680 A   2/1999 Keene et al.

FOREIGN PATENT DOCUMENTS

WO   2011128444 A2   10/2011

OTHER PUBLICATIONS

Keryer-Bobens, Biol. Cell, 2008, 100, 125-138.*
Bharati, A.P., et al., "The mRNA capping enzyme of *Saccharomyces cerevisiae* has dual specificity to interact with CTD of RNA Polymerase II." Scientific Reports, 2016, 6: 31294, pp. 1-12.
Ho, C.K., et al., "A Yeast-Based Genetic System for Functional Analysis of Viral mRNA Capping Enzymes." Journal of Virology, Jun. 2000, 74(12): 5486-5494.
Wen, Y., et al., "Mammalian capping enzyme binds RNA and uses protein tyrosine phosphatase mechanism." Proc. Natl. Acad. Sci. USA, Oct. 1998, 95: 12226-12231.

* cited by examiner

*Primary Examiner* — Maryam Monshipouri
(74) *Attorney, Agent, or Firm* — SALIWANCHIK, LLOYD & EISENSCHENK

(57) ABSTRACT

The present invention relates to a chimeric enzyme comprising or consisting of at least one catalytic domain of a capping enzyme and at least one RNA-binding domain of a protein-RNA tethering system as well as its application for the production of an RNA molecule with a 5'-terminal cap.

6 Claims, 17 Drawing Sheets
Specification includes a Sequence Listing.

Nλ-poly(A) polymerase-G4-NP868R monomer

A | Nλ | Poly(A) polymerases | G4 | NP868R |

---

Nλ-NP868R-G4-poly(A) polymerase monomer

B | Nλ | NP868R | G4 | Poly(A) polymerases |

Figure 10

Nλ-R341-EE$_{1234}$L/RR$_{1234}$L-NP868R heterodimer

A

| Nλ | R341 | EE$_{1234}$L |

⇕

| RR$_{1234}$L | NP868R |

---

Nλ-NP868R-RR$_{1234}$L/EE$_{1234}$L-R341 heterodimer

B

| Nλ | NP868R | RR$_{1234}$L |

⇕

| EE$_{1234}$L | R341 |

Nλ-R341-G$_4$-NP868R-G4-K1ERNAP

| Nλ | R341 | G4 | NP868R | G4 | K1ERNAP |

---

B

Nλ-R341-G$_4$-NP868R-F2A-K1ERNAP

| Nλ | R341 | G4 | NP868R | F2A | K1ERNAP |

---

C

Nλ-R341-F2A-NP868R-G4-K1ERNAP

| Nλ | R341 | F2A | NP868R | G4 | K1ERNAP |

---

D

Nλ-R341-T2A-NP868R-G4-K1ERNAP

| Nλ | R341 | T2A | NP868R | G4 | K1ERNAP |

CHIMERIC ENZYMES AND THEIR APPLICATIONS

CROSS REFERENCE TO RELATED APPLICATIONS

This application is a National Stage Application of International Application No. PCT/EP2018/070479, filed Jul. 27, 2018; which claims priority to European Application No. 17306006.2, filed Jul. 27, 2017.

The present invention relates to the field of expression systems, particularly in eukaryotic cells.

In particular, the invention relates to a chimeric enzyme useful for the production of RNA molecules with 5'-terminal cap structures and preferably with a 3' poly(A) tail.

In the eukaryotes, precursors of messenger RNA (mRNA), i.e. the pre-mRNAs, are synthesized by the RNA polymerase II and then undergoes multiple post-transcriptional modifications, which are required for their biological activities including translation, stability or immune response modulation. Two of these modifications are particularly critical for mRNA metabolism and its translation: the addition of a cap at their 5'-end and a polyadenylation tail at their 3'-end.

The capping is a specialized structure found at the 5'-end of nearly all eukaryotic messenger RNAs. The simplest cap structure, cap-0, results of the addition of a guanine nucleoside methylated at $N^7$ that is joined by 5'-5' triphosphate bound to the end of primary RNA (i.e. $m^7$GpppN where N is any base, p denotes a phosphate and m a methyl group). In the so called canonical pathway, the formation of the cap-0 involves a series of three enzymatic reactions: RNA triphosphatase (RTPase) removes the γ phosphate residue of 5' triphosphate end of nascent pre-mRNA to diphosphate, RNA guanylyltransferase (GTase) transfers GMP from GTP to the diphosphate 5' end of nascent RNA terminus, and RNA $N^7$-guanine methyltransferase (N7-MTase) adds a methyl residue on azote 7 of guanine to the GpppN cap (Furuichi and Shatkin 2000). In higher eukaryotes and some viruses, the 2'-hydroxyl group of the ribose of the first (i.e. cap-1 structures; $m^7$GpppNm$^{2'-O}$pN) and second (i.e. cap2 structures; $m^7$GpppNm$^{2'-O}$pNm$^{2'-O}$) transcribed nucleotides can be methylated by two separate ribose-2'-O MTases, respectively named cap1- and cap2-specific MTases (Langberg and Moss 1981). However, In contrast to the cellular N7-MTase activity that is exclusively nuclear, cap-1 ribose-2'-O MTase activity has been detected in both the cytoplasm and nucleus of HeLa cells, whereas cap2 MTase activity is exclusively found in their cytoplasm (Langberg and Moss 1981).

The formation of the 5'-terminal $m^7$GpppN cap is the first step of pre-mRNA processing. The $m^7$GpppN cap plays important roles in mRNA stability and its transport from the nucleus to the cytoplasm (Huang and Steitz 2005, Kohler and Hurt 2007). In addition, the 5'-terminal $m^7$GpppN cap is important for the translation of mRNA to protein by anchoring the eukaryotic translation initiation factor 4F (eIF4F) complex, which mediates the recruitment of the 16S portion of the small ribosomal subunit to mRNA (Furuichi, LaFiandra et al. 1977, Gingras, Raught et al. 1999, Rhoads 1999). The 5'-terminal $m^7$GpppN cap therefore enhances drastically the translation of mRNA both in vitro (Lo, Huang et al. 1998), and in cellulo (Malone, Feigner et al. 1989, Gallie 1991, Lo, Huang et al. 1998, Kozak 2005). The cap-0, cap-1 and cap-2 modifications participate in the innate immune response, by distinguishing self from non-self RNA through the RNA sensor RIG-1 and MDAS, which in turn induce an interferon type-I response (Hornung, Ellegast et al. 2006, Daffis, Szretter et al. 2010).

Since they are widely used in the life sciences, biotechnology and medicines, many expression systems have been designed to efficiently produce proteins and/or RNAs particularly in eukaryotic cells.

The inventor has developed in the past an artificial expression system (i.e. a chimeric enzyme) for efficient transgenesis in eukaryotic cells, which autonomously generates mRNA molecules, in particular in the cytoplasm of said cells (WO 2011/128444). Using this system, RNA chains are synthesized by RNA polymerase moiety of this chimeric enzyme and are capped at 5'-end by its mRNA capping enzyme moiety. In addition, a poly(A) tail can be produced at the 3'-end of transcripts by transcription of a polyadenosine track from DNA templates. This system has notably the advantage of not using the endogenous RNA transcription machinery of eukaryotic cells, e.g. RNA polymerase II and associated factors involved in transcription and post-transcription.

Other attempts to couple capping to transcription and thus to improve the translatability of uncapped transcripts produced by the T7 RNA polymerase by fusing the carboxyl-terminal domain (CTD) of the largest subunit of the RNA polymerase II (POLR2A), have to enhance the capping of both constitutively and alternatively spliced substrates in cellulo (Kaneko, Chu et al. 2007, Natalizio, Robson-Dixon et al. 2009). The CTD comprises 25-52 heptapeptide repeats of the consensus sequence $^1$YSPTSPS$^7$, which is highly conserved throughout evolution and subject to reversible phosphorylation during the transcription cycle (Palancade and Bensaude 2003). When phosphorylated, the CTD is thought to mediate the coupling of transcription and capping of nascent transcripts, by binding one or more subunits of the mRNA capping enzymes in yeast (Cho, Takagi et al. 1997, McCracken, Fong et al. 1997) and mammals (Mc-Cracken, Fong et al. 1997, Yue, Maldonado et al. 1997). Noticeably, RNA polymerase II with Ser$^5$-phosphorylated CTD repeats undergoes promoter proximal pausing which is coincident with the co-transcriptional capping of the nascent transcripts (Komarnitsky, Cho et al. 2000, Schroeder, Schwer et al. 2000). However, in contrast to what could be expected intuitively, the fusion of the CTD to the single-unit T7 RNA polymerase is not sufficient to enhance the capping of both constitutively and alternatively spliced substrates in vivo (Kaneko, Chu et al. 2007, Natalizio, Robson-Dixon et al. 2009).

There remains therefore a significant need in the art for new and improved expression systems, in particular in eukaryotic cells, which are appropriate for gene therapy and large-scale protein production without cytotoxicity or induced-cytotoxicity. The present inventor has made a significant step forward with the invention disclosed herein.

The purpose of the invention is to fulfill this need by providing new chimeric enzymes, which make it possible to solve in whole or part the problems mentioned-above.

Unexpectedly, the inventor has notably demonstrated that monomeric or oligomeric chimeric (non-natural) enzymes comprising catalytic domains of a capping enzyme, particularly a catalytic domain of a RNA triphosphatase, a catalytic domain of a guanylyltransferase, a catalytic domain of a $N^7$-guanine methyltransferase, and a RNA-binding domain of a protein-RNA tethering system, said RNA-binding domain binding specifically to a RNA element consisting of a specific RNA sequence and/or structure, allows to highly increase the capping rate of specific mRNAs produced by a RNA polymerase.

These results are surprising since the formation of the cap is a complex process and that the capping of exogenous transcripts cannot be achieved by most other approaches, such as the fusion enzyme CTD-T7 RNA polymerase (Kaneko, Chu et al. 2007, Natalizio, Robson-Dixon et al. 2009).

The U.S. Pat. No. 5,866,680 suggests but without any demonstration the use of the nuclear 70K RNA binding-domain to direct RNA modifying activity to specific site in RNAs including different enzymes such as RNA capping enzymes.

Unexpectedly, the inventor has also demonstrated that cytoplasmic monomeric or oligomeric chimeric enzymes comprising catalytic domains of a capping enzyme and a bacteriophage RNA-binding domain of a bacteriophage protein-RNA tethering system allows to highly increase the capping rate of specific mRNAs produced by a bacteriophage DNA-dependant RNA polymerase, compared to other RNA-binding domains of protein-RNA tethering systems, such as the U1-RNA 70K (also known as SNRNP70)-U1snRNA system described in said U.S. Pat. No. 5,866,680.

The inventor has also demonstrated that surprisingly monomeric or oligomeric chimeric enzymes comprising catalytic domains of a capping enzyme, a RNA-binding domain of a protein-RNA tethering system and catalytic domain of a poly(A) polymerase, allows to highly increase, synergistically, the capping rate of specific mRNAs produced by RNA polymerase, compared to the combination of a capping enzyme fused to a RNA-binding domain in presence of a poly(A) polymerase fused to a RNA-binding domain. These results are unexpected since capping enzymes and poly(A) polymerases are not physically linked in the nature and contain no known predicted binding domain for a specific RNA sequence. One skilled in the art could have expected to obtain the same expression rate since the components are the same.

Thus, in one aspect, the invention relates to a chimeric enzyme, in particular cytoplasmic, comprising or consisting of:
- at least one catalytic domain of a capping enzyme, in particular selected in the group consisting of cap-0 canonical capping enzymes, cap-0 non-canonical capping enzymes, cap-1 capping enzymes and cap-2 capping enzymes; and
- at least one RNA-binding domain of a protein-RNA tethering system wherein said RNA-binding domain binds specifically to a RNA element of said protein-RNA tethering system, consisting of a specific RNA sequence and/or structure.

The chimeric enzyme according to the invention has in particular the following advantages:
- It increases the rate of mRNAs produced either by an endogenous DNA-dependent RNA polymerase or a non-endogenous DNA-dependent RNA polymerase;
- It is not expensive, quick and easy to implement and thus appropriate for large-scale assays and protein production.

Unless defined otherwise, all technical and scientific terms used herein have the same meaning as commonly understood to one skilled in the relevant art.

For convenience, the meaning of certain terms and phrases employed in the specification, examples, and claims are provided.

As used herein, the term "chimeric enzyme" refers to an enzyme that is not a native enzyme found in the nature (that is non-natural). Accordingly, a chimeric enzyme may comprise catalytic domains that are derived from different sources (e.g. from different enzymes) or catalytic domains derived from the same source (e.g. from the same enzyme), but arranged in a different manner than that found in nature.

The term "chimeric enzyme" encompasses monomeric (i.e. single-unit) enzyme but also oligomeric (i.e. multi-unit) enzyme, in particular hetero-oligomeric enzyme.

More specifically, the term "chimeric enzyme" may encompasses an enzyme that comprises or consists of a RNA-binding domain of a protein-RNA tethering system linked covalently or noncovalently with one (i.e. single unit) or several (i.e. multi-unit) catalytic domain(s) (at least one catalytic domain of a capping enzyme) or protein(s) (at least one capping enzyme).

The term "catalytic domain" of an enzyme relates to a protein domain, which is necessary and sufficient, in particular in its three-dimensional structure, to assure the enzymatic function. For example, a catalytic domain of a RNA triphosphatase is the domain, which is necessary and sufficient to assure the RNA triphosphatase function. The term "catalytic domain" encompasses catalytic domain of wild type or mutant enzyme.

The term "protein domain" defines distinct functional and/or structural building blocks and elements in a protein which folds and functions independently.

In particular, the chimeric enzyme according to the invention is a monomeric or oligomeric non-natural enzyme.

As used herein, the term "monomeric enzyme" relates to a single-unit enzyme that consists of only one polypeptide chain.

As used herein, the term "oligomeric enzyme" refers to a multi-unit enzyme that consists of at least two polypeptides chains, linked together covalently or noncovalently. The term "oligomeric enzyme" encompasses a multi-unit enzyme, wherein at least two units of said enzyme are linked together covalently or noncovalently. The term "oligomeric enzyme" encompasses homo-oligomeric enzyme that is a multi-unit enzyme consisting of only one type of monomers (subunits) and hetero-oligomeric enzyme consisting of different types of monomers (subunits).

As used herein, the term "protein-RNA tethering system" refers to a system wherein a protein (or a peptide) recognizes and specifically binds (with high affinity) via its RNA-binding domain to a specific RNA element consisting of a specific RNA sequence and/or structure, therefore making possible to tether this protein (or peptide) with this RNA element. The specific binding between the protein (or the peptide) via its RNA binding domain and the specific RNA element implies that the protein (or peptide) and the specific RNA element interact with high affinity. Interaction with high affinity includes interaction with an affinity of about $10^{-6}$ M or stronger, in particular at least $10^{-7}$M, at least $10^{-8}$M, at least $10^{-9}$M and more particularly at least $10^{-10}$ M. Whether a RNA-binding domain specifically binds with high affinity to a specific RNA element can be tested readily by, inter alia, comparing the reaction of said RNA-binding domain with a specific RNA element with the reaction of said RNA-binding domain with RNA other than the specific RNA element.

The RNA-protein affinity can be determined by various methods, well known by one skilled in the art. These methods include, but are not limited to, steady-state fluorescence or electrophoretic measurements, RNA electrophoretic mobility shift assay.

As used herein, the term "RNA-binding domain of a protein-RNA tethering system" refers to the domain of a protein (or a peptide) which is necessary and sufficient, in particular in its three-dimensional structure, to assure the recognition and the interaction with high affinity with a specific RNA element consisting of a specific RNA sequence and/or structure, therefore making possible to tether this protein (or peptide) via said RNA-binding domain with this RNA element. Thus, said "RNA-binding domain" (RNA-tethering domain) binds to RNA with sequence and/or structure specificity, i.e. binds specifically to a RNA element consisting of a specific RNA sequence and/or structure. The term "RNA-binding domain of a protein-RNA tethering system" encompasses RNA-biding domain of wild type or mutant protein (or peptide).

The chimeric enzyme according to the invention comprises at least said RNA-binding domain but can further comprise the whole or part of the protein (or peptide) containing said RNA-binding domain. In fact, according to one embodiment of the chimeric enzyme according to the invention, said RNA-binding domain of a protein-RNA tethering system can be included in the whole or part of a protein (or a peptide) of a protein-RNA tethering system.

Some characterized protein-RNA tethering systems include bacteriophage protein-RNA tethering systems such as the MS2 coat protein-RNA tethering system, the R17 coat protein-RNA tethering system and the lambdoid N antitermination protein-RNA tethering systems. The MS2 coat protein and the R17 coat protein recognize and interact with high affinity with specific RNA elements consisting of stem-loop RNA structures (Valegard, Murray et al. 1994, Valegard, Murray et al. 1997). The lambdoid N antitermination protein-RNA tethering systems recognize and interact with high affinity with specific RNA elements consisting of boxBL and boxBR stem loop RNA structures (Das 1993, Greenblatt, Nodwell et al. 1993, Friedman and Court 1995). The bacteriophages characterized so far that belong either to the lambdoid family (i.e. λ, P22, φ21, HK97 and 933W viruses) or the MS2-related family (i.e. MS2, and R17).

Other well-characterized protein-RNA tethering systems include: (a) TAT binding domain from the Human immunodeficiency virus-1 (HIV-1; e.g. NCBI reference sequence ABY50660.1) (Dingwall, Ernberg et al. 1990, Weeks, Ampe et al. 1990, Karn, Dingwall et al. 1991, Puglisi, Tan et al. 1992, Frankel and Young 1998) and Bovine Immunodeficiency Virus (Puglisi, Chen et al. 1995), (b) Rev protein from HIV-1 and mutants (e.g. UniProtKB P69718) bind to the Rev-binding element (RBE), a short stem-internal stem-loop structure (Karn, Dingwall et al. 1991, Tan and Frankel 1995, Battiste, Mao et al. 1996, Frankel and Young 1998), (c) Jembrana disease virus Tat protein (UniProtKB Q82854) bind its own TAR protein, as well as TAR proteins from human and bovine immunodeficiency viruses (Smith, Calabro et al. 2000), (d) Iron regulatory proteins, such as the iron-responsive element-binding protein 1 (IREB1, e.g. UniProtKB P21399) and 2 (IREB2, e.g. UniProtKB P48200), which bind iron-responsive elements within 5'UTR or 3'UTR of iron metabolism mRNAs (Theil 1994, Rouault 2006), (e) Brome mosaic virus (BMV) coat protein (UniProtKB Q5KSV1_BMV) binds an hairpin of the MP coding region required for packaging of viral RNA (Sacher and Ahlquist 1989, Choi and Rao 2003), (f) U1A small nuclear ribonucleoprotein subunit 70K (SNRNP70), which binds with high specificity and affinity to a 30-nucleotide RNA hairpin within the 3'UTR of U1snRNA (Keene, Query et al. 1999), (g) SLBP (stem-loop binding protein UniProtKB Q14493) that binds the stem-loop structure in the 3'UTR of histone pre-mRNAs (Marzluff, Wagner et al. 2008), (h) 60S ribosomal protein L7 (e.g. UniProtKB P18124) that binds to G-rich structures in 28S rRNA (Hemmerich, Bosbach et al. 1997), (i) Cowpea chlorotic mottle virus capsid protein (UniProtKB P03601) that binds an hairpin required for packaging of viral RNA (Annamalai, Apte et al. 2005), (j) human T-cell leukemia virus type I (HTLV-1) rex protein and related mutants (e.g. HTLV-1 isolate Caribbea HS-35 subtype A, UniProtKB P0C206), which bind to rex-response element (RxRE) located in the 3' long terminal repeat of all human T-cell leukemia virus type I-specific mRNAs (Ballaun, Farrington et al. 1991, Jiang, Gorin et al. 1999), (j) HTLV-2 Rex protein (UniProtKB Q85601) that binds 5' long terminal repeat RNA (Yip, Dynan et al. 1991), (m) RNA splicing component U2 snRNP auxiliary factor U2AF$^{65}$ (e.g. UniProtKB P26368) that binds a polypyrimidine tract that precedes 3' splice sites of pre-mRNA (Zamore, Patton et al. 1992, Banerjee, Rahn et al. 2004), (n) bacterial ribosomal protein S7 (UniProtKB P02359) that binds to the lower half of the 3' major domain of 16S ribosomal RNA (Robert, Gagnon et al. 2000), (o) the archeal L7Ae protein binds to RNA containing a kink-turn with nanomolar affinity (Turner, Melcher et al. 2005, Ye, Yang et al. 2013), (p) RNA binding dormain from the SELENBP2 gene product (Selenium Binding Protein 2, SBP2) binds to the SECIS element in the 3'-UTR of some mRNAs encoding selenoproteins (Mix, Lobanov et al. 2007), (q) the N-terminal domain of Brome mosaic virus (BMV) that can bind a BoxB (Yi, Vaughan et al. 2009), (r) the N-terminus of gp10 head-tail connector which binds φ29 pRNA sequence (Xiao, Moll et al. 2005), (s) Streptavidin that binds the artificial RNA aptamer (Leppek and Stoecklin 2014).

In one embodiment of the chimeric enzyme according to the invention, said RNA-binding domain is a bacteriophage RNA-binding domain of a bacteriophage protein-RNA tethering system, in particular selected in the group consisting of: the MS2 coat protein-RNA tethering system, the R17 coat protein-RNA tethering system and the lambdoid N antitermination protein-RNA tethering systems, more particularly the lambdoid N antitermination protein-RNA tethering systems selected from the group consisting of the lambda N antitermination protein-RNA tethering system, the phi21 N antitermination protein-RNA tethering system, the HK97 N antitermination protein-RNA tethering system and the p22 N antitermination protein-RNA tethering system, and even more particularly the lambda N antitermination protein-RNA tethering system.

Particularly, when the chimeric enzyme of the invention is used to add a 5'-terminal cap to an RNA molecule synthetized by a bacteriophage DNA-dependent polymerase (comprised or not in said chimeric enzyme), said RNA-binding domain is a bacteriophage RNA-binding domain of a bacteriophage protein-RNA tethering system.

In fact, unexpectedly, the inventor has demonstrated that cytoplasmic monomeric or oligomeric chimeric enzymes comprising catalytic domains of a capping enzyme and a bacteriophage RNA-binding domain of a bacteriophage protein-RNA tethering system allows to highly increase the capping rate of specific mRNAs produced by a bacteriophage DNA-dependant RNA polymerase, compared to other RNA-binding domains of protein-RNA tethering systems, including the U1-RNA 70K system described in the U.S. Pat. No. 5,866,680.

In particular, said RNA-binding domain is a bacteriophage RNA-binding domain of a bacteriophage protein selected in the group consisting of: the wild type MS2 coat protein (NCBI accession number NC_001417.2, UniProtKB/Swiss-Prot P03612), the wild type R17 coat protein (NCBI accession numbers EF108465.1, UniProtKB/Swiss-Prot P69170) and the wild type lambdoid N antitermination proteins and mutants and derivatives thereof which are able to recognize and interact with high affinity with the specific RNA element, more particularly the wild type lambdoid N antitermination proteins selected from the group consisting of the wild type lambda N antitermination protein (NCBI accession number NC_001416.1, complete genome sequence; UniProtKB/Swiss-Prot accession number P03045), the wild type phi21 N antitermination protein (NCBI accession number AH007390.1, partial genome sequence; UniProtKB/Swiss-Prot accession number P07243), the wild type HK97 N antitermination protein-RNA tethering system (NCBI accession number NC_002167.1, complete genome sequence; NCBI protein accession number NP_037732.1) and the wild type p22 N antitermination protein (particularly NCBI sequence (NCBI accession number NC_002371.2, complete genome sequence; UniProtKB/Swiss-Prot accession number P04891), and even more particularly the wild type lambda N antitermination protein (NCBI accession number NC_001416.1, complete genome sequence; UniProtKB/Swiss-Prot accession number P03045).

The entire or nearly entire MS2/R17 proteins are needed for proficient binding to the tethered RNA, since multiple amino-acid residues spread in these proteins are involved in stem-loop interaction (Valegard, Murray et al. 1994, Valegard, Murray et al. 1997).

So, in one embodiment, the chimeric enzyme of the invention comprises the wild type MS2 coat protein (NCBI accession number NC_001417.2, UniProtKB/Swiss-Prot P03612) or its isolate the wild type R17 coat protein (NCBI accession numbers EF108465.1, UniProtKB/Swiss-Prot P69170), or a mutant or derivative thereof which is able to recognize and interact with high affinity with the specific RNA element.

Importantly, the 18- to 22-amino-acid region from the N-terminal sequences of the lambdoid N-proteins bind to cognate RNA sequences with an affinity and specificity similar to that of the full-length N-proteins (Franklin 1985, Cilley and Williamson 1997).

In one embodiment of the chimeric of the invention, said RNA-binding domain of a protein-RNA tethering system comprising or consisting of the peptide consisting of amino acids at position 1 to 22, in particular 1 to 18 of the wild type lambda N antitermination protein (NCBI accession number NC_001416.1, complete genome sequence; UniProtKB/Swiss-Prot accession number P03045), or of the wild type phi21 N antitermination protein (NCBI accession number AH007390.1, partial genome sequence; UniProtKB/Swiss-Prot accession number P07243), or of the wild type HK97 N antitermination protein-RNA tethering system (NCBI accession number NC_002167.1, complete genome sequence; NCBI protein accession number NP_037732.1) or of the wild type P22 N antitermination protein (NCBI accession number NC_002371.2, complete genome sequence; UniProtKB/Swiss-Prot accession number P04891) or a mutant or derivative thereof which is able to recognize and interact with high affinity with the specific RNA element, particularly of the wild type lambda N antitermination protein (NCBI accession number NC_001416.1, complete genome sequence; UniProtKB/Swiss-Prot accession number P03045).

In particular, said RNA-binding domain of a protein-RNA tethering system comprising or consisting of the peptide consisting of amino acids at position 1 to 22, of the wild type lambda N antitermination protein (NCBI accession number NC_001416.1, complete genome sequence; UniProtKB/Swiss-Prot accession number P03045), in particular SEQ ID No 2, preferably encoded by SEQ ID No 1.

In particular, said RNA-binding domain of a protein-RNA tethering system does not derive from the same source (e.g. from the same enzyme) than the different catalytic domains of the chimeric enzyme of the invention.

The chimeric enzyme according to the invention can be a nuclear enzyme, a subcellular compartment enzyme or a cytoplasmic enzyme. Thus, the chimeric enzyme according to the invention can comprise a signal peptide well known by one skilled in the art, which directs the transport of the enzyme in cells. For example, the chimeric enzyme according to the invention can comprise a nuclear localization signal (NLS), which directs the enzyme to the nucleus. Such NLS is often a unit consisting of five basic, plus-charged amino acids. The NLS can be located anywhere on the peptide chain.

Preferably, the chimeric enzyme according to the invention is a cytoplasmic chimeric enzyme. In particular, it does not comprise signal peptide that directs the transport of the enzyme, except to the cytoplasm.

The cytoplasmic localization of the chimeric enzyme according to the invention has the advantage that it optimizes the levels of transgene expression by avoiding the active transfer of large DNA molecules (i.e. transgene) from the cytoplasm to the nucleus of eukaryotic cells and the export of RNA molecules from the nucleus to the cytoplasm.

These cytoplasmic chimeric enzymes according to the invention can thus be useful to generate a host-independent, eukaryotic gene expression system that is able to work in the cytoplasm in which significantly higher amounts of transfected DNA are usually found as compared to the nucleus.

There is no competition between the endogenous gene transcription and the transgene transcription, since the endogenous gene transcription occurs in the nucleus of eukaryotic cells in contrast to the transgene transcription, which occurs in the cytoplasm.

The cytoplasmic chimeric enzyme according to the invention is thus notably appropriate for large-scale assays and protein production.

As used herein, the term "capping enzyme" refers to any enzyme able to add a $m^7$ GpppG cap at 5'-end of mRNA and/or to modify the ultimate or penultimate bases of a RNA sequence, including cap-0 canonical or non-canonical capping enzymes and cap-1 or cap-2 nucleoside 2' methyltransferases, N6-methyl-adenosine transferase.

As used herein, the term "cap-0 canonical capping enzymes" refers to enzymes able to add cap-0 structure at the 5'end of RNA molecules by involving a series of three enzymatic reactions: RNA triphosphatase (RTPase) that removes the γ phosphate residue of 5' triphosphate end of nascent pre-mRNA to diphosphate ppRNA, RNA guanylyl-transferase (GTase) that transfers GMP from GTP to the diphosphate ppRNA nascent RNA terminus, and RNA $N^7$-guanine methyltransferase (N7-MTase) that adds a methyl residue on nitrogen 7 of guanine to the GpppRNA cap (Furuichi and Shatkin 2000).

The enzymatic domains of eukaryotic organisms and viruses, which are involved in the canonical formation of cap-0 structure, can be assembled in a variable number of protein subunits:

Single subunit capping enzymes with all three critical enzymatic domains, i.e. RTPase, GTase and N7-MTase. These enzymes include, but are not limited to: (i) *Acanthamoeba polyphaga* mimivirus capping enzyme R382 (Raoult, Audic et al. 2004, Benarroch, Smith et al. 2008) (NCBI APMV genomic sequence NC_006450; UniProtKB/Swiss-Prot accession number Q5UQX1), (ii) ORF3 capping enzyme from yeast *Kluyveromyces lactis* linear extra-chromosomal episome pGKL2 (Tommasino, Ricci et al. 1988, Tiggemann, Jeske et al. 2001) (NCBI *Kluyveromyces lactis* CB 2359 pGKL2 genomic sequence NC_010187; UniProtKB/Swiss-Prot accession number P05469), (iii) African swine fever virus NP868R capping enzyme (Pena, Yanez et al. 1993, Jais 2011, Dixon, Chapman et al. 2013, Jais, Decroly et al. 2018) (NCBI ASFV genomic sequence strain BA71V NC_001659; UniProtKB/Swiss-Prot accession number P32094), VP4 Bluetongue virus capping enzyme (NCBI BTV serotype 10 genomic sequence Y00421; UniProtKB/Swiss-Prot accession number P07132).

Capping enzymes consisting of two subunits which include, but are not limited to: (i) the mammalian capping enzymes that consists of the RNGTT subunit having both RTPase and GTase enzymatic activities (Yue, Maldonado et al. 1997, Pillutla, Yue et al. 1998, Tsukamoto, Shibagaki et al. 1998, Yamada-Okabe, Doi et al. 1998) (also named HCE1; human and mouse UniProtKB/Swiss-Prot accession number O60942 and O55236, respectively) and RNMT having N7-MTase enzymatic activity (Pillutla, Yue et al. 1998, Tsukamoto, Shibagaki et al. 1998) (human and mouse UniProtKB/Swiss-Prot accession number Q05D80 and D3YYS7, respectively), (ii) the vaccinia capping enzyme that consists of the D1R gene product having RTPase, GTase and N7-MTase enzymatic domains (Cong and Shuman 1993, Niles and Christen 1993, Mao and Shuman 1994, Cong and Shuman 1995, Mao and Shuman 1996, Myette and Niles 1996, Yu and Shuman 1996, Yu, Martins et al. 1997, Gong and Shuman 2003) (genomic sequence strain Western Reserve NC_006998.1; UniProtKB/Swiss-Prot accession number P04298) and D12L gene product that has no intrinsic enzymatic activity but enhances drastically the RNA N7-MTase activity of the D1R subunit (Higman, Bourgeois et al. 1992, Higman, Christen et al. 1994, Mao and Shuman 1994, Schwer, Hausmann et al. 2006, De la Pena, Kyrieleis et al. 2007) (genomic sequence strain Western Reserve NC_006998.1; Gene 3707515; UniProtKB/Swiss-Prot accession number P04318).

Capping enzymes that consist of three subunits, such *Saccharomyces cerevisiae* CET1 with RTPase (Tsukamoto, Shibagaki et al. 1997, Gu, Rajashankar et al. 2010) (UniProtKB/Swiss-Prot accession number O13297), CEG1 with GTase (Shibagaki, Itoh et al. 1992, Yamada-Okabe, Doi et al. 1998, Gu, Rajashankar et al. 2010) (UniProtKB/Swiss-Prot accession number Q01159), and ABD1 having N7-MTase catalytic activities (Mao, Schwer et al. 1995, Schwer, Saha et al. 2000) (UniProtKB/Swiss-Prot accession number P32783).

As used herein, the term "cap-0 non canonical capping enzymes" refers to enzymes able to add a cap-0 structure at the 5' end of RNA molecules but in a pathway which differs from the canonical enzymatic process. As of today, three non-canonical 5' RNA cap synthesis mechanisms have been described:

Firstly, the $^{m7}$GTP RNA capping pathway of various ss(+)RNA viruses of the alphavirus (e.g. Semliki Forest virus and Sindbis virus), potexvirus (e.g. Bamboo mosaic virus), tobamovirus (e.g. Tobacco mosaic virus), Togaviridae (e.g. Rubella virus and Chikungunya virus) and Hepeviridae (e.g. Hepatitis E virus) families (Decroly, Ferron et al. 2011). This RNA capping pathway relies on three sequential enzymatic reactions: (a) RTPase similar to the conventional pathway (for example, nsP2 protein of Semliki Forest virus resulting from the apparent cleavage of the non-structural P123 polyprotein; UniProtKB/Swiss-Prot accession number P08411), hydrolyzes the γ-β bond at the 5'-end of the RNA, (b) methylation of GTP molecule by an atypical N7-MTase (for example, nsP1 protein of Semliki Forest virus also resulting from the apparent cleavage of the non-structural P123 polyprotein for example; UniProtKB/Swiss-Prot accession number P08411), (c) $^{m7}$GTP is then recognized as a substrate by an atypical GTase (also nsP1 of protein of Semliki Forest virus for example) and transferred onto the 5'-end of the acceptor ppRNA, to yield a typical $^{m7}$GpppN cap-0 structure (Decroly, Ferron et al. 2011). These three enzymatic activities, in addition to a RNA-dependent RNA polymerase catalytic domain, can be found in a single viral protein, i.e. the Bamboo Mosaic Virus mRNA capping enzyme ORF1 (Li, Shih et al. 2001, Huang, Han et al. 2004, Huang, Hsu et al. 2005, Han, Tsai et al. 2007) (NCBI BMV isolate BaMV-O genomic sequence NC_001642; UniProtKB/Swiss-Prot accession number Q65005).

Secondly, the GDP RNA capping pathway of many ss(−) RNA viruses of the Rhabdoviridae (e.g. vesicular stomatitis virus and Rabies virus), paramyxoviridae (e.g. human respiratory syncytial virus and Measles virus), Bornaviridae (e.g. bornavirus), and Filoviridae (e.g. Ebola virus and Marburg virus) families (Decroly, Ferron et al. 2011), which catalyzes the formation of a cap-0/cap-1 structure in four enzymatic steps. For instance, the single subunit large L protein from the human respiratory syncytial virus (UniProtKB/Swiss-Prot accession number P28887) can complete these four enzymatic steps by itself, in addition of having an RNA dependent RNA polymerase activity: (a) the NTPase activity is responsible for the hydrolysis of a GTP into a GDP, (b) the L protein hydrolyzes the α-β bond of the pppRNA triphosphate moiety, thereby releasing pyrophosphate and creating a covalent enzyme-pRNA intermediate (i.e. RNA with monophosphate 5'-end), (c) the pRNA moiety is then transferred onto the GDP to form a GpppN block RNA. In this case, only the α-phosphate originates from the RNA whereas both the β and γ-phosphates are contributed by the GDP, (d) finally, synthesis of the cap-0 then cap-1 structures is completed by two successive methylations at m$^7$pppN and 2'-residue on the first transcribed nucleotide, respectively (Grdzelishvili, Smallwood et al. 2005, Li, Fontaine-Rodriguez et al. 2005, Grdzelishvili, Smallwood et al. 2006, Ogino and Banerjee 2007, Li, Rahmeh et al. 2008, Ogino and Banerjee 2008, Rahmeh, Li et al. 2009).

Thirdly, RNA cap snatching, which is a process by which some viruses unable to synthesize their own cap structures, acquire capping by stealing it from host mRNA. Viruses belonging to this class include representatives of the Orthomyxoviridae (e.g. Influenza virus, Thogoto virus), Arenaviridae (e.g. Lassa virus, Machupo virus) and Bunyaviridae families (e.g. Hantaan virus, La Crosse virus, Tomato Spotted Wilt virus) (Decroly, Ferron et al. 2011). To acquire their cap structure, nucleotide sequence between 10 and 20 nucleotides in size is cleaved from the 5' end of host capped mRNAs by an endonuclease activity encompassed within the viral RNA dependent RNA polymerase and transferred to the viral genomic RNA. The capped leader obtained is subsequently used to prime transcription on the viral genomic RNA, which ultimately leads to the synthesis of capped, translatable viral mRNAs. The Arenaviridae and Bunyaviridae express a large monomeric polymerase to ensure cap snatching. Orthomyxoviridae influenza virus have heterotrimeric polymerase, consisting of PB1 (UniProtKB/Swiss-Prot accession number strain A/Puerto Rico/8/1934 H1 N1 P03431), PB2 (UniProtKB/Swiss-Prot accession number strain A/Puerto Rico/8/1934 H1 N1 P03428) and PA (UniProtKB/Swiss-Prot accession number strain A/Puerto Rico/8/1934 H1 N1 P03433). All these three subunits are required for endonuclease activity but the enzymatic activity is thought to reside in the amino-terminal domain of the PA subunit (Ohlmann, Rau et al. 1995).

As used herein, the term "cap-1 capping enzymes" refers to enzymes able to add cap-1 structure at the 5'end of RNA molecules.

As used herein, the term "cap-2 capping enzymes" refers to enzymes able to add cap-2 structure at the 5'end of RNA molecules.

In mammalians, higher eukaryotes and some viruses, two cap modifications are found, which are lacking in yeast and plant mRNAs (Langberg and Moss 1981) and are generated by methylation of the 2' hydroxy-groups of the ribose moiety of nucleotides at the 5' end of the mRNA: cap-1 at the first mRNA nucleotide, and cap-2 at the second one. Cap-1 methylation is found on nearly all mammalian mRNA molecules, while only half of the mRNA contain a 2'-O-methylated residue on the second transcribed nucleotide.

In mammalians, cap-1 and cap-2 modifications are performed by two ribose-2'-O methyltransferases, (also named nucleoside-2'-methyltransferase or 2'-O-MTases) (Belanger, Stepinski et al. 2010). Firstly, MTR1 (cap-1 ribose-2'-O MTase activity, also named FTSJD2, KIAA0082 or ISG95; UniProtKB/Swiss-Prot accession number Q8N1G2), which is exclusively found in the nucleus and contains a putative nuclear localization signal and a G-patch domain that is potentially involved in RNA binding (Haline-Vaz, Silva et al. 2008). Noticeably, MRT1 associates with the CTD of RNA polymerase II, which indicate that cap-1 formation occurs early in the synthesis of mRNA (Langberg and Moss 1981). Secondly, MTR2 (cap 2 ribose-2'-O MTase, also named FTSJD1 or FLJ11171; UniProtKB/Swiss-Prot accession number Q8IYT2) transfers a methyl group from S-adenosylmethionine to the 2'-O-ribose of the second nucleotide of mRNA and small nuclear RNA. Nor $N^7$ methylation of the guanosine cap-0 or cap-1 modification is required for MTR2, but the presence of cap-1 increases MTR2 activity. The MTR2 protein is distributed throughout the nucleus and cytosol, in contrast to the nuclear MTR1 (Keith, Ensinger et al. 1978).

Some eukaryotic viruses have their own cap-1 and/or cap-2 2'-O-MTases, including:

VP39 from the vaccinia virus (NCBI genomic sequence NC_006998.1; UniProtKB/Swiss-Prot accession number YP_232977) that has both cap-1 and cap-2 2'-O-MTase enzymatic activities (Schnierle, Gershon et al. 1994, Shi, Yao et al. 1996, Hu, Gershon et al. 1999), Orf69 from the *Autographa californica* Nucleopolyhedrovirus (NCBI genomic sequence NC_001623.1; UniProtKB/Swiss-Prot accession number P41469) (Wu and Guarino 2003), nsp16 from coronavirus (residues 6776-7073 of the polyprotein 1 ab of the human SARS coronavirus NCBI genomic sequence NC_004718.3; UniProtKB/Swiss-Prot accession number POC6X7) (Reinisch, Nibert et al. 2000, Decroly, Imbert et al. 2008, Chen, Cai et al. 2009, Lugari, Betzi et al. 2010), λ2 protein from Reovirus (e.g. mammalian orthoreovirus type 3, strain Dearing; NCBI genomic sequence J03488; UniProtKB/Swiss-Prot accession number P11079), which has 2'-O-MTase in addition to GTase and N7-MTase enzymatic activities (Bujnicki and Rychlewski 2001), VP4 from the bluetongue virus (NCBI BTV serotype 10 genomic sequence ID Y00421; UniProtKB/Swiss-Prot accession number P07132), NS5 from the flaviviruses that include dengue virus yellow fever virus, Zika virus, West Nile virus, Meaban virus, Yokose virus, St. Louis encephalitis virus, Japanese encephalitis virus, tick-borne encephalitis virus (e.g. polyprotein from Dengue virus type 1 strain Nauru/West Pac/1974; NCBI genomic sequence U88535; UniProtKB/Swiss-Prot accession number P17763) can also methylate internal adenosine residues of mRNA (Dong, Chang et al. 2012).

In one embodiment, the chimeric enzyme according to the invention comprises or consists of:
  at least one catalytic domain of a RNA triphosphatase;
  at least one catalytic domain of a guanylyltransferase;
  at least one catalytic domain of a $N^7$-guanine methyltransferase; and
  at least one RNA-binding domain of a protein-RNA tethering system;
in particular, wherein at least one of said catalytic domains is a catalytic domain of a cap-0 canonical capping enzyme, more particularly of a virus cap-0 canonical capping enzyme.

As used herein, the term "RNA triphosphatase" (RTPase) relates to the enzyme, which removes the γ phosphate residue of 5' triphosphate end of nascent pre-mRNA to diphosphate (Furuichi and Shatkin 2000).

As used herein, the term "RNA guanylyltransferase" (GTase) refers to the enzyme, which transfers GMP from GTP to the diphosphate nascent RNA terminus (Furuichi and Shatkin 2000).

As used herein, the term "$N^7$-guanine methyltransferase" (N7-MTase) relates to the enzyme, which adds a methyl residue on azote 7 of guanine to the GpppN cap (Furuichi and Shatkin 2000).

Said catalytic domains of a RNA triphosphatase, of a guanylyltransferase, of a $N^7$-guanine methyltransferase, can be of the same or of different capping enzymes.

Preferably, said catalytic domains of a RNA triphosphatase, of a guanylyltransferase, of a $N^7$-guanine methyltransferase are from one or several cytoplasmic enzymes, which have advantageously relatively simple structure and well-characterized enzymatic activities. Thus, in particular, said catalytic domains of a RNA triphosphatase, of a guanylyltransferase, of a $N^7$-guanine methyltransferase can be catalytic domains of one or several virus capping enzymes, or of capping enzymes of cytoplasmic episomes.

In one embodiment, said catalytic domains of a RNA triphosphatase, of a guanylyltransferase, of a $N^7$-guanine methyltransferase are from one or several virus capping enzymes, in particular selected in the group consisting of the wild type vaccinia virus capping enzyme, the wild type bluetongue virus capping enzyme, the wild type bamboo mosaic virus capping enzyme, the wild type African swine fever virus capping enzyme, the wild type *Acanthamoeba* polyphaga mimivirus capping enzyme, the wild type Organic Lake phycodnavirus 1 (OLPV1) capping enzyme, the wild type Organic Lake phycodnavirus 2 (OLPV2) capping enzyme, the wild type *Phaeocystis globosa* virus capping enzyme, the wild type *Chrysochromulina ericina* virus capping enzyme and mutants or derivatives thereof which are able respectively to remove the γ phosphate residue of 5' triphosphate end of nascent pre-mRNA to diphosphate or transfer GMP from GTP to the diphosphate nascent RNA terminus or add a methyl residue on azote 7 of guanine to the GpppN cap, more particularly of the wild type African swine fever virus capping enzyme and mutants or derivatives thereof which are able respectively to remove the γ phosphate residue of 5' triphosphate end of nascent pre-mRNA to diphosphate or transfer GMP from GTP to the diphosphate nascent RNA terminus or add a methyl residue on azote 7 of guanine to the GpppN cap.

As used herein the term "vaccinia virus capping enzyme" relates to the heterodimeric D1R/D12L capping enzyme of vaccinia virus. The D1R gene product having RTPase, GTase and N7-MTase enzymatic domains (Cong and Shuman 1993, Niles and Christen 1993, Mao and Shuman 1994, Cong and Shuman 1995, Mao and Shuman 1996, Myette and Niles 1996, Yu and Shuman 1996, Yu, Martins et al. 1997, Gong and Shuman 2003) (genomic sequence strain Western Reserve NC_006998.1; UniProtKB/Swiss-Prot accession number P04298) and D12L gene product that has no intrinsic enzymatic activity but enhances drastically the RNA N7-MTase activity of the D1R subunit (Higman, Bourgeois et al. 1992, Higman, Christen et al. 1994, Mao and Shuman 1994, Schwer, Hausmann et al. 2006, De la Pena, Kyrieleis et al. 2007) (genomic sequence strain Western Reserve NC_006998.1; Gene 3707515; UniProtKB/Swiss-Prot accession number P04318).

As used herein the term "bluetongue virus capping enzyme" relates to the single-unit VP4 capping enzyme of Bluetongue virus (BTV), which is a 76 kDa protein (644 amino-acids; for sequence, see for instance NCBI BTV serotype 10 genomic sequence Y00421; Gene 2943157; UniProtKB/Swiss-Prot P07132). This capping enzyme is likely able to homodimerize through the leucine zipper located near its carboxyl-terminus (Ramadevi, Rodriguez et al. 1998). VP4 catalyze all three enzymatic steps required for mRNA $m^7$GpppN capping synthesis: RTPase (Martinez-Costas, Sutton et al. 1998), GTase (Martinez-Costas, Sutton et al. 1998, Ramadevi, Burroughs et al. 1998) and N7-MTase (Ramadevi, Burroughs et al. 1998).

As used herein, the term "bamboo mosaic virus capping enzyme" relates to ORF1, the Bamboo Mosaic Virus (BMV) mRNA capping enzyme, which is a single-unit 155-kDa protein (1365-amino acids; NCBI BMV isolate BaMV-O genomic sequence NC_001642; Gene 1497253; UniProtKB/Swiss-Prot Q65005). ORF1 protein has all the enzymatic activities required to generate $m^7$GpppN mRNA capping, i.e. RTPase (Li, Shih et al. 2001, Han, Tsai et al. 2007), GTase and N7-MTase (Li, Chen et al. 2001, Li, Shih et al. 2001).

As used herein, the term "African swine fever virus capping enzyme" (ASFV) relates to the NP868R capping enzyme (G4R), which is a single-unit 100 kDa protein (868 amino-acids; NCBI ASFV genomic sequence strain BA71V NC_001659; Gene 1488865; UniProtKB/Swiss-Prot P32094), which has all the enzymatic activities required to generate $m^7$GpppN mRNA capping, i.e. RTPase, GTase and N7-MTase (Pena, Yanez et al. 1993, Jais 2011, Dixon, Chapman et al. 2013, Jais, Decroly et al. 2018).

As used herein, the term "*Acanthamoeba Polyphaga* mimivirus capping enzyme" relates to R382, (APMV), which is another single-unit 136.5 kDa protein (1170 amino-acids; NCBI APMV genomic sequence NC_006450; Gene 3162607; UniProtKB/Swiss-Prot Q5UQX1).

As used herein, the term "Organic Lake phycodnavirus 1 (OLPV1) capping enzyme" refers to a 889 single-unit amino-acids, as referenced with NCBI accession number ADX05869.1.

As used herein, the term "Organic Lake phycodnavirus 2 (OLPV2) capping enzyme" refers to a 942 single-unit amino-acids, as referenced with NCBI accession number ADX06468.1.

As used herein, the term "*Phaeocystis globosa* virus capping enzyme" refers to a 1066 single-unit amino-acids as referenced with UniProtKB/Swiss-Prot YP_008052553.1.

As used herein, the term "*Chrysochromulina ericina* virus capping enzyme" refers to a 965 single-unit amino-acids as referenced with UniProtKB/Swiss-Prot YP_009173557.1.

In one embodiment, said catalytic domains of a RNA triphosphatase, of a guanylyltransferase, of a $N^7$-guanine methyltransferase are from the capping enzymes of cytoplasmic episomes, like pGKL2. In particular, said catalytic domains of a RNA triphosphatase, of a guanylyltransferase, of a $N^7$-guanine methyltransferase are included in the whole or part of the capping enzyme of the yeast linear extra-chromosomal episome pGKL2 encoded by the ORF3 gene of *Kluyveromyces lactis* pGKL2 (NCBI *Kluyveromyces lactis* CB 2359 pGKL2 genomic sequence NC_010187; UniProtKB/Swiss-Prot P05469) and which is a 594 amino-acid protein (70.6 kDa protein).

In one embodiment of the chimeric enzyme according to the invention, said catalytic domain of a RNA triphosphatase, said catalytic domain of a guanylyltransferase, said catalytic domain of a $N^7$-guanine methyltransferase, are included in a monomer, i.e. in one polypeptide. For example, said monomer can be a monomeric capping enzyme or a monomeric chimeric enzyme according to the invention.

In particular, said catalytic domain of a RNA triphosphatase, said catalytic domain of a guanylyltransferase, and said catalytic domain of a $N^7$-guanine methyltransferase are included in a monomeric capping enzyme. In this case, the chimeric enzyme according to the invention comprise a monomeric capping enzyme, which includes said catalytic domain of a RNA triphosphatase, said catalytic domain of a guanylyltransferase, and said catalytic domain of a $N^7$-guanine methyltransferase. Said monomeric capping enzyme can be a monomeric virus capping enzyme, in particular selected in the group consisting of the wild type bluetongue virus capping enzyme, the wild type bamboo mosaic virus capping enzyme, the wild type African swine fever virus capping enzyme, the wild type *Acanthamoeba polyphaga* mimivirus capping enzyme, the wild type OLPV1 capping enzyme, the wild type OLPV2 capping enzyme, the wild type *Phaeocystis globosa* virus capping enzyme, the wild type *Chrysochromulina ericina* virus capping enzyme and mutants and derivatives thereof which are able to add a $m^7$GpppN cap at the 5'-terminal end of RNA molecules and, more particularly of the wild type African swine fever virus capping enzyme and mutants and derivatives thereof which are able to add a $m^7$GpppN cap at the 5'-terminal end of RNA molecules, and even more particularly the wild type African swine fever virus capping enzyme The chimeric enzyme according to the invention can also further comprise a domain, which enhances the activity of at least one catalytic domain of the chimeric enzyme of the invention, in particular of at least one catalytic domain of a capping enzyme, more particularly of at least one catalytic domain selected in the group consisting of a catalytic domain of a RNA triphosphatase, a catalytic domain of a guanylyltransferase, a catalytic domain of a $N^7$-guanine methyltransferase, preferably of a $N^7$-guanine methyltransferase.

For example said domain, which enhance the activity of at least one catalytic domain of the chimeric enzyme of the invention, can be a 31-kDa subunit encoded by the vaccinia virus D12L gene (genomic sequence NC_006998.1; Gene3707515; UniProtKB/Swiss-Prot YP_232999.1), which has no intrinsic enzymatic activity, but enhances drastically the RNA $N^7$-guanine methyltransferase activity of the D1R subunit of the vaccinia mRNA capping enzyme (Higman, Bourgeois et al. 1992, Higman, Christen et al. 1994, Mao and Shuman 1994).

In one embodiment, the chimeric enzyme according to the invention further comprises at least one catalytic domain of a 5'-end RNA processing enzyme other than cap-0, cap-1 and cap-2 capping enzymes.

As used herein, the term "5'-end RNA processing enzyme other than cap-0, cap-1 and cap-2 capping enzymes" relates to enzymes able to modify the ultimate or penultimate bases of a mRNA sequence, other than cap-0, cap-1 and cap-2 capping enzymes, including N6-methyl-adenosine transferase and enzymes able to add 2,2,7-trimethylguanosine (TMG) and 2,7-trimethylguanosine (DMG) cap modifications at the 5'end of RNA molecules.

Other capping modifications than cap-0, cap-1, cap-2 modifications have been characterized in eukaryotes or viruses mRNA. For instance, the $m^6A$ methylation by N6-methyl-adenosine transferase of the first base is a reversible modification that influences cellular mRNA fate (Mauer, Luo et al. 2017). 2,2,7-trimethylguanosine (TMG) and 2,7-trimethylguanosine (DMG) cap modifications, which are present on snRNAs, telomerase RNAs, trans-spliced nematode mRNAs and certain viral mRNAs, can confer an advantage of translation (Darzynkiewicz, Stepinski et al. 1988, Cai, Jankowska-Anyszka et al. 1999). TMG and DMG are performed by specialized enzymes from viruses (e.g. L320 from DNA mimivirus, UniProtKB/Swiss-Prot accession number Q5UQR2 (Benarroch, Qiu et al. 2009); protozoan (e.g. *Giardia lamblia* trimethylguanosine synthase (NCBI accession number EAA46438 (Hausmann and Shuman 2005); lower eukaryotes (e.g. *Schizosaccharomyces pombe* trimethylguanosine synthase, UniProtKB/Swiss-Prot accession number Q09814 (Hausmann and Shuman 2005, Hausmann, Zheng et al. 2008, Benarroch, Jankowska-Anyszka et al. 2010) and mammalian (e.g. human trimethylguanosine synthase 1 UniProtKB/Swiss-Prot accession number Q96RS0 (Zhu, Qi et al. 2001, Hausmann, Zheng et al. 2008, Benarroch, Jankowska-Anyszka et al. 2010).

In one embodiment, the chimeric enzyme according to the invention further comprises at least one catalytic domain of a poly(A) polymerase.

In fact, unexpectidely, the inventor has demonstrated that monomeric or oligomeric chimeric enzymes comprising at least one catalytic domain of a capping enzyme, at least one RNA-binding domain of a protein-RNA tethering system and at least one catalytic domain of a poly(A) polymerase allows to highly increase, synergistically, the capping rate of specific mRNAs produced by RNA polymerase, compared to the combination of a capping enzyme fused to a RNA-binding domain in presence of a poly(A) polymerase fused to a RNA-binding domain. These results are unexpected since capping enzymes and poly(A) polymerases are not physically linked in the nature and contain no binding domain for a specific RNA sequence. One skilled in the art could have expected to obtain the same expression rate since the components are the same.

As used herein, the term "poly(A) polymerase" relates to any enzyme able to catalyze the non-templated addition of adenosine residues from ATP onto the 3' end of RNA molecules.

In one embodiment, said catalytic domain of a poly(A) polymerase is a catalytic domain of a canonical poly(A) polymerase including mammalian (such as PAPOLA, PAPOLG), yeast, (such as *Saccharomyces cerevisiae* PAP1, *Schizosaccharomyces pombe* PLA1, *Candida albicans* PAP, *Pneumocystis carinii* PAP), protozoan, viral and bacterial canonical poly(A) polymerases.

In particular said catalytic domain of a poly(A) polymerase is a cytoplasmic canonical poly(A) polymerase, more particularly selected in the group consisting of:
  mammalian cytoplasmic poly(A) polymerase including PAPOLB (human and mouse PAPOLB, UniProtKB/Swiss-Prot accession number Q9NRJ5 and O9WVP6, respectively), which is at least in part a cytoplasmic enzyme (Kashiwabara, Zhuang et al. 2000, Lee, Lee et al. 2000, Kashiwabara, Tsuruta et al. 2016); mutants of PAPOLA (human and mouse PAPOLA, UniProtKB/Swiss-Prot accession number P51003 and Q61183, respectively) wherein mutation or deletion of the nuclear localization signal can relocate the nuclear enzyme to the cytoplasm (Raabe, Murthy et al. 1994, Vethantham, Rao et al. 2008), and mutants of PAPOLG (human and mouse PAPOLG, UniProtKB/Swiss-Prot accession number Q9BWT3 and Q6PCL9, respectively) wherein mutation or deletion of the nuclear localization signal is likely to relocate the nuclear enzyme to the cytoplasm (Kyriakopoulou, Nordvarg et al. 2001),
  yeast or protozoan poly(A) polymerases, e.g. mutants of *Saccharomyces cerevisiae* PAP1, UniProtKB/Swiss-Prot accession number P29468; *Schizosaccharomyces pombe* PLA1, UniProtKB/Swiss-Prot accession number Q10295), *Candida albicans* PAP (UniProtKB/Swiss-Prot accession number Q9UW26), *Pneumocystis carinii* PAP (also named *Pneumocystis jiroveci*; UniProtKB/Swiss-Prot accession number A0A0W4ZDF2), wherein mutation or deletion of the nuclear localization signal is likely to relocate the nuclear enzyme to the cytoplasm (Lingner, Kellermann et al. 1991), as well as other psychrotrophic, mesophilic, thermophilic or hyperthermophilic yeast or protozoan strains,
  viral poly(A) polymerases, including the heterodimeric vaccinia virus poly(A) polymerase that consists of the VP55 catalytic subunit (UniProtKB/Swiss-Prot accession number strain Western Reserve P23371) and VP39 that acts as a processivity factor (UniProtKB/Swiss-Prot accession number strain Western Reserve P07617) (Gershon, Ahn et al. 1991), other poxvirus poly(A) polymerases (e.g. Cowpox virus, Monkeypox virus or Camelpox virus), African Swine Fever Virus (C475L, UniProtKB/Swiss-Prot accession number A0A0A1E081), *Acanthamoeba polyphaga* mimivirus R341 (UniProtKB/Swiss-Prot accession number E3VZZ8) and the *Megavirus chilensis* Mg561 poly(A) polymerases (NCBI Accession number: YP_004894612), Moumouvirus (NCBI accession number AEX62700), Mamavirus (NCBI accession number AEQ60527), Cafeteria roenbergensis BV-PW1 virus (NCBI accession number YP_003969918), *Megavirus* Iba (NCBI accession number AGD92490), Yellowstone lake mimivirus (NCBI accession number YP_009174112), *Chrysochromulina ericina* virus (NCBI accession number YP_009173345), organic lake phycodnavirus 1 (NCBI accession number ADX05881), organic lake phycodnavirus 2 (NCBI accession number ADX06298), Faustovirus (NCBI accession number AMN83802) and *Phaeocystis globosa* virus (NCBI accession number YP_008052392).
and mutants or derivatives thereof which are able to catalyze the non-templated addition of adenosine residues from ATP onto the 3' end of RNA molecules.

In still another embodiment, said catalytic domain of a poly(A) polymerase is a catalytic domain of a non-canonical poly(A) polymerase, in particular of a cytoplasmic non-canonical poly(A) polymerase. "noncanonical poly(A) polymerases", refers to enzymes, that do not have a tripartite structure involving a N-terminal nucleotidyltransferase (NT) catalytic domain, a central domain, and a C-terminal domain corresponding to the RNA binding domain (RBD) (Trippe, Sandrock et al. 1998). As of today, the following non-canonical poly(A) polymerases have been described in mammalians:

Firstly, the poly(A) polymerase GLD2 (also named PAPD4; human and mouse GLD2, UniProtKB/Swiss-Prot accession number Q6PIY7 and 091Y16, respectively), which was initially identified by sequence analogy with the *Caenorhabditis elegans* GLD2 (Wang, Eckmann et al. 2002). In addition, GLD4 (UniProtKB/Swiss-Prot accession number GSEFL0), a GLD2 homolog, has been characterized in *Caenorhabditis elegans* but is lacking in mammals (Schmid, Kuchler et al. 2009)

Secondly, the single-subunit mitochondrial poly(A) polymerase (also named PAPD1, TUTase1 or mtPAP; human and mouse PAPD1, UniProtKB/Swiss-Prot accession number Q9NVV4 and Q9D0D3, respectively), Thirdly, the nucleolar RBM21 poly(A) polymerase (also named U6 TUTase, TUT1 or Star-PAP; Speckle Targeted PIPKIa Regulated Poly(A) Polymerase; human and mouse RBM21, UniProtKB/Swiss-Prot accession number Q9H6E5 and Q8R3F9, respectively), Fourthly and fifthly, the putative cytoplasmic/nuclear PAPD5 (human and mouse PAPD5, UniProtKB/Swiss-Prot accession number Q8NDF8 and Q68ED3, respectively) and PAPD7 (also named POLS, human and mouse PAPD7, UniProtKB/Swiss-Prot accession number Q5XG87 and Q6PB75, respectively), which are orthologs to the yeast poly(A) polymerase TRF4 or TRF5 from the nuclear TRAMP complex (Trf4/Air2/Mtr4p Polyadenylation complex) (Haracska, Johnson et al. 2005), Sixthly and seventhly, the cytoplasmic ZCCHC6 (human and mouse ZCCHC6, UniProtKB/Swiss-Prot accession number Q5VYS8 and Q5BLK4, respectively) and ZCCHC11 poly(A) polymerases (human and mouse ZCCHC11, UniProtKB/Swiss-Prot accession number Q5TAX3 and B2RX14, respectively).

In an embodiment, said catalytic domain of a poly(A) polymerase is a catalytic domain of a yeast or protozoan poly(A) polymerase, in particular selected in the group consisting of the wild type *Saccharomyces cerevisiae* PAP1 poly(A) polymerase, *Schizosaccharomyces pombe* PLA1, *Candida albicans* PAP (UniProtKB/Swiss-Prot accession number Q9UW26), *Pneumocystis carinii* PAP (UniProtKB/Swiss-Prot accession number A0A0W4ZDF2), the cytoplasmic mutants of the *Saccharomyces cerevisiae, Schizosaccharomyces pombe, Candida albicans* or *Pneumocystis carinii* poly(A) polymerases (wherein the nuclear localization signal is non-functional or deleted) and mutants or derivatives thereof, which are able to catalyze the non-templated addition of adenosine residues from ATP onto the 3' end of RNA molecules.

The yeast or protozoan poly(A) polymerases have notably the advantage of its reduced molecular weight in comparison to mammalian canonical poly(A) polymerases (e.g. 568 and 566 amino-acids vs. 745 amino-acids for the *Saccharomyces cerevisiae* PAP1 and *Schizosaccharomyces pombe* PLA1 poly(A) polymerases vs. the human PAPOLA, UniProtKB/Swiss-Prot accession number P51003, respectively), as well as high processivity in tethering assays (Dickson, Thompson et al. 2001), As used herein, the term "PAP1 poly(A) polymerase" refers to the *Saccharomyces cerevisiae* PAP1 poly(A) polymerase (UniProtKB/Swiss-Prot accession number P29468), As used herein, the term "PLA1 poly(A) polymerase" refers to the *Schizosaccharomyces pombe* PLA1 poly(A) polymerase, UniProtKB/Swiss-Prot accession number Q10295), Said catalytic domain of a poly(A) polymerase can be a catalytic domain of a virus poly(A) polymerase, in particular selected in the group consisting of the wild type VP55 poly(A) polymerase, the wild type C475L poly(A) polymerase, the wild type R341 poly(A) polymerase and the wild type MG561 poly(A) polymerase and mutants or derivatives thereof, which are able to catalyze the non-templated addition of adenosine residues from ATP onto the 3' end of RNA molecules.

The virus poly(A) polymerases have notably the advantage of their reduced molecular weight in comparison to mammalian poly(A) polymerases, their strong enzymatic activity and presence in the cytoplasmic compartment when expressed in mammalian cells. In addition, some of these enzymes, such as R341 and MG561 poly(A) polymerases do not require any know accessory protein cofactor.

As used herein, the term "VP55 poly(A) polymerase" relates to the catalytic subunit (UniProtKB/Swiss-Prot accession number strain Western Reserve P23371) of the heterodimeric vaccinia virus poly(A) polymerase. VP39, the second subunit, acts as a processivity factor (UniProtKB/Swiss-Prot accession number strain Western Reserve P07617).

As used herein, the term "C475L poly(A) polymerase" relates to the African Swine Fever Virus poly(A) polymerase (UniProtKB/Swiss-Prot accession number A0A0A1E081).

As used herein, the term "R341 poly(A) polymerase" relates to the *Acanthamoeba polyphaga* mimivirus R341 poly(A) polymerase (UniProtKB/Swiss-Prot accession number E3VZZ8).

As used herein, the term "MG561 poly(A) polymerase" relates to the *Megavirus chilensis* MG561 poly(A) polymerases (NCBI Accession number: YP_004894612).

In one embodiment, the chimeric enzyme according to the invention further comprises at least one catalytic domain of a DNA-dependent RNA polymerase.

As used herein, the term "DNA-dependent RNA polymerase" (RNAPs) relates to nucleotidyl transferases that synthesize complementary strand of RNA from a single- or double-stranded DNA template in the 5'→3' direction.

Preferably, said catalytic domain of a DNA-dependent RNA polymerase is a catalytic domain of an enzyme, which have a relatively simple structure and more preferably, which have characterized genomic enzymatic regulation elements (i.e. promoter and transcription termination signal). Thus, in particular, said catalytic domain of a DNA-dependent RNA polymerase can be a catalytic domain of a bacteriophage DNA-dependent RNA polymerase, of a bacterial DNA-dependent RNA polymerase or of a DNA-dependent RNA polymerase of various eukaryotic organelles (e.g. mitochondria, chloroplast and proplastids).

In one embodiment, said catalytic domain of a DNA-dependent RNA polymerase is a catalytic domain of a bacteriophage DNA-dependent RNA polymerase.

The bacteriophage DNA-dependent RNA polymerases have notably the advantage that they optimize the levels of transgene expression, in particular by having a higher processivity than the eukaryotic RNA polymerases. The bacteriophage DNA-dependent RNA polymerases have also a much simpler structure than most nuclear eukaryotic polymerases, which consist of multiple subunits (e.g. RNA polymerase II) and transcription factors. Most of the bacteriophage DNA-dependent RNA polymerases characterized so far are single-subunit enzymes, which require no accessory proteins for initiation, elongation, or termination of transcription (Chen and Schneider 2005). Several of these enzymes, which are named for the bacteriophages from which they have been cloned, have also well-characterized regulation genomic elements (i.e. promoter and termination signals), which are important for transgenesis.

There is also no competition between the endogenous gene transcription and the transgene transcription. The chimeric enzymes according to the invention, which comprise bacteriophage DNA-dependent RNA-polymerase moieties, allow the production of RNA transcripts in any eukaryotic species (e.g. yeast, rodents, and humans). They are not expensive, quick and easy to implement and thus appropriate for large-scale assays and protein productions; it allows the production of RNA transcripts in any biological system (e.g. acellular reaction mix, cultured cells, and living organisms), since in contrast to eukaryotic RNA polymerase such as RNA polymerase II, most of bacteriophage DNA-dependent RNA polymerases do not require associated factors for initiation, elongation or termination of transcription.

Said catalytic domain of a bacteriophage DNA-dependent RNA polymerase can be a catalytic domain of a bacteriophage DNA-dependent RNA polymerase, in particular selected in the group consisting of the wild type T7 RNA polymerase (NCBI genomic sequence NC_001604; Gene 1261050; UniProtKB/Swiss-Prot P00573), the wild type T3 RNA polymerase (NCBI genomic sequence NC_003298; Gene 927437; UniProtKB/Swiss-Prot Q778M8), the wild type K1E RNA polymerase (NCBI genome sequence AM084415.1, UniProtKB/Swiss-Prot Q2WC24), the wild type K1-5 RNA polymerase (NCBI genome sequence AY370674.1, NCBI YP_654105.1), the wild type K11 RNA polymerase (NCBI genomic K11 RNAP sequence NC_004665; Gene 1258850; UniProtKB/Swiss-Prot Q859H5), the wild type φA1122 RNA polymerase (NCBI genomic sequence NC_004777; Gene 1733944; UniProtKB/Swiss-Prot protein Q858N4), the wild type φYeo3-12 RNA polymerase (NCBI genomic sequence NC_001271; Gene 1262422; UniProtKB/Swiss-Prot Q9T145) and the wild type gh-1 RNA polymerase (NCBI genomic sequence NC_004665; Gene 1258850; UniProtKB/Swiss-Prot protein Q859H5), the wild type SP6 RNA polymerase (NCBI genomic sequence NC_004831; Gene 1481778; UniProtKB/Swiss-Prot protein Q7Y5R1), and mutants or derivatives thereof, which are able to synthesize single-stranded RNA complementary in sequence to the double-stranded template DNA in the 5'→3' direction, more particularly the wild type T7 RNA polymerase, the wild type T3 RNA polymerase, the wild type SP6 RNA polymerase, the wild type K1-5 RNA polymerase and the wild type K1E RNA polymerase and mutants or derivatives thereof, which are able to synthesize single-stranded RNA complementary in sequence to the double-stranded template DNA in the 5'→3' direction.

The prototype of bacteriophage RNA polymerases, i.e. the bacteriophage T7 RNA polymerase, has in particular the advantage that, in vitro, the enzyme is extremely processive and elongates 240-250 nucleotides/s at 37° C. in the 5'→3' direction (Golomb and Chamberlin 1974, Lyakhov, He et al. 1997, Zhang and Studier 1997, Finn, MacLachlan et al. 2005). Moreover, when expressed in eukaryotic cells, the bacteriophage T7 RNA polymerase, remains largely in the cytoplasm (Elroy-Stein and Moss 1990, Gao and Huang 1993, Brisson, He et al. 1999, Jais, Decroly et al. 2018), and thus optimizes the levels of transgene expression by avoiding the active transfer of large DNA molecules (i.e. transgene) from the cytoplasm to the nucleus of eukaryotic cells and the export of RNA molecules from the nucleus to the cytoplasm.

The catalytic domain of a DNA-dependent RNA polymerase can be the one of the wild type of the K1E or K1-5 RNA polymerase but also of mutants of the K1E or K1-5 RNA polymerases, which are able to synthesize single-stranded RNA complementary in sequence to the double-stranded template DNA in the 5'→3' direction, even with processivity. For example, said mutants can be selected in the group consisting of the K1E RNA polymerase mutants R551S (Jais, Decroly et al. 2018), F644A, Q649S, G645A, R627S, 1810S, D812E (Makarova, Makarov et al. 1995), and K631M (Osumi-Davis, de Aguilera et al. 1992, Osumi-Davis, Sreerama et al. 1994), in particular R551 S (Jais, Decroly et al. 2018).

Preferably, said catalytic domain of the DNA-dependent RNA-polymerase of the chimeric enzyme according to the invention is from different enzymes than those of the host cell to prevent the competition between the endogenous gene transcription and said DNA sequence transcription.

The chimeric enzyme according to the invention comprises at least said catalytic domains but can further comprise the whole or part of the enzymes containing said catalytic domains. In fact, according to one embodiment of the chimeric enzyme according to the invention, said catalytic domain of a RNA triphosphatase, said catalytic domain of a guanylyltransferase and said catalytic domain of a $N^7$-guanine methyltransferase can be included in the whole or part of a capping enzyme, preferably of a monomeric capping enzyme. Said catalytic domain of a poly(A) polymerase can also be included in the whole or part of a poly(A) polymerase. Said catalytic domain of a DNA-dependent RNA polymerase can also be included in the whole or part of a DNA-dependent RNA polymerase, preferably of a monomeric DNA-dependent RNA polymerase.

Unexpectedly, the inventor has demonstrated that a chimeric enzyme of the invention is able to generate translatable RNA in the cells, therefore generating the key modifications required for its recognition and use by the host-cell ribosomal machinery.

As used herein, the terms «link» and «bound» encompass covalent and non-covalent linkage.

Said RNA-binding domain can be linked by covalent (directly or indirectly by a linking peptide) linkage to one catalytic domain of the chimeric enzyme according to the invention, in particular selected in the group consisting of:
  said catalytic domain of a capping enzyme, in particular
    said catalytic domain of a RNA triphosphatase, said catalytic domain of a guanylyltransferase, said catalytic domain of a N⁷-guanine methyltransferase;

said catalytic domain of a poly(A) polymerase, said domain which enhances the activity of at least one catalytic domain of the chimeric enzyme of the invention, preferably of at least one catalytic domain selected in the group consisting of a catalytic domain of a RNA triphosphatase, a catalytic domain of a guanylyltransferase, a catalytic domain of a N⁷-guanine methyltransferase, particularly of a N⁷-guanine methyltransferase; and said catalytic domain of a 5'end RNA processing enzyme other than cap-0, cap-1 and cap-2 capping enzymes.

Linking peptide has the advantage of generating fusion proteins in which steric hindrance is minimizes and enough space is provided for the components of the fusion protein to remain in their native conformation.

Said linking peptide of the invention can be selected from the group consisting of:

peptides of formula $(Gly_m Ser_p)_n$, in which:
m represents an integer from 0 to 12, in particular from 1 to 8, and more particularly from 3 to 6 and even more particularly 4;
p represents an integer from 0 to 6, in particular from 0 to 5, more particularly from 0 to 3 and more particularly 1; and
n represents an integer from 0 to 30, in particular from 0 to 12, more particularly from 0 to 8 and even more particularly between 1 and 6 inclusive;

in particular peptides of formula $(Gly_m Ser_p)_n$, in which:
m represents 4;
p represents 0 or 1; and
n represents 1, 2 or 4;

more particularly peptides of formula $Gly_4$, $(Gly_4 Ser)_1$ $(Gly_4 Ser)_2$ and $(Gly_4 Ser)_4$.

The flexible linker peptides of formula $(Gly_m Ser_p)_n$ have the advantages that the glycine residues confer peptide flexibility, while the serine provide some solubility (Huston, Levinson et al. 1988). Furthermore, the absence of sensitive sites for chymotrypsin I, factor Xa, papain, plasmin, thrombin and trypsin in the $(Gly_m Ser_p)_n$ linker sequences is supposed to increase the overall stability of the resulting fusion proteins.

$(Gly_m Ser_p)_n$ linkers of variable lengths are commonly used to engineer single-chain Fv fragment (sFv) antibodies (Huston, Levinson et al. 1988). In addition, $(Gly_m Ser_p)_n$ linkers have been used to generate various fusion proteins, which frequently retain the biological activities of each of their components (Newton, Xue et al. 1996, Lieschke, Rao et al. 1997, Shao, Zhang et al. 2000, Hu, Li et al. 2004).

Other types of peptide linkers can be also considered to generate chimeric enzymes according to the invention, such as GGGGIAPSMVGGGGS (SEQ ID No 48) (Turner, Ritter et al. 1997), SPNGASNSGSAPDTSSAPGSQ (SEQ ID No 49) (Hennecke, Krebber et al. 1998), EGKSSGSGSESKSTE (SEQ ID No 50) (Bird, Hardman et al. 1988), EGKSSGSGSESKEF (SEQ ID No 51) (Newton, Xue et al. 1996), GGGSGGGSGGGTGGGSGGG (SEQ ID No 52) (Robinson and Sauer 1998), GSTSGSGKSSEGKG (SEQ ID No 53) (Bedzyk, Weidner et al. 1990), YPRSIYIRRRHPSPSLTT (SEQ ID No 54) (Tang, Jiang et al. 1996), GSTSGSGKPGSGEGS (SEQ ID No 55) (Ting, Kain et al. 2001), SSADDAKKDAAKKDDAKKDDAKKDA (SEQ ID No 56) (Pantoliano, Bird et al. 1991), GSADDAXXDAAXKDDAKKDDAKKDGS (SEQ ID No 57) (Gregoire, Lin et al. 1996), LSADDAKKDAAKKDDAKKDDAKKDL (SEQ ID No 58) (Pavlinkova, Beresford et al. 1999), AEAAAKEAAAKEAAAKA (SEQ ID No 59) (Wickham, Carrion et al. 1995), GSTSGSGKPGSGEGSTGAGGAGSTSGSGKPSGEG (SEQ ID No 60) (Ting, Kain et al. 2001), LSLEVAEEIARLEAEV (SEQ ID No 61) (Ting, Kain et al. 2001), GTPTPTPTPTGEF (SEQ ID No 62) (Gustaysson, Lehtio et al. 2001), GSTSGSGKPGSGEGSTKG (SEQ ID No 63) (Whitlow, Bell et al. 1993) and GSHSGSGKP (SEQ ID No 64) (Ting, Kain et al. 2001) as described previously in the patent application WO 2011/128444.

Said RNA-binding domain of a protein-RNA tethering system and said catalytic domains can also be assembled by specific protein elements, like leucine zippers.

The C-terminal end or the N-terminal end of said RNA-binding domain can be linked to the N-terminal end or the C-terminal end of one of said catalytic domain of the chimeric enzyme of the invention, respectively.

Preferably, the C-terminal end of said RNA binding domain is linked by covalent (directly or indirectly by a linking peptide preferably of formula $Gly_4$, $(Gly_4 Ser)_1$ $(Gly_4 Ser)_2$ or $(Gly_4 Ser)_4$, even more preferably of formula $(Gly_4 Ser)_1$ or a $Gly_4$) linkage to the N-terminal end of one of the catalytic domain selected in the group consisting of:

said catalytic domain of a capping enzyme, in particular said catalytic domain of a RNA triphosphatase, said catalytic domain of a guanylyltransferase, said catalytic domain of a N⁷-guanine methyltransferase;

said catalytic domain of a poly(A) polymerase, said domain which enhances the activity of at least one catalytic domain of the chimeric enzyme of the invention, preferably of at least one catalytic domain selected in the group consisting of a catalytic domain of a RNA triphosphatase, a catalytic domain of a guanylyltransferase, a catalytic domain of a N⁷-guanine methyltransferase, particularly of a N⁷-guanine methyltransferase; and said catalytic domain of a 5'end RNA processing enzyme other than cap-0, cap-1 and cap-2 capping enzymes.

In one embodiment, the C-terminal end of said RNA binding domain is linked by covalent (directly or indirectly by a linking peptide preferably of formula $Gly_4$, $(Gly_4 Ser)_1$ $(Gly_4 Ser)_2$ or $(Gly_4 Ser)_4$, even more preferably of formula $(Gly_4 Ser)_1$ or a $Gly_4$) linkage to the N-terminal end of one of the catalytic domain selected in the group consisting of:

said catalytic domain of a capping enzyme, in particular said catalytic domain of a RNA triphosphatase, said catalytic domain of a guanylyltransferase, said catalytic domain of a N⁷-guanine methyltransferase; and said catalytic domain of a poly(A) polymerase.

In one embodiment, the chimeric enzyme of the invention is a fusion protein.

As used herein, the term "fusion protein" relates to artificial proteins created through the joining of two or more proteins or protein domains that originally coded for separate proteins. Translation of this fusion gene results in a single or multiple polypeptides with functional properties derived from each of the original proteins.

In one embodiment, the chimeric enzyme of the invention is a fusion protein, wherein:

the C-terminal end of said RNA binding domain is linked by covalent linkage to the N-terminal end of said catalytic domain of a poly(A) polymerase, the C-terminal end of said catalytic domain of a poly(A) polymerase is linked by covalent linkage, in particular by a linking peptide, to the N-terminal end of one of the catalytic domain of a capping enzyme; and the N-terminal end of said catalytic domain of a DNA-dependent RNA polymerase is linked by covalent linkage, in particular by a linking peptide, to the C-terminal end of one of the catalytic domain of a capping enzyme.

In one embodiment, the chimeric enzyme of the invention is a fusion protein, wherein:
   the C-terminal end of said RNA binding domain is linked by covalent linkage to the N-terminal end of said catalytic domain of a poly(A) polymerase,
   the C-terminal end of said catalytic domain of a poly(A) polymerase is linked by covalent linkage to the N-terminal end of one of the catalytic domain selected in the group consisting of:
      said catalytic domain of a RNA triphosphatase,
      said catalytic domain of a guanylyltransferase, and
      said catalytic domain of a $N^7$-guanine methyltransferase,
in particular, of said catalytic domain of a RNA triphosphatase; and
   the N-terminal end of said catalytic domain of a DNA-dependent RNA polymerase is linked by covalent linkage, in particular by a linking peptide, to the C-terminal end of one of the catalytic domain selected in the group consisting of:
      said catalytic domain of a RNA triphosphatase,
      said catalytic domain of a guanylyltransferase, and
      said catalytic domain of a $N^7$-guanine methyltransferase
in particular, of said catalytic domain of a $N^7$-guanine methyltransferase In one embodiment of the chimeric enzyme according to the invention, at least two, in particular at least three, at least four and more particularly the whole catalytic domains can be assembled, fused, or bound directly or indirectly by a linking peptide (particularly by a linking peptide of formula $Gly_4$, $(Gly_4Ser)_1$, $(Gly_4Ser)_2$ or $(Gly_4Ser)_4$, more particularly of formula $(Gly_4Ser)_2$.

In particular, at least two, particularly at least three and more particularly the whole catalytic domains selected in the group consisting of:
   a catalytic domain of a capping enzyme, in particular selected in the group consisting of a catalytic domain of a RNA triphosphatase, a catalytic domain of a guanylyltransferase and a catalytic domain of a $N^7$-guanine methyltransferase,
   a catalytic domain of a DNA-dependent RNA polymerase, and a
   a catalytic domain of a poly(A) polymerase;
particularly consisting of:
   a catalytic domain of a RNA triphosphatase,
   a catalytic domain of a guanylyltransferase,
   a catalytic domain of a $N^7$-guanine methyltransferase, and
   a catalytic domain of a DNA-dependent RNA polymerase
are bound directly or by a linking peptide, particularly selected in the group consisting of linking peptide of formula $Gly_4$, $(Gly_4Ser)_1$, $(Gly_4Ser)_2$ and $(Gly_4Ser)_4$, more particularly of formula $(Gly_4Ser)_2$.

Preferably, at least said catalytic domain of a DNA-dependent RNA polymerase is bound by a linking peptide (particularly selected in the group consisting of linking peptide of formula $Gly_4$, $(Gly_4Ser)_1$, $(Gly_4Ser)_2$ and $(Gly_4Ser)_4$, more particularly of formula $(Gly_4Ser)_2$) to at least one of the catalytic domain of a capping enzyme in particular selected in the group consisting of:
   said catalytic domain of a RNA triphosphatase;
   said catalytic domain of a guanylyltransferase; and
   said catalytic domain of a $N^7$-guanine methyltransferase;
more particularly said catalytic domain of a $N^7$-guanine methyltransferase.

Particularly, the linking peptide can be located N-terminally with respect to said catalytic domain of a DNA-dependent RNA polymerase, in particular of a bacteriophage DNA-dependent RNA polymerase selected in the group consisting of T7, T3, SP6, K1-5 and K1E RNA polymerases, and C-terminally with respect to said catalytic domain of a RNA triphosphatase, said catalytic domain of a guanylyltransferase, and said catalytic domain of a $N^7$-guanine methyltransferase.

In particular, the N-terminal end of said catalytic domain of a DNA-dependent RNA polymerase, in particular of a bacteriophage DNA-dependent RNA polymerase selected in the group consisting of T7, T3, SP6, K1-5 and K1E-RNA polymerases, is linked by covalent linkage, in particular by a linking peptide, to the C-terminal end of one of the catalytic domain selected in the group consisting of:
   said catalytic domain of a RNA triphosphatase,
   said catalytic domain of a guanylyltransferase, and
   said catalytic domain of a $N^7$-guanine methyltransferase;
particularly said catalytic domain of a $N^7$-guanine methyltransferase.

Preferably, at least said catalytic domain of a poly(A) polymerase is bound by a linking peptide to at least one of the catalytic domain of a capping enzyme in particular selected in the group consisting of:
   said catalytic domain of a RNA triphosphatase;
   said catalytic domain of a guanylyltransferase; and
   said catalytic domain of a $N^7$-guanine methyltransferase;
more particularly said catalytic domain of a RNA triphosphatase.

Particularly, the linking peptide can be located C-terminally with respect to said catalytic domain of a poly(A) polymerase and N-terminally with respect to said catalytic domain of a capping enzyme, in particular said catalytic domain of a RNA triphosphatase, said catalytic domain of a guanylyltransferase, and said catalytic domain of a $N^7$-guanine methyltransferase, more particularly said catalytic domain of a RNA triphosphatase.

Said catalytic domains of a capping enzyme (in particular of a RNA triphosphatase, of a guanylyltransferase, of a $N^7$-guanine methyltransferase), of a DNA-dependent RNA polymerase and of a poly(A) polymerase can also be assembled by specific protein elements, like leucine zippers, like biotinylation domain to one of the catalytic domain (e.g. Avi-tag II (Cronan 1990) or PFB-tag (Wu, Yeung et al. 2002)) and a biotin binding domain to one of the other catalytic domain (e.g. Strep-tag II (Schmidt and Skerra 1993) or Nano-tag (Lamla and Erdmann 2004)) in the chimeric enzyme according to the invention.

In one embodiment of the chimeric enzyme according to the invention, at least two of said catalytic domains can be assembled, by non-covalent linkage, in particular by leucine zippers.

Preferably, at least said catalytic domain of a DNA-dependent RNA polymerase or of a poly(A) polymerase is assembled by non-covalent linkage, in particular by leucine zippers, to at least one of the catalytic domain of a capping enzyme, preferably to at least one of the catalytic domain selected in the group consisting of:
   said catalytic domain of a RNA triphosphatase;
   said catalytic domain of a guanylyltransferase; and
   said catalytic domain of a N7-guanine methyltransferase.

In one embodiment, at least said catalytic domain of a poly(A) polymerase is assembled by non-covalent linkage, in particular by leucine zippers, preferably at its C-terminal end, to at least one of the catalytic domain of a capping enzyme, particularly to at least one of the catalytic domain selected in the group consisting of:

said catalytic domain of a RNA triphosphatase;
said catalytic domain of a guanylyltransferase; and
said catalytic domain of a N7-guanine methyltransferase;

and more particularly to said catalytic domain of a RNA triphosphatase.

The leucine zippers, which are dimeric coiled-coil protein structures composed of two amphipathic α-helices that interact with each other, are commonly used to homo- or hetero-dimerize proteins (O'Shea, Klemm et al. 1991). Each helices consist of repeats of seven amino acids, in which the first amino-acid (residue a) is hydrophobic, the fourth (residue d) is usually a leucine, while the other residues are polar. The leucine zippers VELCRO ACID-p1 and BASE-p1, which form a parallel heterodimeric two-stranded coiled coil structures, have high propensity to form parallel protein hetero-dimers (O'Shea, Lumb et al. 1993). They have been used to heterodimerize membrane proteins (Chang, Bao et al. 1994, Pashine, Busch et al. 2003), as well as several soluble proteins (Busch, Reich et al. 1998, Busch, Pashine et al. 2002).

Other types of oligomerisation peptide domains can be also considered to generate chimeric enzyme according to the invention, to assemble at least two of said catalytic domains of the chimeric enzyme according to the invention, especially leucine zippers that form antiparallel heteromeric structures, such as the ACID-a1/BASE-a1 (Oakley and Kim 1998), ACID-Kg/BASE-Eg (McClain, Woods et al. 2001), NZ/CZ (Ghosh, Hamilton et al. 2000), ACID-pLL/BASE-pLL (Lumb and Kim 1995), and EE1234L and RR1234L (Moll, Ruvinov et al. 2001) leucine zippers. Disulfide-linked versions of leucine zippers can be also used to generate disulfide coiled coil-bound heterodimeric chimeric enzyme according to the invention (O'Shea, Lumb et al. 1993), as well as interchain disulfide bridges between cysteine residues under oxidizing conditions (Wells and Powers 1986).

At least two of said catalytic domains of a poly(A) polymerase, of a capping enzyme (in particular of a RNA triphosphatase, of a guanylyltransferase, of a $N^7$-guanine methyltransferase), and of a DNA-dependent RNA polymerase can thus be assembled by leucine zippers, in particular leucine zippers that form antiparallel heteromeric structures, such as the ACID-a1/BASE-a1 (Oakley and Kim 1998), ACID-Kg/BASE-Eg (McClain, Woods et al. 2001), NZ/CZ (Ghosh, Hamilton et al. 2000), and ACID-pLL/BASE-pLL leucine zippers, disulfide coiled coil-bound (O'Shea, Lumb et al. 1993), as well as disulfide bridges between cysteine residues (Wells and Powers 1986).

In one embodiment, the chimeric enzyme according to the invention comprises:

a RNA binding domain of the wild type lambda N antitermination protein fused to
the wild type poly(A) polymerase of the mammalian PAPOLB, vaccinia virus VP55, African Swine Fever Virus C475L, *Acanthamoeba polyphaga* mimivirus R341, *Megavirus chilensis* MG561, *Saccharomyces cerevisiae, Candida albicans, Pneumocystis carinii*, mutant PAPOLA, or a mutant or a derivative thereof, which is able to catalyze the non-templated addition of adenosine residues from ATP onto the 3' end of RNA molecules; or to
the wild type *Saccharomyces cerevisiae* PAP1 poly(A) polymerase, cytoplasmic mutant of the *Saccharomyces cerevisiae* PAP1 poly(A) polymerase (wherein the nuclear localization signal is non-functional or deleted) or a mutant or derivative thereof, which is able to catalyze the non-templated addition of adenosine residues from ATP onto the 3' end of RNA molecules; or to
the wild type *Schizosaccharomyces pombe* PLA1 poly(A) polymerase, cytoplasmic mutant of the *Schizosaccharomyces pombe* PLA1 poly(A) polymerases (wherein the nuclear localization signal is non-functional or deleted) or a mutant or derivative thereof, which is able to catalyze the non-templated addition of adenosine residues from ATP onto the 3' end of RNA molecules;
the wild type mammalian PAPOLA, cytoplasmic mutant of the mammalian PAPOLA poly(A) polymerase (wherein the nuclear localization signal is non-functional or deleted) or a mutant or derivative thereof, which is able to catalyze the non-templated addition of adenosine residues from ATP onto the 3' end of RNA molecules and, fused to, in particular fused to the amino-terminal end of,
the wild type mRNA capping enzyme of the NP868R African Swine Fever virus or a mutant or a derivative thereof, which is able to add a $m^7$GpppN cap at the 5'-terminal end of RNA molecules, in particular the wild type NP868R African swine fever virus capping enzyme, fused to, in particular fused to the amino-terminal end of,
the amino-terminal end of, the wild type T7, T3, SP6, K1-5, K1E RNA polymerase or mutant or derivative thereof which is able to synthesize single-stranded RNA complementary in sequence to the double-stranded template DNA in the 5'→3' direction including the R551 S K1E RNA polymerase mutant, in particular via a linker, preferably selected in the group consisting of linking peptide of formula $Gly_4$, $(Gly_4Ser)_1$, $(Gly_4Ser)_2$ and $(Gly_4Ser)_4$, more preferably of formula $Gly_4$, $(Gly_4Ser)_1$ or $(Gly_4Ser)_2$.

In another embodiment, the chimeric enzyme according to the invention comprises:

a RNA binding domain of the wild type lambda N antitermination protein fused to
the wild type poly(A) polymerase of the R341 virus or a mutant or a derivative thereof, which is able to catalyze the non-templated addition of adenosine residues from ATP onto the 3' end of RNA molecules; or
the wild type *Saccharomyces cerevisiae* PAP1 poly(A) polymerase or a cytoplasmic mutant of the *Saccharomyces cerevisiae* PAP1 poly(A) polymerase (wherein the nuclear localization signal is non-functional) or a mutant or derivative thereof, which is able to catalyze the non-templated addition of adenosine residues from ATP onto the 3' end of RNA molecules; or
the wild type *Schizosaccharomyces pombe* PLA1 poly(A) polymerase, cytoplasmic mutant of the *Schizosaccharomyces pombe* PLA1 poly(A) polymerases (wherein the nuclear localization signal is non-functional or deleted) or a mutant or derivative thereof, which is able to catalyze the non-templated addition of adenosine residues from ATP onto the 3' end of RNA molecules;

and, fused to, in particular fused to the amino-terminal end of,
the wild type mRNA capping enzyme of the NP868R African Swine Fever virus or a mutant or a derivative thereof, which is able to add a $m^7$GpppN cap at the 5'-terminal end of RNA molecules, in particular the wild type NP868R African swine fever virus capping enzyme, fused to, in particular fused to the amino-terminal end of, the amino-terminal end of the wild type K1E RNA polymerase or mutant or derivative thereof which is able to synthesize single-stranded RNA complementary in sequence to the double-stranded template DNA in the 5'→3' direction including the R551 S K1E RNA polymerase mutant, in particular via a linker, preferably selected in the group consisting of linking peptide of formula $Gly_4$, $(Gly_4Ser)_1$, $(Gly_4Ser)_2$ and $(Gly_4Ser)_4$, more preferably of formula $Gly_4$ or $(Gly_4Ser)_2$).

The invention also relates to an isolated nucleic acid molecule or a group of isolated nucleic acid molecules, said nucleic acid molecule(s) encoding a chimeric enzyme according to the invention or an isolated nucleic acid molecule encoding a chimeric enzyme, characterized in that its sequence comprises a nucleic acid sequence encoding a RNA-binding domain of a protein-RNA tethering system fused in frame, in particular in the order, to:
- a nucleic acid sequence encoding at least one catalytic domain of a poly(A) polymerase;
- a nucleic acid sequence encoding at least one catalytic domain of a capping enzyme; and optionally to
- a nucleic acid sequence encoding at least one catalytic domain of a DNA-dependent RNA polymerase, in particular of a bacteriophage DNA-dependent RNA polymerase; wherein said RNA-binding domain binds specifically to a RNA element of said protein-RNA tethering system, consisting of a specific RNA sequence and/or structure.

Said group of isolated nucleic molecules encoding a chimeric enzyme according to the invention comprises or consists of all the nucleic acid molecules which are necessary and sufficient to obtain a chimeric enzyme according to the invention by their expression.

As used herein, the term "nucleic acid molecule" any molecules composed of linked nucleotides, encompassing DNA and RNA molecules.

In one embodiment, said group of isolated nucleic acid molecules encoding a chimeric enzyme according to the invention comprises or consists of:
- a nucleic acid molecule encoding said RNA binding domain of a protein-RNA tethering system, and
- a nucleic acid molecule encoding at least one catalytic domain of a capping enzyme, in particular at least one catalytic domain of a RNA triphosphatase, at least one catalytic domain of a guanylyltransferase and at least one catalytic domain of a N7-guanine methyltransferase;

and optionally:
- a nucleic acid molecule encoding at least one catalytic domain of a poly(A) polymerase; and/or
- a nucleic acid molecule encoding at least one catalytic domain of a DNA-dependent RNA polymerase, in particular of a bacteriophage DNA-dependent RNA polymerase.

In another embodiment, said group of isolated nucleic acid molecules encoding a chimeric enzyme according to the invention comprises or consists of:
- a nucleic acid molecule encoding said RNA binding domain of a protein-RNA tethering system,
- a nucleic acid molecule encoding at least one catalytic domain of a RNA triphosphatase,
- a nucleic acid molecule encoding at least one catalytic domain of a guanylyltransferase,
- a nucleic acid molecule encoding at least one catalytic domain of a N7-guanine methyltransferase;

and optionally:
- a nucleic acid molecule encoding at least one catalytic domain of a poly(A) polymerase; and/or
- a nucleic acid molecule encoding at least one catalytic domain of a DNA-dependent RNA polymerase, in particular of a bacteriophage DNA-dependent RNA polymerase.

In one embodiment, the isolated nucleic acid molecule of the invention comprises or consists of a nucleic acid sequence encoding said RNA-binding domain of a protein-RNA tethering system fused in frame, in particular in the order, to:
- a nucleic acid sequence encoding said catalytic domain of a poly(A) polymerase,
- a nucleic acid sequence encoding said catalytic domain of a capping enzyme, in particular,
  - a nucleic acid sequence encoding said catalytic domain of a RNA triphosphatase,
  - a nucleic acid sequence encoding said catalytic domain of a guanylyltransferase,
  - a nucleic acid sequence encoding said catalytic domain of a $N^7$-guanine methyltransferase, and to
- a nucleic acid sequence encoding said catalytic domain of a DNA-dependent RNA polymerase, in particular of a bacteriophage DNA-dependent RNA polymerase.

Such single nucleic acid sequence has the advantage of facilitating the subunit assembly, since there is only a single open-reading frame.

In one embodiment of the isolated nucleic acid molecule of the invention, its sequence comprises at least one nucleic acid sequence encoding a ribosome skipping motif.

As used herein, the term "ribosome skipping motif" relates to alternate mechanism of translation in which a specific viral peptide prevents the ribosome from covalently linking a new inserted amino-acid, and let it continue translation. This results in apparent co-translational cleavage of the polyprotein.

In particular, said ribosome skipping motif is selected in the group consisting of the 2A sequences from the Foot-and-mouth disease virus Aphtovirus (UniProtKB/Swiss-Prot AAT01756), Avisivirua A (UniProtKB/Swiss-Prot M4PJD6), Duck hepatitis A Avihepatovirus (UniProtKB/Swiss-Prot Q0ZQM1), Encephalomyocarditis Cardiovirus (UniProtKB/Swiss-Prot Q66765), Cosavirus A (UniProtKB/Swiss-Prot B8XTP8), Equine rhinitis B Erbovirus 1 (UniProtKB/Swiss-Prot Q66776), Seneca Valley Erbovirus (UniProtKB/Swiss-Prot Q155Z9), Hunnivirus A (UniProtKB/Swiss-Prot F4YYF3), Kunsagivirus A (UniProtKB/Swiss-Prot S4VD62), Mischivirus A (UniProtKB/Swiss-Prot I3VR62), Mosavirus A2 (UniProtKB/Swiss-Prot X2L6K2), Pasivirus A1 (UniProtKB/Swiss-Prot 16YOK4), Porcine teschovirus 1 (UniProtKB/Swiss-Prot Q9WJ28), Infectious flacherie Iflavirus (UniProtKB/Swiss-Prot Q70710), Thosea asigna Betatetravirus (UniProtKB/Swiss-Prot Q9YK87), Cricket paralysis Cripavirus (UniProtKB/Swiss-Prot Q9IJX4), Human rotavirus C (UniProtKB/Swiss-Prot Q9PY95), and *Lymantria dispar* cypovirus 1 (UniProtKB/Swiss-Prot 0911D7), In particular, said nucleic acid sequence encoding a ribosome skipping motif is selected in the group consisting of the 2A sequences from the Foot-and-mouth disease virus Aphtovirus (also designated as "F2A", UniProtKB/Swiss-Prot AAT01756) or Porcine teschovirus 1 (also designated as "T2A", UniProtKB/Swiss-Prot Q9WJ28).

Said nucleic acid sequence encoding a ribosome skipping motif can be localized between any of the sequence encoding said catalytic domain of the chimeric enzyme of the invention.

In one embodiment, said nucleic acid sequence encoding a ribosome skipping motif can be localized between the sequence encoding said catalytic domain of a poly(A) polymerase fused in frame with the sequence encoding:
- said catalytic domain of a capping enzyme, preferably selected in the group consisting of said catalytic domain of a RNA triphosphatase, said catalytic domain of a guanylyltransferase and said catalytic domain of a $N^7$-guanine methyltransferase, or
- said catalytic domain of a DNA-dependent RNA polymerase, in particular of a bacteriophage DNA-dependent RNA polymerase;

in particular, fused in frame with the sequence encoding said catalytic domain of a capping enzyme, more particularly said catalytic domain of a RNA triphosphatase.

In another embodiment, said nucleic acid sequence encoding a ribosome skipping motif can be localized between the sequence encoding said catalytic domain of a DNA-dependent RNA polymerase fused in frame with the sequence encoding said catalytic domain of a capping enzyme, in particular selected in the group consisting of said catalytic domain of a RNA triphosphatase, said catalytic domain of a guanylyltransferase and said catalytic domain of a $N^7$-guanine methyltransferase, more particularly fused in frame with the sequence encoding said catalytic domain of a $N^7$-guanine methyltransferase.

In one embodiment, the isolated nucleic acid molecule according to the invention is characterized in that its sequence comprises or consists of
- a nucleic acid sequence encoding a RNA-binding domain of a protein-RNA tethering system fused in frame, in particular in the order, to:
  - a nucleic acid sequence encoding a catalytic domain of a poly(A) polymerase;
  - a nucleic acid sequence encoding a catalytic domain of a capping enzyme, and optionally to
  - a nucleic acid sequence encoding said catalytic domain of a DNA-dependent RNA polymerase, in particular of a bacteriophage DNA-dependent RNA polymerase;

and
- a nucleic acid sequence encoding a ribosome skipping motif between said nucleic acid sequence encoding a catalytic domain of a poly(A) polymerase and said nucleic acid sequence encoding one of the catalytic domain selected in the group consisting of:
  - said catalytic domain of a capping enzyme, and
  - said catalytic domain of a DNA-dependent RNA polymerase.

In one embodiment, the isolated nucleic acid molecule according to the invention is characterized in that its sequence comprises or consists of
- a nucleic acid sequence encoding a RNA-binding domain of a protein-RNA tethering system fused in frame, in particular in the order, to:
  - a nucleic acid sequence encoding a catalytic domain of a poly(A) polymerase;
  - a nucleic acid sequence encoding a catalytic domain of a RNA triphosphatase,
  - a nucleic acid sequence encoding a catalytic domain of a guanylyltransferase,
  - a nucleic acid sequence encoding a catalytic domain of a $N^7$-guanine methyltransferase, and optionally to
  - a nucleic acid sequence encoding said catalytic domain of a DNA-dependent RNA polymerase, in particular of a bacteriophage DNA-dependent RNA polymerase;

and
- a nucleic acid sequence encoding a ribosome skipping motif between said nucleic acid sequence encoding a catalytic domain of a poly(A) polymerase and said nucleic acid sequence encoding one of the catalytic domain selected in the group consisting of:
  - said catalytic domain of a RNA triphosphatase,
  - said catalytic domain of a guanylyltransferase,
  - said catalytic domain of a N7-guanine methyltransferase, and
  - said catalytic domain of a DNA-dependent RNA polymerase, preferably said catalytic domain of a RNA triphosphatase.

In one embodiment, the isolated nucleic acid molecule of the invention encoding a chimeric enzyme, is characterized in that its sequence comprises a nucleic acid sequence encoding a RNA-binding domain of a protein-RNA tethering system fused in frame in the order to:
- a nucleic acid sequence encoding at least one catalytic domain of a poly(A) polymerase;
- a nucleic acid sequence encoding at least one catalytic domain of a capping enzyme; and optionally to
- a nucleic acid sequence encoding said catalytic domain of a DNA-dependent RNA polymerase, in particular of a bacteriophage DNA-dependent RNA polymerase;

and in that its sequence further comprises a nucleic acid sequence encoding a ribosome skipping motif between said nucleic acid sequence encoding a catalytic domain of a poly(A) polymerase and said nucleic acid sequence encoding at least one catalytic domain of a capping enzyme.

In fact, unexpectedly, the inventor has demonstrated (as illustrated in Example 8) that such nucleic acid molecule allows higher expression rate by a DNA-dependent RNA polymerase than the combination of a nucleic acid molecule encoding a chimeric enzyme comprising at least one domain of a capping enzyme and a DNA-dependent RNA polymerase associated with a nucleic acid molecule encoding a RNA-binding domain of a protein-RNA tethering system fused in frame to a nucleic acid sequence encoding at least one catalytic domain of a poly(A) polymerase.

These results are really surprising and one skilled in the art could have expected to obtain the same expression rate since the components are the same.

In particular, the nucleic acid molecule according to the invention can be operatively linked to at least one, preferably the whole promoter(s) selected from the group consisting of:
- a promoter for an eukaryotic DNA-dependent RNA polymerase, preferably for RNA polymerase II;
- the promoter for a bacteriophage DNA-dependant RNA polymerase; and
- a promoter for said catalytic domain of a DNA-dependent RNA polymerase of the chimeric enzyme of the invention.

The link of the nucleic acid to a promoter for a eukaryotic DNA-dependent RNA polymerase, preferably for RNA polymerase II has notably the advantage that when the chimeric enzyme of the invention is expressed in an eukaryotic host cell, the expression of the chimeric enzymes is driven by the eukaryotic RNA polymerase, preferably the RNA polymerase II. These chimeric enzymes, in turn, can initiate transcription of the transgene. If tissue-specific RNA polymerase II promoters are used, the chimeric enzyme of the invention can be selectively expressed in the targeted tissues/cells.

Said promoter can be a constitutive promoter or an inducible promoter well known by one skilled in the art. The promoter can be developmentally regulated, inducible or tissue specific.

The invention also relates to a vector comprising a nucleic acid molecule according to the invention. Said vector can be appropriated for semi-stable or stable expression.

The invention also relates to a group of vectors comprising said group of isolated nucleic acid molecules according to the invention.

Particularly said vector according to the invention is a cloning or an expression vector.

The invention also relates to a host cell comprising a nucleic acid molecule according to the invention or a vector according to the invention or a group of vectors according to the invention.

The host cell according to the invention can be useful for large-scale protein production.

Preferably, said catalytic domains of the DNA-polymerase RNA polymerase chimeric enzyme according to the invention are from different enzymes than those of the host cell to prevent the competition between the endogenous gene transcription and the transgene transcription.

The invention also relates to a genetically engineered non-human eukaryotic organism, which expresses a chimeric enzyme encoded by the nucleic acid molecule or the group of isolated nucleic acid molecules according to the invention, in particular a chimeric enzyme according to the invention. Said non-human eukaryotic organism can be any non-human animals, plants.

The invention also relates to the use, particularly in vitro or ex vivo, of a chimeric enzyme according to the invention, for the production of RNA molecule with 5'-terminal cap, in particular 5'-terminal m$^7$GpppN cap and preferably with 3' poly(A) tail and optionally comprising at least one chemical modification.

The invention also relates to the use, particularly in vitro or ex vivo, of a nucleic acid molecule or a group of isolated nucleic acid molecules according to the invention, for the production of RNA molecule with 5'-terminal cap, in particular 5'-terminal m$^7$GpppN cap and preferably with 3' poly(A) tail and optionally comprising at least one chemical modification.

Particularly said RNA molecule is synthetized by a bacteriophage DNA-dependant RNA polymerase.

In fact, the chimeric enzyme according to the invention is suitable for synthetizing a capped RNA with at least one chemical modification.

In particular, the invention relates to the use, particularly in vitro or ex vivo, of a chimeric enzyme according to the invention, for the production of RNA molecule with 5'-terminal cap, in particular 5'-terminal m$^7$GpppN cap and preferably with 3' poly(A) tail and comprising at least one chemical modification selected from the group consisting of pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, pseudouridine, 5-methyl-cytidine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, I-methyl-6-thio-guanosine, N2-methyl-6-thio-guanosine, and N2,N2-dimethyl-6-thio-guanosine.

The invention also relates to the in vitro or ex vivo use of a chimeric enzyme according to the invention or an isolated nucleic acid molecule or a group of isolated nucleic acid molecules according to the invention, for the production of protein, in particular protein of therapeutic interest like antibody, particularly in eukaryotic systems, such as in vitro synthesized protein assay or cultured cells.

The invention also relates to an in vitro or ex vivo method for producing a RNA molecule with a 5'-terminal cap, in particular a 5'-terminal m$^7$ GpppN cap and preferably a 3' poly(A) tail encoded by a DNA sequence, in a host cell, said method comprising the step of expressing in the host cell a nucleic acid molecule or a group of isolated nucleic acid molecules according to the invention, wherein said DNA sequence is covalently linked to at least one sequence encoding the RNA element of said protein-RNA tethering system, which specifically binds to said RNA-binding domain. As used herein the term "the RNA element of a protein-RNA tethering system which specifically binds to said RNA-binding domain" relates to a RNA sequence, usually forming a stem-loop, which is able to bind with high affinity to the corresponding RNA-binding domain of a protein-RNA tethering system.

Particularly, said DNA sequence is operatively linked to the promoter for a bacteriophage DNA-dependant RNA polymerase or to the promoter for said DNA-dependent RNA polymerase of the chimeric of the invention.

In particular, when the RNA-binding domain of a protein-RNA tethering system is the RNA-binding domain of the lambdoid N antitermination protein-RNA tethering systems, the element, which specifically binds to said RNA-binding domain can be a boxBL and/or a boxBR stem loop RNA structure (Das 1993, Greenblatt, Nodwell et al. 1993, Friedman and Court 1995), including the elements encoded by SEQ ID No 7 and SEQ ID No 38.

In particular, when the RNA-binding domain of a protein-RNA tethering system is the RNA-binding domain of the MS2 coat protein-RNA tethering system, the element, which specifically binds to said RNA-binding domain can be the 19 nucleotide or the 21 nucleotide stem-loop sequences, including the element encoded by SEQ ID No 39 (Peabody 1993, Valegard, Murray et al. 1994, LeGuyer, Behlen et al. 1996, Valegard, Murray et al. 1997) (nucleotides 1748-766 from enterobacteriophage MS2 isolate DL52, NCBI accession number J0966307.1), which contains the initiation codon of the gene for the viral replicase (Valegard, Murray et al. 1994, Valegard, Murray et al. 1997).

In particular, when the RNA-binding domain of a protein-RNA tethering system is the RNA-binding domain of the R17 isolate coat protein-RNA tethering system, the element, which specifically binds to said RNA-binding domain can be the 19 nucleotide or the 21 nucleotides stem-loop (nucleotides 1746-764 from enterobacteriophage R17, NCBI accession number EF108465.1), which contains the initiation codon of the gene for the viral replicase (Carey and Uhlenbeck 1983).

In particular, said DNA sequence is operatively linked to the promoter for a bacteriophage DNA-dependant RNA polymerase or to the promoter for said DNA-dependent RNA polymerase of the chimeric of the invention and covalently linked at its 3' terminal end to at least one, preferably at least two, at least three and more preferably at least four sequences encoding the element which specifically binds to said RNA-binding domain.

In particular, said method according to the invention further comprises the step of contacting said DNA sequence encoding the RNA molecule with the enzyme of the invention.

In particular, said DNA sequence is operatively linked to the promoter for a bacteriophage DNA-dependant RNA polymerase or to the promoter for said DNA-dependent RNA polymerase of the chimeric of the invention and covalently linked at its 3' terminal end to at least one sequence encoding the element which specifically binds to said RNA-binding domain covalently linked to a poly(A) track sequence consisting of at least 10, in particular at least 20, 30, and more particularly at least 40 deoxyadenosine residues.

In particular, said poly(A) track sequence can be covalently linked at its 3' terminal end to a self-cleaving RNA sequence and optionally to a transcription stop sequence.

In particular, said self-cleaving RNA sequence can be the self-cleaving RNA sequence from the group comprising the genomic pseudoknot ribozyme of the hepatitis D virus (Genbank accession number AJ000558.1), antigenomic hepatitis-D Virus pseudoknot ribozyme (Genbank accession number AJ000558.1), tobacco Ringspot Virus satellite hairpin ribozyme (Genbank accession number NC_003889.1) or artificial short hairpin RNA (shRNA).

In particular, said transcription stop sequence can be the bacteriophageT7 phi10 transcription stop sequence (Genbank accession number GU071091.1) or E. coli RNA polymerase rrnB t1 stop (Genbank accession number LN832404.1).

In particular, said method according to the invention can further comprise the step of introducing in the host cell said DNA sequence and/or the nucleic acid according to the invention, using well-known methods by one skilled in the art like by transfection using calcium phosphate, by electroporation or by mixing a cationic lipid with DNA to produce liposomes.

In one embodiment, said method according to the invention further comprises the step of inhibiting, in particular silencing, preferably by siRNA (small interfering RNA), miRNA (microRNA) or shRNA, the cellular transcription and post-transcriptional machineries of said host cell.

In one embodiment, said method according to the invention further comprises the step of inhibiting the expression of the endogenous DNA-dependent RNA polymerase and/or the endogenous capping enzyme in said host cell.

As used herein the term "endogenous DNA-dependent RNA polymerase" relates to the endogenous DNA-dependent RNA polymerase of said host cell. When the host cell is a eukaryotic cell, said endogenous DNA-dependent RNA polymerase is the RNA polymerase II.

As used herein the term "endogenous capping enzyme" refers to the endogenous capping enzyme of said host cell.

As used herein the term "inhibiting the expression of a protein" relates to a decrease of at least 20%, particularly at least 35%, at least 50% and more particularly at least 65%, at least 80%, at least 90% of expression of said protein. Inhibition of protein expression can be determined by techniques well known to one skilled in the art, including but not limiting to Northern-Blot, Western-Blot, RT-PCR.

The step of inhibiting the expression of the endogenous DNA-dependent RNA polymerase and/or the endogenous capping enzyme in said host cell can be implemented by any techniques well known to one skilled in the art, including but not limiting to siRNA techniques that target said endogenous DNA-dependent RNA polymerase and/or the endogenous capping enzyme, antisense RNA techniques that target said endogenous DNA-dependent RNA polymerase and/or the endogenous capping enzyme, shRNA techniques that target said endogenous DNA-dependent RNA polymerase and/or the endogenous capping enzyme.

In addition to siRNA (or shRNA), other inhibitory sequences might be also considered for the same purpose including DNA or RNA antisense (Liu and Carmichael 1994, Dias and Stein 2002), hammerhead ribozyme (Salehi-Ashtiani and Szostak 2001), hairpin ribozyme (Lian, De Young et al. 1999) or chimeric snRNA U1-antisense targeting sequence (Fortes, Cuevas et al. 2003). In addition, other cellular target genes might be considered for inhibition, including other genes involved in the cellular transcription (e.g. other subunits of the RNA polymerase II or transcription factors), post-transcriptional processing (e.g. other subunit of the capping enzyme, as well as polyadenylation or spliceosome factors), and mRNA nuclear export pathway.

In one embodiment of the method according to the invention, said RNA molecule can encode a polypeptide of therapeutic interest.

In another embodiment, said RNA molecule can be a non-coding RNA molecule selected in the group comprising siRNA, ribozyme, shRNA and antisense RNA. In particular, said DNA sequence can encode a RNA molecule selected in the group consisting of mRNA, non-coding RNA, particularly siRNA, ribozyme, shRNA and antisense RNA.

The invention also relates to the use of a chimeric enzyme according to the invention as a capping enzyme and preferably a pol(A) polymerase and a DNA-dependent RNA polymerase.

The invention also relates to a kit for the production of a RNA molecule with 5'-terminal cap, in particular 5'-terminal m$^7$GpppN cap, comprising at least one chimeric enzyme according to the invention as defined above, and/or an isolated nucleic acid molecule and/or a group of nucleic acid molecule according to the invention as defined above, and/or a vector according to the invention as defined above, or
a chimeric enzyme, in particular a cytoplasmic chimeric enzyme comprising at least one catalytic domain of a RNA triphosphatase, at least one catalytic domain of a guanylyltransferase, at least one catalytic domain of a $N^7$-guanine methyltransferase, and at least one catalytic domain of a DNA-dependent RNA polymerase and/or an isolated nucleic acid molecule and/or a group of isolated nucleic acid molecules encoding said chimeric enzyme and a poly(A) polymerase, in particular a cytoplasmic poly(A) polymerase, comprising at least one RNA-binding domain of a protein-RNA tethering system linked to at least one catalytic domain of said poly(A) polymerase and/or an isolated nucleic acid molecule encoding said poly(A) polymerase;
and optionally a DNA sequence encoded said RNA molecule, which is covalently linked to at least one sequence encoding the RNA element of said protein-RNA tethering system, which specifically binds to said RNA-binding domain.

Particularly, said kit for the production of an RNA molecule with a 5'-terminal cap, comprises a DNA sequence encoded said RNA molecule, which is operatively linked to the promoter for a bacteriophage DNA-dependant RNA polymerase or to the promoter for said DNA-dependent RNA polymerase of the chimeric enzyme of the invention.

In particular, said kit for the production of an RNA molecule with a 5'-terminal cap, comprises at least one chimeric enzyme according to the invention, and/or an isolated nucleic acid molecule and/or a group of isolated nucleic acid molecules according to the invention, and/or a vector according to the invention and optionally a DNA sequence encoded said RNA molecule, which is covalently linked to at least one sequence encoding the element which specifically binds to said RNA-binding domain and particularly which is operatively linked to the promoter for a bacteriophage DNA-dependant RNA polymerase or to the promoter for said DNA-dependent RNA polymerase of the chimeric enzyme of the invention.

In particular, said kit for the production of an RNA molecule with a 5'-terminal cap, further comprises an isolated nucleic acid molecule encoding at least one catalytic domain of a DNA-dependent RNA polymerase, and/or at least one catalytic domain of a DNA-dependent RNA polymerase, in particular of a bacteriophage DNA-dependent RNA polymerase.

Particularly, said kit further comprises its instructions of use. The invention also relates to a composition (in particular a kit or a pharmaceutical composition) comprising:
  a chimeric enzyme, in particular a cytoplasmic chimeric enzyme, comprising at least one catalytic domain of capping enzyme and at least one catalytic domain of a DNA-dependent RNA polymerase, particularly of a bacteriophage DNA-dependent RNA polymerase and/or an isolated nucleic acid molecule or a group of isolated nucleic acid molecules encoding said chimeric enzyme; and
  a poly(A) polymerase, in particular a cytoplasmic poly(A) polymerase, comprising at least one RNA-binding domain of a protein-RNA tethering system, particularly of a bacteriophage protein-RNA tethering system, linked to at least one catalytic domain of said poly(A) polymerase and/or an isolated nucleic acid molecule encoding said poly(A) polymerase; and optionally
  a DNA sequence, which is operatively linked to the promoter for said DNA-dependent RNA polymerase and covalently linked to at least one sequence encoding the element interacting with high affinity with said RNA-binding domain;
said composition being useful for the production of a RNA molecule with 5'-terminal cap, in particular 5'-terminal $m^7$GpppN cap.

In particular, said composition (in particular a kit or a pharmaceutical composition) comprising:
  a chimeric enzyme, in particular a cytoplasmic chimeric enzyme, comprising at least one catalytic domain of a RNA triphosphatase, at least one catalytic domain of a guanylyltransferase, at least one catalytic domain of a $N^7$-guanine methyltransferase, and at least one catalytic domain of a DNA-dependent RNA polymerase and/or an isolated nucleic acid molecule or a group of isolated nucleic acid molecules encoding said chimeric enzyme; and
  a poly(A) polymerase, in particular a cytoplasmic poly(A) polymerase, comprising at least one RNA-binding domain of a protein-RNA tethering system linked to at least one catalytic domain of said poly(A) polymerase and/or an isolated nucleic acid molecule encoding said poly(A) polymerase; and optionally
  a DNA sequence, which is operatively linked to the promoter for said DNA-dependent RNA polymerase and covalently linked to at least one sequence encoding the element interacting with high affinity with said RNA-binding domain;
said composition being useful for the production of a RNA molecule with 5'-terminal cap, in particular 5'-terminal $m^7$GpppN cap.

More particularly, said composition (in particular a kit or a pharmaceutical composition) comprising:
  a chimeric enzyme, in particular a cytoplasmic chimeric enzyme, comprising the NP868R capping enzyme, and the K1E DNA-dependent RNA polymerase, particularly linked by the $(Gly_4Ser)_2$ linker and/or an isolated nucleic acid molecule or a group of isolated nucleic acid molecules encoding said chimeric enzyme; and
  a poly(A) polymerase, in particular a cytoplasmic poly(A) polymerase comprising at least one catalytic domain of a poly(A) polymerase selected in the group consisting of PAP1, PAPOLA, PAPOLB, VP55, C475L, R341 and MG561 poly(A) polymerase and comprising at least one RNA-binding domain of a protein-RNA tethering system linked to at least one catalytic domain of said poly(A) polymerase and/or an isolated nucleic acid molecule encoding said poly(A) polymerase; and optionally
  a DNA sequence, which is operatively linked to the promoter for said DNA-dependent RNA polymerase and covalently linked to at least one sequence encoding the element interacting with high affinity with said RNA-binding domain;
said composition being useful for the production of a RNA molecule with 5'-terminal cap, in particular 5'-terminal $m^7$GpppN cap.

Advantageously, the kit or the compositions of the invention can be used as an orthogonal gene expression system. As used herein, the term "orthogonal" designate biological systems whose basic structures are independent and generally originates from different species.

The invention also relates to a chimeric enzyme according to the invention, an isolated nucleic acid molecule according to the invention, a group of nucleic acid molecule according to the invention or a vector according to the invention, for its use as a medicament, in particular for the prevention and/or treatment of human or animal pathologies, preferably by means of gene therapy.

The invention also relates to a pharmaceutical composition comprising a chimeric enzyme according to the invention, and/or an isolated nucleic acid molecule according to the invention and/or a group of nucleic acid molecule according to the invention, and/or a vector according to the invention. Preferably, said pharmaceutical composition according to the invention is formulated in a pharmaceutical acceptable carrier.

Pharmaceutical acceptable carriers are well known by one skilled in the art.

The pharmaceutical composition according to the invention can further comprise at least one DNA sequence of interest, wherein said DNA sequence is operatively linked to a promoter for said catalytic domain of a DNA-dependent RNA polymerase and covalently linked to at least one sequence encoding the element which specifically binds to said RNA-binding domain.

Such components (in particular selected in the group consisting of a chimeric enzyme according to the invention, an isolated nucleic acid molecule according to the invention, a vector according to the invention and at least one DNA sequence of interest) can be present in the pharmaceutical composition or medicament according to the invention in a therapeutically amount (active and non-toxic amount).

Such therapeutically amount can be determined by one skilled in the art by routine tests including assessment of the effect of administration of said components on the pathologies and/or disorders which are sought to be prevent and/or to be treated by the administration of said pharmaceutical composition or medicament according to the invention.

For example, such tests can be implemented by analyzing both quantitative and qualitative effect of the administration of different amounts of said aforementioned components (in particular selected in the group consisting of a chimeric enzyme according to the invention, an isolated nucleic acid molecule according to the invention, a vector according to the invention and at least one DNA sequence of interest) on a set of markers (biological and/or clinical) characteristics of said pathologies and/or of said disorders, in particular from a biological sample of a subject.

The invention also relates to a therapeutic method comprising the administration of a chimeric enzyme according to the invention, and/or an isolated nucleic acid molecule according to the invention, and/or a group of nucleic acid molecule according to the invention and/or a vector according to the invention in a therapeutically amount to a subject in need thereof. The therapeutic method according to the invention can further comprise the administration of at least one DNA sequence of interest, wherein said DNA sequence is operatively linked to a promoter for said catalytic domain of a DNA-dependent RNA polymerase and covalently linked to at least one sequence encoding the element which specifically binds to said RNA-binding domain, in a therapeutically amount to a subject in need thereof.

Said chimeric enzyme, nucleic acid molecule and/or said vector according to the invention can be administrated simultaneously, separately or sequentially of said DNA sequence of interest, in particular before said DNA sequence of interest.

The invention also relates to a pharmaceutical composition according to the invention for its use for the prevention and/or treatment of human or animal pathologies, in particular by means of gene therapy.

Said pathologies can be selected from the group consisting of pathologies, which can be improved by the administration of said at least one DNA sequence of interest.

The invention also relates to the use of a chimeric enzyme according to the invention, and/or an isolated nucleic acid molecule according to the invention, and/or a group of nucleic acid molecule according to the invention and/or a vector according to the invention, for the preparation of a medicament for the prevention and/or treatment of human or animal pathologies, in particular by means of gene therapy.

The invention also relates to a first combination product, which comprises as active ingredients:
- at least one chimeric enzyme according to the invention and/or at least one nucleic acid molecule according to the invention and/or a group of nucleic acid molecule according to the invention and/or a at least one vector comprising and/or expressing a nucleic acid molecule according to the invention; and
- at least one DNA sequence of interest, wherein said DNA sequence is operatively linked to a promoter for said catalytic domain of a DNA-dependent RNA polymerase and covalently linked to at least one sequence encoding the element which specifically binds to said RNA-binding domain;

for its use as a medicament, wherein said active ingredients are formulated for separate, simultaneous or sequential administration.

The invention also relates to a second combination product, which comprises as active ingredients:
- a chimeric enzyme, in particular a cytoplasmic chimeric enzyme, comprising at least one catalytic domain of a RNA triphosphatase, at least one catalytic domain of a guanylyltransferase, at least one catalytic domain of a $N^7$-guanine methyltransferase, and at least one catalytic domain of a DNA-dependent RNA polymerase and/or an isolated nucleic acid molecule or a group of isolated nucleic acid molecules encoding said chimeric enzyme; and
- a poly(A) polymerase, in particular a cytoplasmic poly(A) polymerase, comprising at least one RNA-binding domain of a protein-RNA tethering system linked to at least one catalytic domain of said poly(A) polymerase and/or an isolated nucleic acid molecule encoding said poly(A) polymerase; and
- a DNA sequence, which is operatively linked to the promoter for said DNA-dependent RNA polymerase and covalently linked to at least one sequence encoding the element which specifically binds to said RNA-binding domain;

for its use as a medicament, wherein said active ingredients are formulated for separate, simultaneous or sequential administration.

Said DNA sequence of interest can be an anti-oncogene (a tumor suppressor gene).

Said DNA sequence of interest can encode a polypeptide of therapeutic interest or a non-coding RNA selected in the group comprising siRNA, ribozyme, shRNA and antisense RNA.

Said polypeptide of therapeutic interest can be selected from, a monoclonal antibody or its fragments, a growth factor, a cytokine, a cell or nuclear receptor, a ligand, a coagulation factor, the CFTR protein, insulin, dystrophin, a hormone, an enzyme, an enzyme inhibitor, a polypeptide which has an antineoplastic effect, a polypeptide which is capable of inhibiting a bacterial, parasitic or viral, in particular HIV, infection, an antibody, a toxin, an immunotoxin.

Preferably, the combination product according to the invention can be formulated in a pharmaceutical acceptable carrier.

In one embodiment of the combination product according to the invention, said vector is administered before said DNA sequence of interest.

The invention also relates to a combination product according to the invention for its use as a medicament in the prevention and/or treatment of human or animal pathologies, particularly by means of gene therapy.

Said pathologies can be selected from the group consisting of pathologies, which can be improved by the administration of at least one DNA sequence of interest, as described above.

For example, said pathologies, as well as their clinical, biological or genetic subtypes, can be selected from the group comprising liver disorders (e.g. acute liver failure due to acetaminophen intoxication or other causes, prevention of liver failure post-hepatectomy, liver primary cancers including hepatoma or cholangiocarcinoma, nonalcoholic steatohepatitis, as well as liver monogenic disorders such as hemochromatosis, ornithine transarbamylase deficiency, argininosuccinatelyase deficiency, argininosuccinate synthetase 1, hemochromatosis or Wilson's disease), disorders due or associated to deficiencies of secreted proteins (e.g. lysosomal storage diseases such as Gaucher's disease, Niemann-Pick disease, Tay-Sacks or Sandhoff disease, Hunter syndrome, or Hurler disease; deficiencies of coagulation factors including factors VIIIc, IX, Von Willebrand, fibrinogen or other coagulation proteins, as well as colony stimulating factors including erythropoietin, granulocyte colony stimulating factor and thrombopoietin), cancers and their predisposition (e.g. breast, colorectal, pancreas, gastric, esophageal and lung cancers, as well as melanoma), malignant hemopathies (e.g. leukemias, Hodgkin's and non-Hodgkin's lymphomas, myeloma), hemoglobinopathies (e.g. sickle cell anemia, glucose-6-phosphate dehydrogenase deficiency) and thalassemias, autoimmune disorders (e.g. systemic lupus erythematosus, scleroderma, autoimmune hepatitis), cardiovascular disorders (e.g. cardiac rhythm and conduction disorders, hypertrophic cardiomyopathy, cardiovascular disease, or chronic cardiac failure), metabolic disorders (e.g. type I and type II diabetes mellitus and their complications, dyslipidemia, atherosclerosis and their complications), infectious disorders (e.g. AIDS, viral hepatitis B, viral hepatitis C, influenza flu, Zika, Ebola and other viral diseases; botulism, tetanus and other bacterial disorders; malaria and other parasitic disorders), muscular disorders (e.g. Duchenne muscular dystrophy and Steinert myotonic muscular dystrophy), respiratory diseases (e.g. cystic fibrosis, alpha-1 antitrypsin deficiency, acute respiratory distress syndrome, pulmonary arterial hypertension, pulmonary veno-occlusive disease), renal diseases (e.g. polycystic kidney disease, glomerulopathy), colorectal disorders (e.g. Crohn's disease and ulcerative colitis), ocular disorders especially retinal diseases (e.g. Leber's amaurosis, retinitis pigmentosa, age related macular degeneration), central nervous system disorders (e.g. Alzheimer's disease, Parkinson's disease, amyotrophic lateral sclerosis, multiple sclerosis, Huntington's disease, neurofibromatosis, adrenoleukodystrophy, bipolar disease, schizophrenia and autism), bone and joint disorders (e.g. rheumatoid arthritis, ankylosing spondylitis, osteoarthritis) and skin and connective tissue disorders (e.g. neurofibromatosis and psoriasis).

In one embodiment, the combination product of the invention comprises:

- at least one vector comprising and expressing a nucleic acid molecule according to the invention, wherein said catalytic domain of a DNA-dependent RNA polymerase is a catalytic domain of a bacteriophage DNA-dependent RNA polymerase; and
- at least one DNA sequence of interest, wherein said DNA sequence is operatively linked to a promoter for said catalytic domain of a bacteriophage DNA-dependent RNA polymerase and covalently linked to at least one sequence encoding the element which specifically binds to said RNA-binding domain.

The invention also relates to a method for producing the chimeric enzyme according to the invention comprising the step of expressing in at least one host cell said nucleic acid molecule or said group of nucleic acid molecules encoding the chimeric enzyme of the invention in conditions allowing the expression of said nucleic acid molecule(s) in said host cell.

The invention also relates to a method for producing the chimeric enzyme according to the invention comprising the steps of:

- expressing a part of said group of nucleic acid molecules encoding a chimeric enzyme of the invention in a first host cell in conditions allowing the expression of said nucleic acid molecules in said host cell, to obtain a first part of the chimeric enzyme of the invention;
- expressing the other part of said group of nucleic acid molecules encoding the chimeric enzyme of the invention in a second host cell in conditions allowing the expression of said nucleic acid molecules in said host cell to obtain a second part of the chimeric enzyme of the invention; and
- assembling said first part and said second part to obtain the chimeric enzyme of the invention.

BRIEF DESCRIPTION OF DRAWINGS

FIG. 10: structure of constructions resulting of Nλ-tethering domain coupled to the African swine fever virus capping enzyme fused to poly(A) polymerases. (A) Nλ-poly(A) polymerase-G4-NP868R monomer, (B) Nλ-NP868R-G4-poly(A) polymerase monomer.

The present invention will be explained in detail with examples in the following, but the technical scope of the present invention is not limited to these examples.

Example 1: D1R/D12L, the Vaccinia Virus Capping Enzyme Tethered to Luciferase Reporter mRNA Increases its Expression 1. Objectives The objective of this experiment was to determine if the heterodimeric vaccinia virus capping enzyme appropriately tethered to Firefly Luciferase reporter mRNA synthesized in cellulo increases its expression.

The vaccinia virus capping enzyme consist of two subunits, which form a heterodimer: (i) a 95 kDa subunit encoded by the vaccinia virus D1R gene (genomic sequence AY243312.1; UniProtKB/Swiss-Prot accession number P04298), designated hereafter as D1R, which has RNA-triphosphatase, RNA guanylyltransferase and RNA N7-guanine methyltransferase enzymatic activities (Cong and Shuman 1993, Niles and Christen 1993, Higman and Niles 1994, Mao and Shuman 1994, Gong and Shuman 2003), (ii) and a 31-kDa subunit encoded by the vaccinia virus D12L gene (genomic sequence AY243312.1; UniProtKB/Swiss-Prot accession number P04318), designated hereafter as D12L, which has no intrinsic enzymatic activity, but enhances the RNA N7-guanine methyltransferase activity of the D1R subunit (Higman, Bourgeois et al. 1992, Higman, Christen et al. 1994, Mao and Shuman 1994). Cotransfection of plasmids encoding these two subunits therefore generate in cellulo the heterodimer D1R/D12L capping enzyme, which can eventually fused to a protein tethering domain.

2. Methods a. Plasmids

The coding sequences of the following plasmids were optimized for expression in human cells with respect to codon adaptation index using the GeneOptimizer algorithm (Raab, Graf et al. 2010). All gene sequences were artificially synthesized and assembled from stepwise PCR using oligonucleotides, cloned and fully sequenced.

For all the following examples, the conditions tested consist of a variable combination of several plasmids. In the present example, the pK1ERNAP/pT3RNAP plasmids together with Firefly luciferase reporter plasmids were used to generate in cellulo the Firefly Luciferase mRNA with or without tethering domain, which then can be specifically modified by enzyme produced by the test plasmid appropriately tethered to the Firefly Luciferase mRNA.

Figure 1:
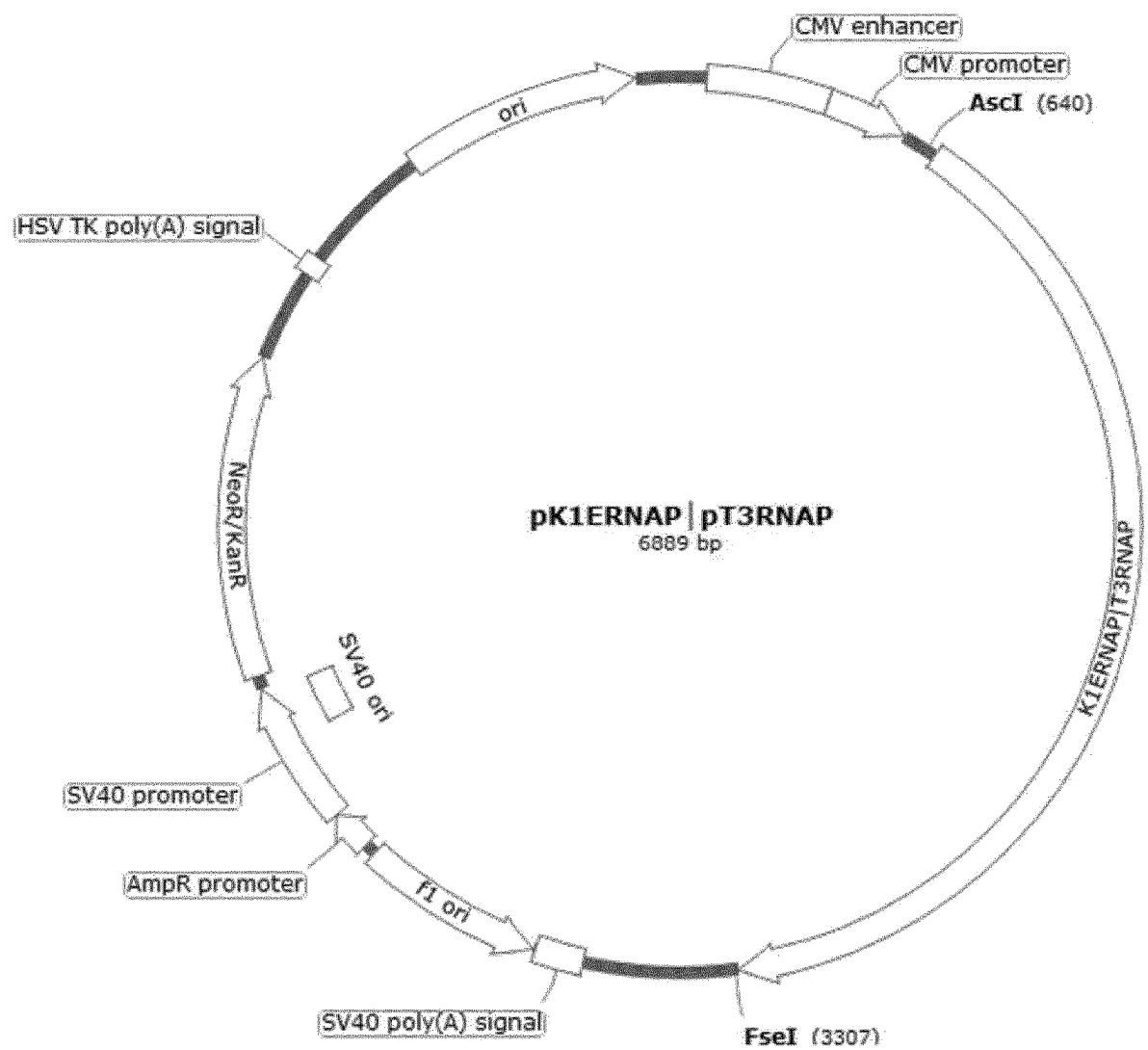
FIG. 1: maps of the pK1ERNAP and pT3RNAP plasmids.

The expression plasmids consisted of the phage T3 and K1E RNA polymerase open reading-frames (ORFs), which were subcloned in the pCMVScript plasmid backbone (Stratagene, La Jolla, Calif.), following the removal of the T7 φ10 promoter sequence. These corresponding plasmids, designated as p-followed by the name of the ORF, have the following design (i.e. pK1ERNAP or pT3RNAP; FIG. 1): IE1 promoter/enhancer from the human cytomegalovirus (CMV), 5'-untranslated region (5'-UTR), Kozak consensus sequence, ORFs, 3'-untranslated region (3'-UTR), and SV40 polyadenylation signal. The corresponding ORFs were subcloned by digestion at endonuclease restriction enzyme sites immediately upstream to the Kozak sequence and downstream to stop codon.

Figure 2:
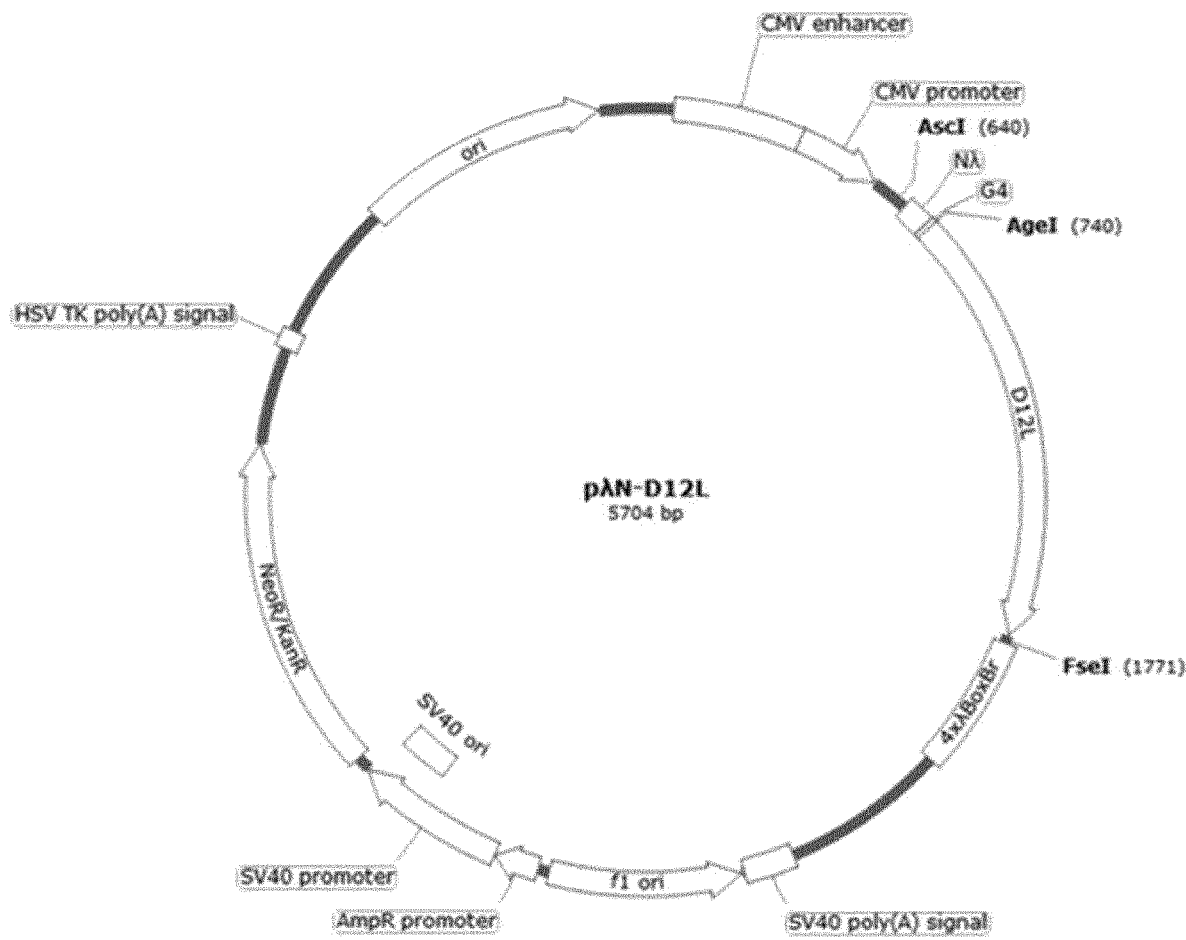
FIG. 2: map of the test tethered pNλ-D12L plasmid. Other test tethered test plasmids have the same general design, except ORFs which were substituted by endonuclease restriction digestion and ligation.
Figure 3:
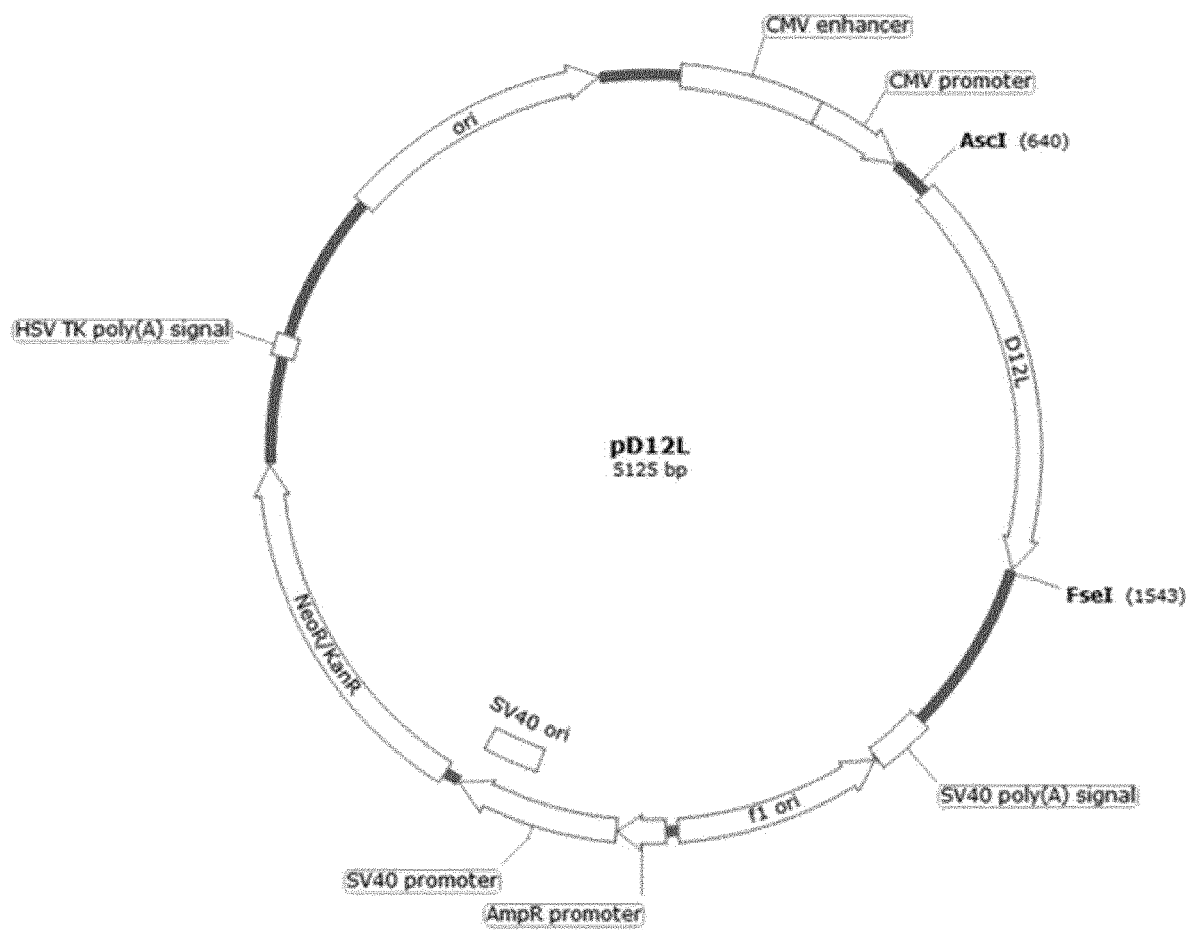
FIG. 3: map of the test pD12L plasmid encoding untethering vaccinia virus capping enzyme D12L subunit. Other untethering test plasmids have the same design, except ORFs which were substituted by endonuclease restriction digestion and ligation.

The test plasmids contained the coding sequence of the capping enzymes under investigation with (FIG. 2 for pNλ-D12L) or without peptide tethering domain (FIG. 3 for pD12L). Peptide tethering domain consist of the 22 aminoacids of antitermination N proteins from the lambda bacteriophage (Nλ; amino-acids 1-22 from Enterobacteria phage lambda nucleocapsid protein AAA32249; SEQ ID No 1 and SEQ ID No 2 corresponding to the nucleotide and amino acid sequences of N-terminal tethering domain from antitermination N protein from A bacteriophage, respectively) was fused to the amino-terminal ends of the D12L protein through a flexible G4 linker. The corresponding ORFs were subcloned by digestion at endonuclease restriction enzyme sites immediately upstream to Kozak sequence or downstream to Nλ-G4 motif, and downstream to stop codon. Two pairs of plasmids were used to encode the tethered or untethered heterodimeric vaccinia virus capping enzyme. Firstly, plasmids containing the D12L coding sequences with the NA tethering domain (pNλ-D12L; SEQ ID No 3 and SEQ ID No 4 corresponding to the nucleotide and amino acid sequences of D12L subunit of vaccinia virus capping enzyme, respectively) and wild-type D1R coding sequence (pD1R; SEQ ID No 5 and SEQ ID No 6 corresponding to the nucleotide and amino acid sequences of D1R subunit of vaccinia virus capping enzyme, respectively), which generate the tethered D1R/Nλ-D12L heterodimer. Secondly, plasmids containing the wild-type D12L coding sequences without the NA tethering domain (pD12L) and wild-type D1R coding sequence (pD1R), which form the untethered D1R/D12L heterodimer.

Figure 4:
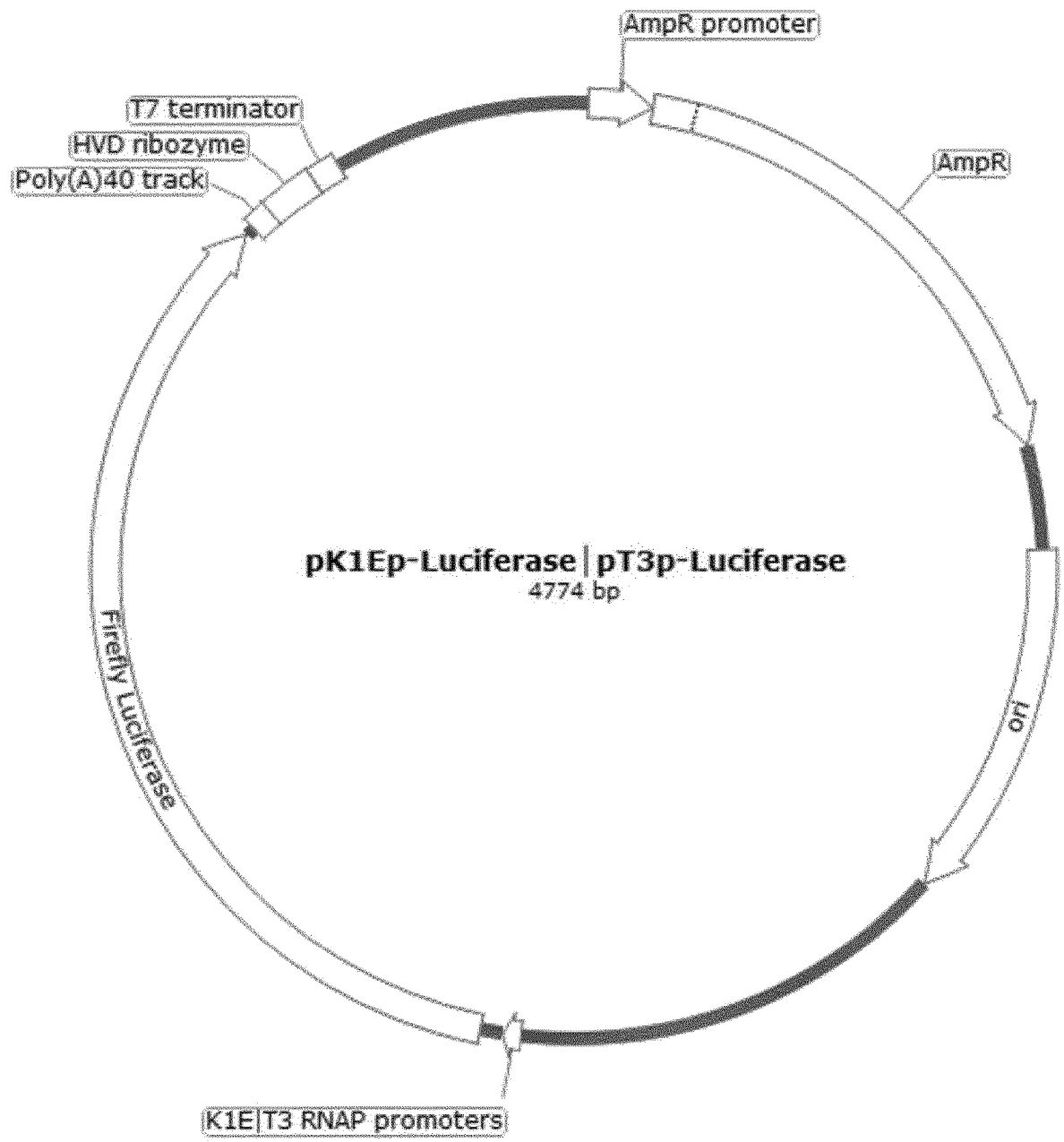
FIG. 4: maps of untethered pK1Ep-Luciferase and pT3p-Luciferase reporter plasmids without 4xλBoxBr repeat.
Figure 5:
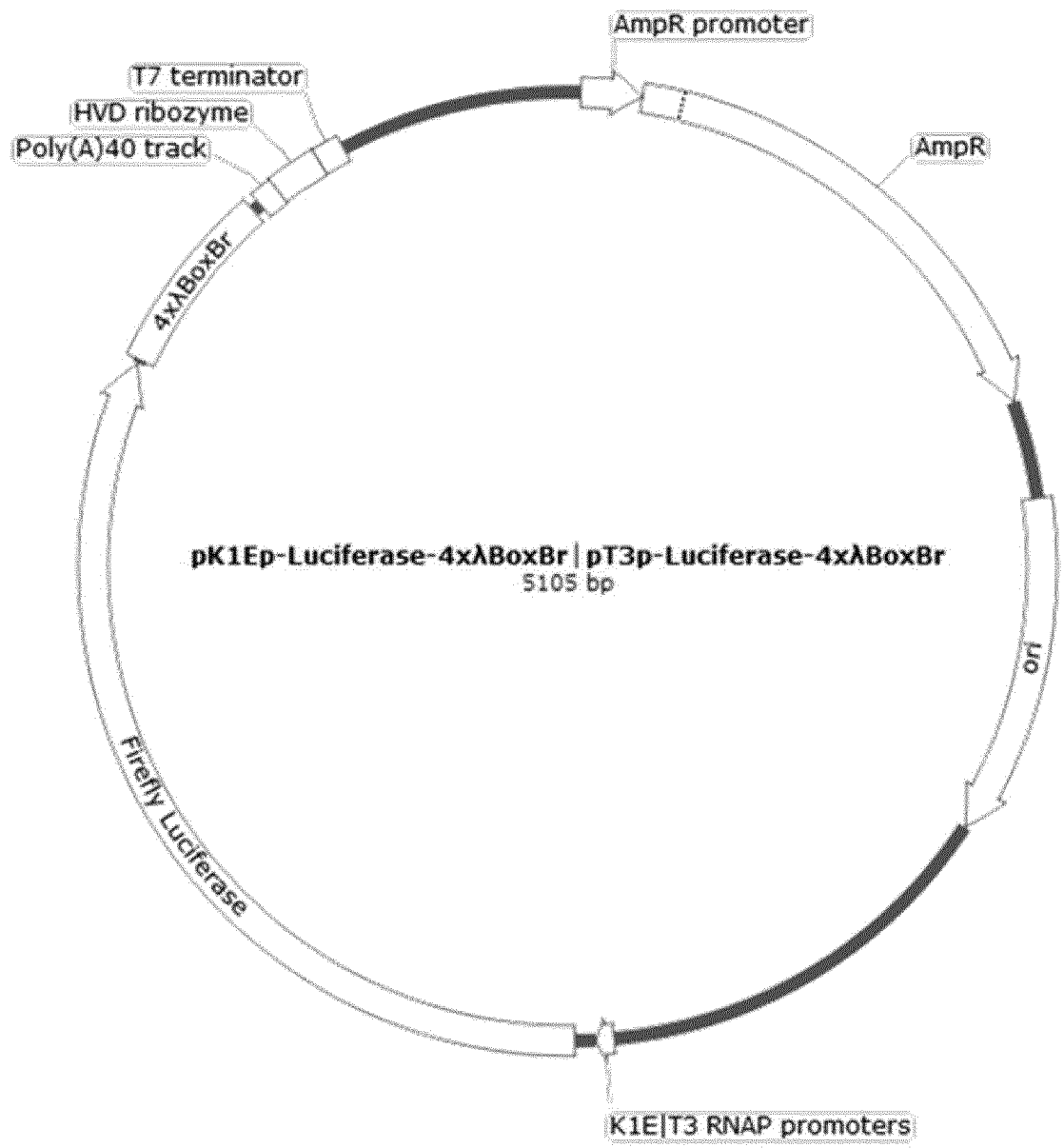
FIG. 5: maps of NA-tethered pK1Ep-Luciferase-4xλBoxBr and pT3p-Luciferase-4xλBoxBr reporter plasmids with 4xλBoxBr repeat.

The Firefly Luciferase reporter plasmids containing the Firefly Luciferase gene under control of the K1E or T3 RNA polymerase promoters, contained a 5'-UTR sequence, Kozak consensus sequence followed by the ORF of Luciferase gene from *Photinus pyralis* and stop codon, RNA tethering domain consisting of four BoxBr in tandem from λ virus (optional, lacking in the untethered version; nucleotides 38312-38298 of genomic sequence of Enterobacteria phage lambda KT232076.1; SEQ ID No 7 corresponding to the nucleotide sequence of the BoxBr RNA stem-loops from A bacteriophage), poly(A) track of 40 adenosine residues, followed by a self-cleaving RNA sequence from the genomic ribozyme of the hepatitis D virus, and terminated by the bacteriophage T7 φ10 transcription stop. These plasmids were designated either pK1Ep-Luciferase/pT3p-Luciferase in their untethered versions (FIG. 4), or pK1Ep-Luciferase-4xλBoxBr/pT3p-Luciferase-4xλBoxBr (FIG. 5) in their 4xBoxBr RNA tethered versions. The RNA molecules produced by this system are therefore uncapped and have a short 3'-end polyadenylation track encoded by 40 adenosine residues in the template Firefly Luciferase reporter plasmids.

b. Cell Culture and Transfection

For standard experiments, the Human Embryonic Kidney 293 (HEK-293, ATCC CRL 1573) were routinely grown at 37° C. in 5% $CO_2$ atmosphere at 100% relative humidity. Cells were maintained in Dulbecco's Modified Eagle's Medium (DMEM) supplemented with 4 mM L-alanyl-L-glutamine, 10% fetal bovine serum (FBS), 1% non-essential amino-acids, 1% sodium pyruvate, 1% penicillin and streptomycin, and 0.25% fungizone.

Cells were routinely plated in 24-well plates at $1\times10^5$ cells per well the day before transfection and transfected at 80% cell confluence. Transient transfection was performed with Lipofectamine 2000 reagent (Invitrogen, Carlsbad, Calif.) according to manufacturer's recommendations. Except otherwise stated, cells were transfected with 2 μl of Lipofectamine 2000 and 0.8 μg of total plasmid DNA. For standard luciferase and hSEAP gene reporter expression assays, cells were analyzed 48 hours after transfection, except otherwise stated.

c. Firefly Luciferase Luminescence and SEAP Colorimetric Assays

Luciferase luminescence was assayed by the Luciferase Assay System (Promega, Madison, Wis.) according to the manufacturer's recommendations. In brief, cells were lysed in Cell Culture Lysis Reagent buffer (CLR), and then centrifuged at 12,000×g for two minutes at 4° C. Luciferase Assay Reagent (Promega; 100 μl/well) diluted at 1:10 was added to supernatant (20 μl/well). Luminescence readout was taken on a Tristar 2 microplate reader (Berthold, Bad Wildbad, Germany) with a read time of one second per well.

In order to normalize for transfection efficacy, cells were transfected with the pORF-eSEAP plasmid (InvivoGen, San Diego, Calif.), which encodes for the human secreted embryonic alkaline phosphatase (hSEAP) driven by the EF-1α/HTLV composite promoter. Enzymatic activity was assayed in cell culture medium using the Quanti-Blue colorimetric enzyme assay kit (InvivoGen). Gene reporter expression was expressed as the ratio of luciferase luminescence (RLU, relative light units) to eSEAP absorbance (OD, optic density).

d. Statistical Analysis

Statistical analyses were performed with paired two-tailed Student's t-test. Results are means (n≥4)±standard deviation. P-value<0.05 was considered statistically significant.

3. Results

Figure 6:
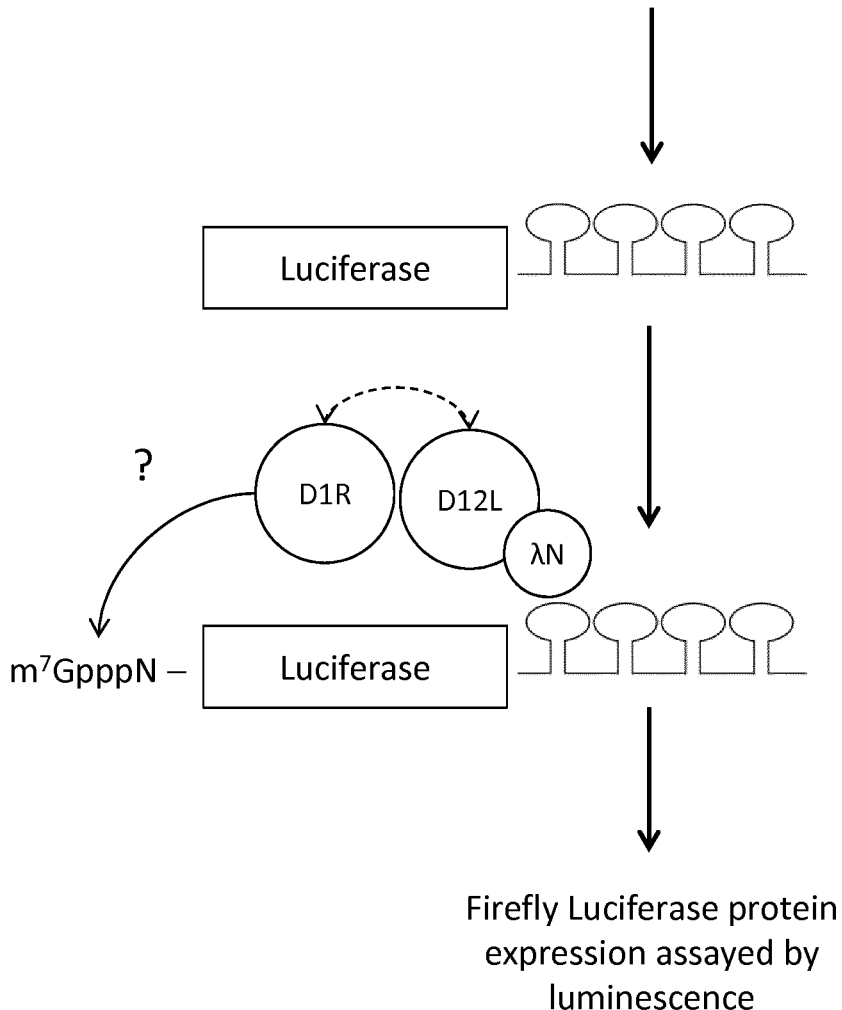
FIG. 6: K1ERNAP or T3RNAP-driven expression systems used to test the activity of NA-tethering system coupled to the vaccinia virus capping enzyme on expression of uncapped 4xλBoxBr-tethered Firefly Luciferase mRNA.
Figure 7:
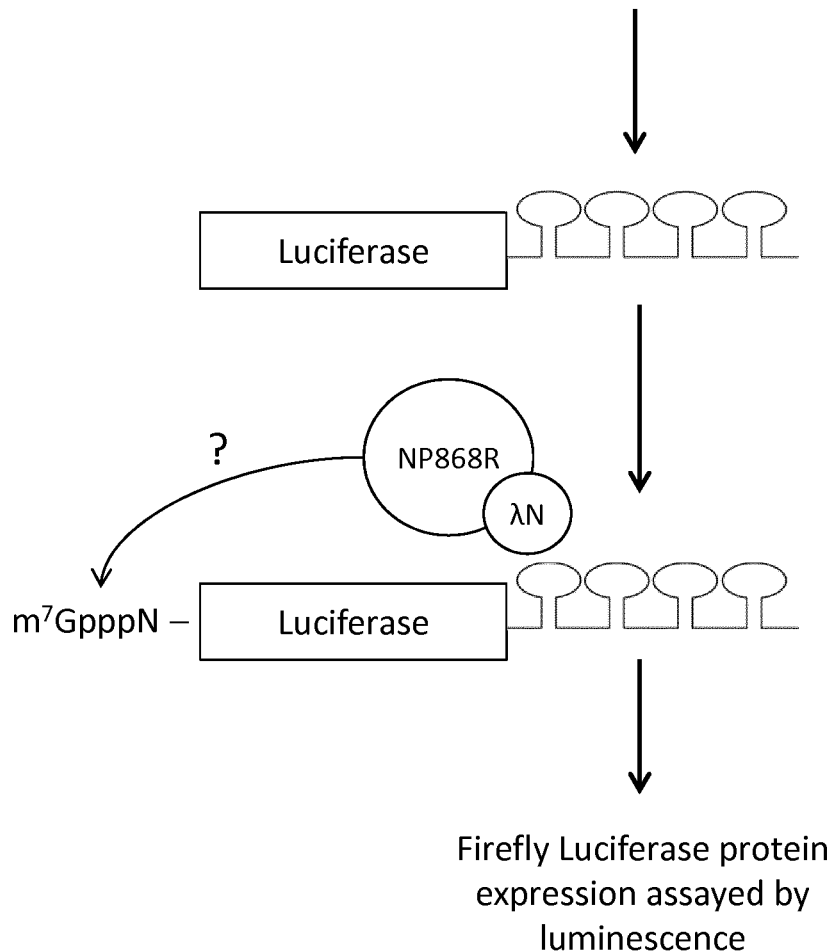
FIG. 7: K1ERNAP or T3RNAP-driven expression systems used to test the activity of NA-tethering system coupled to the African swine fever virus capping enzyme on expression of uncapped 4xλBoxBr-tethered Firefly Luciferase mRNA.

In this set of experiments, the Firefly Luciferase mRNA was produced by the phage K1E or T3 RNA polymerases by cotransfection of pK1ERNAP/pT3RNAP and pK1Ep-Luciferase-4xλBoxBr/pT3p-Luciferase-4xλBoxBr for the tethered version of the Firefly Luciferase reporter plasmids or pK1Ep-Luciferase-4xλBoxBr/pT3p-Luciferase-4xλBoxBr for their untethered version. The test plasmids contain the coding sequence of the D1R/D12L vaccinia virus with or without tethering domain were co-transfected. The translatability of the resulting transcripts, which is expected to increase in case of proficient capping, is measured by the Firefly Luciferase assay. A general depiction of the assay is shown FIG. 6.

Results of the first set of experiments with the K1E-driven system are shown in the table below:

| Plasmids | mean | SEM |
| --- | --- | --- |
| (1) pK1ERNAP, pK1Ep-Luciferase | 35 329 | 3 113 |
| (2) pK1ERNAP, pK1Ep-Luciferase-4xλBoxBr | 34 784 | 4 388 |
| (3) pK1ERNAP, pD1R, pK1Ep-Luciferase-4xλBoxBr | 315 159 | 36 188 |
| (4) pK1ERNAP, pD12L, pK1Ep-Luciferase-4xλBoxBr | 60 212 | 2 219 |
| (5) pK1ERNAP, pD1R, pD12L, pK1Ep-Luciferase-4xλBoxBr | 851 056 | 144 590 |
| (6) pK1ERNAP, pD1R, pNλ-pD12L, pK1Ep-Luciferase-4xλBoxBr | 2 237 689 | 92 709 |
| (7) Baseline | 14 537 | 3 145 |

As expected when capping is lacking, Firefly Luciferase mRNA generated by pK1Ep-Luciferase and pK1Ep-Luciferase-4xλBoxBr cotransfected with the K1ERNAP plasmid alone (designated pK1ERNAP) was poorly expressed (row 1 and 2). Cotransfection of the untethered D1R plasmid (designated pD1R) together with pK1ERNAP/pK1Ep-Luciferase-4xλBoxBr increased the expression by approximately 9-fold in comparison to cotransfection of pK1ERNAP/pK1Ep-Luciferase-4xλBoxBr plasmids only (row 3 vs. 1 or 2, p<0.05, two-way Student t-test), whereas the transfection of the untethered pD12L plasmid with pK1ERNAP/pK1Ep-Luciferase-4xλBoxBr had virtually no effect on Firefly Luciferase expression (row 4 vs. 1 or 2, p=NS, two-way Student t-test). The cotransfection of the untethered pD12L and pD1R plasmids together with pK1ERNAP/pK1Ep-Luciferase-4xλBoxBr, which result in the vaccinia virus D1R/D12L capping enzyme heterodimer without tethering domain, significantly increased the expression of Firefly Luciferase in comparison to previous conditions, therefore confirming that mRNA capping is requested for mRNA translation (row 5 vs. 1 to 4, p=NS, two-way Student t-test p<0.05, two-way Student t-test). Finally, cotransfection of the tethered D12L plasmid (pNλ-D12L) and D1R together with pK1ERNAP/pK1Ep-Luciferase-4xλBoxBr, which produces the tethering vaccinia virus capping enzyme D1R/Nλ-D12L, increased drastically the expression of the Luciferase mRNA by 63.3 (row 6 vs. 2) and 2.6-fold (row 6 vs. 5) in comparison to no vaccinia virus capping enzyme (pK1ERNAP/pK1Ep-Luciferase-4xλBoxBr alone), or untethering vaccinia virus capping enzyme (pK1ERNAP/pK1Ep-Luciferase-4xλBoxBr/pD1R/pD12L), respectively.

In a second set of experiments, the Firefly Luciferase mRNA was produced by the phage T3 RNA polymerase and tethered to the vaccinia virus capping enzyme. Results of the second set of experiments with the T3-driven system are shown in the table below:

| Plasmids | mean | SEM |
| --- | --- | --- |
| (1) pT3RNAP, pT3p-Luciferase | 40 387 | 5 041 |
| (2) pT3RNAP, pT3p-Luciferase-4xλBoxBr | 43 682 | 2 072 |
| (3) pT3RNAP, pD1R, pT3p-Luciferase-4xλBoxBr | 82 445 | 6 913 |
| (4) pT3RNAP, pD12L, pT3p-Luciferase-4xλBoxBr | 47 167 | 1 342 |
| (5) pT3RNAP, pD1R, pD12L, pT3p-Luciferase-4xλBoxBr | 110 371 | 5 390 |
| (6) pT3RNAP, pD1R, pNA-pD12L, pT3p-Luciferase-4xλBoxBr | 353 096 | 12 560 |
| (7) Baseline | 7 269 | 1 901 |

This second set of experiments gave very similar results with cotransfection results in the following order: RNA with no 4xλBoxBr and no capping enzyme (row 1, pT3RNAP/pT3p-Luciferase) 4xλBoxBr-RNA and no capping enzyme (row 2, pT3RNAP/pT3p-Luciferase-4xλBoxBr) 4xλBoxBr-RNA with D12L subunit alone (row 4, pT3RNAP/pD12L/pT3p-Luciferase-4xλBoxBr)<4xλBoxBr-RNA with D1R (row 3, pT3RNAP/pD1R/pT3p-Luciferase-4xλBoxBr)<4xλBoxBr-RNA with untethered D1R/D12L capping enzyme (row 5, pT3RNAP/pD1R/pD12L/UpT3p-Luciferase-4xλBoxBr)<<4xλBoxBr-RNA with tethered D1R/D12L capping enzyme (row 6, pT3RNAP/pD1R/pNλ-D12L/UpT3p-Luciferase-4xλBoxBr). The expression levels of this latter condition was statistically greater than all other conditions, especially 3.2 fold higher than with the untethered D1R/D12L capping enzyme, therefore demonstrating the importance of guiding the D1R/D12L capping enzyme to the target reporter mRNA by tethering domain ($p<0.05$, two-way Student t-test).

4. Conclusions

These experiments show that the vaccinia virus capping enzyme, which contains no known or demonstrated binding domain for a specific RNA sequence, drastically increases gene Firefly Luciferase reporter expression when appropriately tethered to uncapped and polyadenylated Firefly Luciferase reporter mRNA by the Nλ-BoxBr tethering system.

Example 2: NP868R, the African Swine Fever Virus Capping Enzyme Tethered to Luciferase Reporter mRNA Increases its Expression 1. Objectives The objective of this set of experiments was to demonstrate if NP868R, the African swine fever virus capping enzyme, appropriately tethered to polyadenylated Firefly Luciferase reporter mRNA increases its expression in cellulo. NP868R (also named G4R) is a single-unit 868 amino-acids protein, which all enzymatic activities required for cap-0 formation demonstrated in vitro, i.e. RNA-triphosphatase, RNA guanylyltransferase and RNA N7-guanine methyltransferase (Pena, Yanez et al. 1993, Jais 2011, Dixon, Chapman et al. 2013, Jais, Decroly et al. 2018).

2. Methods a. Plasmids

The expression (pK1ERNAP or pT3RNAP), as well as the Firefly Luciferase reporter plasmids in their tethered versions (pK1Ep-Luciferase and pT3p-Luciferase) or untethered versions (pK1Ep-Luciferase-4xλBoxBr and pT3p-Luciferase-4xλBoxBr) were the same as described above.

The test plasmid consisted of the coding sequence from the African swine fever virus NP868R capping enzyme (NCBI ASFV genomic sequence strain BA71V NC_001659; UniProtKB/Swiss-Prot accession number P32094; SEQ ID No 8 and SEQ ID No 9 corresponding to the nucleotide and amino acid sequences of African swine fever virus NP868R capping enzyme, respectively) with (pNλ-NP868R) or without the NA tethering domain (pNP868R) subcloned in the pCMVScript plasmid backbone as described above.

b. Cell Culture and Transfection

Same as described in Example 1.

c. Firefly Luciferase Luminescence and SEAP Colorimetric Assays

Same as described in Example 1.

d. Statistical Analysis

Same as described in Example 1.

3. Results

The design of the assay was very similar to Example 1, except that the single subunit capping enzyme NP868R was used instead of the heterodimeric D1R/D12L capping enzyme. In brief, uncapped but polyadenylated Firefly Luciferase mRNA was synthesized in cellulo by the phage K1E or T3 RNA polymerases and its expression in presence of NP868R was assayed (FIG. 7).

Results of the first set of experiment with the K1E-driven system are shown in the table below:

| Plasmids | mean | SEM |
|---|---|---|
| (1) pK1ERNAP, pK1Ep-Luciferase | 109 401 | 7 601 |
| (2) pK1ERNAP, pK1Ep-Luciferase-4xλBoxBr | 147 494 | 6 310 |
| (3) pK1ERNAP, pNP868R, pK1Ep-Luciferase-4xλBoxBr | 2 433 576 | 226 803 |
| (4) pK1ERNAP, pNλ-pNP868R, pK1Ep-Luciferase-4xλBoxBr | 4 099 936 | 465 513 |
| (5) Baseline | 10 393 | 2 302 |

In this first set of experiments, cells were cotransfected with pK1ERNAP/pK1Ep-Luciferase or pK1ERNAP/pK1Ep-Luciferase-4xλBoxBr plasmids, showed low levels of Firefly Luciferase reporter expression (row 1 and 2). Cotransfection of the pK1ERNAP/pK1Ep-Luciferase-4xλBoxBr with the untethered pNP868R plasmid (pNP868R) increased the expression by approximately 29-fold in comparison to pK1ERNAP/pK1Ep-Luciferase-4xλBoxBr alone (row 3 vs. 1 or 2 respectively, $p<0.05$, two-way Student t-test), therefore confirming that mRNA capping is requested for mRNA translation. Finally, cotransfection of pK1ERNAP/pK1Ep-Luciferase-4xλBoxBr with tethered NP868R (pNλ-NP868R) even increased by 2.1-fold the expression of Firefly Luciferase in comparison to untethered NP868R condition, demonstrating the importance of guiding the enzyme to the target mRNA by tethering domains for proficient mRNA capping (raw 4 vs. 3, $p<0.05$, two-way Student t-test).

Results of the second set of experiments with the T3-driven system are shown in the table below:

| Plasmids | mean | SEM |
|---|---|---|
| (1) pT3RNAP, pT3p-Luciferase | 75 065 | 7 575 |
| (2) pT3RNAP, pT3p-Luciferase-4xλBoxBr | 62 220 | 5 781 |
| (3) pT3RNAP, pNP868R, pT3p-Luciferase-4xλBoxBr | 122 957 | 24 166 |
| (4) pT3RNAP, pNλ-NP868R, pT3p-Luciferase-4xλBoxBr | 352 978 | 16 813 |
| (5) Baseline | 23 464 | 6 302 |

In this second set of experiments, the Firefly Luciferase mRNA was produced by the phage T3 RNA polymerase and tethered to the African swine fever virus capping enzyme. This second set of experiments gave very similar results with cotransfection results in the following order: RNA with no 4xλBoxBr and no capping enzyme (row 1, pT3RNAP/pT3p-Luciferase) 4xλBoxBr-RNA without capping enzyme (row 2, pT3RNAP/pT3p-Luciferase-4xλBoxBr)<4xλBoxBr-RNA with untethered NP868R capping enzyme (row 3, pT3RNAP/pNP868R/pT3p-Luciferase-4xλBoxBr)<<4xλBoxBr-RNA with tethered NP868R capping enzyme (row 4, pT3RNAP/pNλ-NP868R/pT3p-Luciferase-4xλBoxBr). The expression levels of this last condition was statistically greater than all other conditions, especially 2.9 fold higher than with the untethered NP868R capping enzyme, therefore demonstrating the importance of tethering NP868R to the target mRNA by tethering domains for proficient mRNA capping (row 4 vs.3, $p<0.05$, two-way Student t-test).

4. Conclusions

These experiments show that another capping enzyme, NP868R from the African swine fever virus, which contains no known or predicted binding domain for a specific RNA sequence, increases Firefly Luciferase reporter expression when appropriately tethered to uncapped and polyadenylated reporter mRNA by the Nλ-BoxBr tethering system.

Example 3: Various Protein:RNA Tethering Systems, Coupled to African Swine Fever Virus Capping Enzyme NP868R can Increase the Expression of Luciferase Reporter mRNA Produced by K1E Phage RNA Polymerase in Host-Cell Cytoplasm 1. Objectives The objectives of the present experiments were to investigate if other protein:RNA tethering systems than the Nλ-4xBoxBr system can guide the African swine fever virus capping enzyme NP868R in order to increase the expression of appropriately tethered Luciferase reporter mRNA produced by the phage K1E RNA polymerase.

The following tethering systems were presently tested: i) MS2 protein and the RNA stem loop tethered sequence from MS2 virus (Valegard, Murray et al. 1994, Valegard, Murray et al. 1997), ii) NA peptide from the lambda virus and its BoxB1 RNA tethered sequence (Das 1993, Greenblatt, Nodwell et al. 1993, Friedman and Court 1995), iii) NA peptide from the P22 lamboid virus and its BoxBr RNA tethered sequences (Das 1993, Greenblatt, Nodwell et al. 1993, Friedman and Court 1995), iv) NA peptide from the ϕ21 lamboid virus and its BoxBr RNA tethered sequence (Das 1993, Greenblatt, Nodwell et al. 1993, Friedman and Court 1995), v) TAT binding domain from the Human immunodeficiency virus-1 (HIV-1), which contains a biologically validated nuclear localization signal (Duconge and Toulme 1999), and TAR RNA tethered sequence (Dingwall, Ernberg et al. 1990, Weeks, Ampe et al. 1990, Karn, Dingwall et al. 1991, Puglisi, Tan et al. 1992, Frankel and Young 1998), and vi) the human small nuclear ribonucleoprotein U1 subunit 70 (SNRNP70) protein tethering sequence (Romac, Graff et al. 1994), which contains a biologically validated nuclear localization signal (Keene, Query et al. 1999), and its U1snRNA-stem loop tethered sequence.

2. Methods a. Plasmids

The pK1ERNAP expression plasmid was described in Example 1.

The test plasmids consisted of the coding sequence of the African swine fever virus NP868R capping enzyme fused at its amino-terminal end to: i) bacteriophage N-antitermination protein the N-terminus of the entire MS2 protein (pMS2-NP868R, NCBI accession number NC_001417.2, UniProtKB/Swiss-Prot P03612; SEQ ID No 36 and SEQ ID No 37 corresponding to the nucleotide and amino-acid sequences, respectively), ii) N-terminal peptide from lambda bacteriophage previously described, iii)N-terminal peptide from P22 bacteriophage N-antitermination protein (pP22N-NP868R, UniProtKB/Swiss-Prot P04891), iv)N-terminal peptide from ϕ21 bacteriophage N-antitermination protein (pNϕ21-NP868R, UniProtKB/Swiss-Prot P07243), v) the TAT protein binding domain from HIV-1 isolate HXB2 (pTAT-NP868R, NCBI reference sequence: AAB50256.1), and vi) human small nuclear ribonucleoprotein U1 subunit 70 (SNRNP70) RNA-binding protein sequence (pSNRNP70-NP868R, amino-acid 92-202, NCBI accession number NM_003089.5).

The RNA tethering domains of the Firefly Luciferase reporter plasmids substituted by four tandem repeats of: i) MS2 RNA stem-loops (pK1Ep-Luciferase-4xMS2sl plasmid; nucleotides 1748-766 from Enterobacteriophage MS2 isolate DL52, NCBI accession number J0966307.1; SEQ ID No 38), ii) BoxB1 RNA sequence from λ virus (pK1Ep-Luciferase-4xABoxB1; NCBI accession number J02459.1 nucleotides 35518-35534), iii) λBoxBr RNA sequence from P22 lamboid virus (pK1Ep-Luciferase-4xP22BoxBr; NCBI accession number NC_002371.2, nucleotides 31,953-31,971), iv) λBoxBr RNA sequence from ϕ21 lamboid virus (pK1Ep-Luciferase-4xϕ21BoxBr; NCBI accession number AH007390.1, nucleotides 866-883), v) TAR RNA sequence from Human immunodeficiency virus type 1, isolate HXB2 (pK1Ep-Luciferase-4xTAR; NCBI accession number K03455.1, nucleotides 471-497) and vi) U1snRNA RNA stem-loop (pK1Ep-Luciferase-4xU1snRNA; NCBI accession number M28013.1, nucleotides 123-155).

b. Cell Culture and Transfection

Same as described in Example 1.

c. Firefly Luciferase Luminescence and SEAP Colorimetric Assays

Same as described in Example 1.

d. Statistical Analysis

Same as described in Example 1.

3. Results

Figure 8:
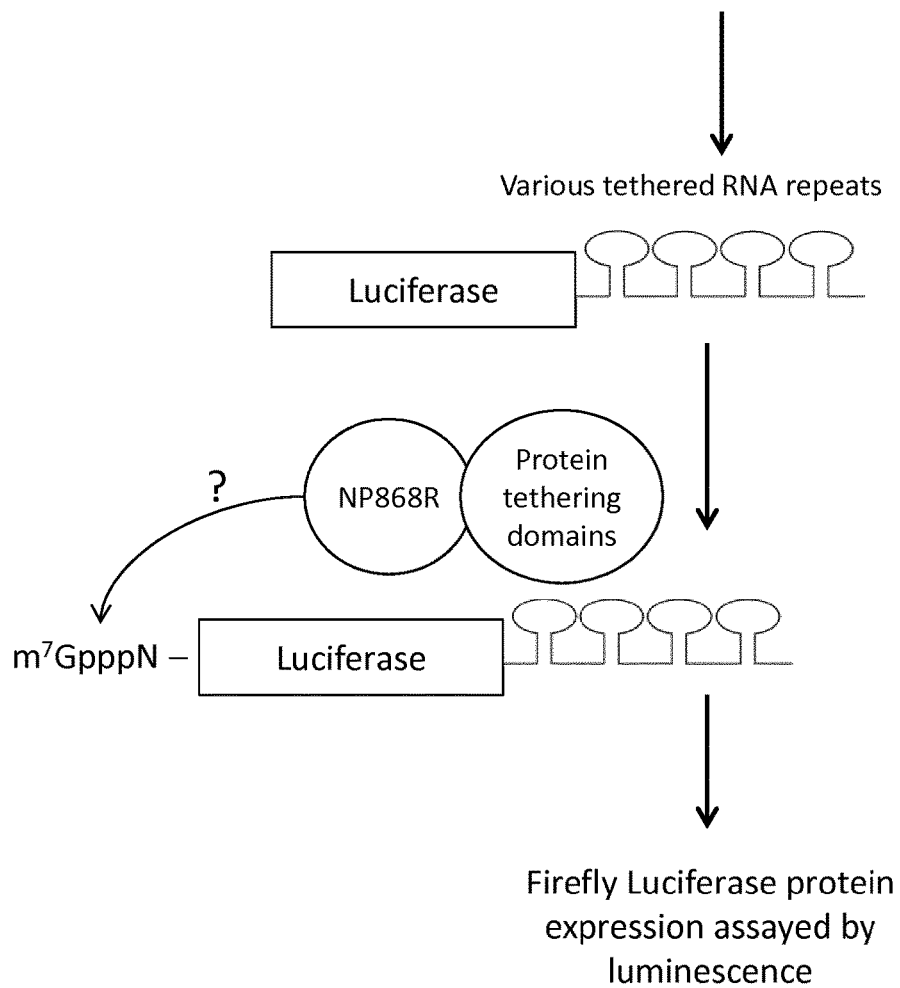
FIG. 8: K1ERNAP-driven expression system used to assay the activity of various protein:RNA binding systems coupled to the African swine fever virus capping enzyme on expression of uncapped 4xλBoxBr-tethered Firefly Luciferase mRNA.

The design of the assay was very similar to Example 2, except that various protein:RNA tethering systems were tested in replacement to the Nλ:BoxBr system. In brief, uncapped Firefly Luciferase mRNA with a short polyadenylation tail of 40 adenosine residues was synthesized in cellulo by the phage K1E RNA polymerase and its expression in presence of NP868R tethered by various systems was assayed (FIG. 8).

Results of these experiments are shown in the table below:

| Plasmids | mean | SEM |
|---|---|---|
| MS2-4xMS2sl tethering system | | |
| (1) pK1ERNAP, pNP868R, pK1Ep-Luciferase | 1 233 076 | 143 402 |
| (2) pK1ERNAP, pNP868R, pK1Ep-Luciferase-4xMS2sl | 1 033 076 | 113 402 |
| (3) pK1ERNAP, pMS2-NP868R, pK1Ep-Luciferase | 1 083 076 | 232 757 |
| (4) pK1ERNAP, pMS2-NP868R, pK1Ep-Luciferase-4xMS2sl | 4 999 936 | 232 757 |
| (5) Baseline | 162 | 150 |
| Nλ-4xλBoxBl tethering system | | |
| (1) pK1ERNAP, pNP868R, pK1Ep-Luciferase | 1 233 076 | 113 402 |
| (2) pK1ERNAP, pNP868R, pK1Ep-Luciferase-4xλBoxBl | 1 433 576 | 113 402 |
| (3) pK1ERNAP, pNλ-NP868R, pK1Ep-Luciferase | 1 430 576 | 232 757 |
| (4) pK1ERNAP, pNλ-NP868R, pK1Ep-Luciferase-4xλBoxBl | 5 699 936 | 332 757 |
| (5) Baseline | 162 | 150 |
| NP22-4xP22BoxBr tethering system | | |
| (1) pK1ERNAP, pNP868R, pK1Ep-Luciferase | 1 233 076 | 113 402 |
| (2) pK1ERNAP, pNP868R, pK1Ep-Luciferase-4xP22BoxBr | 913 576 | 113 402 |
| (3) pK1ERNAP, pNP22-NP868R, pK1Ep-Luciferase | 813 576 | 122 757 |
| (4) pK1ERNAP, pNP22-NP868R, pK1Ep-Luciferase-4xP22BoxBr | 4 699 936 | 232 757 |
| (5) Baseline | 162 | 150 |
| NΦ21-4xΦ21BoxBr tethering system | | |
| (1) pK1ERNAP, pNP868R, pK1Ep-Luciferase | 1 233 076 | 113 402 |
| (2) pK1ERNAP, pNP868R, pK1Ep-Luciferase-4xΦ21BoxBr | 1 313 576 | 113 402 |
| (3) pK1ERNAP, pNΦ21-NP868P, pK1Ep-Luciferase | 1 115 600 | 232 757 |
| (4) pK1ERNAP, pNΦ21-NP868P, pK1Ep-Luciferase-4xΦ21BoxBr | 4 919 936 | 232 757 |
| (5) Baseline | 162 | 150 |
| TAT-4xTAR tethering system | | |
| (1) pK1ERNAP, pNP868R, pK1Ep-Luciferase | 1 233 076 | 113 402 |
| (2) pK1ERNAP, pNP868R, pK1Ep-Luciferase-4xTAR | 1 333 076 | 113 402 |
| (3) pK1ERNAP, pTAT-NP868R, pK1Ep-Luciferase | 1 153 076 | 232 757 |
| (4) pK1ERNAP, pTAT-NP868R, pK1Ep-Luciferase-4xTAR | 1 583 076 | 232 757 |
| (5) Baseline | 162 | 150 |
| SNRNP70-4xU1snRNA tethering system | | |
| (1) pK1ERNAP, pNP868R, pK1Ep-Luciferase | 1 233 076 | 113 402 |
| (2) pK1ERNAP, pNP868R, pK1Ep-Luciferase-4xU1snRNA | 1 331 222 | 38 402 |
| (3) pK1ERNAP, pSNRNP70-NP868R, pK1Ep-Luciferase | 1 153 076 | 232 757 |
| (4) pK1ERNAP, pSNRNP70-NP868R, pK1Ep-Luciferase-4xU1snRNA | 1 423 076 | 157 757 |
| (5) Baseline | 162 | 150 |

The cotransfection of pK1ERNAP with plasmids having only one component of the tethering system, i.e. the protein domains fused to the NP868R capping enzyme of the test plasmid or Firefly Luciferase reporter plasmids with four tandem RNA tethered repeats introduced in their 3'UTR, had no significant effects on the expression of the Firefly Luciferase reporter mRNA with any system when compared to no tethering system (row 2 or 3 vs. 1; p=NS for all comparisons, two-way Student t-test). The cotransfection of pK1ERNAP with plasmids encoding for the components of the MS2-4xMS2sl (i.e. pMS2-NP868R/pK1Ep-Luciferase-4xMS2sl), Nλ-NP868R-4xABoxBl (i.e. pNλ-NP868R/pK1Ep-Luciferase-4xλBoxBl), NP22-NP868R-4xP22BoxBr (i.e. pNP22-NP868R/pK1Ep-Luciferase-4xP22BoxBr), Nφ21-4xφ21BoxBr (i.e. pNφ21-NP868R/pK1Ep-Luciferase-4xφ21BoxBr), tethering system increased significantly by 3.8- to 4.6-fold the expression levels of firefly luciferase reporter in comparison to conditions with the untethering capping enzyme and/or untethered Firefly Luciferase plasmids (row 4 vs. 1-3; p<0.05 for all comparisons, two-way Student t-test). In contrast, the cotransfection of pK1ERNAP with either the TAT/4xTAR tethering system (i.e. pTAT-NP868R/pK1Ep-Luciferase-4xTAR) or the SNRNP70/4xU1snRNA tethering system (i.e. pSNRNP70-NP868R/pK1Ep-Luciferase-4xU1snRNA) shows very low change of Firefly Luciferase in comparison to conditions with the untethering capping enzyme and/or untethered Firefly Luciferase plasmids (row 4 vs. 1-3; p=NS for all comparisons, two-way Student t-test).

In conclusion, the best performances were obtained with the Nλ-4xλBoxBl tethering expression system (i.e. pNλ-NP868R/pK1Ep-Luciferase-4xλBoxBl), with performances of other tethering systems ranging in the following order (i.e. ratio of condition 4 vs.1): Nλ-4xλBoxBl>MS2-4xMS2sl>Nφ21-4xφ21BoxBr>NP22-4xP22BoxBr>>TAT-4xTAR>SNRNP70-4xU1snRNA.

4. Conclusions

The present experiments show that the African swine fever virus capping enzyme NP868R can increase the expression of Firefly Luciferase mRNA produced by the K1E phage RNA polymerase when appropriately tethered to the mRNA by bacteriophage protein-RNA tethering systems.

Example 4: Bacteriophage Protein:RNA Tethering Systems, Coupled to the D12L Subunit of the Vaccinia Virus Capping can Increase the Expression of Luciferase Reporter mRNA Produced by K1E Phage RNA Polymerase in Host-Cell Cytoplasm 1. Objectives The objectives of the present experiments were to investigate if other protein:RNA tethering systems than the Nλ-4xBoxBr system can be used to guide the heterodimeric capping enzyme from the vaccinia virus to the a target mRNA, and thereby increase its expression.

The protein:RNA tethering systems tested hereinafter are the same as described in the previous example.

2. Methods a. Plasmids

The pK1ERNAP expression plasmid was described in Example 1.

The test plasmid consisted of the coding sequence of the D12L subunit from the vaccinia virus capping enzyme fused at its amino-terminal end with the tethering protein sequences described above. The D1R plasmid was the same as previously described.

The Firefly Luciferase reporter plasmids containing the various tethered RNA sequences were the same as described in the previous example.

b. Cell Culture and Transfection

Same as described in Example 1.

c. Firefly Luciferase Luminescence and SEAP Colorimetric Assays

Same as described in Example 1.

d. Statistical Analysis

Same as described in Example 1.

3. Results

Figure 9:
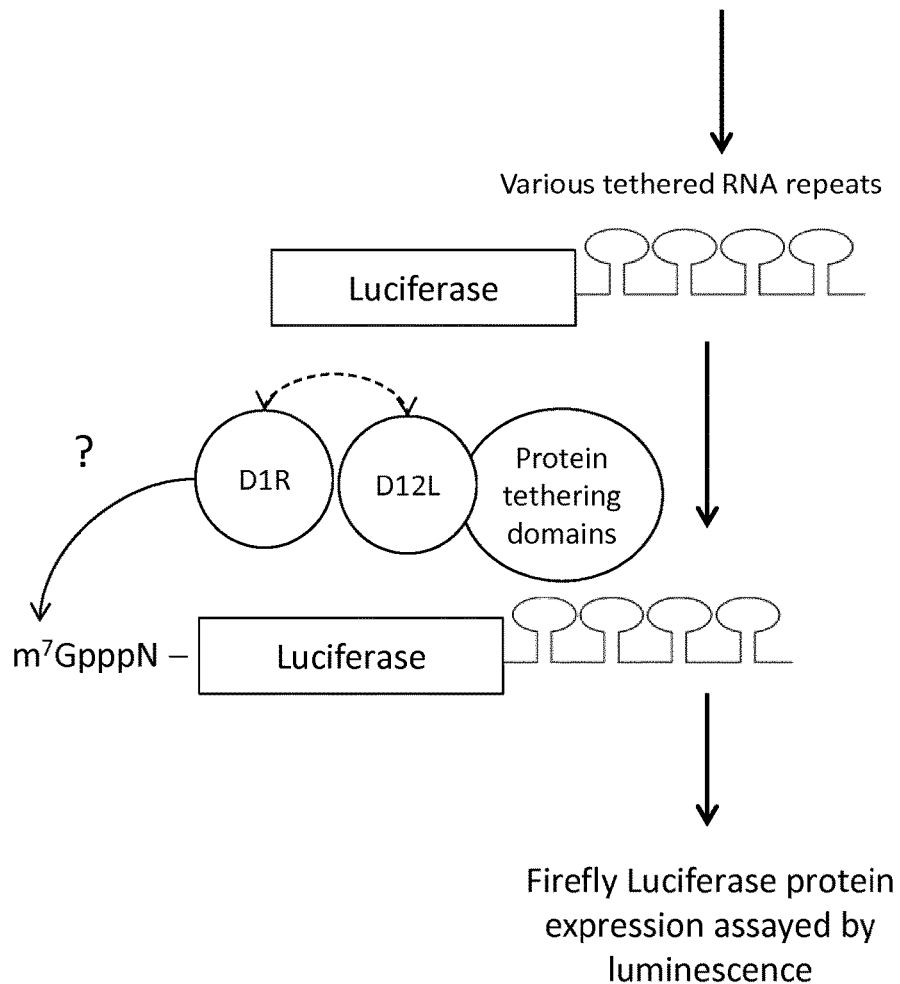
FIG. 9: K1ERNAP-driven expression system used to assay the activity of various protein:RNA binding systems coupled to the vaccinia virus capping enzyme on expression of uncapped 4xλBoxBr-tethered Firefly Luciferase mRNA.

The design of the assay was very similar to Example 1, except that various protein:RNA tethering systems were tested in replacement to the Nλ:BoxBr system (FIG. 9).

Results of these experiments are shown in the table below:

| Plasmids | mean | SEM |
|---|---|---|
| MS2-4xMS2sl tethering system | | |
| (1) pK1ERNAP, pD12L, pD1R, pK1Ep-Luciferase | 573 812 | 41312 |
| (2) pK1ERNAP, pD12L, pD1R, pK1Ep-Luciferase-4xMS2sl | 564 522 | 92952 |
| (3) pK1ERNAP, pMS2-D12L, pD1R, pK1Ep-Luciferase | 687 767 | 84793 |
| (4) pK1ERNAP, pMS2-D12L, pD1R, pK1Ep-Luciferase-4xMS2sl | 1 147 529 | 181568 |
| (5) Baseline | 187 | 173 |
| Nλ-4xλBoxBl tethering system | | |
| (1) pK1ERNAP, pD12L, pD1R, pK1Ep-Luciferase | 573 812 | 41312 |
| (2) pK1ERNAP, pD12L, pD1R, pK1Ep-Luciferase-4xλBoxBl | 566 750 | 60984 |
| (3) pK1ERNAP, pNλ-D12L, pD1R, pK1Ep-Luciferase | 521 157 | 161568 |
| (4) pK1ERNAP, pNλ-D12L, pD1R, pK1Ep-Luciferase-4xλBoxBl | 1 247 165 | 141568 |
| (5) Baseline | 187 | 173 |
| NP22-4xP22BoxBr tethering system | | |
| (1) pK1ERNAP, pD12L, pD1R, pK1Ep-Luciferase | 573 812 | 41312 |
| (2) pK1ERNAP, pD12L, pD1R, pK1Ep-Luciferase-4xP22BoxBr | 748 833 | 41312 |
| (3) pK1ERNAP, pNP22-D12L, pD1R, pK1Ep-Luciferase | 548 192 | 221568 |
| (4) pK1ERNAP, pNP22-D12L, pD1R, pK1Ep-Luciferase-4xP22BoxBr | 1 306 542 | 127189 |
| (5) Baseline | 187 | 173 |
| NΦ21-4xΦ21BoxBr tethering system | | |
| (1) pK1ERNAP, pD12L, pD1R, pK1Ep-Luciferase | 573 812 | 41312 |
| (2) pK1ERNAP, pD12L, pD1R, pK1Ep-Luciferase-4xΦ21BoxBr | 576 702 | 123936 |
| (3) pK1ERNAP, pNΦ21-D12L, pD1R, pK1Ep-Luciferase | 704 808 | 127189 |
| (4) pK1ERNAP, pNΦ21-D12L, pD1R, pK1Ep-Luciferase-4xΦ21BoxBr | 1 432 734 | 127189 |
| (5) Baseline | 187 | 173 |
| TAT-4xTAR tethering system | | |
| (1) pK1ERNAP, pD12L, pD1R, pK1Ep-Luciferase | 573 812 | 41312 |
| (2) pK1ERNAP, pD12L, pD1R, pK1Ep-Luciferase-4xTAR | 489 422 | 81968 |
| (3) pK1ERNAP, pTAT-D12L, pD1R, pK1Ep-Luciferase | 420 064 | 190784 |
| (4) pK1ERNAP, pTAT-D12L, pD1R, pK1Ep-Luciferase-4xTAR | 680 137 | 83594 |
| (5) Baseline | 187 | 173 |
| SNRNP70-4xU1snRNA tethering system | | |
| (1) pK1ERNAP, pD12L, pD1R, pK1Ep-Luciferase | 510 718 | 61968 |
| (2) pK1ERNAP, pD12L, pD1R, pK1Ep-Luciferase-4xU1snRNA | 582 331 | 6995 |
| (3) pK1ERNAP, pSNRNP70-D12L, pD1R, pK1Ep-Luciferase | 630 096 | 190784 |
| (4) pK1ERNAP, pSNRNP70-D12L, pD1R, pK1Ep-Luciferase-4xU1snRNA | 618 425 | 129309 |
| (5) Baseline | 187 | 173 |

The cotransfection of pK1ERNAP with plasmids having only one out of the two components of the tethering system, i.e. the protein domains fused to the D12L subunit of the vaccinia virus capping of the test plasmid or the Firefly Luciferase reporter plasmids with four tandem RNA tethered repeats introduced in their 3'UTR, had no significant effects on the expression of the Firefly Luciferase reporter mRNA with any system when compared to no tethering system (row 2 or 3 vs. 1; p=NS for all comparisons, two-way Student t-test). Similarly to previous findings, the cotransfection of pK1ERNAP with plasmids with all the components of the MS2-4xMS2sl and D1R subunit of the vaccinia virus capping enzyme (i.e. pMS2-D12L/pD1R/pK1Ep-Luciferase-4xMS2sl), Nλ-D12L-4xABoxBl (i.e. pNλ-D12L/pD1R/pK1Ep-Luciferase-4xABoxBl), NP22-D12L-4xP22BoxBr (i.e. pNP22-D12L/pD1R/pK1Ep-Luciferase-4xP22BoxBr), NΦ21-4xφ21BoxBr (i.e. pNφ21-D12L/pD1R/pK1Ep-Luciferase-4xφ21BoxBr), tethering system increased significantly by 2- to 2.5-fold the expression levels of firefly luciferase reporter in comparison to conditions with the untethering capping enzyme and/or untethered Firefly Luciferase plasmids (row 4 vs. 1-3; $p<0.05$ for all comparisons, two-way Student t-test). In contrast, the cotransfection of pK1ERNAP with either the TAT/4xTAR tethering system (i.e. pTAT-D12L/pD1R/pK1Ep-Luciferase-4xTAR) or the SNRNP70/4xU1snRNA tethering system (i.e. pSNRNP70-D12L/pD1R/pK1Ep-Luciferase-4xU1snRNA) shows very low change of Firefly Luciferase in comparison to conditions with the untethering capping enzyme and/or untethered Firefly Luciferase plasmids (p=NS for all comparisons, two-way Student t-test).

Finally, the performances of the tethering systems ranged in a different order than in the previous example (i.e. ratio of condition 4 vs.1): NΦ21-4xφ21BoxBr>NP22-4xP22BoxBr>Nλ-4xλBoxBl>MS2-4xMS2sl>>TAT-4xTAR>SNRNP70-4xU1snRNA.

4. Conclusions

The present experiments show that the heterodimeric D1R/D12L capping enzyme from the vaccinia virus can also increase the expression of Firefly Luciferase mRNA produced by the K1E phage RNA polymerase when appropriately tethered to the mRNA by bacteriophage RNA-binding domain of a bacteriophage protein-RNA tethering system.

Example 5: Fusion Between Poly(A) Polymerases and African Swine Fever Virus NP868R Capping Enzyme Increase the Expression of Luciferase Reporter mRNA Produced by K1E Phage RNA Polymerase when Appropriately Tethered to the Target Transcript 1. Objectives The present experiments aimed to determine if poly(A) polymerases fused to NP868R African Swine Fever virus capping enzyme can increase the expression of Firefly Luciferase reporter mRNA produced by the K1E phage RNA polymerase when appropriately tethered to the target transcript by the Nλ-BoxBl the thering system.

2. Methods a. Plasmids

The ORFs of the following poly(A) polymerases were synthesized: i) PAP1 poly(A) polymerase from *Saccharomyces cerevisiae* sorted to the cytoplasm by deletion of the 42 carboxyl-terminal amino-acids that contains a nuclear localization signal (Zhelkovsky, Helmling et al. 1998) (NCBI accession number: P29468); the vaccinia virus VP55 poly(A) polymerase (UniProtKB/Swiss-Prot accession number P23371 corresponding to the nucleotide and amino-acid sequences, respectively), the viral R341 poly(A) polymerase from *Acanthamoeba polyphaga* mimivirus (UniProtKB/Swiss-Prot accession number: E3VZZ8), iv) the viral MG561 poly(A) polymerase from *Megavirus chilensis* (NCBI Accession number: YP_004894612), v) the viral C475L poly(A) polymerase from the African swine fever virus (UniProtKB/Swiss-Prot accession number: A0A0A1E081), vi) mutant PAPOLA (K656R-K657R mutation of the human PAPOLA, UniProtKB/Swiss-Prot accession number P51003) mutated at its the nuclear localization signal (Raabe, Murthy et al. 1994, Vethantham, Rao et al. 2008), vii) the wild-type canonical *Mus musculus* testis specific PAPOLB (UniProtKB/Swiss-Prot Q9WVP6).

Four types of test plasmids were generated by in-frame subcloning of the poly(A) polymerases ORFs: i) in the pCMV-Script backbone only (e.g. pPAP1), ii) downstream to the Nλ tethering domain (e.g. pNλ-PAP1), iii) downstream to the Nλ-NP868R protein through a G4 flexible linker (e.g. pNλ-NP868R-$G_4$-PAP1) resulting in the expression of monomeric protein, or iv) between the N protein tethering domain from the lambda bacteriophage and NP868R through a G4 flexible linker (e.g. pNλ-PAP1-$G_4$-NP868R) also resulting in the expression of monomeric protein. The design of these two latter constructions is shown FIG. 10.

The Firefly Luciferase reporter plasmids in their untethered (pK1Ep-Luciferase) or tethered version (pK1Ep-Luciferase-4xλBoxBl) were the same as described above.

b. Cell Culture and Transfection

Same as described in Example 1.

c. Firefly Luciferase Luminescence and SEAP Colorimetric Assays

Same as described in Example 1.

d. Statistical Analysis

Same as described in Example 1.

3. Results

Figure 11:
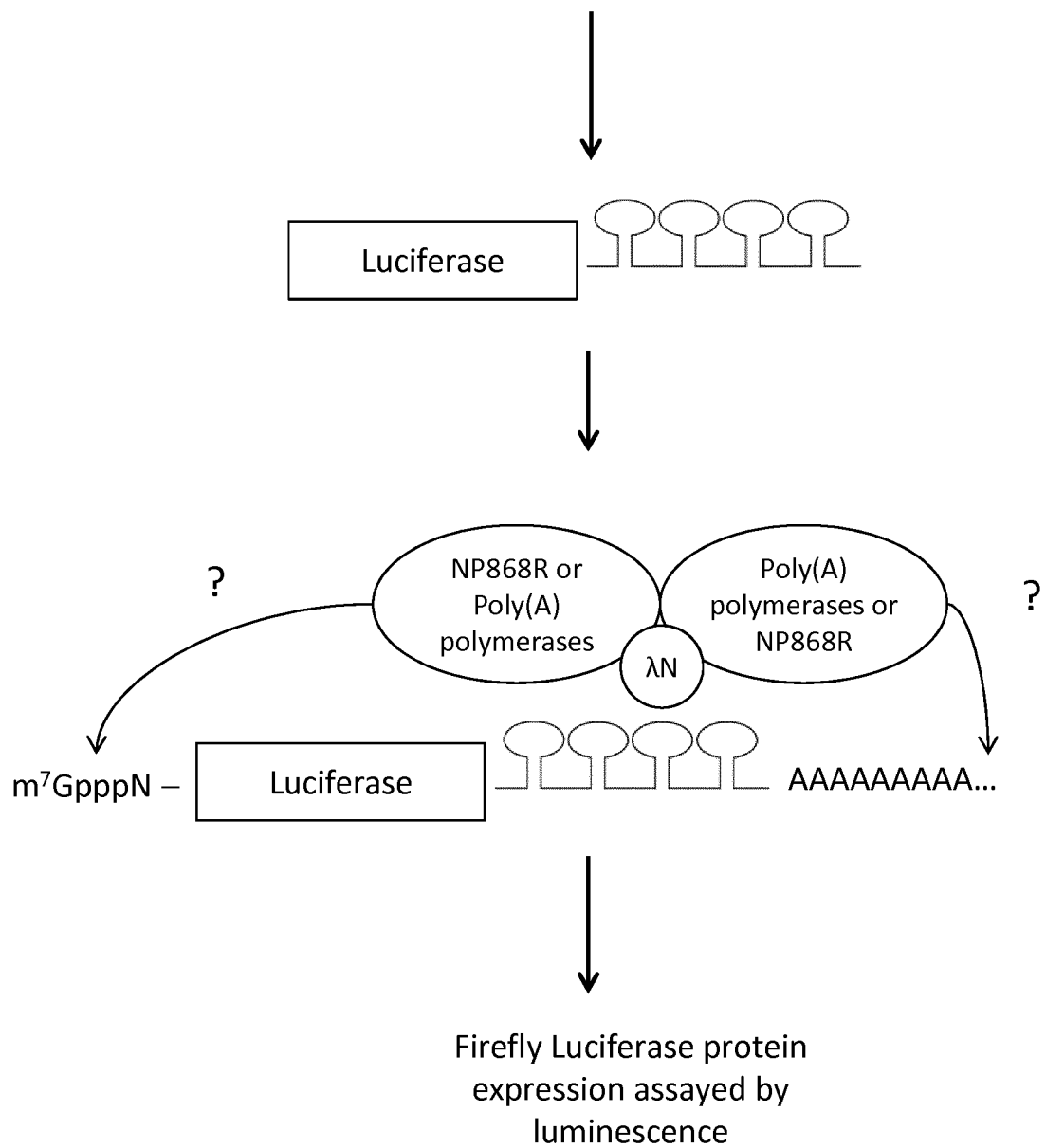
FIG. 11: K1ERNAP-driven expression system used to assay the activity of Nλ-tethering system coupled to the African swine fever virus capping enzyme fused to poly(A) polymerases on expression of uncapped 4xλBoxBr-tethered Firefly Luciferase mRNA.

The design of the assay was very similar to Example 2, except that the poly(A) polymerases were fused to African Swine Fever virus NP868R capping enzyme (FIG. 11).

Results of these experiments are shown in the table below:

| Plasmids | mean | SEM |
|---|---|---|
| C475L poly(A) polymerase series | | |
| (1) pK1ERNAP, pK1Ep-Luciferase-4xλBoxBl | 150 567 | 138 816 |
| (2) pK1ERNAP, C475L, pK1Ep-Luciferase-4xλBoxBl | 240 907 | 386 848 |
| (3) pK1ERNAP, pNλ-C475L, pK1Ep-Luciferase-4xλBoxBl | 301 134 | 499 738 |
| (4) pK1ERNAP, pNλ-NP868R, pK1Ep-Luciferase-4xλBoxBl | 3 538 575 | 414 672 |
| (5) pK1ERNAP, pC475L, pNλ-NP868R, pK1Ep-Luciferase-4xλBoxBl | 4 246 290 | 456 139 |
| (6) pK1ERNAP, pNλ-C475L, pNλ-NP868R, pK1Ep-Luciferase-4xλBoxBl | 6 794 064 | 364 911 |
| (7) pK1ERNAP, pNλ-C475L-G4-NP868R, pK1Ep-Luciferase-4xλBoxBl | 8 685 660 | 414 672 |
| (8) pK1ERNAP, pNλ-NP868R-G4-C475L, pK1Ep-Luciferase-4xλBoxBl | 8 385 560 | 393 938 |
| (9) Baseline | 22 217 | 14 176 |
| MG561 poly(A) polymerase series | | |
| (1) pK1ERNAP, pK1Ep-Luciferase-4xλBoxBl | 150 567 | 138 816 |
| (2) pK1ERNAP, MG561, pK1Ep-Luciferase-4xλBoxBl | 316 191 | 360 922 |
| (3) pK1ERNAP, pNλ-MG561, pK1Ep-Luciferase-4xλBoxBl | 421 588 | 832 896 |
| (4) pK1ERNAP, pNλ-NP868R, pK1Ep-Luciferase-4xλBoxBl | 3 538 575 | 414 672 |
| (5) pK1ERNAP, pMG561, pNλ-NP868R, pK1Ep-Luciferase-4xλBoxBl | 4 246 290 | 456 139 |
| (6) pK1ERNAP, pNλ-MG561, pNλ-NP868R, pK1Ep-Luciferase-4xλBoxBl | 6 199 583 | 364 911 |
| (7) pK1ERNAP, pNλ-MG561-G4-NP868R, pK1Ep-Luciferase-4xλBoxBl | 8 638 575 | 734 672 |
| (8) pK1ERNAP, pNλ-NP868R-G4-MG561, pK1Ep-Luciferase-4xλBoxBl | 9 070 504 | 697 938 |
| (9) Baseline | 22 217 | 14 176 |

| Plasmids | mean | SEM |
|---|---|---|
| PAP1 poly(A) polymerase series | | |
| (1) pK1ERNAP, pK1Ep-Luciferase-4xλBoxBl | 150 567 | 138 816 |
| (2) pK1ERNAP, PAP1, pK1Ep-Luciferase-4xλBoxBl | 225 851 | 277 632 |
| (3) pK1ERNAP, pNλ-PAP1, pK1Ep-Luciferase-4xλBoxBl | 361 361 | 694 080 |
| (4) pK1ERNAP, pNλ-NP868R, pK1Ep-Luciferase-4xλBoxBl | 3 538 575 | 414 672 |
| (5) pK1ERNAP, pPAP1, pNλ-NP868R, pK1Ep-Luciferase-4xλBoxBl | 4 352 447 | 456 139 |
| (6) pK1ERNAP, pNλ-PAP1, pNλ-NP868R, pK1Ep-Luciferase-4xλBoxBl | 6 659 244 | 364 911 |
| (7) pK1ERNAP, pNλ-PAP1-G4-NP868R, pK1Ep-Luciferase-4xλBoxBl | 10 638 575 | 734 688 |
| (8) pK1ERNAP, pNλ-NP868R-G4-PAP1, pK1Ep-Luciferase-4xλBoxBl | 12 538 575 | 404 078 |
| (9) Baseline | 22 217 | 14 176 |
| R341 poly(A) polymerase series | | |
| (1) pK1ERNAP, pK1Ep-Luciferase-4xλBoxBl | 150 567 | 138 816 |
| (2) pK1ERNAP, R341, pK1Ep-Luciferase-4xλBoxBl | 271 021 | 249 869 |
| (3) pK1ERNAP, pNλ-R341, pK1Ep-Luciferase-4xλBoxBl | 338 776 | 430 330 |
| (4) pK1ERNAP, pNλ-NP868R, pK1Ep-Luciferase-4xλBoxBl | 3 538 575 | 414 672 |
| (5) pK1ERNAP, pR341, pNλ-NP868R, pK1Ep-Luciferase-4xλBoxBl | 4 069 361 | 456 139 |
| (6) pK1ERNAP, pNλ-R341, pNλ-NP868R, pK1Ep-Luciferase-4xλBoxBl | 6 673 752 | 364 911 |
| (7) pK1ERNAP, pNλ-R341-G4-NP868R, pK1Ep-Luciferase-4xλBoxBl | 8 992 399 | 734 688 |
| (8) pK1ERNAP, pNλ-NP868R-G4-R341, pK1Ep-Luciferase-4xλBoxBl | 8 522 353 | 881 625 |
| (9) Baseline | 22 217 | 14 176 |
| VP55 poly(A) polymerase series | | |
| (1) pK1ERNAP, pK1Ep-Luciferase-4xλBoxBl | 150 567 | 138 816 |
| (2) pK1ERNAP, VP55, pK1Ep-Luciferase-4xλBoxBl | 271 021 | 388 685 |
| (3) pK1ERNAP, pNλ-VP55, pK1Ep-Luciferase-4xλBoxBl | 331 247 | 291 514 |
| (4) pK1ERNAP, pNλ-NP868R, pK1Ep-Luciferase-4xλBoxBl | 3 538 575 | 414 672 |
| (5) pK1ERNAP, pVP55, pNλ-NP868R, pK1Ep-Luciferase-4xλBoxBl | 4 493 990 | 456 139 |
| (6) pK1ERNAP, pNλ-VP55, pNλ-NP868R, pK1Ep-Luciferase-4xλBoxBl | 6 673 576 | 364 911 |
| (7) pK1ERNAP, pNλ-VP55-G4-NP868R, pK1Ep-Luciferase-4xλBoxBl | 8 638 575 | 134 687 |
| (8) pK1ERNAP, pNλ-NP868R-G4-VP55, pK1Ep-Luciferase-4xλBoxBl | 10 107 133 | 220 406 |
| (9) Baseline | 22 217 | 14 176 |
| PAPOLA poly(A) polymerase series | | |
| (1) pK1ERNAP, pK1Ep-Luciferase-4xλBoxBl | 124 567 | 138 816 |
| (2) pK1ERNAP, PAPOLA, pK1Ep-Luciferase-4xλBoxBl | 267 819 | 388 685 |
| (3) pK1ERNAP, pNλ-PAPOLA, pK1Ep-Luciferase-4xλBoxBl | 274 047 | 291 514 |
| (4) pK1ERNAP, pNλ-NP868R, pK1Ep-Luciferase-4xλBoxBl | 3 538 575 | 414 672 |
| (5) pK1ERNAP, pPAPOLA, pNλ-NP868R, pK1Ep-Luciferase-4xλBoxBl | 4 635 533 | 456 139 |
| (6) pK1ERNAP, pNλ-PAPOLA, pNλ-NP868R, pK1Ep-Luciferase-4xλBoxBl | 7 231 432 | 364 911 |
| (7) pK1ERNAP, pNλ-PAPOLA-G4-NP868R, pK1Ep-Luciferase-4xλBoxBl | 12 203 575 | 734 688 |
| (8) pK1ERNAP, pNλ-NP868R-G4-PAPOLA, pK1Ep-Luciferase-4xλBoxBl | 11 262 433 | 220 406 |
| (9) Baseline | 22 217 | 14 176 |
| PAPOLB polu(A) polymerase series | | |
| (1) pK1ERNAP, pK1Ep-Luciferase-4xλBoxBl | 150 567 | 138 816 |
| (2) pK1ERNAP, PAPOLB, pK1Ep-Luciferase-4xλBoxBl | 251 447 | 360 922 |
| (3) pK1ERNAP, pNλ-PAPOLB, pK1Ep-Luciferase-4xλBoxBl | 337 270 | 832 896 |
| (4) pK1ERNAP, pNλ-NP868R, pK1Ep-Luciferase-4xλBoxBl | 3 538 575 | 414 672 |
| (5) pK1ERNAP, pPAPOLB, pNλ-NP868R, pK1Ep-Luciferase-4xλBoxBl | 5 874 035 | 456 139 |
| (6) pK1ERNAP, pNλ-PAPOLB, pNλ-NP868R, pK1Ep-Luciferase-4xλBoxBl | 7 753 726 | 364 911 |
| (7) pK1ERNAP, pNλ-PAPOLB-G4-NP868R, pK1Ep-Luciferase-4xλBoxBl | 9 338 575 | 734 688 |
| (8) pK1ERNAP, pNλ-NP868R-G4-PAPOLB, pK1Ep-Luciferase-4xλBoxBl | 9 808 575 | 624 484 |
| (9) Baseline | 22 217 | 14 176 |

In the absence of mRNA capping provided by pNλ-NP868R, non-statistically significant increase of Firefly Luciferase mRNA expression of ~1.5-fold and 2.5-fold was observed when untethered (row 2 vs. 1) or tethered poly(A) polymerase plasmids (row 3 vs. 1) were transfected, respectively (p=NS, two-way Student t-test). When the Firefly Luciferase mRNA was capped by co-transfection of pNλ-NP868R, a statistically significant increase of expression of ~1.5-fold (row 5 vs. 4) and ~2-fold (row 6 vs. 4) was observed when the untethered or tethered poly(A) polymerases plasmids were cotransfected, respectively (p<0.05 for all untethered poly(A) polymerases vs. no poly(A) polymerases, two-way Student t-test).

Poly(A) polymerases were fused to NP868R African Swine Fever virus capping enzyme, together with the Nλ-protein tethering domain. Two types of fusion were tested with poly(A) polymerases subcloned either downstream to Nλ-NP868R through a $G_4$ flexible linker or between the N protein tethering domain from the lambda bacteriophage and NP868R through a Ga flexible linker. All tethered fusions genes of both types increased the expression of Firefly Luciferase mRNA in comparison to non-linked enzymes (row 7 and 8 vs. 6; p<0.05 for all comparisons, two-way Student t-test). Activity of the fusion proteins ranged as follows: Nλ-NP868R-$G_4$-C475L<Nλ-NP868R-$G_4$-R341<Nλ-MG561-$G_4$-NP868R<Nλ-VP55-$G_4$-NP868R<Nλ-C475L-$G_4$-NP868R<Nλ-R341-$G_4$-NP868R<Nλ-NP868R-$G_4$-MG561<Nλ-PAPOLB-$G_4$-NP868R<Nλ-NP868R-$G_4$-PAPOLB<Nλ-NP868R-$G_4$-VP55<Nλ-PAP1-$G_4$-NP868R<Nλ-NP868R-$G_4$-PAPOLA<Nλ-PAPOLA-$G_4$-NP868R<Nλ-NP868R-$G_4$-PAP1

4. Conclusions

The present experiments show that various poly(A) polymerases including mammalian, yeast, viral and bacterial enzymes fused to the African Swine Fever virus NP868R capping enzyme increase the expression of transcripts produced by phage RNA polymerase, when appropriately tethered with the Nλ-4xBoxB1 system. Surprisingly, the fusion between various poly(A) polymerases and NP868R capping enzymes, which are not physically linked in the nature and contain no RNA-binding domain, can act synergistically and this effect is even greater when these fusion proteins are appropriately tethered (rows 7 and 8 in the above Table). These results are really surprising and one skilled in the art could have expected to obtain the same expression rate since the components are the same.

Example 6: Fusion of Poly(A) Polymerases and the D12 Subunit of the Heterodimeric Vaccinia Virus Capping Enzyme can Increase the Expression of Luciferase Reporter mRNA Produced by K1E Phage RNA Polymerase when Appropriately Tethered to the Target Transcript 1. Objectives The present experiments aim to determine if fusions of poly(A) polymerases with D12 subunit of the heterodimeric vaccinia virus capping enzyme can increase the expression of transcripts produced by phage RNA polymerase, when appropriately tethered with the Nλ-4xBoxB1 system.

2. Methods a. Plasmids

The pK1ERNAP expression plasmid was described in Example 1.

Figure 12:
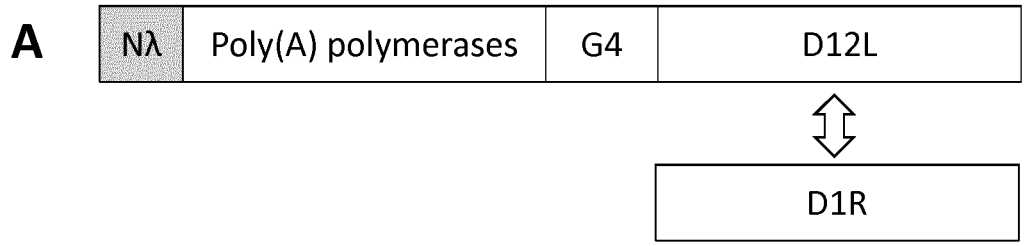
FIG. 12: structure of constructions resulting of Nλ-tethering domain coupled to the vaccinia virus capping enzyme fused to poly(A) polymerases. Arrow indicates D12L-D1R binding. (A) Nλ-poly(A) polymerase-G4-D12L/D1R heterodimer, (B) Nλ-D12L-G4-poly(A) polymerase/D1R heterodimer.
Figure 12:
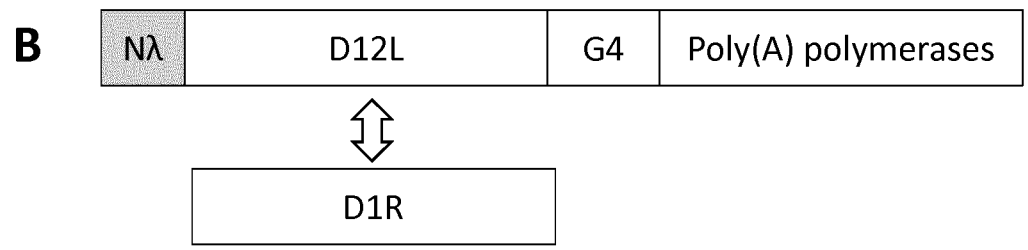

The poly(A) polymerases tested were described in previous example and subcloned in-frame (FIG. 12): i) downstream to the Nλ-D12L protein through a $G_4$ flexible linker (e.g. pNλ-D12L-$G_4$-PAP1), or between the N protein tethering domain from the lambda bacteriophage and D12L through a $G_4$ flexible linker (e.g. pNλ-PAP1-$G_4$-D12L).

The Firefly Luciferase reporter plasmids in their untethered (pK1Ep-Luciferase) or tethered version (pK1Ep-Luciferase-4xλBoxB1) were the same as described above.

b. Cell Culture and Transfection

Same as described in Example 1.

c. Firefly Luciferase Luminescence and SEAP Colorimetric Assays

Same as described in Example 1.

d. Statistical Analysis

Same as described in Example 1.

3. Results

Figure 13:
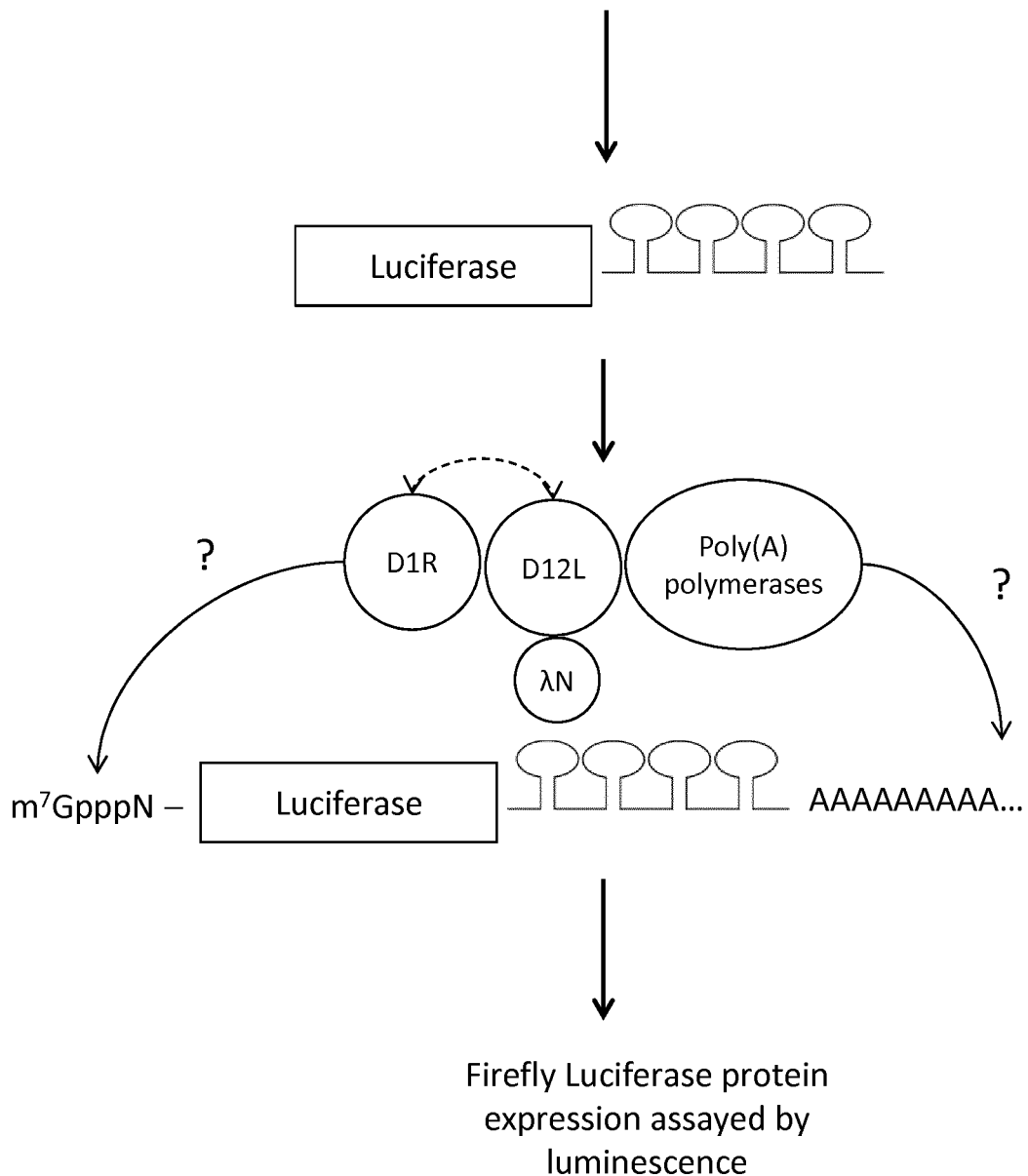
FIG. 13: K1ERNAP-driven expression system used to assay the activity of Nλ-tethering system coupled to the vaccinia virus capping enzyme fused to poly(A) polymerases on expression of uncapped 4xλBoxBr-tethered Firefly Luciferase mRNA FIG. 14 structure of Nλ-tethering system coupled to the vaccinia virus capping enzyme bound to poly(A) polymerases through complementary leucine zippers. Arrow indicates complementary leucines zippers that forms heterodimers. (A) Nλ-R341-EE$_{1234}$L/RR$_{1234}$L-NP868R heterodimer, and (B) Nλ-NP868R-EE$_{1234}$L/RR$_{1234}$L-R341 heterodimer.
Figure 15:
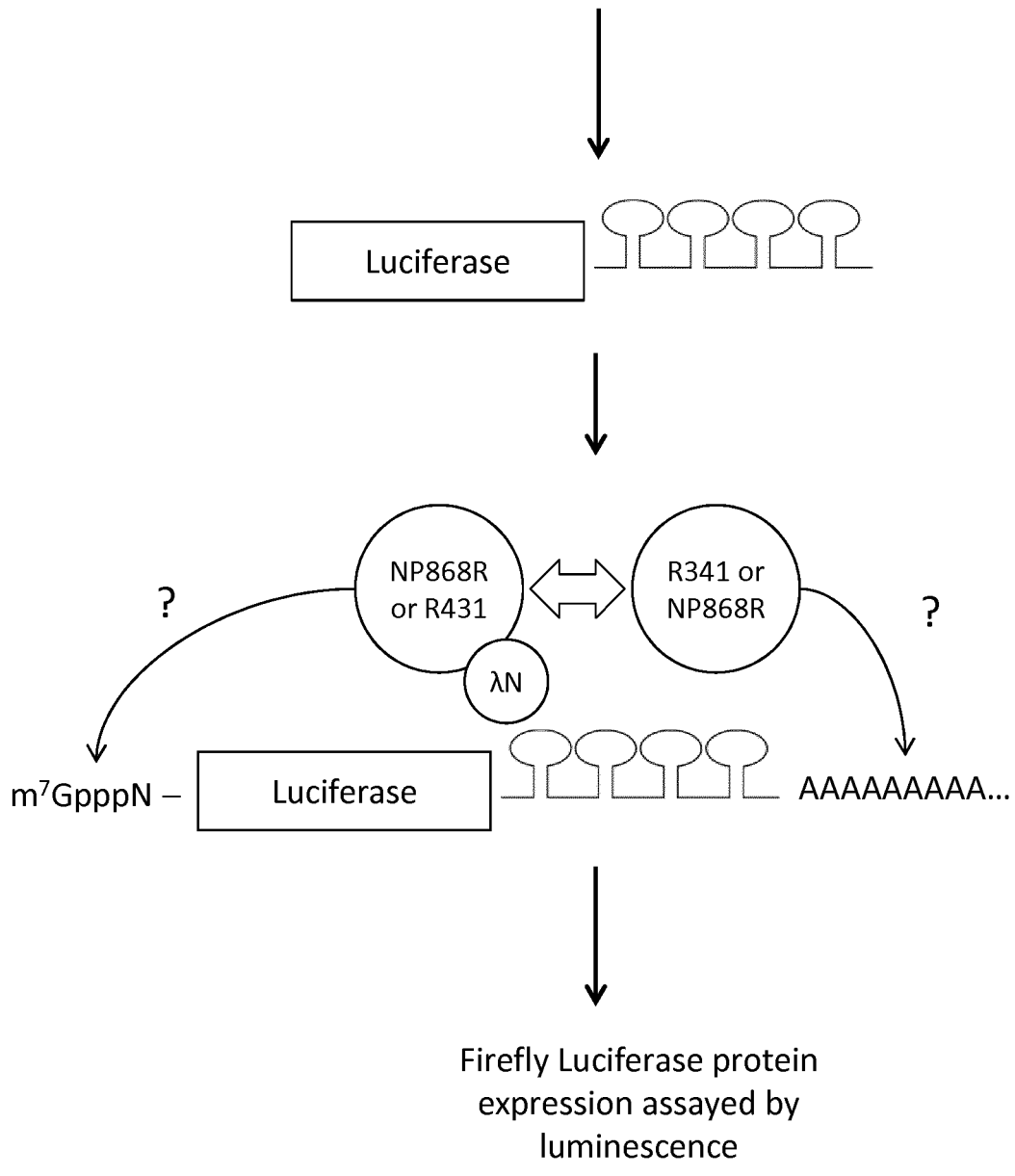
FIG. 15: K1ERNAP-driven expression system used to assay the activity of Nλ-tethering system coupled to the vaccinia virus capping enzyme fused to poly(A) polymerases on expression of uncapped 4xλBoxBr-tethered Firefly Luciferase mRNA. Arrow indicates D12L-D1R binding.

The design of the experiment was similar to previous example, except that the capping enzyme consisted of the vaccinia virus heterodimer D1R/D12 (FIG. 13).

Results of these experiments are shown in the table below:

| Plasmids | mean | SEM |
|---|---|---|
| C475L poly(A) polymerase series | | |
| (1) pK1ERNAP, pK1Ep-Luciferase-4xλBoxB1 | 145 279 | 116 201 |
| (2) pK1ERNAP, C475L, pK1Ep-Luciferase-4xλBoxB1 | 201 661 | 325 912 |
| (3) pK1ERNAP, pNλ-C475L, pK1Ep-Luciferase-4xλBoxB1 | 253 700 | 466 225 |
| (4) pK1ERNAP, pNλ-D12L, pD1R, pK1Ep-Luciferase-4xλBoxB1 | 3 301 279 | 429 341 |
| (5) pK1ERNAP, pC475L, pNλ-D12L, pD1R, pK1Ep-Luciferase-4xλBoxB1 | 4 196 498 | 353 954 |
| (6) pK1ERNAP, pNλ-C475L, pNλ-D12L, pD1R, pK1Ep-Luciferase-4xλBoxB1 | 5 272 046 | 95 796 |
| (7) pK1ERNAP, pNλ-C475L-G4-D12L, pD1R, pK1Ep-Luciferase-4xλBoxB1 | 7 201 395 | 453 620 |
| (8) pK1ERNAP, pNλ-D1R, pD12L-G4-C475L, pK1Ep-Luciferase-4xλBoxB1 | 7 173 174 | 267 557 |
| (9) Baseline | 23 887 | 9 510 |
| MG561 poly(A) polymerase series | | |
| (1) pK1ERNAP, pK1Ep-Luciferase-4xλBoxB1 | 121 133 | 125 248 |
| (2) pK1ERNAP, MG561, pK1Ep-Luciferase-4xλBoxB1 | 285 286 | 334 854 |
| (3) pK1ERNAP, pNλ-MG561, pK1Ep-Luciferase-4xλBoxB1 | 391 138 | 866 711 |

| Plasmids | mean | SEM |
| --- | --- | --- |
| (4) pK1ERNAP, pNλ-D12L, pD1R, pK1Ep-Luciferase-4xλBoxBl | 2 240 943 | 218 840 |
| (5) pK1ERNAP, pMG561, pNλ-D12L, pD1R, pK1Ep-Luciferase-4xλBoxBl | 3 682 240 | 466 962 |
| (6) pK1ERNAP, pNλ-MG561, pNλ-D12L, pD1R, pK1Ep-Luciferase-4xλBoxBl | 5 346 676 | 374 202 |
| (7) pK1ERNAP, pNλ-MG561-G4-D12L, pD1R, pK1Ep-Luciferase-4xλBoxBl | 8 858 505 | 603 377 |
| (8) pK1ERNAP, pNλ-D1R, pD12L-G4-MG561, pK1Ep-Luciferase-4xλBoxBl | 7 449 488 | 527 949 |
| (9) Baseline | 23 887 | 9 510 |
| PAP1 poly(A) polymerase series | | |
| (1) pK1ERNAP, pK1Ep-Luciferase-4xλBoxBl | 120 765 | 132 669 |
| (2) pK1ERNAP, PAP1, pK1Ep-Luciferase-4xλBoxBl | 215 849 | 176 186 |
| (3) pK1ERNAP, pNλ-PAP1, pK1Ep-Luciferase-4xλBoxBl | 229 321 | 646 674 |
| (4) pK1ERNAP, pNλ-D12L, pD1R, pK1Ep-Luciferase-4xλBoxBl | 3 296 890 | 441 173 |
| (5) pK1ERNAP, pPAP1, pNλ-D12L, pD1R, pK1Ep-Luciferase-4xλBoxBl | 4 630 608 | 427 360 |
| (6) pK1ERNAP, pNλ-PAP1, pNλ-D12L, pD1R, pK1Ep-Luciferase-4xλBoxBl | 6 239 087 | 194 450 |
| (7) pK1ERNAP, pNλ-PAP1-G4-D12L, pD1R, pK1Ep-Luciferase-4xλBoxBl | 10 668 967 | 620 415 |
| (8) pK1ERNAP, pNλ-D1R, pD12L-G4-PAP1, pK1Ep-Luciferase-4xλBoxBl | 9 534 665 | 223 391 |
| (9) Baseline | 23 887 | 9 510 |
| R341 poly(A) polymerase series | | |
| (1) pK1ERNAP, pK1Ep-Luciferase-4xλBoxBl | 92 989 | 144 738 |
| (2) pK1ERNAP, R341, pK1Ep-Luciferase-4xλBoxBl | 282 582 | 190 160 |
| (3) pK1ERNAP, pNλ-R341, pK1Ep-Luciferase-4xλBoxBl | 257 822 | 449 340 |
| (4) pK1ERNAP, pNλ-D12L, pD1R, pK1Ep-Luciferase-4xλBoxBl | 2 684 956 | 273 600 |
| (5) pK1ERNAP, pR341, pNλ-D12L, pD1R, pK1Ep-Luciferase-4xλBoxBl | 3 694 895 | 372 489 |
| (6) pK1ERNAP, pNλ-R341, pNλ-D12L, pD1R, pK1Ep-Luciferase-4xλBoxBl | 5 449 865 | 413 128 |
| (7) pK1ERNAP, pNλ-R341-G4-D12L, pD1R, pK1Ep-Luciferase-4xλBoxBl | 10 180 543 | 694 655 |
| (8) pK1ERNAP, pNλ-D1R, pD12L-G4-R341, pK1Ep-Luciferase-4xλBoxBl | 8 057 982 | 766 195 |
| (9) Baseline | 23 887 | 9 510 |
| VP55 poly(A) polymerase series | | |
| (1) pK1ERNAP, pK1Ep-Luciferase-4xλBoxBl | 111 045 | 96 804 |
| (2) pK1ERNAP, VP55, pK1Ep-Luciferase-4xλBoxBl | 188 997 | 328 927 |
| (3) pK1ERNAP, pNλ-VP55, pK1Ep-Luciferase-4xλBoxBl | 280 320 | 285 568 |
| (4) pK1ERNAP, pNλ-D12L, pD1R, pK1Ep-Luciferase-4xλBoxBl | 3 466 398 | 436 289 |
| (5) pK1ERNAP, pVP55, pNλ-D12L, pD1R, pK1Ep-Luciferase-4xλBoxBl | 4 728 261 | 461 933 |
| (6) pK1ERNAP, pNλ-VP55, pNλ-D12L, pD1R, pK1Ep-Luciferase-4xλBoxBl | 5 758 344 | 375 637 |
| (7) pK1ERNAP, pNλ-VP55-G4-D12L, pD1R, pK1Ep-Luciferase-4xλBoxBl | 7 863 085 | 29 635 |
| (8) pK1ERNAP, pNλ-D1R, pD12L-G4-VP55, pK1Ep-Luciferase-4xλBoxBl | 8 601 926 | 252 202 |
| (9) Baseline | 23 887 | 9 510 |
| PAPOLA poly(A) polymerase series | | |
| (1) pK1ERNAP, pK1Ep-Luciferase-4xλBoxBl | 174 916 | 96 128 |
| (2) pK1ERNAP, PAPOLA, pK1Ep-Luciferase-4xλBoxBl | 185 461 | 347 658 |
| (3) pK1ERNAP, pNλ-PAPOLA, pK1Ep-Luciferase-4xλBoxBl | 245 121 | 282 829 |
| (4) pK1ERNAP, pNλ-D12L, pD1R, pK1Ep-Luciferase-4xλBoxBl | 3 433 158 | 309 045 |
| (5) pK1ERNAP, pPAPOLA, pNλ-D12L, pD1R, pK1Ep-Luciferase-4xλBoxBl | 4 454 749 | 385 659 |
| (6) pK1ERNAP, pNλ-PAPOLA, pNλ-D12L, pD1R, pK1Ep-Luciferase-4xλBoxBl | 6 114 076 | 325 113 |
| (7) pK1ERNAP, pNλ-PAPOLA-G4-D12L, pD1R, pK1Ep-Luciferase-4xλBoxBl | 9 230 982 | 731 066 |
| (8) pK1ERNAP, pNλ-D1R, pD12L-G4-PAPOLA, pK1Ep-Luciferase-4xλBoxBl | 10 284 960 | 221 627 |
| (9) Baseline | 23 887 | 9 510 |
| PAPOLB poly(A) polymerase series | | |
| (1) pK1ERNAP, pK1Ep-Luciferase-4xλBoxBl | 134 279 | 130 482 |
| (2) pK1ERNAP, PAPOLB, pK1Ep-Luciferase-4xλBoxBl | 236 351 | 321 719 |
| (3) pK1ERNAP, pNλ-PAPOLB, pK1Ep-Luciferase-4xλBoxBl | 300 637 | 861 464 |

-continued

| Plasmids | mean | SEM |
|---|---|---|
| (4) pK1ERNAP, pNλ-D12L, pD1R, pK1Ep-Luciferase-4xλBoxBl | 3 659 946 | 363 888 |
| (5) pK1ERNAP, pPAPOLB, pNλ-D12L, pD1R, pK1Ep-Luciferase-4xλBoxBl | 4 154 652 | 410 206 |
| (6) pK1ERNAP, pNλ-PAPOLB, pNλ-D12L, pD1R, pK1Ep-Luciferase-4xλBoxBl | 5 972 923 | 350 054 |
| (7) pK1ERNAP, pNλ-PAPOLB-G4-D12L, pD1R, pK1Ep-Luciferase-4xλBoxBl | 7 677 493 | 552 983 |
| (8) pK1ERNAP, pNλ-D1R, pD12L-G4-PAPOLB, pK1Ep-Luciferase-4xλBoxBl | 8 958 357 | 480 636 |
| (9) Baseline | 23 887 | 9 510 |

In the absence of mRNA capping provided by pNλ-D12L/D1R, non-statistically significant change of Firefly Luciferase mRNA expression of ~1.5-fold and 2-fold was observed when untethered (row 2 vs. 1) or tethered poly(A) polymerase plasmids (row 3 vs. 1) were transfected, respectively (p=NS, two-way Student t-test). Similarly to previous findings, when the Firefly Luciferase mRNA was capped by co-transfection of pNλ-D12L/D1R, a statistically significant increase of expression of ~1.5-fold (row 5 vs. 4) and ~2-fold (row 6 vs. 4) was observed when the untethered or tethered poly(A) polymerases plasmids were cotransfected, respectively (p<0.05 for all untethered poly(A) polymerases vs. no poly(A) polymerases, two-way Student t-test).

Poly(A) polymerases were fused to the D12 subunit of the heterodimeric vaccinia virus capping enzyme, together with the Nλ-protein domain as described above. All tethered fusions genes of both types increased the expression of Firefly Luciferase mRNA in comparison to non-linked enzymes (row 7 and 8 vs. 6; p<0.05 for all comparisons, two-way Student t-test). Activity of the fusion complexes ranged as follows: Nλ-D12L/D1R-G$_4$-C475L<Nλ-C475L-G$_4$-D12L/D1R<Nλ-D12L/D1R-G$_4$-MG561<Nλ-PAPOLB-G$_4$-D12L/D1R<Nλ-VP55-G$_4$-D12L/D1R<Nλ-D12L/D1R-G$_4$-R341<Nλ-D12L/D1R-G$_4$-VP55<Nλ-MG561-G$_4$-D12L/D1R<Nλ-D12L/D1R-G$_4$-PAPOLB<Nλ-PAPOLA-G$_4$-D12L/D1R<Nλ-D12L/D1R-G$_4$-PAP1<Nλ-R341-G$_4$-D12L/D1R<Nλ-D12L/D1R-G$_4$-PAPOLA<Nλ-PAP1-G$_4$-D12L/D1R.

4. Conclusions

The present experiments that various poly(A) polymerases fused to the D12 subunit of the heterodimeric vaccinia virus capping enzyme together with D1R subunit, which are not physically linked in the nature and contain no RNA-binding domain, can act synergistically and this effect is even greater when these fusion proteins appropriately tethered.

Example 7: Non-Covalent Tethered Coupling Between *Acanthamoeba polyphaga* Mimivirus R341 Poly(A) Polymerase and African Swine Fever Virus NP868R Capping Enzyme, can Increase the Expression of Luciferase Reporter mRNA Produced by Phage RNA Polymerases 1. Objectives The objectives of this set of experiments were to determine if non-covalent coupling between the R341 poly(A) polymerase and NP868R capping enzyme also results in an active expression system able to enhance the expression of uncapped Firefly Luciferase reporter mRNA when appropriately tethered. In the present experiments, the non-covalent coupling was generated using complementary leucine zippers that form heterodimers.

2. Methods a. Plasmids

The pK1ERNAP expression and Firefly Luciferase reporter plasmids in their untethered (pK1Ep-Luciferase) or tethered version (pK1Ep-Luciferase-4xλBoxBr) were the same as described above.

Non-covalent coupling between the *Acanthamoeba polyphaga* mimivirus R341 poly(A) polymerase and the African swine fever virus NP868R capping enzyme was induced by the $EE_{1234}L$ and $RR_{1234}L$ complementary leucine-zippers (SEQ ID No 28 and SEQ ID No 29 corresponding to the nucleotide and amino-acid sequences of $G_4$-$EE_{1234}L$ leucine-zipper, respectively; SEQ ID No 30 and SEQ ID No 31 corresponding to the nucleotide and amino-acid sequences of $RR_{1234}L$-$G_4$ leucine-zipper, respectively). These amphipathic α-helices form an antiparallel heterodimer with dissociation affinity of $\sim 10^{-15}$M (Moll, Ruvinov et al. 2001). Two non-covalent heterodimeric complexes were generated between NP868R capping enzyme and R341 RNA polymerase (FIG. 14). Firstly, the $EE_{1234}L$ leucine zipper was fused in-frame to the carboxyl-terminal end of Nλ-R41, while $RR_{1234}L$ was fused in-frame to the amino-terminal end of NP868R. Co-expression of these two plasmids, respectively named pNλ-R341-$EE_{1234}L$ and $RR_{1234}L$-NP868R, therefore produces a heterodimer with an Nλ-tethering domain carried by R341. Secondly, $RR_{1234}L$ leucine zipper was fused in-frame to the carboxyl-terminal end of Nλ-NP868R, while the $EE_{1234}L$ was fused in-frame to the amino-terminal end of R341. Co-expression of these two plasmids, respectively named pNλ-NP868R-$RR_{1234}L$ and p$EE_{1234}L$-R341, therefore generates a heterodimer with an Nλ-tethering domain carried by NP868R. These plasmids were synthesized by subcloning the corresponding ORFs in the pCMVScript plasmid backbone at endonuclease restriction enzyme sites.

b. Cell Culture and Transfection

Same as described in Example 1.

c. Firefly Luciferase Luminescence and SEAP Colorimetric Assays

Same as described in Example 1.

d. Statistical Analysis

Same as described in Example 1.

3. Results

Uncapped Firefly Luciferase reporter mRNA was generated by the K1E bacteriophage RNA polymerase, using the pK1Ep-Luciferase and pK1Ep-Luciferase-4xλBoxBr plasmids as previously described (FIG. 15).

Results of these experiments are shown in the table below:

| Plasmids | mean | SEM |
|---|---|---|
| (1) pK1ERNAP, pNλ-R341 | 497 650 | 182 520 |
| (2) pK1ERNAP, pEE1234L-R341 | 257 650 | 109 512 |
| (3) pK1ERNAP, pNλ-R341-EE1234L | 522 533 | 146 016 |
| (4) pK1ERNAP, pNλ-NP868R | 2 377 957 | 237 063 |
| (5) pK1ERNAP, pRR1234L-NP868R | 1 049 099 | 104 587 |
| (6) pK1ERNAP, pNλ-NP868R-RR1234L | 2 331 330 | 232 415 |
| (7) pK1ERNAP, pEE1234L-R341, pRR1234L-NP868R | 4 539 654 | 325 828 |
| (8) pK1ERNAP, pNλ-R341-EE1234L, pRR1234L-NP868R | 12 924 395 | 325 828 |
| (9) pK1ERNAP, pNλ-NP868R-RR1234L, pEE1234L-R341 | 10 191 523 | 270 437 |
| (10) Baseline | 671 | 257 |

The Nλ-tethering of the *Acanthamoeba polyphaga* mimivirus R341 poly(A) polymerase with or without leucine zipper increased modestly the expression of uncapped 4xλBoxBr-Firefly Luciferase mRNA generated by the phage K1E RNA polymerase in comparison to untethered *Acanthamoeba polyphaga* mimivirus R341 poly(A) polymerase (row 1 or 3 vs. 2). The Nλ-tethering of the African Swine Fever Virus NP868R capping enzyme with or without leucine zipper increased frankly the expression of uncapped Firefly Luciferase 4xλBoxBr-mRNA generated by the phage K1E RNA polymerase in comparison to untethered NP868R capping enzyme or no capping enzyme (row 4 or 6 vs. 5).

The non-covalent coupling between the *Acanthamoeba polyphaga* mimivirus R341 poly(A) polymerase and the African swine fever virus NP868R capping enzyme was generated using the $EE_{1234}L$ and $RR_{1234}L$ complementary high-affinity leucine-zippers. This heterodimeric complex without the Nλ-tethering domain resulted in active complex that significantly increased the expression of uncapped Firefly Luciferase mRNA generated by the phage K1E RNA polymerase in comparison to conditions to either untethered R341 or NP868R with leucine zippers alone (row 7 vs. 2 or 5). Noticeably, the addition of Nλ-tethering at amino-terminal end of the *Acanthamoeba polyphaga* mimivirus R341 poly(A) polymerase or the African swine fever virus NP868R capping enzyme of this heterodimeric complex increased by 2.80- and 2.24-fold the expression of uncapped Firefly Luciferase mRNA in comparison to the untethered complex (row 8 or 9 vs. 7; p<0.05 for both comparisons, two-way Student t-test).

4. Conclusions

The present experiments show that the artificial coupling between the R341 poly(A) polymerase and the African swine fever virus NP868R capping enzyme, i.e. non-covalent through leucine zippers, also results in synergistically active heterodimers and this effect is even greater when these fusion proteins appropriately tethered.

Example 8: Assemblies Between the *Acanthamoeba polyphaga* mimivirus R341 Poly(A) Polymerase, African Swine Fever Virus NP868R Capping Enzyme and Phage K1E RNA Polymerase Results in Active Expression Complexes 1. Objectives The objective of the following experiment was to determine if active complexes could be generated by assembling the *Acanthamoeba polyphaga* mimivirus poly(A) polymerase R341, the African swine fever virus NP868R capping enzyme and the phage K1E RNA polymerase when appropriately Nλ-tethered.

The assemblies tested hereinafter are designed according to the common Nλ-R341-[X1]-NP868R-[X2]-K1ERNAP protein scaffold, where [X1] and [X2] are variable.

Figure 16:
FIGS. 16A-D: structures of tethering complexes between the *Acanthamoeba polyphaga* mimivirus poly(A) polymerase R341, the African swine fever virus NP868R capping enzyme and the phage K1E RNA polymerase on expression of polyadenylated 4xλBoxBl-tethered Firefly Luciferase mRNA. [X1] and [X2] designate variable domains, where G4 and (G4S)$_2$ is a flexible linker, T2A and F2A are ribosomal skipping sequences from the porcine teschovirus-1 and picornavirus Foot-and-mouth disease aphtovirus, respectively.
Figure 16:
Figure 16:

The following open-reading-frames were generated to test this hypothesis (FIG. 16):

[X1]=$G_4$, [X2]=$G_4$; i.e. Nλ-R341-$G_4$-NP868R-$G_4$-K1ERNAP construction (NCBI accession number J02459-SEQ ID No 40 and SEQ ID No 41 corresponding to the nucleotide and amino-acid sequences of Nλ-R341-$G_4$-NP868R-$G_4$-K1ERNAP, respectively) featured by the fusion of the three enzymatic subunit through flexible linkers with the Nλ-tethering peptide at its N-terminus,

[X1]=$G_4$, [X2]=F2A; i.e. Nλ-R341-$G_4$-NP868R-F2A-K1ERNAP construction (SEQ ID No 42 and SEQ ID No 43 corresponding to the nucleotide and amino-acid sequences of Nλ-R341-$G_4$-NP868R-F2A-K1ERNAP, respectively) featured by the substitution of the $G_4$ flexible linker located between the African swine fever virus NP868R capping enzyme and the phage K1E RNA polymerase by the F2A ribosomal skipping sequence from the picornavirus aphtovirus (Foot-and-mouth disease aphovirus type 0 polyprotein, UniProtKB/Swiss-Prot accession number AAT01756, residues 934-955). Ribosomal skipping results in apparent co-translational cleavage of the protein (Donnelly, Luke et al. 2001),

[X1]=F2A, [X2]=$G_4$; i.e. Nλ-R341-F2A-NP868R-$G_4$-K1ERNAP construction (SEQ ID No 44 and SEQ ID No 45 corresponding to the nucleotide and amino-acid sequences of Nλ-R341-F2A-NP868R-$G_4$-K1ERNAP, respectively) featured by the substitution of the $G_4$ flexible linker located between the R341 poly(A) polymerase and the African swine fever virus NP868R capping enzyme by the F2A ribosomal skipping sequence.

[X1]=T2A, [X2]=$G_4$; i.e. Nλ-R341-T2A-NP868R-$G_4$-K1ERNAP construction (SEQ ID No 46 and SEQ ID No 47 corresponding to the nucleotide and amino-acid sequences of Nλ-R341-T2A-NP868R-$G_4$-K1ERNAP, respectively) featured by the substitution of the $G_4$ flexible linker located between the R341 poly(A) polymerase and the African swine fever virus NP868R capping enzyme by the T2A ribosomal skipping sequence from the porcine teschovirus-1 (UniProtKB/Swiss-Prot accession number Q9WJ28, residues 979-997).

2. Methods a. Plasmids

The Firefly Luciferase reporter plasmids in their untethered (pK1Ep-Luciferase) or tethered version (pK1Ep-Luciferase-4xλBoxBl) were the same as described above.

The ORFs previously described were subcloned in the pCMVScript backbone, therefore resulting in the pNλ-R341-$G_4$-NP868R-$G_4$-K1ERNAP, pNλ-R341-$G_4$-NP868R-F2A-K1ERNAP, pNλ-R341-F2A-NP868R-$G_4$-K1ERNAP, and pNλ-R341-T2A-NP868R-$G_4$-K1ERNAP plasmids.

b. Cell Culture and Transfection

Same as described in Example 1.

c. Firefly Luciferase Luminescence and SEAP Colorimetric Assays

Same as described in Example 1.

d. Statistical Analysis

Same as described in Example 1.

3. Results

Figure 17:
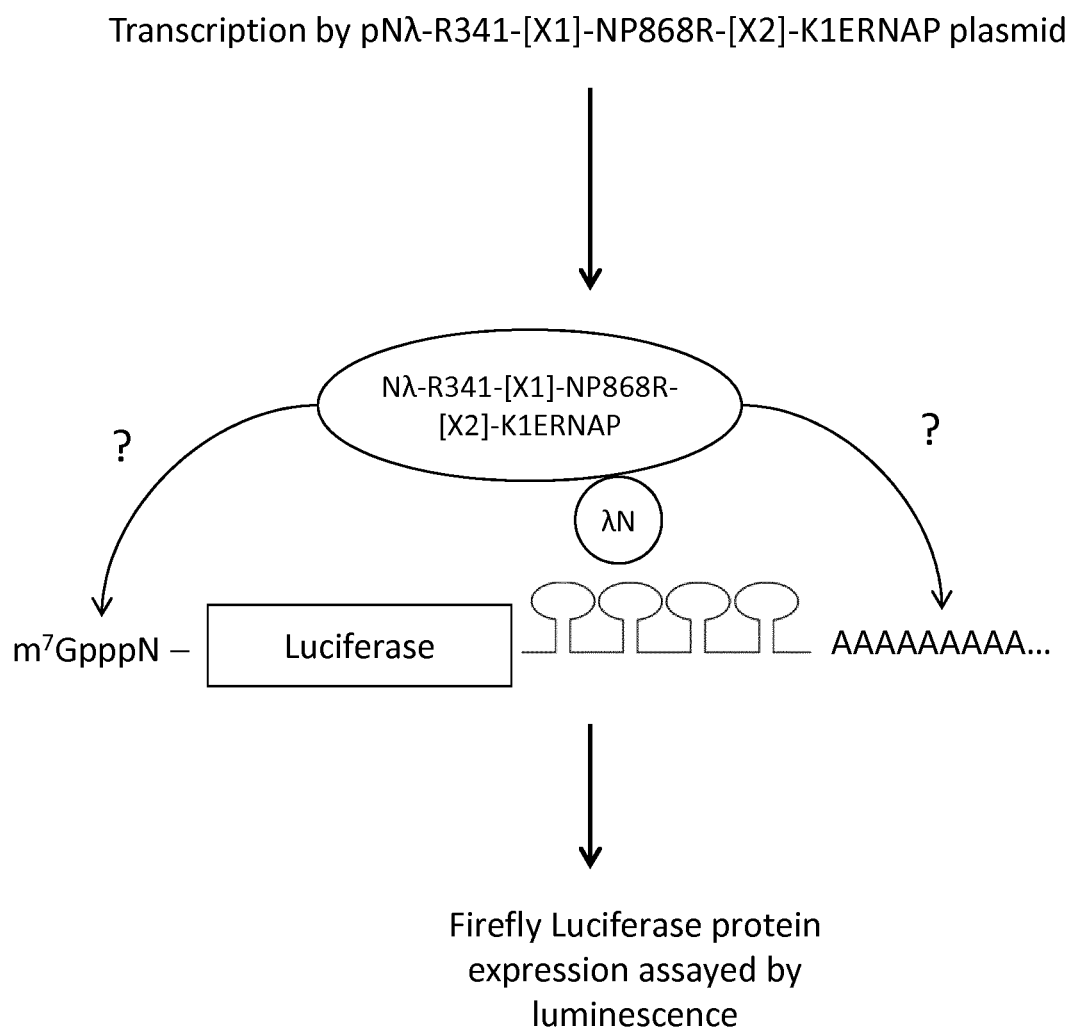
FIG. 17: expression system used to assay the activity of tethering complexes between the *Acanthamoeba polyphaga* mimivirus poly(A) polymerase R341, the African swine fever virus NP868R capping enzyme and the phage K1E RNA polymerase on expression of 4xλBoxBl-tethered Firefly Luciferase mRNA.

A depiction of the assay is shown FIG. 17.

Results of these experiments are shown in the table below:

| Plasmids | mean | SEM |
|---|---|---|
| (1) pNλ-R341-G4-NP868R, pK1ERNAP, pK1Ep-Luciferase-4xλBoxBl | 2 989 500 | 321 841 |
| (2) pNλ-R341-G4-NP868R-G4-K1ERNAP, pK1Ep-Luciferase-4xλBoxBl | 3 882 614 | 649 466 |
| (3) pNλ-R341-G4-NP868R-F2A-K1ERNAP, pK1Ep-Luciferase-4xλBoxBl | 4 393 507 | 928 702 |
| (4) pNλ-R341-F2A-NP868R-G4-K1ERNAP, pK1Ep-Luciferase-4xλBoxBl | 7 778 512 | 219 138 |
| (5) pNλ-R341-T2A-NP868R-G4-K1ERNAP, pK1Ep-Luciferase-4xλBoxBl | 7 861 869 | 1 120 056 |
| (6) Baseline | 162 088 | 56 504 |

The various fusion of K1ERNAP coding sequence with Nλ-R341-F2A-NP868R were compared with non-linked Nλ-R341-F2A-NP868R and K1ERNAP. All fusions constructions gave significantly greater expression levels than non-linked Nλ-R341-F2A-NP868R and K1ERNAP (row 2-to-5 vs. 1; p<0.05, two-way Student t-test for all comparisons). Best results were obtained with Nλ-R341-T2A-NP868R-$G_4$-K1ERNAP and Nλ-R341-F2A-NP868R-$G_4$-K1ERNAP fusions, with other conditions ranging in the following order: Nλ-R341-T2A-NP868R-$G_4$-K1ERNAP Nλ-R341-F2A-NP868R-$G_4$-K1ERNAP>>Nλ-R341-$G_4$-NP868R-F2A-K1ERNAP>Nλ-R341-$G_4$-NP868R-$G_4$-K1ERNAP>pNλ-R341-$G_4$-NP868R, pK1ERNAP.

4. Conclusions

The present experiments show that active tethered expression systems can be generated by assembling the poly(A) polymerase R341, African swine fever virus NP868R capping enzyme and phage K1E RNA polymerase under a Nλ-R341-[X1]-NP868R-[X2]-K1ERNAP scaffold, preferably where [X1]=T2A or F2A, and [X2]=$G_4$. Unexpectedly, the construction Nλ-R341-F2A-NP868R-$G_4$-K1ERNAP and Nλ-R341-T2A-NP868R-$G_4$-K1ERNAP allow higher expression rate than the association of the constructions Nλ-R341 with NP868R-$G_4$-K1ERNAP (row 4 and 5 vs. 1). These results are really surprising and one skilled in the art could have expected to obtain the same expression rate since the components are the same and are not physically linked in the nature and nor contain any RNA-binding domain.

BIBLIOGRAPHY

Annamalai, P., S. Apte, S. Wilkens and A. L. Rao (2005). "Deletion of highly conserved arginine-rich RNA binding motif in cowpea chlorotic mottle virus capsid protein results in virion structural alterations and RNA packaging constraints." *J Virol* 79(6): 3277-3288.

Ballaun, C., G. K. Farrington, M. Dobrovnik, J. Rusche, J. Hauber and E. Bohnlein (1991). "Functional analysis of human T-cell leukemia virus type I rex-response element: direct RNA binding of Rex protein correlates with in vivo activity." *J Virol* 65(8): 4408-4413.

Banerjee, H., A. Rahn, B. Gawande, S. Guth, J. Valcarcel and R. Singh (2004). "The conserved RNA recognition motif 3 of U2 snRNA auxiliary factor (U2AF 65) is essential in vivo but dispensable for activity in vitro." *RNA* 10(2): 240-253.

Battiste, J. L., H. Mao, N. S. Rao, R. Tan, D. R. Muhandiram, L. E. Kay, A. D. Frankel and J. R. Williamson (1996). "Alpha helix-RNA major groove recognition in an HIV-1 rev peptide-RRE RNA complex." *Science* 273 (5281): 1547-1551.

Bedzyk, W. D., K. M. Weidner, L. K. Denzin, L. S. Johnson, K. D. Hardman, M. W. Pantoliano, E. D. Asel and E. W. Voss, Jr. (1990). "Immunological and structural characterization of a high affinity anti-fluorescein single-chain antibody." *J Biol Chem* 265(30): 18615-18620.

Belanger, F., J. Stepinski, E. Darzynkiewicz and J. Pelletier (2010). "Characterization of hMTr1, a human Cap1 2'-O-ribose methyltransferase." *J Biol Chem* 285(43): 33037-33044.

Benarroch, D., M. Jankowska-Anyszka, J. Stepinski, E. Darzynkiewicz and S. Shuman (2010). "Cap analog substrates reveal three clades of cap guanine-N2 methyltransferases with distinct methyl acceptor specificities." *RNA* 16(1): 211-220.

Benarroch, D., Z. R. Qiu, B. Schwer and S. Shuman (2009). "Characterization of a mimivirus RNA cap guanine-N2 methyltransferase." *RNA* 15(4): 666-674.

Benarroch, D., P. Smith and S. Shuman (2008). "Characterization of a trifunctional mimivirus mRNA capping enzyme and crystal structure of the RNA triphosphatase domain." *Structure* 16(4): 501-512.

Bird, R. E., K. D. Hardman, J. W. Jacobson, S. Johnson, B. M. Kaufman, S. M. Lee, T. Lee, S. H. Pope, G. S. Riordan and M. Whitlow (1988). "Single-chain antigen-binding proteins." *Science* 242(4877): 423-426.

Brisson, M., Y. He, S. Li, J. P. Yang and L. Huang (1999). "A novel T7 RNA polymerase autogene for efficient cytoplasmic expression of target genes." *Gene Ther* 6(2): 263-270.

Bujnicki, J. M. and L. Rychlewski (2001). "Reassignment of specificities of two cap methyltransferase domains in the reovirus lambda 2 protein." *Genome Biol* 2(9): RESEARCH0038.

Busch, R., A. Pashine, K. C. Garcia and E. D. Mellins (2002). "Stabilization of soluble, low-affinity HLA-DM/HLA-DR1 complexes by leucine zippers." *J Immunol Methods* 263(1-2): 111-121.

Busch, R., Z. Reich, D. M. Zaller, V. Sloan and E. D. Mellins (1998). "Secondary structure composition and pH-dependent conformational changes of soluble recombinant HLA-DM." *J Biol Chem* 273(42): 27557-27564.

Cai, A., M. Jankowska-Anyszka, A. Centers, L. Chlebicka, J. Stepinski, R. Stolarski, E. Darzynkiewicz and R. E. Rhoads (1999). "Quantitative assessment of mRNA cap analogues as inhibitors of in vitro translation." *Biochemistry* 38(26): 8538-8547.

Carey, J. and O. C. Uhlenbeck (1983). "Kinetic and thermodynamic characterization of the R17 coat protein-ribonucleic acid interaction." *Biochemistry* 22(11): 2610-2615.

Chang, H. C., Z. Bao, Y. Yao, A. G. Tse, E. C. Goyarts, M. Madsen, E. Kawasaki, P. P. Brauer, J. C. Sacchettini, S. G. Nathenson and et al. (1994). "A general method for facilitating heterodimeric pairing between two proteins: application to expression of alpha and beta T-cell receptor extracellular segments." *Proc Natl Acad Sci USA* 91(24): 11408-11412.

Chen, Y., H. Cai, J. Pan, N. Xiang, P. Tien, T. Ahola and D. Guo (2009). "Functional screen reveals SARS coronavirus nonstructural protein nsp14 as a novel cap N7 methyltransferase." *Proc Natl Acad Sci USA* 106(9): 3484-3489.

Chen, Z. and T. D. Schneider (2005). "Information theory based T7-like promoter models: classification of bacteriophages and differential evolution of promoters and their polymerases." *Nucleic Acids Res* 33(19): 6172-6187.

Cho, E. J., T. Takagi, C. R. Moore and S. Buratowski (1997). "mRNA capping enzyme is recruited to the transcription complex by phosphorylation of the RNA polymerase II carboxy-terminal domain." *Genes Dev* 11(24): 3319-3326.

Choi, Y. G. and A. L. Rao (2003). "Packaging of brome mosaic virus RNA3 is mediated through a bipartite signal." *J Virol* 77(18): 9750-9757.

Cilley, C. D. and J. R. Williamson (1997). "Analysis of bacteriophage N protein and peptide binding to boxB RNA using polyacrylamide gel coelectrophoresis (PACE)." *RNA* 3(1): 57-67.

Cong, P. and S. Shuman (1993). "Covalent catalysis in nucleotidyl transfer. A KTDG motif essential for enzyme-GMP complex formation by mRNA capping enzyme is conserved at the active sites of RNA and DNA ligases." *J Biol Chem* 268(10): 7256-7260.

Cong, P. and S. Shuman (1995). "Mutational analysis of mRNA capping enzyme identifies amino acids involved in GTP binding, enzyme-guanylate formation, and GMP transfer to RNA." *Mol Cell Biol* 15(11): 6222-6231.

Cronan, J. E., Jr. (1990). "Biotination of proteins in vivo. A post-translational modification to label, purify, and study proteins." *J Biol Chem* 265(18): 10327-10333.

Daffis, S., K. J. Szretter, J. Schriewer, J. Li, S. Youn, J. Errett, T. Y. Lin, S. Schneller, R. Zust, H. Dong, V. Thiel, G. C. Sen, V. Fensterl, W. B. Klimstra, T. C. Pierson, R. M. Buller, M. Gale, Jr., P. Y. Shi and M. S. Diamond (2010). "2'-O methylation of the viral mRNA cap evades host restriction by IFIT family members." *Nature* 468(7322): 452-456.

Darzynkiewicz, E., J. Stepinski, I. Ekiel, Y. Jin, D. Haber, T. Sijuwade and S. M. Tahara (1988). "Beta-globin mRNAs capped with m7G, m2.7(2)G or m2.2.7(3)G differ in intrinsic translation efficiency." *Nucleic Acids Res* 16(18): 8953-8962.

Das, A. (1993). "Control of transcription termination by RNA-binding proteins." *Annu Rev Biochem* 62: 893-930.

De la Pena, M., 0. J. Kyrieleis and S. Cusack (2007). "Structural insights into the mechanism and evolution of the vaccinia virus mRNA cap N7 methyl-transferase." *EMBO J* 26(23): 4913-4925.

Decroly, E., F. Ferron, J. Lescar and B. Canard (2011). "Conventional and unconventional mechanisms for capping viral mRNA." *Nat Rev Microbiol* 10(1): 51-65.

Decroly, E., I. Imbert, B. Coutard, M. Bouvet, B. Selisko, K. Alvarez, A. E. Gorbalenya, E. J. Snijder and B. Canard (2008). "Coronavirus nonstructural protein 16 is a cap-0 binding enzyme possessing (nucleoside-2'O)-methyl-transferase activity." *J Virol* 82(16): 8071-8084.

Dias, N. and C. A. Stein (2002). "Antisense oligonucleotides: basic concepts and mechanisms." *Mol Cancer Ther* 1(5): 347-355.

Dickson, K. S., S. R. Thompson, N. K. Gray and M. Wickens (2001). "Poly(A) polymerase and the regulation of cytoplasmic polyadenylation." *J Biol Chem* 276(45): 41810-41816.

Dingwall, C., I. Ernberg, M. J. Gait, S. M. Green, S. Heaphy, J. Karn, A. D. Lowe, M. Singh and M. A. Skinner (1990). "HIV-1 tat protein stimulates transcription by binding to a U-rich bulge in the stem of the TAR RNA structure." *EMBO J* 9(12): 4145-4153.

Dixon, L. K., D. A. Chapman, C. L. Netherton and C. Upton (2013). "African swine fever virus replication and genomics." *Virus Res* 173(1): 3-14.

Dong, H., D. C. Chang, M. H. Hua, S. P. Lim, Y. H. Chionh, F. Hia, Y. H. Lee, P. Kukkaro, S. M. Lok, P. C. Dedon and P. Y. Shi (2012). "2'-O methylation of internal adenosine by flavivirus NS5 methyltransferase." *PLoS Pathog* 8(4): e1002642.

Donnelly, M. L., G. Luke, A. Mehrotra, X. Li, L. E. Hughes, D. Gani and M. D. Ryan (2001). "Analysis of the aphthovirus 2A/2B polyprotein 'cleavage' mechanism indicates not a proteolytic reaction, but a novel translational effect: a putative ribosomal 'skip'." *J Gen Virol* 82(Pt 5): 1013-1025.

Duconge, F. and J. J. Toulme (1999). "In vitro selection identifies key determinants for loop-loop interactions: RNA aptamers selective for the TAR RNA element of HIV-1." *RNA* 5(12): 1605-1614.

Elroy-Stein, O. and B. Moss (1990). "Cytoplasmic expression system based on constitutive synthesis of bacteriophage T7 RNA polymerase in mammalian cells." *Proc Natl Acad Sci USA* 87(17): 6743-6747.

Finn, J., I. MacLachlan and P. Cullis (2005). "Factors limiting autogene-based cytoplasmic expression systems." *FASEB J* 19(6): 608-610.

Fortes, P., Y. Cuevas, F. Guan, P. Liu, S. Pentlicky, S. P. Jung, M. L. Martinez-Chantar, J. Prieto, D. Rowe and S. I. Gunderson (2003). "Inhibiting expression of specific genes in mammalian cells with 5' end-mutated U1 small nuclear RNAs targeted to terminal exons of pre-mRNA." *Proc Natl Acad Sci USA* 100(14): 8264-8269.

Frankel, A. D. and J. A. Young (1998). "HIV-1: fifteen proteins and an RNA." *Annu Rev Biochem* 67:1-25.

Franklin, N. C. (1985). ""N" transcription antitermination proteins of bacteriophages lambda, phi 21 and P22." *J Mol Biol* 181(1): 85-91.

Friedman, D. I. and D. L. Court (1995). "Transcription antitermination: the lambda paradigm updated." *Mol Microbiol* 18(2): 191-200.

Furuichi, Y., A. LaFiandra and A. J. Shatkin (1977). "5'-Terminal structure and mRNA stability." *Nature* 266 (5599): 235-239.

Furuichi, Y. and A. J. Shatkin (2000). "Viral and cellular mRNA capping: past and prospects." *Adv Virus Res* 55: 135-184.

Gallie, D. R. (1991). "The cap and poly(A) tail function synergistically to regulate mRNA translational efficiency." *Genes Dev* 5(11): 2108-2116.

Gao, X. and L. Huang (1993). "Cytoplasmic expression of a reporter gene by co-delivery of T7 RNA polymerase and T7 promoter sequence with cationic liposomes." *Nucleic Acids Res* 21(12): 2867-2872.

Gershon, P. D., B. Y. Ahn, M. Garfield and B. Moss (1991). "Poly(A) polymerase and a dissociable polyadenylation stimulatory factor encoded by vaccinia virus." *Cell* 66(6): 1269-1278.

Ghosh, I., A. D. Hamilton and L. Regan (2000). "Antiparallel Leucine Zipper-Directed Protein Reassembly: Application to the Green Fluorescent Protein." *Journal of the American Chemical Society* 122(23): 5658-5659.

Gingras, A. C., B. Raught and N. Sonenberg (1999). "eIF4 initiation factors: effectors of mRNA recruitment to ribosomes and regulators of translation." *Annu Rev Biochem* 68: 913-963.

Golomb, M. and M. Chamberlin (1974). "Characterization of T7-specific ribonucleic acid polymerase. IV. Resolution of the major in vitro transcripts by gel electrophoresis." *J Biol Chem* 249(9): 2858-2863.

Gong, C. and S. Shuman (2003). "Mapping the active site of vaccinia virus RNA triphosphatase." *Virology* 309(1): 125-134.

Grdzelishvili, V. Z., S. Smallwood, D. Tower, R. L. Hall, D. M. Hunt and S. A. Moyer (2005). "A single amino acid change in the L-polymerase protein of vesicular stomatitis virus completely abolishes viral mRNA cap methylation." *J Virol* 79(12): 7327-7337.

Grdzelishvili, V. Z., S. Smallwood, D. Tower, R. L. Hall, D. M. Hunt and S. A. Moyer (2006). "Identification of a new region in the vesicular stomatitis virus L polymerase protein which is essential for mRNA cap methylation." *Virology* 350(2): 394-405.

Greenblatt, J., J. R. Nodwell and S. W. Mason (1993). "Transcriptional antitermination." *Nature* 364(6436): 401-406.

Gregoire, C., S. Y. Lin, G. Mazza, N. Rebai, I. F. Luescher and B. Malissen (1996). "Covalent assembly of a soluble T cell receptor-peptide-major histocompatibility class I complex." *Proc Natl Acad Sci USA* 93(14): 7184-7189.

Gu, M., K. R. Rajashankar and C. D. Lima (2010). "Structure of the *Saccharomyces cerevisiae* Cet1-Ceg1 mRNA capping apparatus." *Structure* 18(2): 216-227.

Gustaysson, M., J. Lehtio, S. Denman, T. T. Teeri, K. Hult and M. Martinelle (2001). "Stable linker peptides for a cellulose-binding domain-lipase fusion protein expressed in *Pichia pastoris*." *Protein Eng* 14(9): 711-715.

Haline-Vaz, T., T. C. Silva and N. I. Zanchin (2008). "The human interferon-regulated ISG95 protein interacts with RNA polymerase II and shows methyltransferase activity." *Biochem Biophys Res Commun* 372(4): 719-724.

Han, Y. T., C. S. Tsai, Y. C. Chen, M. K. Lin, Y. H. Hsu and M. Meng (2007). "Mutational analysis of a helicase motif-based RNA 5'-triphosphatase/NTPase from bamboo mosaic virus." *Virology* 367(1): 41-50.

Haracska, L., R. E. Johnson, L. Prakash and S. Prakash (2005). "Trf4 and Trf5 proteins of *Saccharomyces cerevisiae* exhibit poly(A) RNA polymerase activity but no DNA polymerase activity." *Mol Cell Biol* 25(22): 10183-10189.

Hausmann, S. and S. Shuman (2005). "*Giardia lamblia* RNA cap guanine-N2 methyltransferase (Tgs2)." *J Biol Chem* 280(37): 32101-32106.

Hausmann, S. and S. Shuman (2005). "Specificity and mechanism of RNA cap guanine-N2 methyltransferase (Tgs1)." *J Biol Chem* 280(6): 4021-4024.

Hausmann, S., S. Zheng, M. Costanzo, R. L. Brost, D. Garcin, C. Boone, S. Shuman and B. Schwer (2008). "Genetic and biochemical analysis of yeast and human cap trimethylguanosine synthase: functional overlap of 2,2,7-trimethylguanosine caps, small nuclear ribonucleoprotein components, pre-mRNA splicing factors, and RNA decay pathways." *J Biol Chem* 283(46): 31706-31718.

Hemmerich, P., S. Bosbach, A. von Mikecz and U. Krawinkel (1997). "Human ribosomal protein L7 binds RNA with an alpha-helical arginine-rich and lysine-rich domain." *Eur J Biochem* 245(3): 549-556.

Hennecke, F., C. Krebber and A. Pluckthun (1998). "Non-repetitive single-chain Fv linkers selected by selectively infective phage (SIP) technology." *Protein Eng* 11(5): 405-410.

Higman, M. A., N. Bourgeois and E. G. Niles (1992). "The vaccinia virus mRNA (guanine-N7-)-methyltransferase requires both subunits of the mRNA capping enzyme for activity." *J Biol Chem* 267(23): 16430-16437.

Higman, M. A., L. A. Christen and E. G. Niles (1994). "The mRNA (guanine-7-)methyltransferase domain of the vaccinia virus mRNA capping enzyme. Expression in *Escherichia coli* and structural and kinetic comparison to the intact capping enzyme." *J Biol Chem* 269(21): 14974-14981.

Higman, M. A. and E. G. Niles (1994). "Location of the S-adenosyl-L-methionine binding region of the vaccinia virus mRNA (guanine-7-)methyltransferase." *J Biol Chem* 269(21): 14982-14987.

Hornung, V., J. Ellegast, S. Kim, K. Brzozka, A. Jung, H. Kato, H. Poeck, S. Akira, K. K. Conzelmann, M. Schlee, S. Endres and G. Hartmann (2006). "5'-Triphosphate RNA is the ligand for RIG-I." *Science* 314(5801): 994-997.

Hu, G., P. D. Gershon, A. E. Hodel and F. A. Quiocho (1999). "mRNA cap recognition: dominant role of enhanced stacking interactions between methylated bases and protein aromatic side chains." *Proc Natl Acad Sci USA* 96(13): 7149-7154.

Hu, W., F. Li, X. Yang, Z. Li, H. Xia, G. Li, Y. Wang and Z. Zhang (2004). "A flexible peptide linker enhances the immunoreactivity of two copies HBsAg preS1 (21-47) fusion protein." *J Biotechnol* 107(1): 83-90.

Huang, Y. and J. A. Steitz (2005). "SRprises along a messenger's journey." *Mol Cell* 17(5): 613-615.

Huang, Y. L., Y. T. Han, Y. T. Chang, Y. H. Hsu and M. Meng (2004). "Critical residues for GTP methylation and formation of the covalent m7GMP-enzyme intermediate in the capping enzyme domain of bamboo mosaic virus." *J Virol* 78(3): 1271-1280.

Huang, Y. L., Y. H. Hsu, Y. T. Han and M. Meng (2005). "mRNA guanylation catalyzed by the S-adenosylmethionine-dependent guanylyltransferase of bamboo mosaic virus." *J Biol Chem* 280(13): 13153-13162.

Huston, J. S., D. Levinson, M. Mudgett-Hunter, M. S. Tai, J. Novotny, M. N. Margolies, R. J. Ridge, R. E. Bruccoleri, E. Haber, R. Crea and et al. (1988). "Protein engineering of antibody binding sites: recovery of specific activity in an anti-digoxin single-chain Fv analogue produced in *Escherichia coli*." *Proc Natl Acad Sci USA* 85(16): 5879-5883.

Jais, P. (2011). Capping-prone RNA polymerase enzymes and their applications. Eukarÿs. France.

Jais, P. H., E. Decroly, E. Jacquet, M. Le Boulch, A. Jais, H. Eaton, P. Ponien, F. Verdier, B. Canard, S. Gonvalves, S. Chiron, M. Le Gall, P. Mayeux and M. Shmulevitz (2018). "C3P3-G1: first generation of an artificial cytoplasmic expression system that recapitulates mRNA capping and polyadenylation." Under review.

Jiang, F., A. Gorin, W. Hu, A. Majumdar, S. Baskerville, W. Xu, A. Ellington and D. J. Patel (1999). "Anchoring an extended HTLV-1 Rex peptide within an RNA major groove containing junctional base triples." *Structure* 7(12): 1461-1472.

Kaneko, S., C. Chu, A. J. Shatkin and J. L. Manley (2007). "Human capping enzyme promotes formation of transcriptional R loops in vitro." *Proc Natl Acad Sci USA* 104(45): 17620-17625.

Karn, J., C. Dingwall, J. T. Finch, S. Heaphy and M. J. Gait (1991). "RNA binding by the tat and rev proteins of HIV-1." *Biochimie* 73(1): 9-16.

Kashiwabara, S., T. Zhuang, K. Yamagata, J. Noguchi, A. Fukamizu and T. Baba (2000). "Identification of a novel isoform of poly(A) polymerase, TPAP, specifically present in the cytoplasm of spermatogenic cells." *Dev Biol* 228(1): 106-115.

Kashiwabara, S. I., S. Tsuruta, K. Okada, Y. Yamaoka and T. Baba (2016). "Adenylation by testis-specific cytoplasmic poly(A) polymerase, PAPOLB/TPAP, is essential for spermatogenesis." *J Reprod Dev* 62(6): 607-614.

Keene, J. D., C. C. Query and R. O. Bentley (1999). Ribonucleoproteins and RNA-binding proteins useful for the specific recognition and binding to RNA, and for control of cellular genetic processing and expression. U.S. Pat. No. 5,866,680A.

Keith, J. M., M. J. Ensinger and B. Mose (1978). "HeLa cell RNA (2'-O-methyladenosine-N6-)-methyltransferase specific for the capped 5'-end of messenger RNA." *J Biol Chem* 253(14): 5033-5039.

Kohler, A. and E. Hurt (2007). "Exporting RNA from the nucleus to the cytoplasm." *Nat Rev Mol Cell Biol* 8(10): 761-773.

Komarnitsky, P., E. J. Cho and S. Buratowski (2000). "Different phosphorylated forms of RNA polymerase II and associated mRNA processing factors during transcription." *Genes Dev* 14(19): 2452-2460.

Kozak, M. (2005). "Regulation of translation via mRNA structure in prokaryotes and eukaryotes." *Gene* 361: 13-37.

Kyriakopoulou, C. B., H. Nordvarg and A. Virtanen (2001). "A novel nuclear human poly(A) polymerase (PAP), PAP gamma." *J Biol Chem* 276(36): 33504-33511.

Lamla, T. and V. A. Erdmann (2004). "The Nano-tag, a streptavidin-binding peptide for the purification and detection of recombinant proteins." *Protein Expr Purif* 33(1): 39-47.

Langberg, S. R. and B. Moss (1981). "Post-transcriptional modifications of mRNA. Purification and characterization of cap I and cap II RNA (nucleoside-2'-)-methyltransferases from HeLa cells." *J Biol Chem* 256(19): 10054-10060.

LeGuyer, K. A., L. S. Behlen and O. C. Uhlenbeck (1996). "Mutagenesis of a stacking contact in the MS2 coat protein-RNA complex." *EMBO J* 15(24): 6847-6853.

Lee, Y. J., Y. Lee and J. H. Chung (2000). "An intronless gene encoding a poly(A) polymerase is specifically expressed in testis." *FEBS Lett* 487(2): 287-292.

Leppek, K. and G. Stoecklin (2014). "An optimized streptavidin-binding RNA aptamer for purification of ribonucleoprotein complexes identifies novel ARE-binding proteins." *Nucleic Acids Res* 42(2): e13.

Li, J., E. C. Fontaine-Rodriguez and S. P. Whelan (2005). "Amino acid residues within conserved domain VI of the vesicular stomatitis virus large polymerase protein essential for mRNA cap methyltransferase activity." *J Virol* 79(21): 13373-13384.

Li, J., A. Rahmeh, M. Morelli and S. P. Whelan (2008). "A conserved motif in region v of the large polymerase proteins of nonsegmented negative-sense RNA viruses that is essential for mRNA capping." *J Virol* 82(2): 775-784.

Li, Y. I., Y. J. Chen, Y. H. Hsu and M. Meng (2001). "Characterization of the AdoMet-dependent guanylyltransferase activity that is associated with the N terminus of bamboo mosaic virus replicase." *J Virol* 75(2): 782-788.

Li, Y. I., T. W. Shih, Y. H. Hsu, Y. T. Han, Y. L. Huang and M. Meng (2001). "The helicase-like domain of plant potexvirus replicase participates in formation of RNA 5' cap structure by exhibiting RNA 5'-triphosphatase activity." *J Virol* 75(24): 12114-12120.

Lian, Y., M. B. De Young, A. Siwkowski, A. Hampel and J. Rappaport (1999). "The sCYMV1 hairpin ribozyme: targeting rules and cleavage of heterologous RNA." *Gene Ther* 6(6): 1114-1119.

Lieschke, G. J., P. K. Rao, M. K. Gately and R. C. Mulligan (1997). "Bioactive murine and human interleukin-12 fusion proteins which retain antitumor activity in vivo." *Nat Biotechnol* 15(1): 35-40.

Lingner, J., J. Kellermann and W. Keller (1991). "Cloning and expression of the essential gene for poly(A) polymerase from *S. cerevisiae*." *Nature* 354(6353): 496-498.

Liu, Z. and G. G. Carmichael (1994). "Nuclear antisense RNA. An efficient new method to inhibit gene expression." *Mol Biotechnol* 2(2): 107-118.

Lo, H. J., H. K. Huang and T. F. Donahue (1998). "RNA polymerase I-promoted HIS4 expression yields uncapped, polyadenylated mRNA that is unstable and inefficiently translated in *Saccharomyces cerevisiae*." *Mol Cell Biol* 18(2): 665-675.

Lugari, A., S. Betzi, E. Decroly, E. Bonnaud, A. Hermant, J. C. Guillemot, C. Debarnot, J. P. Borg, M. Bouvet, B. Canard, X. Morelli and P. Lecine (2010). "Molecular mapping of the RNA Cap 2'-O-methyltransferase activation interface between severe acute respiratory syndrome coronavirus nsp10 and nsp16." *J Biol Chem* 285(43): 33230-33241.

Lumb, K. J. and P. S. Kim (1995). "A buried polar interaction imparts structural uniqueness in a designed heterodimeric coiled coil." *Biochemistry* 34(27): 8642-8648.

Lyakhov, D. L., B. He, X. Zhang, F. W. Studier, J. J. Dunn and W. T. McAllister (1997). "Mutant bacteriophage T7 RNA polymerases with altered termination properties." *J Mol Biol* 269(1): 28-40.

Makarova, 0. V., E. M. Makarov, R. Sousa and M. Dreyfus (1995). "Transcribing of *Escherichia coli* genes with mutant T7 RNA polymerases: stability of lacZ mRNA inversely correlates with polymerase speed." *Proc Natl Acad Sci USA* 92(26): 12250-12254.

Malone, R. W., P. L. Feigner and I. M. Verma (1989). "Cationic liposome-mediated RNA transfection." *Proc Natl Acad Sci USA* 86(16): 6077-6081.

Mao, X., B. Schwer and S. Shuman (1995). "Yeast mRNA cap methyltransferase is a 50-kilodalton protein encoded by an essential gene." *Mol Cell Biol* 15(8): 4167-4174.

Mao, X. and S. Shuman (1994). "Intrinsic RNA (guanine-7) methyltransferase activity of the vaccinia virus capping enzyme D1 subunit is stimulated by the D12 subunit. Identification of amino acid residues in the D1 protein required for subunit association and methyl group transfer." *J Biol Chem* 269(39): 24472-24479.

Mao, X. and S. Shuman (1996). "Vaccinia virus mRNA (guanine-7-)methyltransferase: mutational effects on cap methylation and AdoHcy-dependent photo-cross-linking of the cap to the methyl acceptor site." *Biochemistry* 35(21): 6900-6910.

Martinez-Costas, J., G. Sutton, N. Ramadevi and P. Roy (1998). "Guanylyltransferase and RNA 5'-triphosphatase activities of the purified expressed VP4 protein of bluetongue virus." *J Mol Biol* 280(5): 859-866.

Marzluff, W. F., E. J. Wagner and R. J. Duronio (2008). "Metabolism and regulation of canonical histone mRNAs: life without a poly(A) tail." *Nat Rev Genet* 9(11): 843-854.

Mauer, J., X. Luo, A. Blanjoie, X. Jiao, A. V. Grozhik, D. P. Patil, B. Linder, B. F. Pickering, J. J. Vasseur, Q. Chen, S. S. Gross, O. Elemento, F. Debart, M. Kiledjian and S. R.

Jaffrey (2017). "Reversible methylation of m(6)Am in the 5' cap controls mRNA stability." *Nature* 541(7637): 371-375.

McClain, D. L., H. L. Woods and M. G. Oakley (2001). "Design and characterization of a heterodimeric coiled coil that forms exclusively with an antiparallel relative helix orientation." *J Am Chem Soc* 123(13): 3151-3152.

McCracken, S., N. Fong, E. Rosonina, K. Yankulov, G. Brothers, D. Siderovski, A. Hessel, S. Foster, S. Shuman and D. L. Bentley (1997). "5'-Capping enzymes are targeted to pre-mRNA by binding to the phosphorylated carboxy-terminal domain of RNA polymerase II." *Genes Dev* 11(24): 3306-3318.

Mix, H., A. V. Lobanov and V. N. Gladyshev (2007). "SECIS elements in the coding regions of selenoprotein transcripts are functional in higher eukaryotes." *Nucleic Acids Res* 35(2): 414-423.

Moll, J. R., S. B. Ruvinov, I. Pastan and C. Vinson (2001). "Designed heterodimerizing leucine zippers with a ranger of pIs and stabilities up to 10(-15) M." *Protein Sci* 10(3): 649-655.

Myette, J. R. and E. G. Niles (1996). "Domain structure of the vaccinia virus mRNA capping enzyme. Expression in Escherichia coli of a subdomain possessing the RNA 5'-triphosphatase and guanylyltransferase activities and a kinetic comparison to the full-size enzyme." *J Biol Chem* 271(20): 11936-11944.

Natalizio, B. J., N. D. Robson-Dixon and M. A. Garcia-Blanco (2009). "The Carboxyl-terminal Domain of RNA Polymerase II Is Not Sufficient to Enhance the Efficiency of Pre-mRNA Capping or Splicing in the Context of a Different Polymerase." *J Biol Chem* 284(13): 8692-8702.

Newton, D. L., Y. Xue, K. A. Olson, J. W. Fett and S. M. Rybak (1996). "Angiogenin single-chain immunofusions: influence of peptide linkers and spacers between fusion protein domains." *Biochemistry* 35(2): 545-553.

Niles, E. G. and L. Christen (1993). "Identification of the vaccinia virus mRNA guanyltransferase active site lysine." *J Biol Chem* 268(33): 24986-24989.

O'Shea, E. K., J. D. Klemm, P. S. Kim and T. Alber (1991). "X-ray structure of the GCN4 leucine zipper, a two-stranded, parallel coiled coil." *Science* 254(5031): 539-544.

O'Shea, E. K., K. J. Lumb and P. S. Kim (1993). "Peptide 'Velcro': design of a heterodimeric coiled coil." *Curr Biol* 3(10): 658-667.

Oakley, M. G. and P. S. Kim (1998). "A buried polar interaction can direct the relative orientation of helices in a coiled coil." *Biochemistry* 37(36): 12603-12610.

Ogino, T. and A. K. Banerjee (2007). "Unconventional mechanism of mRNA capping by the RNA-dependent RNA polymerase of vesicular stomatitis virus." *Mol Cell* 25(1): 85-97.

Ogino, T. and A. K. Banerjee (2008). "Formation of guanosine(5')tetraphospho(5')adenosine cap structure by an unconventional mRNA capping enzyme of vesicular stomatitis virus." *J Virol* 82(15): 7729-7734.

Ohlmann, T., M. Rau, S. J. Morley and V. M. Pain (1995). "Proteolytic cleavage of initiation factor eIF-4 gamma in the reticulocyte lysate inhibits translation of capped mRNAs but enhances that of uncapped mRNAs." *Nucleic Acids Res* 23(3): 334-340.

Osumi-Davis, P. A., M. C. de Aguilera, R. W. Woody and A. Y. Woody (1992). "Asp537, Asp812 are essential and Lys631, His811 are catalytically significant in bacteriophage T7 RNA polymerase activity." *J Mol Biol* 226(1): 37-45.

Osumi-Davis, P. A., N. Sreerama, D. B. Volkin, C. R. Middaugh, R. W. Woody and A. Y. Woody (1994). "Bacteriophage T7 RNA polymerase and its active-site mutants. Kinetic, spectroscopic and calorimetric characterization." *J Mol Biol* 237(1): 5-19.

Palancade, B. and O. Bensaude (2003). "Investigating RNA polymerase II carboxyl-terminal domain (CTD) phosphorylation." *Eur J Biochem* 270(19): 3859-3870.

Pantoliano, M. W., R. E. Bird, S. Johnson, E. D. Asel, S. W. Dodd, J. F. Wood and K. D. Hardman (1991). "Conformational stability, folding, and ligand-binding affinity of single-chain Fv immunoglobulin fragments expressed in Escherichia coli." *Biochemistry* 30(42): 10117-10125.

Pashine, A., R. Busch, M. P. Belmares, J. N. Munning, R. C. Doebele, M. Buckingham, G. P. Nolan and E. D. Mellins (2003). "Interaction of HLA-DR with an acidic face of HLA-DM disrupts sequence-dependent interactions with peptides." *Immunity* 19(2): 183-192.

Pavlinkova, G., G. W. Beresford, B. J. Booth, S. K. Batra and D. Colcher (1999). "Pharmacokinetics and biodistribution of engineered single-chain antibody constructs of MAb CC49 in colon carcinoma xenografts." *J Nucl Med* 40(9): 1536-1546.

Peabody, D. S. (1993). "The RNA binding site of bacteriophage MS2 coat protein." *EMBO J* 12(2): 595-600.

Pena, L., R. J. Yanez, Y. Revilla, E. Vinuela and M. L. Salas (1993). "African swine fever virus guanylyltransferase." *Virology* 193(1): 319-328.

Pillutla, R. C., Z. Yue, E. Maldonado and A. J. Shatkin (1998). "Recombinant human mRNA cap methyltransferase binds capping enzyme/RNA polymerase IIo complexes." *J Biol Chem* 273(34): 21443-21446.

Puglisi, J. D., L. Chen, S. Blanchard and A. D. Frankel (1995). "Solution structure of a bovine immunodeficiency virus Tat-TAR peptide-RNA complex." *Science* 270 (5239): 1200-1203.

Puglisi, J. D., R. Tan, B. J. Calnan, A. D. Frankel and J. R. Williamson (1992). "Conformation of the TAR RNA-arginine complex by NMR spectroscopy." *Science* 257 (5066): 76-80.

Raab, D., M. Graf, F. Notka, T. Schodl and R. Wagner (2010). "The GeneOptimizer Algorithm: using a sliding window approach to cope with the vast sequence space in multiparameter DNA sequence optimization." *Syst Synth Biol* 4(3): 215-225.

Raabe, T., K. G. Murthy and J. L. Manley (1994). "Poly(A) polymerase contains multiple functional domains." *Mol Cell Biol* 14(5): 2946-2957.

Rahmeh, A. A., J. Li, P. J. Kranzusch and S. P. Whelan (2009). "Ribose 2'-O methylation of the vesicular stomatitis virus mRNA cap precedes and facilitates subsequent guanine-N-7 methylation by the large polymerase protein." *J Virol* 83(21): 11043-11050.

Ramadevi, N., N. J. Burroughs, P. P. Mertens, I. M. Jones and P. Roy (1998). "Capping and methylation of mRNA by purified recombinant VP4 protein of bluetongue virus." *Proc Natl Acad Sci USA* 95(23): 13537-13542.

Ramadevi, N., J. Rodriguez and P. Roy (1998). "A leucine zipper-like domain is essential for dimerization and encapsidation of bluetongue virus nucleocapsid protein VP4." *J Virol* 72(4): 2983-2990.

Raoult, D., S. Audic, C. Robert, C. Abergel, P. Renesto, H. Ogata, B. La Scola, M. Suzan and J. M. Claverie (2004). "The 1.2-megabase genome sequence of Mimivirus." *Science* 306(5700): 1344-1350.

Reinisch, K. M., M. L. Nibert and S. C. Harrison (2000). "Structure of the reovirus core at 3.6 A resolution." *Nature* 404(6781): 960-967.

Rhoads, R. E. (1999). "Signal transduction pathways that regulate eukaryotic protein synthesis." *J Biol Chem* 274(43): 30337-30340.

Robert, F., M. Gagnon, D. Sans, S. Michnick and L. Brakier-Gingras (2000). "Mapping of the RNA recognition site of *Escherichia coli* ribosomal protein S7." *RNA* 6(11): 1649-1659.

Robinson, C. R. and R. T. Sauer (1998). "Optimizing the stability of single-chain proteins by linker length and composition mutagenesis." *Proc Natl Acad Sci USA* 95(11): 5929-5934.

Romac, J. M., D. H. Graff and J. D. Keene (1994). "The U1 small nuclear ribonucleoprotein (snRNP) 70K protein is transported independently of U1 snRNP particles via a nuclear localization signal in the RNA-binding domain." *Molecular and Cellular Biology* 14(7): 4662-4670.

Rouault, T. A. (2006). "The role of iron regulatory proteins in mammalian iron homeostasis and disease." *Nat Chem Biol* 2(8): 406-414.

Sacher, R. and P. Ahlquist (1989). "Effects of deletions in the N-terminal basic arm of brome mosaic virus coat protein on RNA packaging and systemic infection." *J Virol* 63(11): 4545-4552.

Salehi-Ashtiani, K. and J. W. Szostak (2001). "In vitro evolution suggests multiple origins for the hammerhead ribozyme." *Nature* 414(6859): 82-84.

Schmid, M., B. Kuchler and C. R. Eckmann (2009). "Two conserved regulatory cytoplasmic poly(A) polymerases, GLD-4 and GLD-2, regulate meiotic progression in *C. elegans*." *Genes Dev* 23(7): 824-836.

Schmidt, T. G. and A. Skerra (1993). "The random peptide library-assisted engineering of a C-terminal affinity peptide, useful for the detection and purification of a functional Ig Fv fragment." *Protein Eng* 6(1): 109-122.

Schnierle, B. S., P. D. Gershon and B. Moss (1994). "Mutational analysis of a multifunctional protein, with mRNA 5' cap-specific (nucleoside-2'-O-)-methyltransferase and 3'-adenylyltransferase stimulatory activities, encoded by vaccinia virus." *The Journal of biological chemistry* 269(32): 20700-20706.

Schroeder, S. C., B. Schwer, S. Shuman and D. Bentley (2000). "Dynamic association of capping enzymes with transcribing RNA polymerase II." *Genes Dev* 14(19): 2435-2440.

Schwer, B., S. Hausmann, S. Schneider and S. Shuman (2006). "Poxvirus mRNA cap methyltransferase. Bypass of the requirement for the stimulatory subunit by mutations in the catalytic subunit and evidence for intersubunit allostery." *J Biol Chem* 281(28): 18953-18960.

Schwer, B., N. Saha, X. Mao, H. W. Chen and S. Shuman (2000). "Structure-function analysis of yeast mRNA cap methyltransferase and high-copy suppression of conditional mutants by AdoMet synthase and the ubiquitin conjugating enzyme Cdc34p." *Genetics* 155(4): 1561-1576.

Shao, W. H., X. E. Zhang, H. Liu, Z. P. Zhang and A. E. Cass (2000). "Anchor-chain molecular system for orientation control in enzyme immobilization." *Bioconjug Chem* 11(6): 822-826.

Shi, X., P. Yao, T. Jose and P. Gershon (1996). "Methyltransferase-specific domains within VP-39, a bifunctional protein that participates in the modification of both mRNA ends." *RNA* 2(1): 88-101.

Shibagaki, Y., N. Itoh, H. Yamada, S. Nagata and K. Mizumoto (1992). "mRNA capping enzyme. Isolation and characterization of the gene encoding mRNA guanylytransferase subunit from *Saccharomyces cerevisiae*." *J Biol Chem* 267(14): 9521-9528.

Smith, C. A., V. Calabro and A. D. Frankel (2000). "An RNA-binding chameleon." *Mol Cell* 6(5): 1067-1076.

Tan, R. and A. D. Frankel (1995). "Structural variety of arginine-rich RNA-binding peptides." *Proc Natl Acad Sci USA* 92(12): 5282-5286.

Tang, Y., N. Jiang, C. Parakh and D. Hilvert (1996). "Selection of linkers for a catalytic single-chain antibody using phage display technology." *J Biol Chem* 271(26): 15682-15686.

Theil, E. C. (1994). "Iron regulatory elements (IREs): a family of mRNA non-coding sequences." *Biochem J* 304 (Pt 1): 1-11.

Tiggemann, M., S. Jeske, M. Larsen and F. Meinhardt (2001). "*Kluyveromyces lactis* cytoplasmic plasmid pGKL2: heterologous expression of Orf3p and proof of guanylyltransferase and mRNA-triphosphatase activities." *Yeast* 18(9): 815-825.

Ting, A. Y., K. H. Kain, R. L. Klemke and R. Y. Tsien (2001). "Genetically encoded fluorescent reporters of protein tyrosine kinase activities in living cells." *Proc Natl Acad Sci USA* 98(26): 15003-15008.

Tommasino, M., S. Ricci and C. L. Galeotti (1988). "Genome organization of the killer plasmid pGK12 from *Kluyveromyces lactis*." *Nucleic Acids Res* 16(13): 5863-5878.

Trippe, R., B. Sandrock and B. J. Benecke (1998). "A highly specific terminal uridylyl transferase modifies the 3'-end of U6 small nuclear RNA." *Nucleic Acids Res* 26(13): 3119-3126.

Tsukamoto, T., Y. Shibagaki, S. Imajoh-Ohmi, T. Murakoshi, M. Suzuki, A. Nakamura, H. Gotoh and K. Mizumoto (1997). "Isolation and characterization of the yeast mRNA capping enzyme beta subunit gene encoding RNA 5'-triphosphatase, which is essential for cell viability." *Biochem Biophys Res Commun* 239(1): 116-122.

Tsukamoto, T., Y. Shibagaki, Y. Niikura and K. Mizumoto (1998). "Cloning and characterization of three human cDNAs encoding mRNA (guanine-7-)-methyltransferase, an mRNA cap methylase." *Biochem Biophys Res Commun* 251(1): 27-34.

Turner, B., S. E. Melcher, T. J. Wilson, D. G. Norman and D. M. Lilley (2005). "Induced fit of RNA on binding the L7Ae protein to the kink-turn motif." *RNA* 11(8): 1192-1200.

Turner, D. J., M. A. Ritter and A. J. George (1997). "Importance of the linker in expression of single-chain Fv antibody fragments: optimisation of peptide sequence using phage display technology." *J Immunol Methods* 205(1): 43-54.

Valegard, K., J. B. Murray, P. G. Stockley, N. J. Stonehouse and L. Liljas (1994). "Crystal structure of an RNA bacteriophage coat protein-operator complex." *Nature* 371(6498): 623-626.

Valegard, K., J. B. Murray, N. J. Stonehouse, S. van den Worm, P. G. Stockley and L. Liljas (1997). "The three-dimensional structures of two complexes between recombinant MS2 capsids and RNA operator fragments reveal sequence-specific protein-RNA interactions." *J Mol Biol* 270(5): 724-738.

Vethantham, V., N. Rao and J. L. Manley (2008). "Sumoylation regulates multiple aspects of mammalian poly(A) polymerase function." *Genes Dev* 22(4): 499-511.

Wang, L., C. R. Eckmann, L. C. Kadyk, M. Wickens and J. Kimble (2002). "A regulatory cytoplasmic poly(A) polymerase in Caenorhabditis elegans." Nature 419(6904): 312-316.

Weeks, K. M., C. Ampe, S. C. Schultz, T. A. Steitz and D. M. Crothers (1990). "Fragments of the HIV-1 Tat protein specifically bind TAR RNA." Science 249(4974): 1281-1285.

Wells, J. A. and D. B. Powers (1986). "In vivo formation and stability of engineered disulfide bonds in subtilisin." J Biol Chem 261(14): 6564-6570.

Whitlow, M., B. A. Bell, S. L. Feng, D. Filpula, K. D. Hardman, S. L. Hubert, M. L. Rollence, J. F. Wood, M. E. Schott, D. E. Milenic and et al. (1993). "An improved linker for single-chain Fv with reduced aggregation and enhanced proteolytic stability." Protein Eng 6(8): 989-995.

Wickham, T. J., M. E. Carrion and I. Kovesdi (1995). "Targeting of adenovirus penton base to new receptors through replacement of its RGD motif with other receptor-specific peptide motifs." Gene Ther 2(10): 750-756.

Wu, S. C., J. C. Yeung, P. M. Hwang and S. L. Wong (2002). "Design, production, and characterization of an engineered biotin ligase (BirA) and its application for affinity purification of staphylokinase produced from Bacillus subtilis via secretion." Protein Expr Purif 24(3): 357-365.

Wu, X. and L. A. Guarino (2003). "Autographa californica nucleopolyhedrovirus orf69 encodes an RNA cap (nucleoside-2'-O)-methyltransferase." J Virol 77(6): 3430-3440.

Xiao, F., W. D. Moll, S. Guo and P. Guo (2005). "Binding of pRNA to the N-terminal 14 amino acids of connector protein of bacteriophage phi29." Nucleic Acids Res 33(8): 2640-2649.

Yamada-Okabe, T., R. Doi, O. Shimmi, M. Arisawa and H. Yamada-Okabe (1998). "Isolation and characterization of a human cDNA for mRNA 5'-capping enzyme." Nucleic Acids Res 26(7): 1700-1706.

Ye, W., J. Yang, Q. Yu, W. Wang, J. Nancy, R. Luo and H. F. Chen (2013). "Kink turn sRNA folding upon L7Ae binding using molecular dynamics simulations." Phys Chem Chem Phys 15(42): 18510-18522.

Yi, G., R. C. Vaughan, I. Yarbrough, S. Dharmaiah and C. C. Kao (2009). "RNA binding by the brome mosaic virus capsid protein and the regulation of viral RNA accumulation." J Mol Biol 391(2): 314-326.

Yip, M. T., W. S. Dynan, P. L. Green, A. C. Black, S. J. Arrigo, A. Torbati, S. Heaphy, C. Ruland, J. D. Rosenblatt and I. S. Chen (1991). "Human T-cell leukemia virus (HTLV) type II Rex protein binds specifically to RNA sequences of the HTLV long terminal repeat but poorly to the human immunodeficiency virus type 1 Rev-responsive element." J Virol 65(5): 2261-2272.

Yu, L., A. Martins, L. Deng and S. Shuman (1997). "Structure-function analysis of the triphosphatase component of vaccinia virus mRNA capping enzyme." J Virol 71(12): 9837-9843.

Yu, L. and S. Shuman (1996). "Mutational analysis of the RNA triphosphatase component of vaccinia virus mRNA capping enzyme." J Virol 70(9): 6162-6168.

Yue, Z., E. Maldonado, R. Pillutla, H. Cho, D. Reinberg and A. J. Shatkin (1997). "Mammalian capping enzyme complements mutant Saccharomyces cerevisiae lacking mRNA guanylyltransferase and selectively binds the elongating form of RNA polymerase II." Proc Natl Acad Sci USA 94(24): 12898-12903.

Zamore, P. D., J. G. Patton and M. R. Green (1992). "Cloning and domain structure of the mammalian splicing factor U2AF." Nature 355(6361): 609-614.

Zhang, X. and F. W. Studier (1997). "Mechanism of inhibition of bacteriophage T7 RNA polymerase by T7 lysozyme." J Mol Biol 269(1): 10-27.

Zhelkovsky, A., S. Helmling and C. Moore (1998). "Processivity of the Saccharomyces cerevisiae poly(A) polymerase requires interactions at the carboxyl-terminal RNA binding domain." Mol Cell Biol 18(10): 5942-5951.

Zhu, Y., C. Qi, W. Q. Cao, A. V. Yeldandi, M. S. Rao and J. K. Reddy (2001). "Cloning and characterization of PIMT, a protein with a methyltransferase domain, which interacts with and enhances nuclear receptor coactivator PRIP function." Proc Natl Acad Sci USA 98(18): 10380-10385.

The invention claimed is:

1. A non-natural hetero-oligomeric enzyme comprising components i) through iv) linked together covalently or non-covalently:
   i) at least one catalytic domain of a RNA triphosphatase;
   ii) at least one catalytic domain of a guanylyltransferase;
   iii) at least one catalytic domain of a N7-guanine methyltransferase; and
   iv) at least one RNA-binding domain of a protein-RNA tethering system; and
      wherein said RNA-binding domain is a bacteriophage RNA-binding domain of a bacteriophage protein-RNA tethering system, and wherein said non-natural hetero-oligomeric enzyme adds a cap to RNA produced by a RNA polymerase.

2. The non-natural hetero-oligomeric enzyme according to claim 1, wherein the RNA-binding domain is a bacteriophage RNA-binding domain of a bacteriophage protein selected from the group consisting of the MS2 coat protein, the R17 coat protein and lambdoid N antitermination proteins.

3. A method for the in vitro or ex vivo production of an RNA molecule with a 5'-terminal cap, and optionally said method comprising at least one chemical modification, wherein said method comprises in vitro or ex vivo use of:
   A) expressing, in a host cell:
      an isolated nucleic acid molecule encoding a non-natural hetero-oligomeric enzyme according to claim 1; and/or
   B) expressing in one or more host cells a group of isolated nucleic acid molecules encoding a non-natural hetero-oligomeric enzyme according to claim 1.

4. A kit for the production of an RNA molecule with a 5'-terminal cap, comprising:
   i) at least one non-natural hetero-oligomeric enzyme according to claim 1; and/or
   ii) an isolated nucleic acid molecule encoding a non-natural hetero-oligomeric enzyme according to claim 1; and/or
   iii) a group of isolated nucleic acid molecules encoding a non-natural hetero-oligomeric enzyme according to claim 1.

5. A pharmaceutical composition comprising:
at least one non-natural hetero-oligomeric enzyme according to claim 1.

6. A pharmaceutical composition comprising an isolated nucleic acid molecule encoding a non-natural hetero-oligomeric enzyme according to claim 1.

* * * * *

SEQUENCE LISTING

```
<160> NUMBER OF SEQ ID NOS: 64

<210> SEQ ID NO 1
<211> LENGTH: 66
<212> TYPE: DNA
<213> ORGANISM: Bacteriophage lambda

<400> SEQUENCE: 1
atggatgctc agaccagacg cagagaacgg cgggcagaga agcaggcaca gtggaaggcc      60
gctaat                                                                66

<210> SEQ ID NO 2
<211> LENGTH: 22
<212> TYPE: PRT
<213> ORGANISM: Bacteriophage lambda

<400> SEQUENCE: 2

Met Asp Ala Gln Thr Arg Arg Arg Glu Arg Arg Ala Glu Lys Gln Ala
 1               5                  10                  15

Gln Trp Lys Ala Ala Asn
            20
```

<210> SEQ ID NO 3
<211> LENGTH: 870
<212> TYPE: DNA
<213> ORGANISM: Vaccinia virus

<400> SEQUENCE: 3

```
atggaattcg acgagatcgt gaagaacatc cgcgagggca cccacgtgct gctgcccttc      60
tacgagacac tgcccgagct gaacctgtcc ctgggcaagt ccccccctgcc ctccctggaa     120 tacggcgcca actacttcct gcagatctcc agagtgaacg acctgaaccg gatgcccacc     180
gacatgctga agctgttcac ccacgacatc atgctgcccg agtccgacct ggacaaggtg     240
tacgagattc tgaagatcaa ctccgtgaag tactacggcc ggtccacaaa ggctgacgcc     300
gtggtggccg acctgtctgc ccggaacaag ctgttcaaga gagagcggga cgccatcaag     360
tccaacaacc acctgaccga gaacaacctg tacatctccg actacaagat gctgaccttc     420
gacgtgttcc ggcccctgtt cgacttcgtg aacgagaagt actgcatcat caagctgccc     480
accctgttcg gcagaggcgt gatcgacacc atgcggatct actgctccct gttcaagaac     540
gtgcggctgc tgaagtgcgt gtccgactcc tggctgaagg actccgccat catggtggcc     600
tccgacgtgt gcaagaagaa cctggacctg ttcatgtccc acgtgaagtc cgtgaccaag     660
tcatccagct ggaaggacgt gaactccgtg cagttctcca tcctgaacaa ccccgtggac     720
accgagttca tcaacaagtt tctggaattt tccaaccggg tgtacgaggc cctgtactac     780
gtgcactccc tgctgtactc ctccatgacc tccgactcca agtccatcga gaacaaacat     840
cagcgacggc tggtcaagct gctgctgtaa                                      870
```

<210> SEQ ID NO 4
<211> LENGTH: 287
<212> TYPE: PRT
<213> ORGANISM: Vaccinia virus

<400> SEQUENCE: 4

```
Met Asp Glu Ile Val Lys Asn Ile Arg Glu Gly Thr His Val Leu Leu
1               5                   10                  15

Pro Phe Tyr Glu Thr Leu Pro Glu Leu Asn Leu Ser Leu Gly Lys Ser
            20                  25                  30

Pro Leu Pro Ser Leu Glu Tyr Gly Ala Asn Tyr Phe Leu Gln Ile Ser
        35                  40                  45

Arg Val Asn Asp Leu Asn Arg Met Pro Thr Asp Met Leu Lys Leu Phe
    50                  55                  60

Thr His Asp Ile Met Leu Pro Glu Ser Asp Leu Asp Lys Val Tyr Glu
65                  70                  75                  80

Ile Leu Lys Ile Asn Ser Val Lys Tyr Tyr Gly Arg Ser Thr Lys Ala
                85                  90                  95

Asp Ala Val Val Ala Asp Leu Ser Ala Arg Asn Lys Leu Phe Lys Arg
            100                 105                 110

Glu Arg Asp Ala Ile Lys Ser Asn Asn His Leu Thr Glu Asn Asn Leu
        115                 120                 125

Tyr Ile Ser Asp Tyr Lys Met Leu Thr Phe Asp Val Phe Arg Pro Leu
    130                 135                 140

Phe Asp Phe Val Asn Glu Lys Tyr Cys Ile Ile Lys Leu Pro Thr Leu
145                 150                 155                 160

Phe Gly Arg Gly Val Ile Asp Thr Met Arg Ile Tyr Cys Ser Leu Phe
                165                 170                 175
```

```
Lys Asn Val Arg Leu Leu Lys Cys Val Ser Asp Ser Trp Leu Lys Asp
                180                 185                 190

Ser Ala Ile Met Val Ala Ser Asp Val Cys Lys Lys Asn Leu Asp Leu
            195                 200                 205

Phe Met Ser His Val Lys Ser Val Thr Lys Ser Ser Trp Lys Asp
        210                 215                 220

Val Asn Ser Val Gln Phe Ser Ile Leu Asn Asn Pro Val Asp Thr Glu
225                 230                 235                 240

Phe Ile Asn Lys Phe Leu Glu Phe Ser Asn Arg Val Tyr Glu Ala Leu
                245                 250                 255

Tyr Tyr Val His Ser Leu Leu Tyr Ser Ser Met Thr Ser Asp Ser Lys
            260                 265                 270

Ser Ile Glu Asn Lys His Gln Arg Arg Leu Val Lys Leu Leu Leu
                275                 280                 285

<210> SEQ ID NO 5
<211> LENGTH: 2541
<212> TYPE: DNA
<213> ORGANISM: Vaccinia virus

<400> SEQUENCE: 5
atggaattcg acgccaacgt ggtgtcctcc tccacaatcg ccacctacat cgacgccctg      60
gccaagaacg cctccgagct ggaacagcgg tccaccgcct acgagatcaa caatgagctg     120
gaactggtgt tcatcaagcc ccccctgatc accctgacca acgtggtcaa catcagcacc     180
atccaggaat ccttcatccg gttcaccgtg accaacaaag aaggcgtgaa gatccggacc     240
aagatccccc tgtccaaggt gcacggcctg gacgtgaaga acgtgcagct ggtggacgcc     300
atcgacaaca tcgtgtggga agaagtcc ctggtcaccg agaacggct gcacaaagag       360 tgcctgctgc ggctgtccac cgaggaacgg cacatctttc tggactacaa gaagtacggc     420
tcctccatca gactggaact ggtcaacctg atccaggcca agaccaagaa cttcaccatc     480
gacttcaagc tgaagtactt cctgggctct ggcgcccagt ccaagtcctc tctgctgcac     540
gccatcaacc cccccaagtc ccggcccaac acctccctgg aaatcgagtt cacccctcgg     600
gacaacgaga cagtgcccta cgacgagctg atcaagagc tgaccaccct gtccagacac      660
atcttcatgg cctcccccga aacgtgatc ctgtcccccc ccatcaacgc ccccatcaag      720
accttcatgc tgcccaagca ggacatcgtg ggcctggacc tggaaaacct gtacgccgtg     780
accaagaccg acggcatccc catcaccatc agagtgacct ccaacggcct gtactgctac     840
ttcacccacc tgggctacat catcagatac cccgtgaagc ggatcatcga ctccgaggtg     900
gtggtgttcg cgaggccgt gaaggacaag aactggaccg tgtacctgat caagctgatc      960
gagcccgtga acgccatcaa tgaccggctg gaagagtcca aatacgtgga atccaagctg    1020
gtggatatct gcgaccggat cgtgttcaag tctaagaagt acgagggacc cttcactaca    1080
acttcagagg tggtcgacat gctgtccacc tacctgccta gcagcccga gggcgtcatc     1140 ctgttctact ccaagggacc caagtccaac atcgatttca gatcaagaa agagaacacc     1200 atcgaccaga ccgccaatgt ggtgttccgg tacatgtcct ccgagcccat catcttcggc    1260
gagtcctcca tcttcgtcga gtacaagaag ttctccaacg acaagggctt ccccaaagag    1320
tacggcagcg gcaagatcgt gctgtacaac ggcgtgaact acctgaacaa catctactgc    1380
ctggagtaca tcaacaccca acgcgaagtg ggcatcaagt ccgtggtggt gcccatcaag    1440
tttatcgccg agttcctggt caacggcgag atcctgaagc cccggatcga caagaccatg    1500
```

```
aagtacatca attccgagga ctactacggc aaccagcaca acatcatcgt ggaacacctg      1560
agggaccagt ccatcaagat cggcgacatc ttcaacgagg acaagctgtc cgacgtgggc      1620
caccagtacg ccaacaacga caagttccgg ctgaaccccg aggtgtccta cttcaccaac      1680
aagagaaccc gaggcccact gggcatcctg tccaactacg tgaaaaccct gctgatctcc      1740
atgtactgct ccaagacctt cctggacgac tccaacaagc ggaaggtgct ggccatcgat      1800
ttcggcaacg cgccgatct ggaaaagtac ttctatggcg agatcgccct gctggtggct       1860
accgaccctg acgccgacgc tatcgccaga ggcaacgagc ggtacaacaa gctgaactcc      1920
ggcatcaaga ccaagtacta caagttcgac tacatccagg aaaccatccg ctccgacacc      1980
ttcgtgtcct ccgtgcgcga ggtgttctat ttcggcaagt tcaatatcat cgactggcag      2040
ttcgccatcc actacagctt ccaccccgg cactacgcca ccgtgatgaa caacctgtcc       2100
gagctgaccg cctccggcgg caaggtgctg atcaccacca tggacggcga caagctgagc      2160
aagctgaccg acaagaaaac cttcatcatc cacaagaacc tgccctccag cgagaactac      2220
atgtccgtgg aaaagatcgc cgacgacaga atcgtggtgt acaatccctc caccatgtcc      2280
acccccatga ccgagtacat catcaagaag aacgacatcg tccgggtgtt caacgagtac      2340
ggcttcgtgc tggtggacaa cgtggacttc gccaccatca tcgagcggtc caaaaagttc      2400
atcaatggag ccagcaccat ggaagatcgg ccctctaccc ggaacttctt cgagctgaac      2460
agaggcgcca tcaagtgcga gggcctggat gtggaagatc tgctgagcta ctacgtggtg      2520
tacgtgttct ccaagagata a                                                2541

<210> SEQ ID NO 6
<211> LENGTH: 844
<212> TYPE: PRT
<213> ORGANISM: Vaccinia virus

<400> SEQUENCE: 6

Met Asp Ala Asn Val Val Ser Ser Ser Thr Ile Ala Thr Tyr Ile Asp
1               5                   10                  15

Ala Leu Ala Lys Asn Ala Ser Glu Leu Glu Gln Arg Ser Thr Ala Tyr
                20                  25                  30

Glu Ile Asn Asn Glu Leu Glu Leu Val Phe Ile Lys Pro Pro Leu Ile
            35                  40                  45

Thr Leu Thr Asn Val Val Asn Ile Ser Thr Ile Gln Glu Ser Phe Ile
        50                  55                  60

Arg Phe Thr Val Thr Asn Lys Glu Gly Val Lys Ile Arg Thr Lys Ile
65                  70                  75                  80

Pro Leu Ser Lys Val His Gly Leu Asp Val Lys Asn Val Gln Leu Val
                85                  90                  95

Asp Ala Ile Asp Asn Ile Val Trp Glu Lys Lys Ser Leu Val Thr Glu
            100                 105                 110

Asn Arg Leu His Lys Glu Cys Leu Leu Arg Leu Ser Thr Glu Glu Arg
        115                 120                 125

His Ile Phe Leu Asp Tyr Lys Lys Tyr Gly Ser Ser Ile Arg Leu Glu
    130                 135                 140

Leu Val Asn Leu Ile Gln Ala Lys Thr Lys Asn Phe Thr Ile Asp Phe
145                 150                 155                 160

Lys Leu Lys Tyr Phe Leu Gly Ser Gly Ala Gln Ser Lys Ser Ser Leu
                165                 170                 175

Leu His Ala Ile Asn His Pro Lys Ser Arg Pro Asn Thr Ser Leu Glu
```

-continued

```
                180                 185                 190
Ile Glu Phe Thr Pro Arg Asp Asn Glu Thr Val Pro Tyr Asp Glu Leu
            195                 200                 205

Ile Lys Glu Leu Thr Thr Leu Ser Arg His Ile Phe Met Ala Ser Pro
        210                 215                 220

Glu Asn Val Ile Leu Ser Pro Pro Ile Asn Ala Pro Ile Lys Thr Phe
225                 230                 235                 240

Met Leu Pro Lys Gln Asp Ile Val Gly Leu Asp Leu Glu Asn Leu Tyr
                245                 250                 255

Ala Val Thr Lys Thr Asp Gly Ile Pro Ile Thr Ile Arg Val Thr Ser
            260                 265                 270

Asn Gly Leu Tyr Cys Tyr Phe Thr His Leu Gly Tyr Ile Ile Arg Tyr
        275                 280                 285

Pro Val Lys Arg Ile Ile Asp Ser Glu Val Val Phe Gly Glu Ala
                290                 295                 300

Val Lys Asp Lys Asn Trp Thr Val Tyr Leu Ile Lys Leu Ile Glu Pro
305                 310                 315                 320

Val Asn Ala Ile Asn Asp Arg Leu Glu Glu Ser Lys Tyr Val Glu Ser
                325                 330                 335

Lys Leu Val Asp Ile Cys Asp Arg Ile Val Phe Lys Ser Lys Lys Tyr
            340                 345                 350

Glu Gly Pro Phe Thr Thr Thr Ser Glu Val Val Asp Met Leu Ser Thr
        355                 360                 365

Tyr Leu Pro Lys Gln Pro Glu Gly Val Ile Leu Phe Tyr Ser Lys Gly
        370                 375                 380

Pro Lys Ser Asn Ile Asp Phe Lys Ile Lys Lys Glu Asn Thr Ile Asp
385                 390                 395                 400

Gln Thr Ala Asn Val Val Phe Arg Tyr Met Ser Ser Glu Pro Ile Ile
                405                 410                 415

Phe Gly Glu Ser Ser Ile Phe Val Glu Tyr Lys Lys Phe Ser Asn Asp
                420                 425                 430

Lys Gly Phe Pro Lys Glu Tyr Gly Ser Gly Lys Ile Val Leu Tyr Asn
            435                 440                 445

Gly Val Asn Tyr Leu Asn Asn Ile Tyr Cys Leu Glu Tyr Ile Asn Thr
        450                 455                 460

His Asn Glu Val Gly Ile Lys Ser Val Val Pro Ile Lys Phe Ile
465                 470                 475                 480

Ala Glu Phe Leu Val Asn Gly Glu Ile Leu Lys Pro Arg Ile Asp Lys
                485                 490                 495

Thr Met Lys Tyr Ile Asn Ser Glu Asp Tyr Tyr Gly Asn Gln His Asn
            500                 505                 510

Ile Ile Val Glu His Leu Arg Asp Gln Ser Ile Lys Ile Gly Asp Ile
        515                 520                 525

Phe Asn Glu Asp Lys Leu Ser Asp Val Gly His Gln Tyr Ala Asn Asn
        530                 535                 540

Asp Lys Phe Arg Leu Asn Pro Glu Val Ser Tyr Phe Thr Asn Lys Arg
545                 550                 555                 560

Thr Arg Gly Pro Leu Gly Ile Leu Ser Asn Tyr Val Lys Thr Leu Leu
                565                 570                 575

Ile Ser Met Tyr Cys Ser Lys Thr Phe Leu Asp Asp Ser Asn Lys Arg
            580                 585                 590

Lys Val Leu Ala Ile Asp Phe Gly Asn Gly Ala Asp Leu Glu Lys Tyr
        595                 600                 605
```

Phe Tyr Gly Glu Ile Ala Leu Leu Val Ala Thr Asp Pro Asp Ala Asp
            610                 615                 620
Ala Ile Ala Arg Gly Asn Glu Arg Tyr Asn Lys Leu Asn Ser Gly Ile
625                 630                 635                 640
Lys Thr Lys Tyr Tyr Lys Phe Asp Tyr Ile Gln Glu Thr Ile Arg Ser
                645                 650                 655
Asp Thr Phe Val Ser Ser Val Arg Glu Val Phe Tyr Phe Gly Lys Phe
            660                 665                 670
Asn Ile Ile Asp Trp Gln Phe Ala Ile His Tyr Ser Phe His Pro Arg
        675                 680                 685
His Tyr Ala Thr Val Met Asn Asn Leu Ser Glu Leu Thr Ala Ser Gly
            690                 695                 700
Gly Lys Val Leu Ile Thr Thr Met Asp Gly Asp Lys Leu Ser Lys Leu
705                 710                 715                 720
Thr Asp Lys Lys Thr Phe Ile Ile His Lys Asn Leu Pro Ser Ser Glu
                725                 730                 735
Asn Tyr Met Ser Val Glu Lys Ile Ala Asp Asp Arg Ile Val Val Tyr
            740                 745                 750
Asn Pro Ser Thr Met Ser Thr Pro Met Thr Glu Tyr Ile Ile Lys Lys
        755                 760                 765
Asn Asp Ile Val Arg Val Phe Asn Glu Tyr Gly Phe Val Leu Val Asp
            770                 775                 780
Asn Val Asp Phe Ala Thr Ile Ile Glu Arg Ser Lys Lys Phe Ile Asn
785                 790                 795                 800
Gly Ala Ser Thr Met Glu Asp Arg Pro Ser Thr Arg Asn Phe Phe Glu
                805                 810                 815
Leu Asn Arg Gly Ala Ile Lys Cys Glu Gly Leu Asp Val Glu Asp Leu
            820                 825                 830
Leu Ser Tyr Tyr Val Val Tyr Val Phe Ser Lys Arg
        835                 840

<210> SEQ ID NO 7
<211> LENGTH: 15
<212> TYPE: DNA
<213> ORGANISM: Bacteriophage lambda

<400> SEQUENCE: 7
gccctgaaaa agggc                                                      15

<210> SEQ ID NO 8
<211> LENGTH: 2613
<212> TYPE: DNA
<213> ORGANISM: African swine fever virus

<400> SEQUENCE: 8
atggaattcg ccagcctgga caacctggtg gccagatacc agcggtgctt caacgaccag      60
agcctgaaga acagcaccat cgagctggaa atccggttcc agcagatcaa cttcctgctg     120
ttcaagaccg tgtacgaggc cctggtcgcc aggaaatccc cagcaccat cagccacagc      180 atccggtgca tcaagaaggt gcaccacgag aaccactgcc gggagaagat cctgcccagc     240
gagaacctgt acttcaagaa cagcccctg atgttcttca gttcagcga gcccgccagc      300 ctgggctgta aagtgtccct ggccatcgag cagcccatcc ggaagttcat cctggacagc     360
agcgtgctgg tccggctgaa gaaccggacc accttccggg tgtccgagct gtggaagatc     420
gagctgacca tcgtgaagca gctgatgggc agcgaggtgt cagccaagct ggccgccttc     480

```
aagaccctgc tgttcgacac ccccgagcag cagaccacca agaacatgat gaccctgatc      540
aaccccgacg acgagtacct gtacgagatc gagatcgagt acaccggcaa gcctgagagc      600
ctgacagccg ccgacgtgat caagatcaag aacaccgtgc tgacactgat cagccccaac      660
cacctgatgc tgaccgccta ccaccaggcc atcgagttta cgccagcca catcctgagc       720 agcgagatcc tgctggcccg gatcaagagc ggcaagtggg gcctgaagag actgctgccc      780
caggtcaagt ccatgaccaa ggccgactac atgaagttct accccccgt gggctactac       840 gtgaccgaca aggccgacgg catccggggc attgccgtga tccaggacac ccagatctac      900
gtggtggccg accagctgta cagcctgggc accaccggca tcgagcccct gaagcccacc      960
atcctggacg gcgagttcat gcccgagaag aaagagttct acggctttga cgtgatcatg     1020
tacgagggca acctgctgac ccagcagggc ttcgagacac ggatcgagag cctgagcaag     1080
ggcatcaagg tgctgcaggc cttcaacatc aaggccgaga tgaagccctt catcagcctg     1140
acctccgccg accccaacgt gctgctgaag aatttcgaga gcatcttcaa gaagaaaacc     1200
cggccctaca gcatcgacgg catcatcctg gtggagcccg gcaacagcta cctgaacacc     1260
aacaccttca gtggaagcc cacctgggac aacaccctgg actttctggt ccggaagtgc      1320
cccgagtccc tgaacgtgcc cgagtacgcc cccaagaagg gcttcagcct gcatctgctg     1380
ttcgtgggca tcagcggcga gctgtttaag aagctggccc tgaactggtg ccccggctac     1440
accaagctgt tccccgtgac ccagcggaac cagaactact tccccgtgca gttccagccc     1500
agcgacttcc ccctggcctt cctgtactac caccccgaca ccagcagctt cagcaacatc     1560
gatggcaagg tgctggaaat cggtgcctg aagcgggaga tcaactacgt gcgctgggag      1620
atcgtgaaga tccgggagga ccggcagcag gatctgaaaa ccggcggcta cttcggcaac     1680
gacttcaaga ccgccgagct gacctggctg aactacatgg ccccttcag cttcgaggaa      1740 ctggccaagg gacccagcgg catgtacttc gctggcgcca agaccggcat ctacagagcc     1800
cagaccgccc tgatcagctt catcaagcag gaaatcatcc agaagatcag ccaccagagc     1860
tgggtgatcg acctgggcat cggcaagggc caggacctgg gcagatacct ggacgccggc     1920
gtgagacacc tggtcggcat cgataaggac cagacagccc tggccgagct ggtgtaccgg     1980
aagttctccc acgccaccac cagacagcac aagcacgcca ccaacatcta cgtgctgcac     2040
caggatctgg ccgagcctgc caaagaaatc agcgagaaag tgcaccagat ctatggcttc     2100
cccaaagagg gcgccagcag catcgtgtcc aacctgttca tccactacct gatgaagaac     2160
acccagcagg tcgagaacct ggctgtgctg tgccacaagc tgctgcagcc tggcggcatg     2220
gtctggttca ccaccatgct gggcgaacag gtgctggaac tgctgcacga aaccggatc     2280 gaactgaacg aagtgtggga ggcccggag aacgaggtgg tcaagttcgc catcaagcgg      2340
ctgttcaaag aggacatcct gcaggaaacc ggccaggaaa tcggcgtcct gctgcccttc     2400
agcaacggcg acttctacaa tgagtacctg gtcaacaccg cctttctgat caagattttc     2460
aagcaccatg gctttagcct cgtgcagaag cagagcttca aggactggat ccccgagttc     2520
cagaacttca gcaagagcct gtacaagatc ctgaccgagg ccgacaagac ctggaccagc     2580
ctgttcggct tcatctgcct gcggaagaac taa                                 2613
```

<210> SEQ ID NO 9
<211> LENGTH: 868
<212> TYPE: PRT
<213> ORGANISM: African swine fever virus

<400> SEQUENCE: 9

Met Ala Ser Leu Asp Asn Leu Val Ala Arg Tyr Gln Arg Cys Phe Asn
1               5                   10                  15

Asp Gln Ser Leu Lys Asn Ser Thr Ile Glu Leu Glu Ile Arg Phe Gln
            20                  25                  30

Gln Ile Asn Phe Leu Leu Phe Lys Thr Val Tyr Glu Ala Leu Val Ala
        35                  40                  45

Gln Glu Ile Pro Ser Thr Ile Ser His Ser Ile Arg Cys Ile Lys Lys
    50                  55                  60

Val His His Glu Asn His Cys Arg Glu Lys Ile Leu Pro Ser Glu Asn
65              70                  75                  80

Leu Tyr Phe Lys Lys Gln Pro Leu Met Phe Lys Phe Ser Glu Pro
                85                  90                  95

Ala Ser Leu Gly Cys Lys Val Ser Leu Ala Ile Glu Gln Pro Ile Arg
            100                 105                 110

Lys Phe Ile Leu Asp Ser Ser Val Leu Val Arg Leu Lys Asn Arg Thr
        115                 120                 125

Thr Phe Arg Val Ser Glu Leu Trp Lys Ile Glu Leu Thr Ile Val Lys
    130                 135                 140

Gln Leu Met Gly Ser Glu Val Ser Ala Lys Leu Ala Ala Phe Lys Thr
145                 150                 155                 160

Leu Leu Phe Asp Thr Pro Glu Gln Gln Thr Thr Lys Asn Met Met Thr
                165                 170                 175

Leu Ile Asn Pro Asp Asp Glu Tyr Leu Tyr Glu Ile Glu Ile Glu Tyr
            180                 185                 190

Thr Gly Lys Pro Glu Ser Leu Thr Ala Ala Asp Val Ile Lys Ile Lys
        195                 200                 205

Asn Thr Val Leu Thr Leu Ile Ser Pro Asn His Leu Met Leu Thr Ala
    210                 215                 220

Tyr His Gln Ala Ile Glu Phe Ile Ala Ser His Ile Leu Ser Ser Glu
225                 230                 235                 240

Ile Leu Leu Ala Arg Ile Lys Ser Gly Lys Trp Gly Leu Lys Arg Leu
                245                 250                 255

Leu Pro Gln Val Lys Ser Met Thr Lys Ala Asp Tyr Met Lys Phe Tyr
            260                 265                 270

Pro Pro Val Gly Tyr Tyr Val Thr Asp Lys Ala Asp Gly Ile Arg Gly
        275                 280                 285

Ile Ala Val Ile Gln Asp Thr Gln Ile Tyr Val Val Ala Asp Gln Leu
    290                 295                 300

Tyr Ser Leu Gly Thr Thr Gly Ile Glu Pro Leu Lys Pro Thr Ile Leu
305                 310                 315                 320

Asp Gly Glu Phe Met Pro Glu Lys Lys Glu Phe Tyr Gly Phe Asp Val
                325                 330                 335

Ile Met Tyr Glu Gly Asn Leu Leu Thr Gln Gln Gly Phe Glu Thr Arg
            340                 345                 350

Ile Glu Ser Leu Ser Lys Gly Ile Lys Val Leu Gln Ala Phe Asn Ile
        355                 360                 365

Lys Ala Glu Met Lys Pro Phe Ile Ser Leu Thr Ser Ala Asp Pro Asn
    370                 375                 380

Val Leu Leu Lys Asn Phe Glu Ser Ile Phe Lys Lys Thr Arg Pro
385                 390                 395                 400

Tyr Ser Ile Asp Gly Ile Ile Leu Val Glu Pro Gly Asn Ser Tyr Leu
                405                 410                 415

-continued

Asn Thr Asn Thr Phe Lys Trp Lys Pro Thr Trp Asp Asn Thr Leu Asp
            420                 425                 430

Phe Leu Val Arg Lys Cys Pro Glu Ser Leu Asn Val Pro Glu Tyr Ala
            435                 440                 445

Pro Lys Lys Gly Phe Ser Leu His Leu Leu Phe Val Gly Ile Ser Gly
            450                 455                 460

Glu Leu Phe Lys Lys Leu Ala Leu Asn Trp Cys Pro Gly Tyr Thr Lys
465                 470                 475                 480

Leu Phe Pro Val Thr Gln Arg Asn Gln Asn Tyr Phe Pro Val Gln Phe
                485                 490                 495

Gln Pro Ser Asp Phe Pro Leu Ala Phe Leu Tyr Tyr His Pro Asp Thr
            500                 505                 510

Ser Ser Phe Ser Asn Ile Asp Gly Lys Val Leu Glu Met Arg Cys Leu
            515                 520                 525

Lys Arg Glu Ile Asn Tyr Val Arg Trp Glu Ile Val Lys Ile Arg Glu
            530                 535                 540

Asp Arg Gln Gln Asp Leu Lys Thr Gly Gly Tyr Phe Gly Asn Asp Phe
545                 550                 555                 560

Lys Thr Ala Glu Leu Thr Trp Leu Asn Tyr Met Asp Pro Phe Ser Phe
                565                 570                 575

Glu Glu Leu Ala Lys Gly Pro Ser Gly Met Tyr Phe Ala Gly Ala Lys
            580                 585                 590

Thr Gly Ile Tyr Arg Ala Gln Thr Ala Leu Ile Ser Phe Ile Lys Gln
            595                 600                 605

Glu Ile Ile Gln Lys Ile Ser His Gln Ser Trp Val Ile Asp Leu Gly
            610                 615                 620

Ile Gly Lys Gly Gln Asp Leu Gly Arg Tyr Leu Asp Ala Gly Val Arg
625                 630                 635                 640

His Leu Val Gly Ile Asp Lys Asp Gln Thr Ala Leu Ala Glu Leu Val
                645                 650                 655

Tyr Arg Lys Phe Ser His Ala Thr Thr Arg Gln His Lys His Ala Thr
            660                 665                 670

Asn Ile Tyr Val Leu His Gln Asp Leu Ala Glu Pro Ala Lys Glu Ile
            675                 680                 685

Ser Glu Lys Val His Gln Ile Tyr Gly Phe Pro Lys Glu Gly Ala Ser
            690                 695                 700

Ser Ile Val Ser Asn Leu Phe Ile His Tyr Leu Met Lys Asn Thr Gln
705                 710                 715                 720

Gln Val Glu Asn Leu Ala Val Leu Cys His Lys Leu Leu Gln Pro Gly
                725                 730                 735

Gly Met Val Trp Phe Thr Thr Met Leu Gly Glu Gln Val Leu Glu Leu
            740                 745                 750

Leu His Glu Asn Arg Ile Glu Leu Asn Glu Val Trp Glu Ala Arg Glu
            755                 760                 765

Asn Glu Val Val Lys Phe Ala Ile Lys Arg Leu Phe Lys Glu Asp Ile
            770                 775                 780

Leu Gln Glu Thr Gly Gln Glu Ile Gly Val Leu Leu Pro Phe Ser Asn
785                 790                 795                 800

Gly Asp Phe Tyr Asn Glu Tyr Leu Val Asn Thr Ala Phe Leu Ile Lys
                805                 810                 815

Ile Phe Lys His His Gly Phe Ser Leu Val Gln Lys Gln Ser Phe Lys
            820                 825                 830

```
Asp Trp Ile Pro Glu Phe Gln Asn Phe Ser Lys Ser Leu Tyr Lys Ile
    835                 840                 845

Leu Thr Glu Ala Asp Lys Thr Trp Thr Ser Leu Phe Gly Phe Ile Cys
    850                 855                 860

Leu Arg Lys Asn
865

<210> SEQ ID NO 10
<211> LENGTH: 5277
<212> TYPE: DNA
<213> ORGANISM: Artificial Sequence
<220> FEATURE:
<223> OTHER INFORMATION: Nucleotide sequence of C3P3-K1E chimeric enzyme
      consisting of fusion between African swine fever virus NP868R
      capping enzyme and mutant phage K1E-RNA polymerase

<400> SEQUENCE: 10
atggaattcg ccagcctgga caacctggtg gccagatacc agcggtgctt caacgaccag      60
agcctgaaga acagcaccat cgagctggaa atccggttcc agcagatcaa cttcctgctg     120
ttcaagaccg tgtacgaggc cctggtcgcc aggaaatccc cagcaccat cagccacagc     180 atccggtgca tcaagaaggt gcaccacgag aaccactgcc gggagaagat cctgcccagc     240
gagaacctgt acttcaagaa cagcccctg atgttcttca gttcagcga gcccgccagc     300 ctgggctgta aagtgtccct ggccatcgag cagcccatcc ggaagttcat cctggacagc     360
agcgtgctgg tccggctgaa gaaccggacc accttccggg tgtccgagct gtggaagatc     420
gagctgacca tcgtgaagca gctgatgggc agcgaggtgt cagccaagct ggccgccttc     480
aagaccctgc tgttcgacac ccccgagcag cagaccacca gaacatgat gaccctgatc     540 aaccccgacg acgagtacct gtacgagatc gagatcgagt acaccggcaa gcctgagagc     600
ctgacagccg ccgacgtgat caagatcaag aacaccgtgc tgacactgat cagccccaac     660
cacctgatgc tgaccgccta ccaccaggcc atcgagttta cgccagcca tcctgagc      720 agcgagatcc tgctggcccg gatcaagagc ggcaagtggg gcctgaagag actgctgccc     780
caggtcaagt ccatgaccaa ggccgactac atgaagttct accccccgt gggctactac     840 gtgaccgaca aggccgacgg catccggggc attgccgtga tccaggacac ccagatctac     900
gtggtggccg accagctgta cagcctgggc accaccggca tcgagcccct gaagcccacc     960
atcctggacg gcgagttcat gcccgagaag aaagagttct acggctttga cgtgatcatg    1020
tacgagggca acctgctgac ccagcagggc ttcgagacac ggatcgagag cctgagcaag    1080
ggcatcaagt gctgcaggc cttcaacatc aaggccgaga tgaagccctt catcagcctg    1140
acctccgccg accccaacgt gctgctgaag aatttcgaga gcatcttcaa gaagaaaacc    1200
cggccctaca gcatcgacgg catcatcctg gtggagcccg caacagcta cctgaacacc    1260 aacaccttca gtggaagcc cacctgggac aaccccttgg actttctggt ccggaagtgc    1320
cccgagtccc tgaacgtgcc cgagtacgcc ccaagaagg cttcagcct gcatctgctg    1380 ttcgtgggca tcagcggcga gctgtttaag aagctggccc tgaactggtg ccccggctac    1440
accaagctgt ccccgtgac ccagcggaac cagaactact ccccgtgca gttccagccc    1500 agcgacttcc ctggccttt cctgtactac caccccgaca ccagcagctt cagcaacatc    1560
gatggcaagg tgctggaaat gcggtgcctg aagcgggaga tcaactacgt cgctgggag    1620 atcgtgaaga tccggggagga ccggcagcag atctgaaaa ccggcggcta cttcggcaac    1680
gacttcaaga ccgccgagct gacctggctg aactacatgg acccccttcag cttcgaggaa    1740
```

```
ctggccaagg gacccagcgg catgtacttc gctggcgcca agaccggcat ctacagagcc      1800
cagaccgccc tgatcagctt catcaagcag gaaatcatcc agaagatcag ccaccagagc      1860
tgggtgatcg acctgggcat cggcaagggc caggacctgg gcagatacct ggacgccggc      1920
gtgagacacc tggtcggcat cgataaggac cagacagccc tggccgagct ggtgtaccgg      1980
aagttctccc acgccaccac cagacagcac aagcacgcca ccaacatcta cgtgctgcac      2040
caggatctgg ccgagcctgc caaagaaatc agcgagaaag tgcaccagat ctatggcttc      2100
cccaaagagg gcgccagcag catcgtgtcc aacctgttca tccactacct gatgaagaac      2160
acccagcagg tcgagaacct ggctgtgctg tgccacaagc tgctgcagcc tggcggcatg      2220
gtctggttca ccaccatgct gggcgaacag gtgctggaac tgctgcacga accggatc       2280 gaactgaacg aagtgtggga ggcccgggag aacgaggtgg tcaagttcgc catcaagcgg      2340
ctgttcaaag aggacatcct gcaggaaacc ggccaggaaa tcggcgtcct gctgcccttc      2400
agcaacggcg acttctacaa tgagtacctg gtcaacaccg cctttctgat caagattttc      2460
aagcaccatg gctttagcct cgtgcagaag cagagcttca aggactggat ccccgagttc      2520
cagaacttca gcaagagcct gtacaagatc ctgaccgagg ccgacaagac ctggaccagc      2580
ctgttcggct tcatctgcct gcggaagaac ctcgaggag gaggaggatc aggcggaggc      2640
ggaagtgtcg agcaggacct gcacgccatc cagctgcagc tcgaagagga aatgttcaac      2700
ggcggcatca agagattcga ggccgaccag cagagacaga tcgcctctgg caacgagagc      2760
gacaccgcct ggaatagaag gctgctgtct gagctgatcg cccctatggc cgaaggcatc      2820
caggcctaca agaggaata cgagggcaag agaggcagag cccctagagc cctggccttc      2880
atcaactgtg tgggcaatga ggtggccgcc tacatcacca tgaagatcgt gatggacatg      2940
ctgaacaccg acgtgaccct gcaggccatt gccatgaacg tggccgacag aatcgaggac      3000
caggtccgat tcagcaagct ggaaggacac gccgccaagt acttcgagaa agtgaagaag      3060
tccctgaagg ccagcaagac caagagctac agacacgccc acaacgtggc cgtggtggcc      3120
gaaaaatctg tggccgatag ggacgccgac ttctctagat gggaggcctg gcctaaggac      3180
accctgctgc agatcggcat gaccctgctg aaatcctgg aaaacagcgt gttcttcaac      3240
ggccagcccg tgttcctgag aaccctgagg acaaatggcg gcaagcacgg cgtgtactac      3300
ctgcagacat ctgagcacgt gggcgagtgg atcaccgcct tcaaagaaca tgtggcccag      3360
ctgagccctg cctatgcccc ttgtgtgatc cctcctagac cctgggtgtc cccttttcaat      3420 ggcggctttc acaccgagaa ggtggccagc agaatcagac tggtcaaggg caaccgggaa      3480
cacgtgcgga agctgaccaa gaaacagatg cccgccgtgt acaaggccgt gaatgctctg      3540
caggccacca gtggcaggt caacaaagag gtgctgcagg tcgtcgagga cgtgatcaga      3600
ctggatctgg gctacggcgt gccaagcttt aagcccctga tcgacagaga gaacaagccc      3660
gccaaccctg tgcccctgga atttcagcac ctgagaggcc gcgagctgaa agagatgctg      3720
acacctgaac agtggcaggc ctttatcaat tggaagggcg agtgcaccaa gctgtacacc      3780
gccgagacaa gagggggctc taagtctgcc gccacagtgc gaatggtcgg acaggccaga      3840
aagtacagcc agttcgacgc catctacttc gtgtacgccc tggacagccg gtctagagtg      3900
tatgcccaga gcagcacact gagcccccag tctaacgatc tgggaaaggc cctgctgaga      3960
ttcaccgagg ccagagact ggattctgcc gaagccctga gtggttcct ggtcaacggc      4020 gccaacaact ggggctggga caagaaaacc ttcgatgtgc ggaccgccaa cgtgctggat      4080
agcgagttcc aggacatgtg cagagatatc gccgccgacc ctctgaccct tacccagtgg      4140
```

```
gtcaacgccg atagcccta tggattcctg gcctggtgct tcgagtacgc cagatacctg    4200
gacgccctgg atgagggaac ccaggatcag ttcatgaccc atctgcccgt gcaccaggat    4260
ggctcttgtt ctggcatcca gcactacagc gccatgctga gcgatgccgt gggagccaaa    4320
gccgtgaacc tgaagcctag cgacagcccc caggatatct atggcgctgt ggcccaggtg    4380
gtcatccaga aaactacgc ctacatgaac gccgaggacg ccgagacatt cacaagcgga    4440
agcgtgacac tgacaggcgc cgagctgaga tctatggcct ctgcctggga catgatcggc    4500
atcacacggg gcctgaccaa aaagcctgtg atgacactgc cctacggcag caccagactg    4560
acctgtagag aaagcgtgat cgactacatc gtggacctgg aagagaaaga ggcccagaga    4620
gccattgccg agggcagaac agccaatcct gtgcacccct tcgacaacga ccggaaggat    4680
agcctgacac ctagcgccgc ctacaactac atgaccgccc tgatctggcc cagcatctct    4740
gaagtggtca aggcccctat cgtggccatg aagatgatca gacagctggc cagattcgcc    4800
gccaagagaa atgagggcct ggaataccct ctgcccaccg gctttatcct gcagcagaaa    4860
atcatggcca ccgacatgct gcgggtgtcc acatgtctga tgggcgagat caagatgagc    4920
ctgcagatcg agacagacgt ggtggacgag acagccatga tgggagccgc cgctcctaat    4980
tttgtgcacg acacgatgc cagccacctg atcctgaccg tgtgcgatct ggtggacaag    5040
ggcatcacta gcgtggccgt gatccacgat agctttggaa cacacgccgg cagaaccgcc    5100
gacctgagag attctctgcg ggaagagatg gtcaagatgt accagaacca caacgccctg    5160
cagaacctgc tggacgtgca cgaagaaaga tggctggtgg acaccggcat ccaggtgcca    5220
gaacagggag agttcgacct gaacgagatc ctggtgtccg actactgctt cgcctaa       5277
```

<210> SEQ ID NO 11
<211> LENGTH: 1758
<212> TYPE: PRT
<213> ORGANISM: Artificial Sequence
<220> FEATURE:
<223> OTHER INFORMATION: Amino-acid sequence of C3P3-K1E chimeric enzyme
    consisting of fusion between African swine fever NP868R virus
    capping enzyme and mutant phage K1E-RNA polymerase

<400> SEQUENCE: 11

```
Met Glu Phe Ala Ser Leu Asp Asn Leu Val Ala Arg Tyr Gln Arg Cys
1               5                   10                  15

Phe Asn Asp Gln Ser Leu Lys Asn Ser Thr Ile Glu Leu Glu Ile Arg
            20                  25                  30

Phe Gln Gln Ile Asn Phe Leu Leu Phe Lys Thr Val Tyr Glu Ala Leu
        35                  40                  45

Val Ala Gln Glu Ile Pro Ser Thr Ile Ser His Ser Ile Arg Cys Ile
    50                  55                  60

Lys Lys Val His His Glu Asn His Cys Arg Glu Lys Ile Leu Pro Ser
65                  70                  75                  80

Glu Asn Leu Tyr Phe Lys Lys Gln Pro Leu Met Phe Phe Lys Phe Ser
                85                  90                  95

Glu Pro Ala Ser Leu Gly Cys Lys Val Ser Leu Ala Ile Glu Gln Pro
            100                 105                 110

Ile Arg Lys Phe Ile Leu Asp Ser Ser Val Leu Val Arg Leu Lys Asn
        115                 120                 125

Arg Thr Thr Phe Arg Val Ser Glu Leu Trp Lys Ile Glu Leu Thr Ile
    130                 135                 140

Val Lys Gln Leu Met Gly Ser Glu Val Ser Ala Lys Leu Ala Ala Phe
```

-continued

```
        145                 150                 155                 160
Lys Thr Leu Leu Phe Asp Thr Pro Glu Gln Gln Thr Thr Lys Asn Met
                165                 170                 175

Met Thr Leu Ile Asn Pro Asp Asp Glu Tyr Leu Tyr Glu Ile Glu Ile
                180                 185                 190

Glu Tyr Thr Gly Lys Pro Glu Ser Leu Thr Ala Ala Asp Val Ile Lys
                195                 200                 205

Ile Lys Asn Thr Val Leu Thr Leu Ile Ser Pro Asn His Leu Met Leu
                210                 215                 220

Thr Ala Tyr His Gln Ala Ile Glu Phe Ile Ala Ser His Ile Leu Ser
225                 230                 235                 240

Ser Glu Ile Leu Leu Ala Arg Ile Lys Ser Gly Lys Trp Gly Leu Lys
                245                 250                 255

Arg Leu Leu Pro Gln Val Lys Ser Met Thr Lys Ala Asp Tyr Met Lys
                260                 265                 270

Phe Tyr Pro Pro Val Gly Tyr Tyr Val Thr Asp Lys Ala Asp Gly Ile
                275                 280                 285

Arg Gly Ile Ala Val Ile Gln Asp Thr Gln Ile Tyr Val Val Ala Asp
                290                 295                 300

Gln Leu Tyr Ser Leu Gly Thr Thr Gly Ile Glu Pro Leu Lys Pro Thr
305                 310                 315                 320

Ile Leu Asp Gly Glu Phe Met Pro Glu Lys Lys Glu Phe Tyr Gly Phe
                325                 330                 335

Asp Val Ile Met Tyr Glu Gly Asn Leu Leu Thr Gln Gln Gly Phe Glu
                340                 345                 350

Thr Arg Ile Glu Ser Leu Ser Lys Gly Ile Lys Val Leu Gln Ala Phe
                355                 360                 365

Asn Ile Lys Ala Glu Met Lys Pro Phe Ile Ser Leu Thr Ser Ala Asp
                370                 375                 380

Pro Asn Val Leu Leu Lys Asn Phe Glu Ser Ile Phe Lys Lys Lys Thr
385                 390                 395                 400

Arg Pro Tyr Ser Ile Asp Gly Ile Ile Leu Val Glu Pro Gly Asn Ser
                405                 410                 415

Tyr Leu Asn Thr Asn Thr Phe Lys Trp Lys Pro Thr Trp Asp Asn Thr
                420                 425                 430

Leu Asp Phe Leu Val Arg Lys Cys Pro Glu Ser Leu Asn Val Pro Glu
                435                 440                 445

Tyr Ala Pro Lys Lys Gly Phe Ser Leu His Leu Leu Phe Val Gly Ile
                450                 455                 460

Ser Gly Glu Leu Phe Lys Lys Leu Ala Leu Asn Trp Cys Pro Gly Tyr
465                 470                 475                 480

Thr Lys Leu Phe Pro Val Thr Gln Arg Asn Gln Asn Tyr Phe Pro Val
                485                 490                 495

Gln Phe Gln Pro Ser Asp Phe Pro Leu Ala Phe Leu Tyr Tyr His Pro
                500                 505                 510

Asp Thr Ser Ser Phe Ser Asn Ile Asp Gly Lys Val Leu Glu Met Arg
                515                 520                 525

Cys Leu Lys Arg Glu Ile Asn Tyr Val Arg Trp Glu Ile Val Lys Ile
                530                 535                 540

Arg Glu Asp Arg Gln Gln Asp Leu Lys Thr Gly Gly Tyr Phe Gly Asn
545                 550                 555                 560

Asp Phe Lys Thr Ala Glu Leu Thr Trp Leu Asn Tyr Met Asp Pro Phe
                565                 570                 575
```

```
Ser Phe Glu Glu Leu Ala Lys Gly Pro Ser Gly Met Tyr Phe Ala Gly
            580                 585                 590

Ala Lys Thr Gly Ile Tyr Arg Ala Gln Thr Ala Leu Ile Ser Phe Ile
        595                 600                 605

Lys Gln Glu Ile Ile Gln Lys Ile Ser His Gln Ser Trp Val Ile Asp
610                 615                 620

Leu Gly Ile Gly Lys Gly Gln Asp Leu Gly Arg Tyr Leu Asp Ala Gly
625                 630                 635                 640

Val Arg His Leu Val Gly Ile Asp Lys Asp Gln Thr Ala Leu Ala Glu
                645                 650                 655

Leu Val Tyr Arg Lys Phe Ser His Ala Thr Thr Arg Gln His Lys His
            660                 665                 670

Ala Thr Asn Ile Tyr Val Leu His Gln Asp Leu Ala Glu Pro Ala Lys
        675                 680                 685

Glu Ile Ser Glu Lys Val His Gln Ile Tyr Gly Phe Pro Lys Glu Gly
    690                 695                 700

Ala Ser Ser Ile Val Ser Asn Leu Phe Ile His Tyr Leu Met Lys Asn
705                 710                 715                 720

Thr Gln Gln Val Glu Asn Leu Ala Val Leu Cys His Lys Leu Leu Gln
                725                 730                 735

Pro Gly Gly Met Val Trp Phe Thr Thr Met Leu Gly Glu Gln Val Leu
            740                 745                 750

Glu Leu Leu His Glu Asn Arg Ile Glu Leu Asn Glu Val Trp Glu Ala
        755                 760                 765

Arg Glu Asn Glu Val Val Lys Phe Ala Ile Lys Arg Leu Phe Lys Glu
    770                 775                 780

Asp Ile Leu Gln Glu Thr Gly Gln Glu Ile Gly Val Leu Leu Pro Phe
785                 790                 795                 800

Ser Asn Gly Asp Phe Tyr Asn Glu Tyr Leu Val Asn Thr Ala Phe Leu
                805                 810                 815

Ile Lys Ile Phe Lys His His Gly Phe Ser Leu Val Gln Lys Gln Ser
            820                 825                 830

Phe Lys Asp Trp Ile Pro Glu Phe Gln Asn Phe Ser Lys Ser Leu Tyr
        835                 840                 845

Lys Ile Leu Thr Glu Ala Asp Lys Thr Trp Thr Ser Leu Phe Gly Phe
    850                 855                 860

Ile Cys Leu Arg Lys Asn Leu Glu Gly Gly Gly Ser Gly Gly Gly
865                 870                 875                 880

Gly Ser Val Glu Gln Asp Leu His Ala Ile Gln Leu Gln Leu Glu Glu
                885                 890                 895

Glu Met Phe Asn Gly Gly Ile Arg Arg Phe Glu Ala Asp Gln Gln Arg
            900                 905                 910

Gln Ile Ala Ser Gly Asn Glu Ser Asp Thr Ala Trp Asn Arg Arg Leu
        915                 920                 925

Leu Ser Glu Leu Ile Ala Pro Met Ala Glu Gly Ile Gln Ala Tyr Lys
    930                 935                 940

Glu Glu Tyr Glu Gly Lys Arg Gly Arg Ala Pro Arg Ala Leu Ala Phe
945                 950                 955                 960

Ile Asn Cys Val Gly Asn Glu Val Ala Ala Tyr Ile Thr Met Lys Ile
                965                 970                 975

Val Met Asp Met Leu Asn Thr Asp Val Thr Leu Gln Ala Ile Ala Met
            980                 985                 990
```

```
Asn Val Ala Asp Arg Ile Glu Asp  Gln Val Arg Phe  Ser Lys Leu Glu
            995               1000                1005

Gly His Ala Ala Lys Tyr Phe  Glu Lys Val Lys  Ser Leu Lys
1010                1015                1020

Ala Ser Lys Thr Lys Ser Tyr  Arg His Ala His  Asn Val Ala Val
1025                1030                1035

Val Ala Glu Lys Ser Val Ala  Asp Arg Asp Ala  Asp Phe Ser Arg
1040                1045                1050

Trp Glu Ala Trp Pro Lys Asp  Thr Leu Leu Gln  Ile Gly Met Thr
1055                1060                1065

Leu Leu Glu Ile Leu Glu Asn  Ser Val Phe Phe  Asn Gly Gln Pro
1070                1075                1080

Val Phe Leu Arg Thr Leu Arg  Thr Asn Gly Gly  Lys His Gly Val
1085                1090                1095

Tyr Tyr Leu Gln Thr Ser Glu  His Val Gly Glu  Trp Ile Thr Ala
1100                1105                1110

Phe Lys Glu His Val Ala Gln  Leu Ser Pro Ala  Tyr Ala Pro Cys
1115                1120                1125

Val Ile Pro Pro Arg Pro Trp  Val Ser Pro Phe  Asn Gly Gly Phe
1130                1135                1140

His Thr Glu Lys Val Ala Ser  Arg Ile Arg Leu  Val Lys Gly Asn
1145                1150                1155

Arg Glu His Val Arg Lys Leu  Thr Lys Lys Gln  Met Pro Ala Val
1160                1165                1170

Tyr Lys Ala Val Asn Ala Leu  Gln Ala Thr Lys  Trp Gln Val Asn
1175                1180                1185

Lys Glu Val Leu Gln Val Val  Glu Asp Val Ile  Arg Leu Asp Leu
1190                1195                1200

Gly Tyr Gly Val Pro Ser Phe  Lys Pro Leu Ile  Asp Arg Glu Asn
1205                1210                1215

Lys Pro Ala Asn Pro Val Pro  Leu Glu Phe Gln  His Leu Arg Gly
1220                1225                1230

Arg Glu Leu Lys Glu Met Leu  Thr Pro Glu Gln  Trp Gln Ala Phe
1235                1240                1245

Ile Asn Trp Lys Gly Glu Cys  Thr Lys Leu Tyr  Thr Ala Glu Thr
1250                1255                1260

Lys Arg Gly Ser Lys Ser Ala  Ala Thr Val Arg  Met Val Gly Gln
1265                1270                1275

Ala Arg Lys Tyr Ser Gln Phe  Asp Ala Ile Tyr  Phe Val Tyr Ala
1280                1285                1290

Leu Asp Ser Arg Ser Arg Val  Tyr Ala Gln Ser  Ser Thr Leu Ser
1295                1300                1305

Pro Gln Ser Asn Asp Leu Gly  Lys Ala Leu Leu  Arg Phe Thr Glu
1310                1315                1320

Gly Gln Arg Leu Asp Ser Ala  Glu Ala Leu Lys  Trp Phe Leu Val
1325                1330                1335

Asn Gly Ala Asn Asn Trp Gly  Trp Asp Lys Lys  Thr Phe Asp Val
1340                1345                1350

Arg Thr Ala Asn Val Leu Asp  Ser Glu Phe Gln  Asp Met Cys Arg
1355                1360                1365

Asp Ile Ala Ala Asp Pro Leu  Thr Phe Thr Gln  Trp Val Asn Ala
1370                1375                1380

Asp Ser Pro Tyr Gly Phe Leu  Ala Trp Cys Phe  Glu Tyr Ala Arg
```

```
            1385                1390                1395

Tyr Leu Asp Ala Leu Asp Glu Gly Thr Gln Asp Gln Phe Met Thr
    1400                1405                1410

His Leu Pro Val His Gln Asp Gly Ser Cys Ser Gly Ile Gln His
    1415                1420                1425

Tyr Ser Ala Met Leu Ser Asp Ala Val Gly Ala Lys Ala Val Asn
    1430                1435                1440

Leu Lys Pro Ser Asp Ser Pro Gln Asp Ile Tyr Gly Ala Val Ala
    1445                1450                1455

Gln Val Val Ile Gln Lys Asn Tyr Ala Tyr Met Asn Ala Glu Asp
    1460                1465                1470

Ala Glu Thr Phe Thr Ser Gly Ser Val Thr Leu Thr Gly Ala Glu
    1475                1480                1485

Leu Arg Ser Met Ala Ser Ala Trp Asp Met Ile Gly Ile Thr Arg
    1490                1495                1500

Gly Leu Thr Lys Lys Pro Val Met Thr Leu Pro Tyr Gly Ser Thr
    1505                1510                1515

Arg Leu Thr Cys Arg Glu Ser Val Ile Asp Tyr Ile Val Asp Leu
    1520                1525                1530

Glu Glu Lys Glu Ala Gln Arg Ala Ile Ala Glu Gly Arg Thr Ala
    1535                1540                1545

Asn Pro Val His Pro Phe Asp Asn Asp Arg Lys Asp Ser Leu Thr
    1550                1555                1560

Pro Ser Ala Ala Tyr Asn Tyr Met Thr Ala Leu Ile Trp Pro Ser
    1565                1570                1575

Ile Ser Glu Val Val Lys Ala Pro Ile Val Ala Met Lys Met Ile
    1580                1585                1590

Arg Gln Leu Ala Arg Phe Ala Ala Lys Arg Asn Glu Gly Leu Glu
    1595                1600                1605

Tyr Pro Leu Pro Thr Gly Phe Ile Leu Gln Gln Lys Ile Met Ala
    1610                1615                1620

Thr Asp Met Leu Arg Val Ser Thr Cys Leu Met Gly Glu Ile Lys
    1625                1630                1635

Met Ser Leu Gln Ile Glu Thr Asp Val Val Asp Glu Thr Ala Met
    1640                1645                1650

Met Gly Ala Ala Ala Pro Asn Phe Val His Gly His Asp Ala Ser
    1655                1660                1665

His Leu Ile Leu Thr Val Cys Asp Leu Val Asp Lys Gly Ile Thr
    1670                1675                1680

Ser Val Ala Val Ile His Asp Ser Phe Gly Thr His Ala Gly Arg
    1685                1690                1695

Thr Ala Asp Leu Arg Asp Ser Leu Arg Glu Glu Met Val Lys Met
    1700                1705                1710

Tyr Gln Asn His Asn Ala Leu Gln Asn Leu Leu Asp Val His Glu
    1715                1720                1725

Glu Arg Trp Leu Val Asp Thr Gly Ile Gln Val Pro Glu Gln Gly
    1730                1735                1740

Glu Phe Asp Leu Asn Glu Ile Leu Val Ser Asp Tyr Cys Phe Ala
    1745                1750                1755

<210> SEQ ID NO 12
<211> LENGTH: 7929
<212> TYPE: DNA
<213> ORGANISM: Artificial Sequence
```

<220> FEATURE:
<223> OTHER INFORMATION: Nucleotide sequence of C3P3-T3 chimeric enzyme
consisting of fusion between African swine fever virus NP868R
capping enzyme and phage T3-RNA polymerase

<400> SEQUENCE: 12

```
atggaattcg ccagcctgga caacctggtg gccagatacc agcggtgctt caacgaccag      60
agcctgaaga acagcaccat cgagctggaa atccggttcc agcagatcaa cttcctgctg     120
ttcaagaccg tgtacgaggc cctggtcgcc caggaaatcc ccagcaccat cagccacagc     180
atccggtgca tcaagaaggt gcaccacgag aaccactgcc gggagaagat cctgcccagc     240
gagaacctgt acttcaagaa cagcccctg atgttcttca gttcagcga gcccgccagc      300
ctgggctgta aagtgtccct ggccatcgag cagcccatcc ggaagttcat cctggacagc     360
agcgtgctgg tccggctgaa gaaccggacc accttccggg tgtccgagct gtggaagatc     420
gagctgacca tcgtgaagca gctgatgggc agcgaggtgt cagccaagct ggccgccttc     480
aagaccctgc tgttcgacac ccccgagcag cagaccacca gaacatgat gaccctgatc      540
aaccccgacg acgagtacct gtacgagatc gagatcgagt acaccggcaa gcctgagagc     600
ctgacagccg ccgacgtgat caagatcaag aacaccgtgc tgacactgat cagccccaac     660
cacctgatgc tgaccgccta ccaccaggcc atcgagtttta tcgccagcca tcctgagc      720
agcgagatcc tgctggcccg gatcaagagc ggcaagtggg gcctgaagag actgctgccc     780
caggtcaagt ccatgaccaa ggccgactac atgaagttct accccccgt gggctactac      840
gtgaccgaca ggccgacgg catccggggc attgccgtga tccaggacac ccagatctac      900
gtggtggccg accagctgta cagcctgggc accaccggca tcgagcccct gaagcccacc     960
atcctggacg gcgagttcat gcccgagaag aaagagttct acggctttga cgtgatcatg    1020
tacgagggca acctgctgac ccagcagggc ttcgagacac ggatcgagag cctgagcaag    1080
ggcatcaagg tgctgcaggc cttcaacatc aaggccgaga tgaagccctt catcagcctg    1140
acctccgccg accccaacgt gctgctgaag aatttcgaga gcatcttcaa gagaaaacc     1200
cggccctaca gcatcgacgg catcatcctg tggagcccg gcaacagcta cctgaacacc     1260
aacaccttca gtggaagcc cacctgggac aacaccctgg actttctggt ccggaagtgc     1320
cccgagtccc tgaacgtgcc cgagtacgcc cccaagaagg gcttcagcct gcatctgctg    1380
ttcgtgggca tcagcggcga gctgttttaag aagctggccc tgaactggtg ccccggctac    1440
accaagctgt cccccgtgac ccagcggaac cagaactact ccccgtgca gttccagccc     1500
agcgacttcc ccctggcctt cctgtactac caccccgaca ccagcagctt cagcaacatc    1560
gatggcaagg tgctggaaat gcggtgcctg aagcgggaga tcaactacgt gcgctgggag    1620
atcgtgaaga tccgggagga ccggcagcag atctgaaaa ccggcggcta cttcggcaac     1680
gacttcaaga ccgccgagct gacctggctg aactacatgg accccttcag cttcgaggaa    1740
ctggccaagg acccagcgg catgtacttc gctggcgcca agaccggcat ctacagagcc     1800
cagaccgccc tgatcagctt catcaagcag gaaatcatcc agaagatcag ccaccagagc    1860
tgggtgatcg acctgggcat cggcaagggc caggacctgg cagataacct ggacgccggc    1920
gtgagacacc tggtcggcat cgataaggac cagacagccc tggccgagct ggtgtaccgg    1980
aagttctccc acgccaccac cagacagcac aagcacgcca ccaacatcta cgtgctgcac    2040
caggatctgg ccgagcctgc caaagaaatc agcgagaaag tgcaccagat ctatggcttc    2100
cccaaagagg gcgccagcag catcgtgtcc aacctgttca ccactacct gatgaagaac    2160
```

```
acccagcagg tcgagaacct ggctgtgctg tgccacaagc tgctgcagcc tggcggcatg    2220
gtctggttca ccaccatgct gggcgaacag gtgctggaac tgctgcacga gaaccggatc    2280
gaactgaacg aagtgtggga ggcccgggag aacgaggtgg tcaagttcgc catcaagcgg    2340
ctgttcaaag aggacatcct gcaggaaacc ggccaggaaa tcggcgtcct gctgcccttc    2400
agcaacggcg acttctacaa tgagtacctg gtcaacaccg cctttctgat caagattttc    2460
aagcaccatg gctttagcct cgtgcagaag cagagcttca aggactggat ccccgagttc    2520
cagaacttca gcaagagcct gtacaagatc ctgaccgagg ccgacaagac ctggaccagc    2580
ctgttcggct tcatctgcct gcggaagaac ctcgagggag gaggaggatc aggcggaggc    2640
ggaagtgtcg agatggaatt cgccagcctg acaacctgg tggccagata ccagcggtgc    2700
ttcaacgacc agagcctgaa gaacagcacc atcgagctgg aaatccggtt ccagcagatc    2760
aacttcctgc tgttcaagac cgtgtacgag gccctggtcg cccaggaaat ccccagcacc    2820
atcagccaca gcatccggtg catcaagaag gtgcaccacg agaaccactg ccgggagaag    2880
atcctgccca gcgagaacct gtacttcaag aaacagcccc tgatgttctt caagttcagc    2940
gagcccgcca gctgggctg taaagtgtcc ctggccatcg agcagcccat ccggaagttc    3000
atcctggaca gcagcgtgct ggtccggctg aagaaccgga ccaccttccg ggtgtccgag    3060
ctgtggaaga tcgagctgac catcgtgaag cagctgatgg gcagcgaggt gtcagccaag    3120
ctggccgcct tcaagaccct gctgttcgac accccccgagc agcagaccac caagaacatg    3180
atgaccctga tcaaccccga cgacgagtac ctgtacgaga tcgagatcga gtacaccggc    3240
aagcctgaga gcctgacagc cgccgacgtg atcaagatca gaacaccgt gctgacactg    3300 atcagcccca accacctgat gctgaccgcc taccaccagg ccatcgagtt tatcgccagc    3360
cacatcctga gcagcgagat cctgctggcc cggatcaaga gcggcaagtg gggcctgaag    3420
agactgctgc cccaggtcaa gtccatgacc aaggccgact acatgaagtt ctaccccccc    3480
gtgggctact acgtgaccga caaggccgac ggcatccggg gcattgccgt gatccaggac    3540
acccagatct acgtggtggc cgaccagctg tacagcctgg gcaccaccgg catcgagccc    3600
ctgaagccca ccatcctgga cggcgagttc atgcccgaga gaaagagtt ctacggcttt    3660 gacgtgatca tgtacgaggg caacctgctg acccagcagg gcttcgagac acggatcgag    3720
agcctgagca agggcatcaa ggtgctgcag gccttcaaca tcaaggccga gatgaagccc    3780
ttcatcagcc tgacctccgc cgaccccaac gtgctgctga agaatttcga gagcatcttc    3840
aagaagaaaa cccggcccta cagcatcgac ggcatcatcc tggtggagcc cggcaacagc    3900
tacctgaaca ccaacaccctt caagtggaag cccacctggg acaacaccct ggactttctg    3960
gtccggaagt gccccgagtc cctgaacgtg cccgagtacg cccccaagaa gggcttcagc    4020
ctgcatctgc tgttcgtggg catcagcggc gagctgttta agaagctggc cctgaactgg    4080
tgccccggct acaccaagct gttccccgtg acccagcgga accagaacta cttccccgtg    4140
cagttccagc ccagcgactt cccctgcc ttcctgtact accacccccga caccagcagc    4200 ttcagcaaca tcgatggcaa ggtgctggaa atgcggtgcc tgaagcggga gatcaactac    4260
gtgcgctggg agatcgtgaa gatccggag accggcagc aggatctgaa accggcggc    4320 tacttcggca acgacttcaa gaccgccgag ctgacctggc tgaactacat ggaccccttc    4380
agcttcgagg aactggccaa gggaccagc ggcatgtact cgctggcgc caagaccggc    4440 atctacagag cccagaccgc cctgatcagc ttcatcaagc aggaaatcat ccagaagatc    4500
agccaccaga gctgggtgat cgacctgggc atcggcaagg gccaggacct gggcagatac    4560
```

```
ctggacgccg gcgtgagaca cctggtcggc atcgataagg accagacagc cctggccgag   4620
ctggtgtacc ggaagttctc ccacgccacc accagacagc acaagcacgc caccaacatc   4680
tacgtgctgc accaggatct ggccgagcct gccaaagaaa tcagcgagaa agtgcaccag   4740
atctatggct tccccaaaga gggcgccagc agcatcgtgt ccaacctgtt catccactac   4800
ctgatgaaga cacccagca ggtcgagaac ctggctgtgc tgtgccacaa gctgctgcag   4860
cctggcggca tggtctggtt caccaccatg ctgggcgaac aggtgctgga actgctgcac   4920
gagaaccgga tcgaactgaa cgaagtgtgg gaggcccggg agaacgaggt ggtcaagttc   4980
gccatcaagg ggctgttcaa agaggacatc ctgcaggaaa ccggccagga aatcggcgtc   5040
ctgctgccct tcagcaacgg cgacttctac aatgagtacc tggtcaacac cgcctttctg   5100
atcaagattt tcaagcacca tggctttagc ctcgtgcaga agcagagctt caaggactgg   5160
atccccgagt tccagaactt cagcaagagc ctgtacaaga tcctgaccga ggccgacaag   5220
acctggacca gcctgttcgg cttcatctgc ctgcggaaga acctcgaggg aggaggagga   5280
tcaggcggag gcggaagtgt cgagcaggac ctgcacgcca tccagctgca gctcgaagag   5340
gaaatgttca acggcggcat cagaagattc gaggccgacc agcagagaca gatcgcctct   5400
ggcaacgaga gcgacaccgc ctggaataga aggctgctgt ctgagctgat cgcccctatg   5460
gccgaaggca tccaggccta caaagaggaa tacgagggca agagaggcag agccctaga    5520 gccctggcct tcatcaactg tgtgggcaat gaggtggccg cctacatcac catgaagatc   5580
gtgatggaca tgctgaacac cgacgtgacc ctgcaggcca ttgccatgaa cgtggccgac   5640
agaatcgagg accaggtccg attcagcaag ctggaaggac acgccgccaa gtacttcgag   5700
aaagtgaaga agtccctgaa ggccagcaag accaagagct acagacacgc ccacaacgtg   5760
gccgtggtgg ccgaaaaatc tgtggccgat agggacgccg acttctctag atgggaggcc   5820
tggcctaagg acaccctgct gcagatcggc atgaccctgc tggaaatcct ggaaaacagc   5880
gtgttcttca acgccagcc cgtgttcctg agaacccctga ggacaaatgg cggcaagcac   5940
ggcgtgtact acctgcagac atctgagcac gtgggcgagt ggatcaccgc cttcaaagaa   6000
catgtggccc agctgagccc tgcctatgcc ccttgtgtga tccctcctag accctgggtg   6060 tccccttca atggcggctt tcacaccgag aaggtggcca gcagaatcag actggtcaag   6120
ggcaaccggg aacacgtgcg gaagctgacc aagaaacaga tgcccgccgt gtacaaggcc   6180
gtgaatgctc tgcaggccac caagtggcag gtcaacaaag aggtgctgca ggtcgtcgag   6240
gacgtgatca gactggatct gggctacggc gtgccaagct taagcccct gatcgacaga   6300 gagaacaagc ccgccaaccc tgtgcccctg gaatttcagc acctgagagg ccgcgagctg   6360
aaagagatgc tgacacctga acagtggcag gcctttatca attggaaggg cgagtgcacc   6420
aagctgtaca ccgccgagac aaagaggggc tctaagtctg ccgccacagt gcgaatggtc   6480
ggacaggcca gaaagtacag ccagttcgac gccatctact tcgtgtacgc cctggacagc   6540
cggtctagag tgtatgccca gagcagcaca ctgagccccc agtctaacga tctgggaaag   6600
gccctgctga gattcaccga gggccagaga ctggattctg ccgaagccct gaagtggttc   6660
ctggtcaacg gcgccaacaa ctgggcctgg acaagaaaa ccttcgatgt gcggaccgcc   6720
aacgtgctgg atagcgagtt ccaggacatg tgcagagata tcgccgccga ccctctgacc   6780
tttacccagt gggtcaacgc cgatagcccc tatggattcc tggcctggtg cttcgagtac   6840
gccagatacc tggacgccct ggatgaggga acccaggatc agttcatgac ccatctgccc   6900
```

```
gtgcaccagg atggctcttg ttctggcatc cagcactaca gcgccatgct gagcgatgcc    6960
gtgggagcca aagccgtgaa cctgaagcct agcgacagcc cccaggatat ctatggcgct    7020
gtggcccagg tggtcatcca gaaaaactac gcctacatga acgccgagga cgccgagaca    7080
ttcacaagcg gaagcgtgac actgacaggc gccgagctga gatctatggc ctctgcctgg    7140
gacatgatcg gcatcacacg gggcctgacc aaaaagcctg tgatgacact gccctacggc    7200
agcaccagac tgacctgtag agaaagcgtg atcgactaca tcgtggacct ggaagagaaa    7260
gaggcccaga gagccattgc cgagggcaga acagccaatc tgtgcacccc cttcgacaac    7320
gaccggaagg atagcctgac acctagcgcc gcctacaact acatgaccgc cctgatctgg    7380
cccagcatct ctgaagtggt caaggcccct atcgtggcca tgaagatgat cagacagctg    7440
gccagattcg ccgccaagag aaatgagggc ctggaatacc ctctgcccac cggctttatc    7500
ctgcagcaga aaatcatggc caccgacatg ctgcgggtgt ccacatgtct gatgggcgag    7560
atcaagatga gcctgcagat cgagacagac gtggtggacg agacagccat gatgggagcc    7620
gccgctccta attttgtgca cggacacgat gccagccacc tgatcctgac cgtgtgcgat    7680
ctggtggaca agggcatcac tagcgtggcc gtgatccacg atagctttgg aacacacgcc    7740
ggcagaaccg ccgacctgag agattctctg cgggaagaga tggtcaagat gtaccagaac    7800
cacaacgccc tgcagaacct gctggacgtg cacgaagaaa gatggctggt ggacaccggc    7860
atccaggtgc agaacaggg agagttcgac ctgaacgaga tcctggtgtc cgactactgc    7920
ttcgcctaa                                                             7929

<210> SEQ ID NO 13
<211> LENGTH: 2642
<212> TYPE: PRT
<213> ORGANISM: Artificial Sequence
<220> FEATURE:
<223> OTHER INFORMATION: Amino-acid sequence of C3P3-T3 chimeric enzyme
      consisting of fusion between African swine fever virus NP868R
      capping enzyme and phage T3-RNA polymerase

<400> SEQUENCE: 13

Met Glu Phe Ala Ser Leu Asp Asn Leu Val Ala Arg Tyr Gln Arg Cys
1               5                   10                  15

Phe Asn Asp Gln Ser Leu Lys Asn Ser Thr Ile Glu Leu Glu Ile Arg
            20                  25                  30

Phe Gln Gln Ile Asn Phe Leu Leu Phe Lys Thr Val Tyr Glu Ala Leu
        35                  40                  45

Val Ala Gln Glu Ile Pro Ser Thr Ile Ser His Ser Ile Arg Cys Ile
    50                  55                  60

Lys Lys Val His His Glu Asn His Cys Arg Glu Lys Ile Leu Pro Ser
65                  70                  75                  80

Glu Asn Leu Tyr Phe Lys Lys Gln Pro Leu Met Phe Phe Lys Phe Ser
                85                  90                  95

Glu Pro Ala Ser Leu Gly Cys Lys Val Ser Leu Ala Ile Glu Gln Pro
            100                 105                 110

Ile Arg Lys Phe Ile Leu Asp Ser Ser Val Leu Val Arg Leu Lys Asn
        115                 120                 125

Arg Thr Thr Phe Arg Val Ser Glu Leu Trp Lys Ile Glu Leu Thr Ile
    130                 135                 140

Val Lys Gln Leu Met Gly Ser Glu Val Ser Ala Lys Leu Ala Ala Phe
145                 150                 155                 160

Lys Thr Leu Leu Phe Asp Thr Pro Glu Gln Gln Thr Thr Lys Asn Met
```

```
                    165                 170                 175
Met Thr Leu Ile Asn Pro Asp Asp Glu Tyr Leu Tyr Glu Ile Glu Ile
                180                 185                 190
Glu Tyr Thr Gly Lys Pro Glu Ser Leu Thr Ala Ala Asp Val Ile Lys
                195                 200                 205
Ile Lys Asn Thr Val Leu Thr Leu Ile Ser Pro Asn His Leu Met Leu
210                 215                 220
Thr Ala Tyr His Gln Ala Ile Glu Phe Ile Ala Ser His Ile Leu Ser
225                 230                 235                 240
Ser Glu Ile Leu Leu Ala Arg Ile Lys Ser Gly Lys Trp Gly Leu Lys
                245                 250                 255
Arg Leu Leu Pro Gln Val Lys Ser Met Thr Lys Ala Asp Tyr Met Lys
                260                 265                 270
Phe Tyr Pro Pro Val Gly Tyr Tyr Val Thr Asp Lys Ala Asp Gly Ile
                275                 280                 285
Arg Gly Ile Ala Val Ile Gln Asp Thr Gln Ile Tyr Val Val Ala Asp
                290                 295                 300
Gln Leu Tyr Ser Leu Gly Thr Thr Gly Ile Glu Pro Leu Lys Pro Thr
305                 310                 315                 320
Ile Leu Asp Gly Glu Phe Met Pro Glu Lys Lys Glu Phe Tyr Gly Phe
                325                 330                 335
Asp Val Ile Met Tyr Glu Gly Asn Leu Leu Thr Gln Gln Gly Phe Glu
                340                 345                 350
Thr Arg Ile Glu Ser Leu Ser Lys Gly Ile Lys Val Leu Gln Ala Phe
                355                 360                 365
Asn Ile Lys Ala Glu Met Lys Pro Phe Ile Ser Leu Thr Ser Ala Asp
                370                 375                 380
Pro Asn Val Leu Leu Lys Asn Phe Glu Ser Ile Phe Lys Lys Lys Thr
385                 390                 395                 400
Arg Pro Tyr Ser Ile Asp Gly Ile Ile Leu Val Glu Pro Gly Asn Ser
                405                 410                 415
Tyr Leu Asn Thr Asn Thr Phe Lys Trp Lys Pro Thr Trp Asp Asn Thr
                420                 425                 430
Leu Asp Phe Leu Val Arg Lys Cys Pro Glu Ser Leu Asn Val Pro Glu
                435                 440                 445
Tyr Ala Pro Lys Lys Gly Phe Ser Leu His Leu Leu Phe Val Gly Ile
                450                 455                 460
Ser Gly Glu Leu Phe Lys Lys Leu Ala Leu Asn Trp Cys Pro Gly Tyr
465                 470                 475                 480
Thr Lys Leu Phe Pro Val Thr Gln Arg Asn Gln Asn Tyr Phe Pro Val
                485                 490                 495
Gln Phe Gln Pro Ser Asp Phe Pro Leu Ala Phe Leu Tyr Tyr His Pro
                500                 505                 510
Asp Thr Ser Ser Phe Ser Asn Ile Asp Gly Lys Val Leu Glu Met Arg
                515                 520                 525
Cys Leu Lys Arg Glu Ile Asn Tyr Val Arg Trp Glu Ile Val Lys Ile
                530                 535                 540
Arg Glu Asp Arg Gln Gln Asp Leu Lys Thr Gly Gly Tyr Phe Gly Asn
545                 550                 555                 560
Asp Phe Lys Thr Ala Glu Leu Thr Trp Leu Asn Tyr Met Asp Pro Phe
                565                 570                 575
Ser Phe Glu Glu Leu Ala Lys Gly Pro Ser Gly Met Tyr Phe Ala Gly
                580                 585                 590
```

```
Ala Lys Thr Gly Ile Tyr Arg Ala Gln Thr Ala Leu Ile Ser Phe Ile
        595                 600                 605

Lys Gln Glu Ile Ile Gln Lys Ile Ser His Gln Ser Trp Val Ile Asp
610                 615                 620

Leu Gly Ile Gly Lys Gly Gln Asp Leu Gly Arg Tyr Leu Asp Ala Gly
625                 630                 635                 640

Val Arg His Leu Val Gly Ile Asp Lys Asp Gln Thr Ala Leu Ala Glu
                645                 650                 655

Leu Val Tyr Arg Lys Phe Ser His Ala Thr Thr Arg Gln His Lys His
            660                 665                 670

Ala Thr Asn Ile Tyr Val Leu His Gln Asp Leu Ala Glu Pro Ala Lys
        675                 680                 685

Glu Ile Ser Glu Lys Val His Gln Ile Tyr Gly Phe Pro Lys Glu Gly
    690                 695                 700

Ala Ser Ser Ile Val Ser Asn Leu Phe Ile His Tyr Leu Met Lys Asn
705                 710                 715                 720

Thr Gln Gln Val Glu Asn Leu Ala Val Leu Cys His Lys Leu Leu Gln
                725                 730                 735

Pro Gly Gly Met Val Trp Phe Thr Thr Met Leu Gly Glu Gln Val Leu
            740                 745                 750

Glu Leu Leu His Glu Asn Arg Ile Glu Leu Asn Glu Val Trp Glu Ala
        755                 760                 765

Arg Glu Asn Glu Val Val Lys Phe Ala Ile Lys Arg Leu Phe Lys Glu
    770                 775                 780

Asp Ile Leu Gln Glu Thr Gly Gln Glu Ile Gly Val Leu Leu Pro Phe
785                 790                 795                 800

Ser Asn Gly Asp Phe Tyr Asn Glu Tyr Leu Val Asn Thr Ala Phe Leu
                805                 810                 815

Ile Lys Ile Phe Lys His His Gly Phe Ser Leu Val Gln Lys Gln Ser
            820                 825                 830

Phe Lys Asp Trp Ile Pro Glu Phe Gln Asn Phe Ser Lys Ser Leu Tyr
        835                 840                 845

Lys Ile Leu Thr Glu Ala Asp Lys Thr Trp Thr Ser Leu Phe Gly Phe
    850                 855                 860

Ile Cys Leu Arg Lys Asn Leu Glu Gly Gly Gly Ser Gly Gly Gly
865                 870                 875                 880

Gly Ser Val Glu Met Glu Phe Ala Ser Leu Asp Asn Leu Val Ala Arg
                885                 890                 895

Tyr Gln Arg Cys Phe Asn Asp Gln Ser Leu Lys Asn Ser Thr Ile Glu
            900                 905                 910

Leu Glu Ile Arg Phe Gln Gln Ile Asn Phe Leu Leu Phe Lys Thr Val
        915                 920                 925

Tyr Glu Ala Leu Val Ala Gln Glu Ile Pro Ser Thr Ile Ser His Ser
    930                 935                 940

Ile Arg Cys Ile Lys Lys Val His His Glu Asn His Cys Arg Glu Lys
945                 950                 955                 960

Ile Leu Pro Ser Glu Asn Leu Tyr Phe Lys Lys Gln Pro Leu Met Phe
                965                 970                 975

Phe Lys Phe Ser Glu Pro Ala Ser Leu Gly Cys Lys Val Ser Leu Ala
            980                 985                 990

Ile Glu Gln Pro Ile Arg Lys Phe Ile Leu Asp Ser Ser Val Leu Val
        995                 1000                1005
```

| | | | | | | | | | | | | |
|---|---|---|---|---|---|---|---|---|---|---|---|---|
| Arg | Leu | Lys | Asn | Arg | Thr | Thr | Phe | Arg | Val | Ser | Glu | Leu | Trp | Lys |
| 1010 | | | | | 1015 | | | | | 1020 | | | | |
| Ile | Glu | Leu | Thr | Ile | Val | Lys | Gln | Leu | Met | Gly | Ser | Glu | Val | Ser |
| 1025 | | | | | 1030 | | | | | 1035 | | | | |
| Ala | Lys | Leu | Ala | Ala | Phe | Lys | Thr | Leu | Leu | Phe | Asp | Thr | Pro | Glu |
| 1040 | | | | | 1045 | | | | | 1050 | | | | |
| Gln | Gln | Thr | Thr | Lys | Asn | Met | Met | Thr | Leu | Ile | Asn | Pro | Asp | Asp |
| 1055 | | | | | 1060 | | | | | 1065 | | | | |
| Glu | Tyr | Leu | Tyr | Glu | Ile | Ile | Glu | Tyr | Thr | Gly | Lys | Pro | Glu |
| 1070 | | | | | 1075 | | | | | 1080 | | | | |
| Ser | Leu | Thr | Ala | Ala | Asp | Val | Ile | Lys | Ile | Lys | Asn | Thr | Val | Leu |
| 1085 | | | | | 1090 | | | | | 1095 | | | | |
| Thr | Leu | Ile | Ser | Pro | Asn | His | Leu | Met | Leu | Thr | Ala | Tyr | His | Gln |
| 1100 | | | | | 1105 | | | | | 1110 | | | | |
| Ala | Ile | Glu | Phe | Ile | Ala | Ser | His | Ile | Leu | Ser | Ser | Glu | Ile | Leu |
| 1115 | | | | | 1120 | | | | | 1125 | | | | |
| Leu | Ala | Arg | Ile | Lys | Ser | Gly | Lys | Trp | Gly | Leu | Lys | Arg | Leu | Leu |
| 1130 | | | | | 1135 | | | | | 1140 | | | | |
| Pro | Gln | Val | Lys | Ser | Met | Thr | Lys | Ala | Asp | Tyr | Met | Lys | Phe | Tyr |
| 1145 | | | | | 1150 | | | | | 1155 | | | | |
| Pro | Pro | Val | Gly | Tyr | Tyr | Val | Thr | Asp | Lys | Ala | Asp | Gly | Ile | Arg |
| 1160 | | | | | 1165 | | | | | 1170 | | | | |
| Gly | Ile | Ala | Val | Ile | Gln | Asp | Thr | Gln | Ile | Tyr | Val | Val | Ala | Asp |
| 1175 | | | | | 1180 | | | | | 1185 | | | | |
| Gln | Leu | Tyr | Ser | Leu | Gly | Thr | Gly | Ile | Glu | Pro | Leu | Lys | Pro |
| 1190 | | | | | 1195 | | | | | 1200 | | | | |
| Thr | Ile | Leu | Asp | Gly | Glu | Phe | Met | Pro | Glu | Lys | Lys | Glu | Phe | Tyr |
| 1205 | | | | | 1210 | | | | | 1215 | | | | |
| Gly | Phe | Asp | Val | Ile | Met | Tyr | Glu | Gly | Asn | Leu | Leu | Thr | Gln | Gln |
| 1220 | | | | | 1225 | | | | | 1230 | | | | |
| Gly | Phe | Glu | Thr | Arg | Ile | Glu | Ser | Leu | Ser | Lys | Gly | Ile | Lys | Val |
| 1235 | | | | | 1240 | | | | | 1245 | | | | |
| Leu | Gln | Ala | Phe | Asn | Ile | Lys | Ala | Glu | Met | Lys | Pro | Phe | Ile | Ser |
| 1250 | | | | | 1255 | | | | | 1260 | | | | |
| Leu | Thr | Ser | Ala | Asp | Pro | Asn | Val | Leu | Leu | Lys | Asn | Phe | Glu | Ser |
| 1265 | | | | | 1270 | | | | | 1275 | | | | |
| Ile | Phe | Lys | Lys | Lys | Thr | Arg | Pro | Tyr | Ser | Ile | Asp | Gly | Ile | Ile |
| 1280 | | | | | 1285 | | | | | 1290 | | | | |
| Leu | Val | Glu | Pro | Gly | Asn | Ser | Tyr | Leu | Asn | Thr | Asn | Thr | Phe | Lys |
| 1295 | | | | | 1300 | | | | | 1305 | | | | |
| Trp | Lys | Pro | Thr | Trp | Asp | Asn | Thr | Leu | Asp | Phe | Leu | Val | Arg | Lys |
| 1310 | | | | | 1315 | | | | | 1320 | | | | |
| Cys | Pro | Glu | Ser | Leu | Asn | Val | Pro | Glu | Tyr | Ala | Pro | Lys | Lys | Gly |
| 1325 | | | | | 1330 | | | | | 1335 | | | | |
| Phe | Ser | Leu | His | Leu | Leu | Phe | Val | Gly | Ile | Ser | Gly | Glu | Leu | Phe |
| 1340 | | | | | 1345 | | | | | 1350 | | | | |
| Lys | Lys | Leu | Ala | Leu | Asn | Trp | Cys | Pro | Gly | Tyr | Thr | Lys | Leu | Phe |
| 1355 | | | | | 1360 | | | | | 1365 | | | | |
| Pro | Val | Thr | Gln | Arg | Asn | Gln | Asn | Tyr | Phe | Pro | Val | Gln | Phe | Gln |
| 1370 | | | | | 1375 | | | | | 1380 | | | | |
| Pro | Ser | Asp | Phe | Pro | Leu | Ala | Phe | Leu | Tyr | Tyr | His | Pro | Asp | Thr |
| 1385 | | | | | 1390 | | | | | 1395 | | | | |
| Ser | Ser | Phe | Ser | Asn | Ile | Asp | Gly | Lys | Val | Leu | Glu | Met | Arg | Cys |

```
                    1400              1405              1410
Leu Lys Arg Glu Ile Asn Tyr Val Arg Trp Glu Ile Val Lys Ile
    1415              1420              1425

Arg Glu Asp Arg Gln Gln Asp Leu Lys Thr Gly Gly Tyr Phe Gly
    1430              1435              1440

Asn Asp Phe Lys Thr Ala Glu Leu Thr Trp Leu Asn Tyr Met Asp
    1445              1450              1455

Pro Phe Ser Phe Glu Glu Leu Ala Lys Gly Pro Ser Gly Met Tyr
    1460              1465              1470

Phe Ala Gly Ala Lys Thr Gly Ile Tyr Arg Ala Gln Thr Ala Leu
    1475              1480              1485

Ile Ser Phe Ile Lys Gln Glu Ile Ile Gln Lys Ile Ser His Gln
    1490              1495              1500

Ser Trp Val Ile Asp Leu Gly Ile Gly Lys Gly Gln Asp Leu Gly
    1505              1510              1515

Arg Tyr Leu Asp Ala Gly Val Arg His Leu Val Gly Ile Asp Lys
    1520              1525              1530

Asp Gln Thr Ala Leu Ala Glu Leu Val Tyr Arg Lys Phe Ser His
    1535              1540              1545

Ala Thr Thr Arg Gln His Lys His Ala Thr Asn Ile Tyr Val Leu
    1550              1555              1560

His Gln Asp Leu Ala Glu Pro Ala Lys Glu Ile Ser Glu Lys Val
    1565              1570              1575

His Gln Ile Tyr Gly Phe Pro Lys Glu Gly Ala Ser Ser Ile Val
    1580              1585              1590

Ser Asn Leu Phe Ile His Tyr Leu Met Lys Asn Thr Gln Gln Val
    1595              1600              1605

Glu Asn Leu Ala Val Leu Cys His Lys Leu Leu Gln Pro Gly Gly
    1610              1615              1620

Met Val Trp Phe Thr Thr Met Leu Gly Glu Gln Val Leu Glu Leu
    1625              1630              1635

Leu His Glu Asn Arg Ile Glu Leu Asn Glu Val Trp Glu Ala Arg
    1640              1645              1650

Glu Asn Glu Val Val Lys Phe Ala Ile Lys Arg Leu Phe Lys Glu
    1655              1660              1665

Asp Ile Leu Gln Glu Thr Gly Gln Glu Ile Gly Val Leu Leu Pro
    1670              1675              1680

Phe Ser Asn Gly Asp Phe Tyr Asn Glu Tyr Leu Val Asn Thr Ala
    1685              1690              1695

Phe Leu Ile Lys Ile Phe Lys His His Gly Phe Ser Leu Val Gln
    1700              1705              1710

Lys Gln Ser Phe Lys Asp Trp Ile Pro Glu Phe Gln Asn Phe Ser
    1715              1720              1725

Lys Ser Leu Tyr Lys Ile Leu Thr Glu Ala Asp Lys Thr Trp Thr
    1730              1735              1740

Ser Leu Phe Gly Phe Ile Cys Leu Arg Lys Asn Leu Glu Gly Gly
    1745              1750              1755

Gly Gly Ser Gly Gly Gly Ser Val Glu Gln Asp Leu His Ala
    1760              1765              1770

Ile Gln Leu Gln Leu Glu Glu Glu Met Phe Asn Gly Gly Ile Arg
    1775              1780              1785

Arg Phe Glu Ala Asp Gln Gln Arg Gln Ile Ala Ser Gly Asn Glu
    1790              1795              1800
```

Ser Asp Thr Ala Trp Asn Arg Arg Leu Leu Ser Glu Leu Ile Ala
1805                1810                1815

Pro Met Ala Glu Gly Ile Gln Ala Tyr Lys Glu Glu Tyr Glu Gly
1820                1825                1830

Lys Arg Gly Arg Ala Pro Arg Ala Leu Ala Phe Ile Asn Cys Val
1835                1840                1845

Gly Asn Glu Val Ala Ala Tyr Ile Thr Met Lys Ile Val Met Asp
1850                1855                1860

Met Leu Asn Thr Asp Val Thr Leu Gln Ala Ile Ala Met Asn Val
1865                1870                1875

Ala Asp Arg Ile Glu Asp Gln Val Arg Phe Ser Lys Leu Glu Gly
1880                1885                1890

His Ala Ala Lys Tyr Phe Glu Lys Val Lys Lys Ser Leu Lys Ala
1895                1900                1905

Ser Lys Thr Lys Ser Tyr Arg His Ala His Asn Val Ala Val Val
1910                1915                1920

Ala Glu Lys Ser Val Ala Asp Arg Asp Ala Asp Phe Ser Arg Trp
1925                1930                1935

Glu Ala Trp Pro Lys Asp Thr Leu Leu Gln Ile Gly Met Thr Leu
1940                1945                1950

Leu Glu Ile Leu Glu Asn Ser Val Phe Phe Asn Gly Gln Pro Val
1955                1960                1965

Phe Leu Arg Thr Leu Arg Thr Asn Gly Gly Lys His Gly Val Tyr
1970                1975                1980

Tyr Leu Gln Thr Ser Glu His Val Gly Glu Trp Ile Thr Ala Phe
1985                1990                1995

Lys Glu His Val Ala Gln Leu Ser Pro Ala Tyr Ala Pro Cys Val
2000                2005                2010

Ile Pro Pro Arg Pro Trp Val Ser Pro Phe Asn Gly Gly Phe His
2015                2020                2025

Thr Glu Lys Val Ala Ser Arg Ile Arg Leu Val Lys Gly Asn Arg
2030                2035                2040

Glu His Val Arg Lys Leu Thr Lys Lys Gln Met Pro Ala Val Tyr
2045                2050                2055

Lys Ala Val Asn Ala Leu Gln Ala Thr Lys Trp Gln Val Asn Lys
2060                2065                2070

Glu Val Leu Gln Val Val Glu Asp Val Ile Arg Leu Asp Leu Gly
2075                2080                2085

Tyr Gly Val Pro Ser Phe Lys Pro Leu Ile Asp Arg Glu Asn Lys
2090                2095                2100

Pro Ala Asn Pro Val Pro Leu Glu Phe Gln His Leu Arg Gly Arg
2105                2110                2115

Glu Leu Lys Glu Met Leu Thr Pro Glu Gln Trp Gln Ala Phe Ile
2120                2125                2130

Asn Trp Lys Gly Glu Cys Thr Lys Leu Tyr Thr Ala Glu Thr Lys
2135                2140                2145

Arg Gly Ser Lys Ser Ala Ala Thr Val Arg Met Val Gly Gln Ala
2150                2155                2160

Arg Lys Tyr Ser Gln Phe Asp Ala Ile Tyr Phe Val Tyr Ala Leu
2165                2170                2175

Asp Ser Arg Ser Arg Val Tyr Ala Gln Ser Ser Thr Leu Ser Pro
2180                2185                2190

```
Gln Ser Asn Asp Leu Gly Lys Ala Leu Leu Arg Phe Thr Glu Gly
    2195                2200                2205

Gln Arg Leu Asp Ser Ala Glu Ala Leu Lys Trp Phe Leu Val Asn
    2210                2215                2220

Gly Ala Asn Asn Trp Gly Trp Asp Lys Lys Thr Phe Asp Val Arg
    2225                2230                2235

Thr Ala Asn Val Leu Asp Ser Glu Phe Gln Asp Met Cys Arg Asp
    2240                2245                2250

Ile Ala Ala Asp Pro Leu Thr Phe Thr Gln Trp Val Asn Ala Asp
    2255                2260                2265

Ser Pro Tyr Gly Phe Leu Ala Trp Cys Phe Glu Tyr Ala Arg Tyr
    2270                2275                2280

Leu Asp Ala Leu Asp Glu Gly Thr Gln Asp Gln Phe Met Thr His
    2285                2290                2295

Leu Pro Val His Gln Asp Gly Ser Cys Ser Gly Ile Gln His Tyr
    2300                2305                2310

Ser Ala Met Leu Ser Asp Ala Val Gly Ala Lys Ala Val Asn Leu
    2315                2320                2325

Lys Pro Ser Asp Ser Pro Gln Asp Ile Tyr Gly Ala Val Ala Gln
    2330                2335                2340

Val Val Ile Gln Lys Asn Tyr Ala Tyr Met Asn Ala Glu Asp Ala
    2345                2350                2355

Glu Thr Phe Thr Ser Gly Ser Val Thr Leu Thr Gly Ala Glu Leu
    2360                2365                2370

Arg Ser Met Ala Ser Ala Trp Asp Met Ile Gly Ile Thr Arg Gly
    2375                2380                2385

Leu Thr Lys Lys Pro Val Met Thr Leu Pro Tyr Gly Ser Thr Arg
    2390                2395                2400

Leu Thr Cys Arg Glu Ser Val Ile Asp Tyr Ile Val Asp Leu Glu
    2405                2410                2415

Glu Lys Glu Ala Gln Arg Ala Ile Ala Glu Gly Arg Thr Ala Asn
    2420                2425                2430

Pro Val His Pro Phe Asp Asn Asp Arg Lys Asp Ser Leu Thr Pro
    2435                2440                2445

Ser Ala Ala Tyr Asn Tyr Met Thr Ala Leu Ile Trp Pro Ser Ile
    2450                2455                2460

Ser Glu Val Val Lys Ala Pro Ile Val Ala Met Lys Met Ile Arg
    2465                2470                2475

Gln Leu Ala Arg Phe Ala Ala Lys Arg Asn Glu Gly Leu Glu Tyr
    2480                2485                2490

Pro Leu Pro Thr Gly Phe Ile Leu Gln Gln Lys Ile Met Ala Thr
    2495                2500                2505

Asp Met Leu Arg Val Ser Thr Cys Leu Met Gly Glu Ile Lys Met
    2510                2515                2520

Ser Leu Gln Ile Glu Thr Asp Val Val Asp Glu Thr Ala Met Met
    2525                2530                2535

Gly Ala Ala Ala Pro Asn Phe Val His Gly His Asp Ala Ser His
    2540                2545                2550

Leu Ile Leu Thr Val Cys Asp Leu Val Asp Lys Gly Ile Thr Ser
    2555                2560                2565

Val Ala Val Ile His Asp Ser Phe Gly Thr His Ala Gly Arg Thr
    2570                2575                2580

Ala Asp Leu Arg Asp Ser Leu Arg Glu Glu Met Val Lys Met Tyr
```

| | | | |
|---|---|---|---|
| | 2585 | 2590 | 2595 |

Gln Asn His Asn Ala Leu Gln Asn Leu Leu Asp Val His Glu Glu
    2600                  2605                  2610

Arg Trp Leu Val Asp Thr Gly Ile Gln Val Pro Glu Gln Gly Glu
    2615                  2620                  2625

Phe Asp Leu Asn Glu Ile Leu Val Ser Asp Tyr Cys Phe Ala
    2630                  2635                  2640

<210> SEQ ID NO 14
<211> LENGTH: 1578
<212> TYPE: DNA
<213> ORGANISM: Saccharomyces cerevisiae

<400> SEQUENCE: 14

| | |
|---|---|
| atgagtagtc agaaggtgtt tggcatcact ggaccagtaa gtacggtcgg tgctactgcc | 60 |
| gctgaaaaca agctgaatga ttcttaatc caggagctga aaaggaagg ctcatttgaa | 120 |
| actgaacagg agaccgccaa tagggtccaa gtgctgaaaa ttctgcaaga actggctcag | 180 |
| cgcttcgttt acgaggttag taagaaaaag aatatgagcg acggcatggc ccgcgacgca | 240 |
| ggaggcaaaa ttttcaccta tggtagctat agactggggg tccatggtcc cggaagcgac | 300 |
| atcgataccttagtcgtggt tcctaagcac gttacccgcg aggacttctt cacagtgttc | 360 |
| gactcactac tgagggaaag aaaagaatta atgaaatcg cgcccgtgcc tgatgcgttt | 420 |
| gtgcccatta tcaagattaa gttctcaggc attagtattg atctgatatg cgcacgtctc | 480 |
| gatcagccac aggttccact gagcctgacc ttgagcgata aaaacctgtt aaggaaccta | 540 |
| gacgaaaagg accttagggc actgaatggt actagagtga ctgatgagat actggagcta | 600 |
| gtccccaagc ccaatgtttt caggatagcc ctccgcgcta tcaagctctg gcacagaga | 660 |
| cgggcggtat acgctaatat atttggcttc cccggaggcg tcgcctgggc aatgctagtc | 720 |
| gctcgaattt gtcagctcta ccccaatgcc tgctcggcgg tcattctgaa tcgtttcttt | 780 |
| ataatcctgt cagaatggaa ttggccccaa cctgtgattc tcaagcctat tgaggatggc | 840 |
| ccactgcaag tgagagtctg gaaccctaaa atatacgccc aggacagatc ccatcggatg | 900 |
| cccgttatca cccctgctta cccttccatg tgcgctacac acaatattac ggaatccact | 960 |
| aaaaaagtga tattgcagga atttgtgaga ggtgtgcaaa tcaccaacga catctttcc | 1020 |
| aacaaaaat cttgggcaaa cctttttgag aagaatgact ttttcttcg ctacaagttt | 1080 |
| tatctggaaa tcaccgctta tacacgcggg tccgacgagc agcatctcaa atggtctggc | 1140 |
| ctggtagagt ctaaggtccg cttgttagtg atgaaactcg aggtgctagc tggcattaag | 1200 |
| atcgcccatc cctttaccaa gcccttgag tcttcctact gctgcccgac tgaggacgat | 1260 |
| tatgagatga tccaagacaa gtacggttcc cataaaactg aaacagctct gaacgccctg | 1320 |
| aaactcgtta ccgatgaaaa caagaggaa gaatcaatta aggatgctcc caaggcgtac | 1380 |
| ctcagcacta tgtacatcgg gctcgacttc aatatcgaga ataagaagga gaaggtcgac | 1440 |
| atccatatcc cctgtaccga gttcgtgaac ctctgtcgga gctttaatga ggactacggg | 1500 |
| gatcacaagg tgttcaatct ggccctccgg ttcgtcaaag gatacgatct gcccgacgag | 1560 |
| gtattcgacg aaaatgag | 1578 |

<210> SEQ ID NO 15
<211> LENGTH: 526
<212> TYPE: PRT
<213> ORGANISM: Saccharomyces cerevisiae

```
<400> SEQUENCE: 15

Met Ser Ser Gln Lys Val Phe Gly Ile Thr Gly Pro Val Ser Thr Val
1               5                   10                  15

Gly Ala Thr Ala Ala Glu Asn Lys Leu Asn Asp Ser Leu Ile Gln Glu
            20                  25                  30

Leu Lys Lys Glu Gly Ser Phe Glu Thr Glu Gln Glu Thr Ala Asn Arg
        35                  40                  45

Val Gln Val Leu Lys Ile Leu Gln Glu Leu Ala Gln Arg Phe Val Tyr
    50                  55                  60

Glu Val Ser Lys Lys Lys Asn Met Ser Asp Gly Met Ala Arg Asp Ala
65                  70                  75                  80

Gly Gly Lys Ile Phe Thr Tyr Gly Ser Tyr Arg Leu Gly Val His Gly
                85                  90                  95

Pro Gly Ser Asp Ile Asp Thr Leu Val Val Pro Lys His Val Thr
            100                 105                 110

Arg Glu Asp Phe Phe Thr Val Phe Asp Ser Leu Leu Arg Glu Arg Lys
        115                 120                 125

Glu Leu Asp Glu Ile Ala Pro Val Pro Asp Ala Phe Val Pro Ile Ile
    130                 135                 140

Lys Ile Lys Phe Ser Gly Ile Ser Ile Asp Leu Ile Cys Ala Arg Leu
145                 150                 155                 160

Asp Gln Pro Gln Val Pro Leu Ser Leu Thr Leu Ser Asp Lys Asn Leu
                165                 170                 175

Leu Arg Asn Leu Asp Glu Lys Asp Leu Arg Ala Leu Asn Gly Thr Arg
            180                 185                 190

Val Thr Asp Glu Ile Leu Glu Leu Val Pro Lys Pro Asn Val Phe Arg
        195                 200                 205

Ile Ala Leu Arg Ala Ile Lys Leu Trp Ala Gln Arg Arg Ala Val Tyr
    210                 215                 220

Ala Asn Ile Phe Gly Phe Pro Gly Gly Val Ala Trp Ala Met Leu Val
225                 230                 235                 240

Ala Arg Ile Cys Gln Leu Tyr Pro Asn Ala Cys Ser Ala Val Ile Leu
                245                 250                 255

Asn Arg Phe Phe Ile Ile Leu Ser Glu Trp Asn Trp Pro Gln Pro Val
            260                 265                 270

Ile Leu Lys Pro Ile Glu Asp Gly Pro Leu Gln Val Arg Val Trp Asn
        275                 280                 285

Pro Lys Ile Tyr Ala Gln Asp Arg Ser His Arg Met Pro Val Ile Thr
    290                 295                 300

Pro Ala Tyr Pro Ser Met Cys Ala Thr His Asn Ile Thr Glu Ser Thr
305                 310                 315                 320

Lys Lys Val Ile Leu Gln Glu Phe Val Arg Gly Val Gln Ile Thr Asn
                325                 330                 335

Asp Ile Phe Ser Asn Lys Lys Ser Trp Ala Asn Leu Phe Glu Lys Asn
            340                 345                 350

Asp Phe Phe Phe Arg Tyr Lys Phe Tyr Leu Glu Ile Thr Ala Tyr Thr
        355                 360                 365

Arg Gly Ser Asp Glu Gln His Leu Lys Trp Ser Gly Leu Val Glu Ser
    370                 375                 380

Lys Val Arg Leu Leu Val Met Lys Leu Glu Val Leu Ala Gly Ile Lys
385                 390                 395                 400

Ile Ala His Pro Phe Thr Lys Pro Phe Glu Ser Ser Tyr Cys Cys Pro
                405                 410                 415
```

| | | | | | | | | | | | | |
|---|---|---|---|---|---|---|---|---|---|---|---|---|
|Thr|Glu|Asp|Asp|Tyr|Glu|Met|Ile|Gln|Asp|Lys|Tyr|Gly|Ser|His|Lys|
| | | |420| | |425| | | |430| | | | | |

Thr Glu Thr Ala Leu Asn Ala Leu Lys Leu Val Thr Asp Glu Asn Lys
            435                 440                 445

Glu Glu Glu Ser Ile Lys Asp Ala Pro Lys Ala Tyr Leu Ser Thr Met
450                 455                 460

Tyr Ile Gly Leu Asp Phe Asn Ile Glu Asn Lys Lys Glu Lys Val Asp
465                 470                 475                 480

Ile His Ile Pro Cys Thr Glu Phe Val Asn Leu Cys Arg Ser Phe Asn
                485                 490                 495

Glu Asp Tyr Gly Asp His Lys Val Phe Asn Leu Ala Leu Arg Phe Val
            500                 505                 510

Lys Gly Tyr Asp Leu Pro Asp Glu Val Phe Asp Glu Asn Glu
            515                 520                 525

<210> SEQ ID NO 16
<211> LENGTH: 1932
<212> TYPE: DNA
<213> ORGANISM: Mus musculus

<400> SEQUENCE: 16

```
atgcctttcg cagtcacaac ccagggagcc agcagccag ccccagcacc taaacaattc      60
ggaatctcca gcccgatttc tttagctgcc cccaaagaca ccgatagaga attaacacag     120
aagctgattg aaactttgca gcccttggc gtcttcgagg aagaggagga gcttcaacgc     180
cgaatcttaa ttctgcagaa gttgaataac ctggtcaagg agtggatccg ggaaatatcc     240
gagtctagaa atctacctca ggcggtgatc gaaaacgtgg aggcaaaat attcactttc     300
ggctcttacc gctgggggt gcacacaaaa ggggcagaca ttgacgccct ttgcgtggct     360
cctaggcatg tcgatcggaa cgacttcttt actagtttct atgataaact taaacttcaa     420
gaggaggtga agatctgcg ggcggtggaa gaggcgttcg tacctgttat caaactctgt     480
tttgacggga tcgagattga catccttttc gcccgactcg cattgcagac aatacctgag     540
gatcttgatc tgcgtgatga ttcactgtta aaaaatctgg atattaggtg cattcgcagc     600
ctgaatggat gtcgggttac agacgagatt ttgcacctgg tccctaacat cgattctttt     660
cgactgaccc ttagggctat caaactatgg gctaaatgtc ataatatcta tagcaatata     720
ctgggctttc ttggaggcgt cagctgggcc atgctggtcg ctagaacttg tcagctctat     780
cccaacgcca tcgcatctac tcttgtccgt aaattcttc tggtgttttc cgaatgggag     840
tggcctaatc cggtgctcct caaagagcca gaagagcgta accttaacct gccggtctgg     900
gaccccgtg taaatccttc cgataggtat cacctgatgc cgataattac ccctgcgtac     960
ccccagcaga acagtactta aacgtcagt gtgtctacaa ggatggtgat gatcgaggaa    1020
tttaagcaag gcctggctat cacgcacgag attctactta ataaggccga gtggtccaag    1080
ctgttcgagg cccctagttt ctttcagaag tataagcact acatcgtcct tttggcatct    1140
gcacccacag aaaagcaaca cctggaatgg gttgggctgg ttgagagcaa gattcgcatt    1200
ctggttggga gcttggagaa aaatgagttc attaccctgg ctcacgttaa ccccagtcc     1260
tttcccgccc caaggagac cgccgacaag gaggagtttc gtacgatgtg ggtgataggt    1320
ctcgtgctga aaaacccga gaacagcgag attctttcca tagacctgac ctatgacatc    1380
caaagtttca ccgacaccgt gtacagacag gcaataaact cgaaaatgtt tgagatggat    1440
atgaagattg ccgccatgca ccttagaaga aaggagctgc atcagctgct gcctaaccat    1500
```

```
gtactgcaga agaaagaaac ccacctgacc gagtccgtgc gactgaccgc cgtcaccgat    1560
agttccctgc ttctgtccat cgacagcgag aactcgatga ccgctccgtc accaacagga    1620
accatgaaaa ccgggcctct gacaggcaat ccacagggac gtaacagtcc cgctttggcc    1680
gttatggccg cgtcggtgac taacattcag ttccctgatg tgtctctgca acatgtaaat    1740
ccaatcgaaa gctctggcat cgccctgtct gagagcatac ctcaaatacc tagtcagcct    1800
acaatatccc ccccacccaa gcctactatg accagagtgg tgagttctac tcacttagtg    1860
aatcacccat cgagaccctc cggcaacacc gctacaaaca tccccaaccc cattctgggc    1920
gtcgggccct aa                                                        1932
```

<210> SEQ ID NO 17
<211> LENGTH: 641
<212> TYPE: PRT
<213> ORGANISM: Mus musculus
<400> SEQUENCE: 17

```
Met Pro Phe Ala Val Thr Thr Gln Gly Ala Gln Gln Pro Ala Pro Ala
1               5                   10                  15

Pro Lys Gln Phe Gly Ile Ser Ser Pro Ile Ser Leu Ala Ala Pro Lys
            20                  25                  30

Asp Thr Asp Arg Glu Leu Thr Gln Lys Leu Ile Glu Thr Leu Gln Pro
        35                  40                  45

Phe Gly Val Phe Glu Glu Glu Glu Leu Gln Arg Arg Ile Leu Ile
    50                  55                  60

Leu Gln Lys Leu Asn Asn Leu Val Lys Glu Trp Ile Arg Glu Ile Ser
65                  70                  75                  80

Glu Ser Arg Asn Leu Pro Gln Ala Val Ile Glu Asn Val Gly Gly Lys
                85                  90                  95

Ile Phe Thr Phe Gly Ser Tyr Arg Leu Gly Val His Thr Lys Gly Ala
            100                 105                 110

Asp Ile Asp Ala Leu Cys Val Ala Pro Arg His Val Asp Arg Asn Asp
        115                 120                 125

Phe Phe Thr Ser Phe Tyr Asp Lys Leu Lys Leu Gln Glu Glu Val Lys
    130                 135                 140

Asp Leu Arg Ala Val Glu Glu Ala Phe Val Pro Val Ile Lys Leu Cys
145                 150                 155                 160

Phe Asp Gly Ile Glu Ile Asp Ile Leu Phe Ala Arg Leu Ala Leu Gln
                165                 170                 175

Thr Ile Pro Glu Asp Leu Asp Leu Arg Asp Asp Ser Leu Leu Lys Asn
            180                 185                 190

Leu Asp Ile Arg Cys Ile Arg Ser Leu Asn Gly Cys Arg Val Thr Asp
        195                 200                 205

Glu Ile Leu His Leu Val Pro Asn Ile Asp Ser Phe Arg Leu Thr Leu
    210                 215                 220

Arg Ala Ile Lys Leu Trp Ala Lys Cys His Asn Ile Tyr Ser Asn Ile
225                 230                 235                 240

Leu Gly Phe Leu Gly Gly Val Ser Trp Ala Met Leu Val Ala Arg Thr
                245                 250                 255

Cys Gln Leu Tyr Pro Asn Ala Ile Ala Ser Thr Leu Val Arg Lys Phe
            260                 265                 270

Phe Leu Val Phe Ser Glu Trp Glu Trp Pro Asn Pro Val Leu Leu Lys
        275                 280                 285
```

Glu Pro Glu Glu Arg Asn Leu Asn Leu Pro Val Trp Asp Pro Arg Val
290                 295                 300

Asn Pro Ser Asp Arg Tyr His Leu Met Pro Ile Ile Thr Pro Ala Tyr
305                 310                 315                 320

Pro Gln Gln Asn Ser Thr Tyr Asn Val Ser Val Ser Thr Arg Met Val
            325                 330                 335

Met Ile Glu Glu Phe Lys Gln Gly Leu Ala Ile Thr His Glu Ile Leu
        340                 345                 350

Leu Asn Lys Ala Glu Trp Ser Lys Leu Phe Glu Ala Pro Ser Phe Phe
    355                 360                 365

Gln Lys Tyr Lys His Tyr Ile Val Leu Leu Ala Ser Ala Pro Thr Glu
370                 375                 380

Lys Gln His Leu Glu Trp Val Gly Leu Val Glu Ser Lys Ile Arg Ile
385                 390                 395                 400

Leu Val Gly Ser Leu Glu Lys Asn Glu Phe Ile Thr Leu Ala His Val
                405                 410                 415

Asn Pro Gln Ser Phe Pro Ala Pro Lys Glu Thr Ala Asp Lys Glu Glu
            420                 425                 430

Phe Arg Thr Met Trp Val Ile Gly Leu Val Leu Lys Lys Pro Glu Asn
        435                 440                 445

Ser Glu Ile Leu Ser Ile Asp Leu Thr Tyr Asp Ile Gln Ser Phe Thr
450                 455                 460

Asp Thr Val Tyr Arg Gln Ala Ile Asn Ser Lys Met Phe Glu Met Asp
465                 470                 475                 480

Met Lys Ile Ala Ala Met His Leu Arg Arg Lys Glu Leu His Gln Leu
                485                 490                 495

Leu Pro Asn His Val Leu Gln Lys Lys Glu Thr His Leu Thr Glu Ser
            500                 505                 510

Val Arg Leu Thr Ala Val Thr Asp Ser Ser Leu Leu Leu Ser Ile Asp
        515                 520                 525

Ser Glu Asn Ser Met Thr Ala Pro Ser Pro Thr Gly Thr Met Lys Thr
530                 535                 540

Gly Pro Leu Thr Gly Asn Pro Gln Gly Arg Asn Ser Pro Ala Leu Ala
545                 550                 555                 560

Val Met Ala Ala Ser Val Thr Asn Ile Gln Phe Pro Asp Val Ser Leu
                565                 570                 575

Gln His Val Asn Pro Ile Glu Ser Ser Gly Ile Ala Leu Ser Glu Ser
            580                 585                 590

Ile Pro Gln Ile Pro Ser Gln Pro Thr Ile Ser Pro Pro Lys Pro
        595                 600                 605

Thr Met Thr Arg Val Val Ser Ser Thr His Leu Val Asn His Pro Ser
610                 615                 620

Arg Pro Ser Gly Asn Thr Ala Thr Asn Ile Pro Asn Pro Ile Leu Gly
625                 630                 635                 640

Val

<210> SEQ ID NO 18
<211> LENGTH: 1365
<212> TYPE: DNA
<213> ORGANISM: Escherichia coli

<400> SEQUENCE: 18
aaggttttgt cgagagaaga gtccgaggct gagcaggcgg tcgcccgacc tcaagtgaca    60
gtgattccga gggagcaaca tgcgatcagc cgcaaagata tctccgaaaa cgctctgaaa   120

```
gtgatgtata ggctcaataa agccggatac gaagcctggc ttgttggcgg cggtgtgcgc        180
gatctcctcc tgggaaagaa acccaaagat tttgacgtaa ccacaaacgc taccccagag        240
caggtgagaa aactgttccg aaattgccgt cttgtgggac gcagatttag actcgctcac        300
gtcatgttcg gcccagagat cattgaggtg gctactttta ggggtcatca tgagggcaat        360
gtttcggacc gaacgacttc acaacgaggg cagaacggta tgctcctccg ggataatatt        420
ttcggttcca tcgaggagga cgcccaacgg cgcgacttta ccattaacag cctgtactac        480
agcgtcgccg actttactgt cagggactat gtcggggca tgaaagacct gaaggacggc        540
gtgatccgcc taattggtaa tcctgagact cggtatagag aggacccagt gcgtatgttg        600
agggctgtga ggttcgcagc aaagcttggt atgagaattt ccccagagac agctgagccc        660
attcctcgac tagcgacact gctgaacgac ataccacctg cccgattgtt tgaagaatcg        720
ttgaagctgc tacaggccgg gtatggctat gagacataca agctgctctg cgaataccac        780
ctgttccaac cgttgttccc aacaatcact agatacttta ccgagaatgg ggactctcca        840
atggagcgga ttatcgagca ggtgctgaag aacactgaca cacgtattca caatgacatg        900
cgcgtgaatc cagccttcct attcgccgcc atgtttttggt atcctttact agaaacagcc        960
cagaagatcg cccaggagag cggtctgacc taccatgatg catttgccct cgcaatgaac       1020
gacgtgcttg acgaggcatg cagatccctg gccatcccta acgtttgac tacactgaca       1080 agagacatct ggcaattgca attacggatg agtcgaagac aaggcaaacg cgcttggaag       1140
cttctggaac atcctaaatt tcgggccgcc tacgacctgt tagccttaag ggcagaagtc       1200
gaacgaaacg ctgagttaca gaggcttgtc aaatggtggg gtgaatttca ggtgtcagcc       1260
ccccctgatc agaagggat gctaaacgag ctagatgaag aaccatcacc gcggcggaga       1320
acgcgtcgcc ctagaaaacg ggcgccaagg agagagggta cagcc                       1365
```

<210> SEQ ID NO 19
<211> LENGTH: 455
<212> TYPE: PRT
<213> ORGANISM: Escherichia coli

<400> SEQUENCE: 19

```
Lys Val Leu Ser Arg Glu Glu Ser Glu Ala Glu Gln Ala Val Ala Arg
1               5                   10                  15

Pro Gln Val Thr Val Ile Pro Arg Glu Gln His Ala Ile Ser Arg Lys
                20                  25                  30

Asp Ile Ser Glu Asn Ala Leu Lys Val Met Tyr Arg Leu Asn Lys Ala
            35                  40                  45

Gly Tyr Glu Ala Trp Leu Val Gly Gly Gly Val Arg Asp Leu Leu Leu
        50                  55                  60

Gly Lys Lys Pro Lys Asp Phe Asp Val Thr Thr Asn Ala Thr Pro Glu
65                  70                  75                  80

Gln Val Arg Lys Leu Phe Arg Asn Cys Arg Leu Val Gly Arg Arg Phe
                85                  90                  95

Arg Leu Ala His Val Met Phe Gly Pro Glu Ile Ile Glu Val Ala Thr
            100                 105                 110

Phe Arg Gly His His Glu Gly Asn Val Ser Asp Arg Thr Thr Ser Gln
        115                 120                 125

Arg Gly Gln Asn Gly Met Leu Leu Arg Asp Asn Ile Phe Gly Ser Ile
    130                 135                 140

Glu Glu Asp Ala Gln Arg Arg Asp Phe Thr Ile Asn Ser Leu Tyr Tyr
```

```
              145                 150                 155                 160
        Ser Val Ala Asp Phe Thr Val Arg Asp Tyr Val Gly Gly Met Lys Asp
                        165                 170                 175

Leu Lys Asp Gly Val Ile Arg Leu Ile Gly Asn Pro Glu Thr Arg Tyr
                        180                 185                 190

Arg Glu Asp Pro Val Arg Met Leu Arg Ala Val Arg Phe Ala Ala Lys
                        195                 200                 205

Leu Gly Met Arg Ile Ser Pro Glu Thr Ala Glu Pro Ile Pro Arg Leu
                        210                 215                 220

Ala Thr Leu Leu Asn Asp Ile Pro Pro Ala Arg Leu Phe Glu Glu Ser
        225                 230                 235                 240

Leu Lys Leu Leu Gln Ala Gly Tyr Gly Tyr Glu Thr Tyr Lys Leu Leu
                        245                 250                 255

Cys Glu Tyr His Leu Phe Gln Pro Leu Phe Pro Thr Ile Thr Arg Tyr
                        260                 265                 270

Phe Thr Glu Asn Gly Asp Ser Pro Met Glu Arg Ile Ile Glu Gln Val
                        275                 280                 285

Leu Lys Asn Thr Asp Thr Arg Ile His Asn Asp Met Arg Val Asn Pro
                        290                 295                 300

Ala Phe Leu Phe Ala Ala Met Phe Trp Tyr Pro Leu Leu Glu Thr Ala
        305                 310                 315                 320

Gln Lys Ile Ala Gln Glu Ser Gly Leu Thr Tyr His Asp Ala Phe Ala
                        325                 330                 335

Leu Ala Met Asn Asp Val Leu Asp Glu Ala Cys Arg Ser Leu Ala Ile
                        340                 345                 350

Pro Lys Arg Leu Thr Thr Leu Thr Arg Asp Ile Trp Gln Leu Gln Leu
                        355                 360                 365

Arg Met Ser Arg Arg Gln Gly Lys Arg Ala Trp Lys Leu Leu Glu His
                        370                 375                 380

Pro Lys Phe Arg Ala Ala Tyr Asp Leu Leu Ala Leu Arg Ala Glu Val
        385                 390                 395                 400

Glu Arg Asn Ala Glu Leu Gln Arg Leu Val Lys Trp Trp Gly Glu Phe
                        405                 410                 415

Gln Val Ser Ala Pro Pro Asp Gln Lys Gly Met Leu Asn Glu Leu Asp
                        420                 425                 430

Glu Glu Pro Ser Pro Arg Arg Thr Arg Arg Pro Arg Lys Arg Ala
                        435                 440                 445

Pro Arg Arg Glu Gly Thr Ala
            450                 455

<210> SEQ ID NO 20
<211> LENGTH: 1440
<212> TYPE: DNA
<213> ORGANISM: Vaccinia virus

<400> SEQUENCE: 20
atgaatcgga atcccgacca aaatacattt cctaacatca cactgaaaat tatcgaaaca        60
tacctgggcc gcgtcccctc tgtgaatgaa taccacatgc tcaagctcca ggccagaaat       120
attcagaaga tcaccgtgtt caataaagac attttcgtct cactggtcaa aaaaaacaag       180
aagagatttt tttctgacgt tgacacctcc gccagtgaaa ttaagacag atactgagc         240 tatttctcta agcaaactca gacatacaac atcgggaagc tgtttacgat catagagctg       300
caaagcgtcc tagtgacaac atacaccgat atactcggtg tgctcacgat taagccccc       360
```

-continued

```
aacgttatct cctcgaagat cagctacaat gttacaagca tggaggagct cgcaagagat    420
atgctcaata gcatgaatgt ggccgtgatc gataaggcga aagtcatggg gaggcacaat    480
gtcagctccc tcgtgaaaaa cgtcaacaag ctgatggagg agtacttgcg gcggcacaat    540
aagtcctgca tttgctatgg ctcctactcc ttgtacctca tcaatcccaa cattctttac    600
ggggacattg acatcctgca gaccaattct cgcacatttt tgattgatct cgcgttcctg    660
atcaagttca taaccggcaa caacattatc ctctccaaga tcccatatct gcgaaattat    720
atggtcatta aggacgagaa cgataaccac attatagact cgttcaacat ccgccaggac    780
acgatgaatg tggtgccgaa aattttcata gacaatatct atatcgtaga ccccactttt    840
cagctcctga acatgattaa aatgttttct cagattgaca ggctagaaga tctgtccaaa    900
gatccagaaa agtttaacgc tcgtatggct accatgctgg agtacgtccg gtacactcat    960
ggtatagttt ttgacggcaa gcggaataat atgcccatga aatgtatcat cgatgaaaat   1020
aaccgcatcg taacagtaac gacaaaagat tactttagtt tcaagaaatg cctggtatac   1080
cttgacgaga atgttctgtc atccgacatt ttagacctta acgcggacac atcatgcgat   1140
tttgagagtg tgactaactc cgtctatctt atacacgata atattatgta tacctacttt   1200
tccaacacga tcctgctttc cgacaagggt aaagtccatg aaatcagcgc caggggactc   1260
tgcgcccata tattgcttta tcagatgttg acatctggag aatacaaaca gtgtctgtcc   1320
gaccttctca attccatgat gaaccgagac aagatcccta tctactccca cacagagagg   1380
gataaaaagc ccggacggca tggattcatc aatatcgaga aggatatcat cgtgttttaa   1440
```

<210> SEQ ID NO 21
<211> LENGTH: 479
<212> TYPE: PRT
<213> ORGANISM: Vaccinia virus

<400> SEQUENCE: 21

```
Met Asn Arg Asn Pro Asp Gln Asn Thr Leu Pro Asn Ile Thr Leu Lys
1               5                   10                  15

Ile Ile Glu Thr Tyr Leu Gly Arg Val Pro Ser Val Asn Glu Tyr His
            20                  25                  30

Met Leu Lys Leu Gln Ala Arg Asn Ile Gln Lys Ile Thr Val Phe Asn
        35                  40                  45

Lys Asp Ile Phe Val Ser Leu Val Lys Asn Lys Lys Arg Phe Phe
    50                  55                  60

Ser Asp Val Asn Thr Ser Ala Ser Glu Ile Lys Asp Arg Ile Leu Ser
65                  70                  75                  80

Tyr Phe Ser Lys Gln Thr Gln Thr Tyr Asn Ile Gly Lys Leu Phe Thr
                85                  90                  95

Ile Ile Glu Leu Gln Ser Val Leu Val Thr Thr Tyr Thr Asp Ile Leu
            100                 105                 110

Gly Val Leu Thr Ile Lys Ala Pro Asn Val Ile Ser Ser Lys Ile Ser
        115                 120                 125

Tyr Asn Val Thr Ser Met Glu Glu Leu Ala Arg Asp Met Leu Asn Ser
    130                 135                 140

Met Asn Val Ala Val Ile Asp Lys Ala Lys Val Met Gly Arg His Asn
145                 150                 155                 160

Val Ser Ser Leu Val Lys Asn Val Asn Lys Leu Met Glu Glu Tyr Leu
                165                 170                 175

Arg Arg His Asn Lys Ser Cys Ile Cys Tyr Gly Ser Tyr Ser Leu Tyr
            180                 185                 190
```

Leu Ile Asn Pro Asn Ile Arg Tyr Gly Asp Ile Asp Ile Leu Gln Thr
            195                 200                 205

Asn Ser Arg Thr Phe Leu Ile Asp Leu Ala Phe Leu Ile Lys Phe Ile
    210                 215                 220

Thr Gly Asn Asn Ile Ile Leu Ser Lys Ile Pro Tyr Leu Arg Asn Tyr
225                 230                 235                 240

Met Val Ile Lys Asp Glu Asn Asp His Ile Ile Asp Ser Phe Asn
                245                 250                 255

Ile Arg Gln Asp Thr Met Asn Val Val Pro Lys Ile Phe Ile Asp Asn
                260                 265                 270

Ile Tyr Ile Val Asp Pro Thr Phe Gln Leu Leu Asn Met Ile Lys Met
            275                 280                 285

Phe Ser Gln Ile Asp Arg Leu Glu Asp Leu Ser Lys Asp Pro Glu Lys
    290                 295                 300

Phe Asn Ala Arg Met Ala Thr Met Leu Glu Tyr Val Arg Tyr Thr His
305                 310                 315                 320

Gly Ile Val Phe Asp Gly Lys Arg Asn Asn Met Pro Met Lys Cys Ile
                325                 330                 335

Ile Asp Glu Asn Asn Arg Ile Val Thr Val Thr Thr Lys Asp Tyr Phe
            340                 345                 350

Ser Phe Lys Lys Cys Leu Val Tyr Leu Asp Glu Asn Val Leu Ser Ser
    355                 360                 365

Asp Ile Leu Asp Leu Asn Ala Asp Thr Ser Cys Asp Phe Glu Ser Val
    370                 375                 380

Thr Asn Ser Val Tyr Leu Ile His Asp Asn Ile Met Tyr Thr Tyr Phe
385                 390                 395                 400

Ser Asn Thr Ile Leu Leu Ser Asp Lys Gly Lys Val His Glu Ile Ser
                405                 410                 415

Ala Arg Gly Leu Cys Ala His Ile Leu Leu Tyr Gln Met Leu Thr Ser
            420                 425                 430

Gly Glu Tyr Lys Gln Cys Leu Ser Asp Leu Leu Asn Ser Met Met Asn
    435                 440                 445

Arg Asp Lys Ile Pro Ile Tyr Ser His Thr Glu Arg Asp Lys Lys Pro
    450                 455                 460

Gly Arg His Gly Phe Ile Asn Ile Glu Lys Asp Ile Ile Val Phe
465                 470                 475

<210> SEQ ID NO 22
<211> LENGTH: 1761
<212> TYPE: DNA
<213> ORGANISM: Acanthamoeba polyphaga

<400> SEQUENCE: 22
atgctcaaaa acaagaccag ggctgagaag tatcagacct actacaccac caatgaatat    60
cagatcgtta agaaaaaact accagacatt ataagagacg cggaaattaa ggcgtctgaa   120
gtgctcgagc caaccatcta cgagaagcgc gcaatcatgg aagtcattaa ggatttcatt   180
cgggatcatc aaaggaaagt gtatggcgga acagccctga tgaggcatt gaaacaggtg    240 aatcccaagg atgccatcta tgataactat tccttcagcg catcgagtt ttattcccct    300 accccgtgc aggatctcgt ggatctctgc aacatcctgt atagaaaagg gtataagttc    360
gtccagggga aggacgctca gcatgaggaa acctattcta tctttgtaaa tttccagctc   420
tactgtgaca ttaccattc gccaaccccgg gtcttttatg gtattaaaac gatagaaatt   480

```
gacggcatta actataccga tcctcatttc atgctcatag attacctccg aatggtgaac    540
cagcccttga ctgccgccgg ccagcgctgg gagaaagcgt tcgaacggat gtacaggctg    600
ctcaaagact atcccattga ggattttgac aagaggctgg atattcctga gccacccgaa    660
gaaatccaga gttatatttc tcggattaag accgagtttc tgagcgataa caagctgaat    720
gaaagcttcc tcatctccgg catcgaggct tacaacttct acattcgcca tgctgcctct    780
agcaaagatg aagaacagat ggcccggaca aaccgcaatg tggtcaatct taataacttt    840
attgcaaatg tcccctttag cgagctgatc tccgtgaact atcgcgaaga tgtcaagaat    900
acctataact cctgcggat gatcgtcgag gataaagaga aaatcagtgt tgacgaatat    960
ttccctctct ttcaattcac tggctattcc actgtcatca aatacgatga tcaccccata   1020
attaggatct acgagggcga cggttattgt attcctaacg tcaagaccgt taaaacggtg   1080
gagaatgaca acggaacgaa gacaaagtac gagtacaagt acgtatcctt ccagtacgtc   1140
ctcatgattc tatatatcaa caaatttcgt gcgcacttgg acaagaataa gcctatgtat   1200
tttaactacg gtattgccat atccaatctg gtcaaagctc gcaatatata cctggaccag   1260
accgggaaaa gcgtccttga caacactgtg tttaaggagt tccgcactaa ctgtaccgga   1320
aatacgatct ctttcacacg gatgaacaga ctgagattac tcgagaaaag aaagcagggc   1380
aagcagactt cgttcgttta caccctgaa gacttcttta agaaggatct ggaaacccaa   1440
gccaagcttg acccgtcgaa agcgagattc aaaaatacca gtggtaacaa gattatggtg   1500
ccaaagtacc tgctgttcaa aatagataac aacggaaata ttgaagataa catacatagc   1560
gaagaggcag aaatctcaga gaagaagaa acttccggtg gctcttctat atccactgat   1620
aaatcattcg aagaatcacc taattcctcc cctaacagct ctcctaacaa ctcgttgaat   1680
aattctattg atatcagtac aaataattac gacgaccgct cggaaaacag cctggactca   1740
ctcacgtctg atgggcccta a                                             1761
```

<210> SEQ ID NO 23
<211> LENGTH: 584
<212> TYPE: PRT
<213> ORGANISM: Acanthamoeba polyphaga

<400> SEQUENCE: 23

```
Met Leu Lys Asn Lys Thr Arg Ala Glu Lys Tyr Gln Thr Tyr Tyr Thr
1               5                   10                  15

Thr Asn Glu Tyr Gln Ile Val Lys Glu Lys Leu Pro Asp Ile Ile Arg
            20                  25                  30

Asp Ala Glu Ile Lys Ala Ser Glu Val Leu Glu Pro Thr Ile Tyr Glu
        35                  40                  45

Lys Arg Ala Ile Met Glu Val Ile Lys Asp Phe Ile Arg Asp His Gln
    50                  55                  60

Arg Lys Val Tyr Gly Gly Thr Ala Leu Asn Glu Ala Leu Lys Gln Val
65                  70                  75                  80

Asn Pro Lys Asp Ala Ile Tyr Asp Asn Tyr Ser Phe Ser Asp Ile Glu
                85                  90                  95

Phe Tyr Ser Pro Thr Pro Val Gln Asp Leu Val Asp Leu Cys Asn Ile
            100                 105                 110

Leu Tyr Arg Lys Gly Tyr Lys Phe Val Gln Gly Lys Asp Ala Gln His
        115                 120                 125

Glu Glu Thr Tyr Ser Ile Phe Val Asn Phe Gln Leu Tyr Cys Asp Ile
    130                 135                 140
```

```
Thr Tyr Ser Pro Thr Arg Val Phe Tyr Gly Ile Lys Thr Ile Glu Ile
145                 150                 155                 160

Asp Gly Ile Asn Tyr Thr Asp Pro His Phe Met Leu Ile Asp Tyr Leu
                165                 170                 175

Arg Met Val Asn Gln Pro Leu Thr Ala Ala Gly Gln Arg Trp Glu Lys
            180                 185                 190

Ala Phe Glu Arg Met Tyr Arg Leu Leu Lys Asp Tyr Pro Ile Glu Asp
        195                 200                 205

Phe Asp Lys Arg Leu Asp Ile Pro Glu Pro Pro Glu Ile Gln Ser
    210                 215                 220

Tyr Ile Ser Arg Ile Lys Thr Glu Phe Leu Ser Asp Asn Lys Leu Asn
225                 230                 235                 240

Glu Ser Phe Leu Ile Ser Gly Ile Glu Ala Tyr Asn Phe Tyr Ile Arg
                245                 250                 255

His Ala Ala Ser Ser Lys Asp Glu Glu Gln Met Ala Arg Thr Asn Arg
            260                 265                 270

Asn Val Val Asn Leu Asn Asn Phe Ile Ala Asn Val Pro Phe Ser Glu
        275                 280                 285

Leu Ile Ser Val Asn Tyr Arg Glu Asp Val Lys Asn Thr Tyr Asn Phe
290                 295                 300

Leu Arg Met Ile Val Glu Asp Lys Glu Lys Ile Ser Val Asp Glu Tyr
305                 310                 315                 320

Phe Pro Leu Phe Gln Phe Thr Gly Tyr Ser Thr Val Ile Lys Tyr Asp
                325                 330                 335

Asp His Pro Ile Ile Arg Ile Tyr Glu Gly Asp Gly Tyr Cys Ile Pro
            340                 345                 350

Asn Val Lys Thr Val Lys Thr Val Glu Asn Asp Asn Gly Thr Lys Thr
        355                 360                 365

Lys Tyr Glu Tyr Lys Tyr Val Ser Phe Gln Tyr Val Leu Met Ile Leu
370                 375                 380

Tyr Ile Asn Lys Phe Arg Ala His Leu Asp Lys Asn Lys Pro Met Tyr
385                 390                 395                 400

Phe Asn Tyr Gly Ile Ala Ile Ser Asn Leu Val Lys Ala Arg Asn Ile
                405                 410                 415

Tyr Leu Asp Gln Thr Gly Lys Ser Val Leu Asp Asn Thr Val Phe Lys
            420                 425                 430

Glu Phe Arg Thr Asn Cys Thr Gly Asn Thr Ile Ser Phe Thr Arg Met
        435                 440                 445

Asn Arg Leu Arg Leu Leu Glu Lys Arg Lys Gln Gly Lys Gln Thr Ser
450                 455                 460

Phe Val Tyr Thr Pro Glu Asp Phe Phe Lys Lys Asp Leu Glu Thr Gln
465                 470                 475                 480

Ala Lys Leu Asp Pro Ser Lys Ala Arg Phe Lys Asn Thr Ser Gly Asn
                485                 490                 495

Lys Ile Met Val Pro Lys Tyr Leu Leu Phe Lys Ile Asp Asn Asn Gly
            500                 505                 510

Asn Ile Glu Asp Asn Ile His Ser Glu Glu Ala Glu Ile Ser Glu Lys
        515                 520                 525

Glu Glu Thr Ser Gly Gly Ser Ser Ile Ser Thr Asp Lys Ser Phe Glu
530                 535                 540

Glu Ser Pro Asn Ser Ser Pro Asn Ser Ser Pro Asn Asn Ser Leu Asn
545                 550                 555                 560

Asn Ser Ile Asp Ile Ser Thr Asn Asn Tyr Asp Asp Arg Ser Glu Asn
```

Ser Leu Asp Ser Leu Thr Ser Asp
        580

<210> SEQ ID NO 24
<211> LENGTH: 1593
<212> TYPE: DNA
<213> ORGANISM: Megavirus chilensis

<400> SEQUENCE: 24

| | | | | | |
|---|---|---|---|---|---|
| atgtctgaaa | ataggaatag | gaagctctca | taccaagaat | attatgtaga | cggggattac | 60 |
| gaggaggtcc | gtaaaaagct | gcccgagata | attaaacagg | ctagaatcaa | agcctcccaa | 120 |
| gtgatggagc | ccacaatcta | tgagaagcgg | gtggtgatgg | aaataatcaa | ggattttatt | 180 |
| cgggacaagg | ggagaaaggt | ctatgggggg | accgcactca | acgagaccat | taagaagaag | 240 |
| aatcccgaag | acgcgatcta | cgacagctac | ctgttttcag | atatcgagtt | ttactcacca | 300 |
| acacctgtgc | ctgatctaaa | ggagctgtgt | gacattttat | accacaaagg | ctatgacccg | 360 |
| gtacagggaa | aggaggcgca | gcacgaggaa | acttattcta | tcttcgtcaa | tctgcagttg | 420 |
| tattgtgaca | tcacatacgt | ccctactaaa | gtatatcatg | ggattaagac | cattgaaatc | 480 |
| gatgggatca | actacacaca | cccgcatttc | atgctgatcg | attacctgcg | gatgatcaac | 540 |
| cagccattaa | cagcagcgga | acagaggtgg | gaaaaggcct | tcgacaggat | gtacgtgctg | 600 |
| ctgaagaatt | atccgatgga | gaaatatgat | aattcaatgc | gaatcaccag | tccgcgggac | 660 |
| gatatccaaa | tgtacatcgg | aaaagtcaag | tccgagttca | tgaagatacc | ggaaattcag | 720 |
| gaaagttgct | taatctcagg | ctttgacgca | tacaactttt | ttatcagaca | cgcaatgggg | 780 |
| gacaggaagg | tcgaacagat | ggcccgcatc | aaaaatgact | acaacagcct | gaagaacttc | 840 |
| attactgtgc | tgccttttat | ggagttaatc | agtgtaaagt | acaaagacac | tgtggaaaag | 900 |
| ctctataatt | ttctccggga | gaaagtcgtt | aacccagact | tgatcactat | cgatgagtac | 960 |
| ttcccgttgt | tccagttcac | tgggtattct | gtctctatca | actatgacgg | cattccaatc | 1020 |
| gtgaaggttt | acgaggcgga | tggctattgc | gtcccggata | ttaagacgac | ctcaggatac | 1080 |
| cgatacgtct | cctatcagta | tatcctgatg | attatgtata | tctccaaatt | caaagctcac | 1140 |
| ctggataaga | acaaggaaat | gtattttaat | tatggcatcg | ccatttccaa | tctggtacaa | 1200 |
| gctcgcaact | cctatctgaa | ccagaaaaat | atcggtgtta | taacgacac | cgttttagc | 1260 |
| gagttcagga | taggctgtat | aggcacaact | gtctcctata | caagaatgtc | aagacttaga | 1320 |
| atgttggaga | aaagaaaaca | aggaaaggtt | atccaatttg | tctataccccc | taaacagtac | 1380 |
| tttagtcaga | cccccgagca | gcagaacaat | ttcgacgaga | gcatgaagaa | gtaccgcttt | 1440 |
| aaaaacactt | ccggcaataa | gattactatt | cctaagaacc | tgctgtttaa | gatagacgag | 1500 |
| agaggaaata | tttctgagga | gatctcaacc | gaggaagcct | atataacaga | agatactacc | 1560 |
| agcatcaata | caaccacgga | tatcaatact | aat | | | 1593 |

<210> SEQ ID NO 25
<211> LENGTH: 531
<212> TYPE: PRT
<213> ORGANISM: Megavirus chilensis

<400> SEQUENCE: 25

Met Ser Glu Asn Arg Asn Arg Lys Leu Ser Tyr Gln Glu Tyr Tyr Val
1               5                   10                  15

Asp Gly Asp Tyr Glu Glu Val Arg Lys Lys Leu Pro Glu Ile Ile Lys

-continued

```
            20                  25                  30
Gln Ala Arg Ile Lys Ala Ser Gln Val Met Glu Pro Thr Ile Tyr Glu
            35                  40                  45
Lys Arg Val Val Met Glu Ile Ile Lys Asp Phe Ile Arg Asp Lys Gly
    50                  55                  60
Arg Lys Val Tyr Gly Gly Thr Ala Leu Asn Glu Thr Ile Lys Lys Lys
65                  70                  75                  80
Asn Pro Glu Asp Ala Ile Tyr Asp Ser Tyr Leu Phe Ser Asp Ile Glu
                85                  90                  95
Phe Tyr Ser Pro Thr Pro Val Pro Asp Leu Lys Glu Leu Cys Asp Ile
            100                 105                 110
Leu Tyr His Lys Gly Tyr Asp Pro Val Gln Gly Lys Glu Ala Gln His
            115                 120                 125
Glu Glu Thr Tyr Ser Ile Phe Val Asn Leu Gln Leu Tyr Cys Asp Ile
        130                 135                 140
Thr Tyr Val Pro Thr Lys Val Tyr His Gly Ile Lys Thr Ile Glu Ile
145                 150                 155                 160
Asp Gly Ile Asn Tyr Thr His Pro His Phe Met Leu Ile Asp Tyr Leu
                165                 170                 175
Arg Met Ile Asn Gln Pro Leu Thr Ala Ala Glu Gln Arg Trp Glu Lys
            180                 185                 190
Ala Phe Asp Arg Met Tyr Val Leu Leu Lys Asn Tyr Pro Met Glu Lys
            195                 200                 205
Tyr Asp Asn Ser Met Arg Ile Thr Ser Pro Arg Asp Asp Ile Gln Met
        210                 215                 220
Tyr Ile Gly Lys Val Lys Ser Glu Phe Met Lys Ile Pro Glu Ile Gln
225                 230                 235                 240
Glu Ser Cys Leu Ile Ser Gly Phe Asp Ala Tyr Asn Phe Phe Ile Arg
                245                 250                 255
His Ala Met Gly Asp Arg Lys Val Glu Gln Met Ala Arg Ile Lys Asn
            260                 265                 270
Asp Tyr Asn Ser Leu Lys Asn Phe Ile Thr Val Leu Pro Phe Met Glu
            275                 280                 285
Leu Ile Ser Val Lys Tyr Lys Asp Thr Val Glu Lys Leu Tyr Asn Phe
        290                 295                 300
Leu Arg Glu Lys Val Val Asn Pro Asp Leu Ile Thr Ile Asp Glu Tyr
305                 310                 315                 320
Phe Pro Leu Phe Gln Phe Thr Gly Tyr Ser Val Ser Ile Asn Tyr Asp
                325                 330                 335
Gly Ile Pro Ile Val Lys Val Tyr Glu Ala Asp Gly Tyr Cys Val Pro
            340                 345                 350
Asp Ile Lys Thr Thr Ser Gly Tyr Arg Tyr Val Ser Tyr Gln Tyr Ile
            355                 360                 365
Leu Met Ile Met Tyr Ile Ser Lys Phe Lys Ala His Leu Asp Lys Asn
        370                 375                 380
Lys Glu Met Tyr Phe Asn Tyr Gly Ile Ala Ile Ser Asn Leu Val Gln
385                 390                 395                 400
Ala Arg Asn Ser Tyr Leu Asn Gln Lys Asn Ile Gly Val Ile Asn Asp
                405                 410                 415
Thr Val Phe Ser Glu Phe Arg Ile Gly Cys Ile Gly Thr Thr Val Ser
            420                 425                 430
Tyr Thr Arg Met Ser Arg Leu Arg Met Leu Glu Lys Lys Lys Gln Gly
            435                 440                 445
```

```
Lys Val Ile Gln Phe Val Tyr Thr Pro Lys Gln Tyr Phe Ser Gln Thr
            450                 455                 460

Pro Glu Gln Gln Asn Asn Phe Asp Glu Ser Met Lys Lys Tyr Arg Phe
465                 470                 475                 480

Lys Asn Thr Ser Gly Asn Lys Ile Thr Ile Pro Lys Asn Leu Leu Phe
                485                 490                 495

Lys Ile Asp Glu Arg Gly Asn Ile Ser Glu Glu Ile Ser Thr Glu Glu
                500                 505                 510

Ala Tyr Ile Thr Glu Asp Thr Thr Ser Ile Asn Thr Thr Thr Asp Ile
            515                 520                 525

Asn Thr Asn
    530

<210> SEQ ID NO 26
<211> LENGTH: 1434
<212> TYPE: DNA
<213> ORGANISM: African swine fever virus

<400> SEQUENCE: 26
atgagtagtc tcctcaagac tgatttcaac gtgtctaagt accgcctgat cgcgcagaag      60
cgggaggcaa atgccgttga atcgaggct gcactcgaag tagtgaggga atttataatt     120
aagaagaaac tgatcctgta cggtgggatc gccatcgatt acgccctcca ccttaaagga     180
tcttccattt acccagaagg tgaaaggccc gacttcgaca tgttcagccc aaaccacgtc     240
gaggacgctt acgagctggc agacatactg tacgagaagg ggtttaaaca ggtgggtacg     300
gtgcgtgcaa tacacgttca gacgatgcgg gtgcgtactg acttcgtgtg ggtcgcagac     360
ttatcctaca tgccaccaaa tatctttaat acaatcccga cactgaccta caaaaacttg     420
aagattattc accccgacta tcagagggca gggctacatc ttgctttctg ctttccgttt     480
gataaccctc ctagggagga cgttttagt cgatttaaga aagacttgca acgctataac     540
ctcattgaaa agtactaccc tatccccgtc gtgcctgtaa agtcgatcta cgaatcaaag     600 acatttctcta tcccctccaa acaggttgcc atacacggtt tgctgcata cgcgctcctg     660 tatcagactc tgaacgagtt acgtatcacc tgtaaagtac ctgagtggaa gaccgagttt     720
ccccagccta gctactccta tcacaagaac gacaaaaaca tcacacttac agtggacatg     780
cctaaagcct accctgcgct ggtgctggca acctacaatc ccgaagaggt gatcaaggag     840
atgggactgc atctgactga gatatgcgaa ccatacatgg actactcacc gcctattttc     900
aagacaaacg acattcactt ttttttcgact atgtttaaag agctggccat cagcattatc     960
caagataacc tgattgtggt gagccctcaa tatttactgt tgtatttcct gtatggcgca    1020
ttcgccactc cagcggataa aagtctgttt ttatttatt ataacgccac actgtggatc    1080
ctggagaaag ccgactccct gttgaacatc attcagaagc agaccagccc cgaggagttc    1140
accagatttg ccaatacctc accattcgtc ctgaccacga gagtgctatc atgctcgcaa    1200
gagcgctgca cattctctcc agcatacaga atctctctgg ccaatgacgt acagcagtcc    1260
cagctcccat gccgaagac acacttcctg agtaacagtt tgccggatgt gtcaactttg    1320
ccatataatt attaccctgg aaaagggaag gaccgaccca caaatttctc gtacgaaaag    1380
aatctgttat ttaatattgg gggaaagtgc actccctccg ctatggggcc ctaa          1434

<210> SEQ ID NO 27
<211> LENGTH: 475
<212> TYPE: PRT
```

<213> ORGANISM: African swine fever virus

<400> SEQUENCE: 27

```
Met Ser Ser Leu Leu Lys Thr Asp Phe Asn Val Ser Lys Tyr Arg Leu
1               5                   10                  15

Ile Ala Gln Lys Arg Glu Ala Asn Ala Val Glu Ile Glu Ala Ala Leu
            20                  25                  30

Glu Val Val Arg Glu Phe Ile Ile Lys Lys Lys Leu Ile Leu Tyr Gly
        35                  40                  45

Gly Ile Ala Ile Asp Tyr Ala Leu His Leu Lys Gly Ser Ser Ile Tyr
    50                  55                  60

Pro Glu Gly Glu Arg Pro Asp Phe Asp Met Phe Ser Pro Asn His Val
65                  70                  75                  80

Glu Asp Ala Tyr Glu Leu Ala Asp Ile Leu Tyr Glu Lys Gly Phe Lys
                85                  90                  95

Gln Val Gly Thr Val Arg Ala Ile His Val Gln Thr Met Arg Val Arg
            100                 105                 110

Thr Asp Phe Val Trp Val Ala Asp Leu Ser Tyr Met Pro Pro Asn Ile
        115                 120                 125

Phe Asn Thr Ile Pro Thr Leu Thr Tyr Lys Asn Leu Lys Ile Ile His
130                 135                 140

Pro Asp Tyr Gln Arg Ala Gly Leu His Leu Ala Phe Cys Phe Pro Phe
145                 150                 155                 160

Asp Asn Pro Pro Arg Glu Asp Val Phe Ser Arg Phe Lys Lys Asp Leu
                165                 170                 175

Gln Arg Tyr Asn Leu Ile Glu Lys Tyr Tyr Pro Ile Pro Val Val Pro
            180                 185                 190

Val Lys Ser Ile Tyr Glu Ser Lys Thr Phe Ser Ile Pro Phe Lys Gln
        195                 200                 205

Val Ala Ile His Gly Phe Ala Ala Tyr Ala Leu Leu Tyr Gln Thr Leu
    210                 215                 220

Asn Glu Leu Arg Ile Thr Cys Lys Val Pro Glu Trp Lys Thr Glu Phe
225                 230                 235                 240

Pro Gln Pro Ser Tyr Ser Tyr His Lys Asn Asp Lys Asn Ile Thr Leu
                245                 250                 255

Thr Val Asp Met Pro Lys Ala Tyr Pro Ala Leu Val Leu Ala Thr Tyr
            260                 265                 270

Asn Pro Glu Glu Val Ile Lys Glu Met Gly Leu His Leu Thr Glu Ile
        275                 280                 285

Cys Glu Pro Tyr Met Asp Tyr Ser Pro Pro Ile Phe Lys Thr Asn Asp
    290                 295                 300

Ile His Phe Phe Ser Thr Met Phe Lys Glu Leu Ala Ile Ser Ile Ile
305                 310                 315                 320

Gln Asp Asn Leu Ile Val Val Ser Pro Gln Tyr Leu Leu Tyr Phe
                325                 330                 335

Leu Tyr Gly Ala Phe Ala Thr Pro Ala Asp Lys Ser Leu Phe Leu Phe
            340                 345                 350

Tyr Tyr Asn Ala Thr Leu Trp Ile Leu Glu Lys Ala Asp Ser Leu Leu
        355                 360                 365

Asn Ile Ile Gln Lys Gln Thr Ser Pro Glu Glu Phe Thr Arg Phe Ala
    370                 375                 380

Asn Thr Ser Pro Phe Val Leu Thr Thr Arg Val Leu Ser Cys Ser Gln
385                 390                 395                 400
```

```
Glu Arg Cys Thr Phe Ser Pro Ala Tyr Arg Ile Ser Leu Ala Asn Asp
                405                 410                 415

Val Gln Gln Ser Gln Leu Pro Leu Pro Lys Thr His Phe Leu Ser Asn
        420                 425                 430

Ser Leu Pro Asp Val Ser Thr Leu Pro Tyr Asn Tyr Tyr Pro Gly Lys
        435                 440                 445

Gly Lys Asp Arg Pro Thr Asn Phe Ser Tyr Glu Lys Asn Leu Leu Phe
    450                 455                 460

Asn Ile Gly Gly Lys Cys Thr Pro Ser Ala Met
465                 470                 475

<210> SEQ ID NO 28
<211> LENGTH: 141
<212> TYPE: DNA
<213> ORGANISM: Artificial Sequence
<220> FEATURE:
<223> OTHER INFORMATION: Nucleotide sequence of G4-EE1234L leucine-
      zipper

<400> SEQUENCE: 28
ggcggcggag gcctggaaat cgaggccgcc ttcctggaac aggaaaacac cgccctggaa     60
accgaggtgg ccgagctgga acaggaagtg cagcggctgg aaaacatcgt gtcccagtac   120
gagacaagat acggcccct g                                              141

<210> SEQ ID NO 29
<211> LENGTH: 47
<212> TYPE: PRT
<213> ORGANISM: Artificial Sequence
<220> FEATURE:
<223> OTHER INFORMATION: Amino-acid sequence of G4-EE1234L leucine-
      zipper

<400> SEQUENCE: 29

Gly Gly Gly Gly Leu Glu Ile Glu Ala Ala Phe Leu Glu Gln Glu Asn
1               5                   10                  15

Thr Ala Leu Glu Thr Glu Val Ala Glu Leu Glu Gln Glu Val Gln Arg
            20                  25                  30

Leu Glu Asn Ile Val Ser Gln Tyr Glu Thr Arg Tyr Gly Pro Leu
        35                  40                  45

<210> SEQ ID NO 30
<211> LENGTH: 141
<212> TYPE: DNA
<213> ORGANISM: Artificial Sequence
<220> FEATURE:
<223> OTHER INFORMATION: Nucleotide sequence of RR1234L-G4 leucine-
      zipper

<400> SEQUENCE: 30
ctggaaatca gggccgcctt cctgcggaga agaaacaccg ccctgcggac cagagtggcc     60
gagctgagac agcgggtgca gcggctgcgg aacatcgtgt cccagtacga gacaagatac   120 ggcccctgg gcggaggcgg c                                              141

<210> SEQ ID NO 31
<211> LENGTH: 47
<212> TYPE: PRT
<213> ORGANISM: Artificial Sequence
<220> FEATURE:
<223> OTHER INFORMATION: Amino-acid sequence of RR1234L-G4 leucine-
      zipper

<400> SEQUENCE: 31
```

```
Leu Glu Ile Arg Ala Ala Phe Leu Arg Arg Arg Asn Thr Ala Leu Arg
1               5                   10                  15

Thr Arg Val Ala Glu Leu Arg Gln Arg Val Gln Arg Leu Arg Asn Ile
            20                  25                  30

Val Ser Gln Tyr Glu Thr Arg Tyr Gly Pro Leu Gly Gly Gly Gly
        35                  40                  45

<210> SEQ ID NO 32
<211> LENGTH: 4467
<212> TYPE: DNA
<213> ORGANISM: Artificial Sequence
<220> FEATURE:
<223> OTHER INFORMATION: Nucleotide sequence of lambdaN-R341-G4-NP868R

<400> SEQUENCE: 32
atggatgctc agaccagacg cagagaacgg cgggcagaga agcaggcaca gtggaaggcc      60
gctaatggcg gtggcggcac cggtctcaaa aacaagacca gggctgagaa gtatcagacc     120
tactacacca ccaatgaata tcagatcgtt aaagaaaaac taccagacat tataagagac     180
gcggaaatta aggcgtctga agtgctcgag ccaaccatct acgagaagcg cgcaatcatg     240
gaagtcatta aggatttcat tcgggatcat caaaggaaag tgtatggcgg aacagccctg     300
aatgaggcat tgaaacaggt gaatcccaag gatgccatct atgataacta ttccttcagc     360
gacatcgagt tttattcccc taccccgtg caggatctcg tggatctctg caacatcctg     420
tatagaaaag ggtataagtt cgtccagggg aaggacgctc agcatgagga aacctattct     480
atctttgtaa atttccagct ctactgtgac attacctatt cgccaacccg ggtcttttat     540
ggtattaaaa cgatagaaat tgacggcatt aactataccg atcctcattt catgctcata     600
gattacctcc gaatggtgaa ccagcccttg actgccgccg ccagcgctg ggagaaagcg      660 ttcgaacgga tgtacaggct gctcaaagac tatcccattg aggattttga caagaggctg     720
gatattcctg agccacccga agaaatccag agttatattt ctcggattaa gaccgagttt     780
ctgagcgata caagctgaa tgaaagcttc ctcatctccg gcatcgaggc ttacaacttc      840
tacattcgcc atgctgcctc tagcaaagat gaagaacaga tggcccggac aaaccgcaat     900
gtggtcaatc ttaataactt tattgcaaat gtcccccttta gcgagctgat ctccgtgaac     960
tatcgcgaag atgtcaagaa tacctataac ttcctgcgga tgatcgtcga ggataaagag    1020
aaaatcagtg ttgacgaata tttccctctc tttcaattca ctggctattc cactgtcatc    1080
aaatacgatg atcaccccat aattaggatc tacgagggcg acggttattg tattcctaac    1140
gtcaagaccg ttaaaacggt ggagaatgac aacggaacga agacaaagta cgagtacaag    1200
tacgtatcct ccagtacgt cctcatgatt ctatatatca acaaatttcg tgcgcacttg     1260
gacaagaata agcctatgta ttttaactac ggtattgcca tatccaatct ggtcaaagct    1320
cgcaatatat acctggacca gaccgggaaa agcgtccttg acaacactgt gtttaaggag    1380
ttccgcacta actgtaccgg aaatacgatc tctttcacac ggatgaacag actgagatta    1440
ctcgagaaaa gaaagcaggg caagcagact tcgttcgttt acacccctga agacttcttt    1500
aagaaggatc tggaacccca agccaagctt gacccgtcga aagcgagatt caaaaatacc    1560
agtggtaaca agattatggt gccaaagtac ctgctgttca aaatagataa caacggaaat    1620
attgaagata acatacatag cgaagaggca gaaatctcag agaaagaaga aacttccggt    1680
ggctcttcta tatccactga taatatcatt gaagaatcac ctaattcctc ccctaacagc    1740
tctcctaaca actcgttgaa taattctatt gatatcagta caaataatta cgacgaccgc    1800
```

```
tcggaaaaca gcctggactc actcacgtct gatgggcccg gcggtggcgg cgaattcgcc      1860
agcctggaca acctggtggc cagataccag cggtgcttca acgaccagag cctgaagaac      1920
agcaccatcg agctggaaat ccggttccag cagatcaact tcctgctgtt caagaccgtg      1980
tacgaggccc tggtcgccca ggaaatcccc agcaccatca gccacagcat ccggtgcatc      2040
aagaaggtgc accacgagaa ccactgccgg gagaagatcc tgcccagcga gaacctgtac      2100
ttcaagaaac agcccctgat gttcttcaag ttcagcgagc ccgccagcct gggctgtaaa      2160
gtgtccctgg ccatcgagca gcccatccgg aagttcatcc tggacagcag cgtgctggtc      2220
cggctgaaga accggaccac cttccgggtg tccgagctgt ggaagatcga gctgaccatc      2280
gtgaagcagc tgatgggcag cgaggtgtca gccaagctgg ccgccttcaa gaccctgctg      2340
ttcgacaccc ccgagcagca gaccaccaag aacatgatga ccctgatcaa ccccgacgac      2400
gagtacctgt acgagatcga gatcgagtac accggcaagc tgagagcct gacagccgcc      2460
gacgtgatca agatcaagaa caccgtgctg acactgatca gccccaacca cctgatgctg      2520
accgcctacc accaggccat cgagtttatc gccagccaca tcctgagcag cgagatcctg      2580
ctggcccgga tcaagagcgg caagtggggc ctgaagagac tgctgcccca ggtcaagtcc      2640
atgaccaagg ccgactacat gaagttctac ccccccgtgg gctactacgt gaccgacaag      2700
gccgacggca tccgggggcat tgccgtgatc caggacaccc agatctacgt ggtggccgac      2760
cagctgtaca gcctgggcac caccggcatc gagcccctga gcccaccat cctggacggc      2820
gagttcatgc ccgagaagaa agagttctac ggctttgacg tgatcatgta cgagggcaac      2880
ctgctgaccc agcagggctt cgagacacgg atcgagagcc tgagcaaggg catcaaggtg      2940
ctgcaggcct tcaacatcaa ggccgagatg aagcccttca tcagcctgac ctccgccgac      3000
cccaacgtgc tgctgaagaa tttcgagagc atcttcaaga gaaaacccg gccctacagc      3060
atcgacggca tcatcctggt ggagcccggc aacagctacc tgaacaccaa cacccttcaag      3120
tggaagccca cctgggacaa caccctggac tttctggtcc ggaagtgccc cgagtccctg      3180
aacgtgcccg agtacgcccc caagaagggc ttcagcctgc atctgctgtt cgtgggcatc      3240
agcggcgagc tgtttaagaa gctggccctg aactggtgcc ccggctacac caagctgttc      3300
cccgtgaccc agcggaacca gaactacttc cccgtgcagt tccagcccag cgacttcccc      3360
ctggccttcc tgtactacca ccccgacacc agcagcttca gcaacatcga tggcaaggtg      3420
ctggaaatgc ggtgcctgaa gcgggagatc aactacgtgc gctgggagat cgtgaagatc      3480
cgggaggacc ggcagcagga tctgaaaacc ggcggctact tcggcaacga cttcaagacc      3540
gccgagctga cctggctgaa ctacatggac cccttcagct tcgaggaact ggccaaggga      3600
cccagcggca tgtacttcgc tggcgccaag accggcatct acagagccca gaccgccctg      3660
atcagcttca tcaagcagga aatcatccag aagatcagcc accagagctg ggtgatcgac      3720
ctgggcatcg gcaagggcca ggacctgggc agatacctgg acgccggcgt gagacacctg      3780
gtcggcatcg ataaggacca gacagccctg gccgagctgg tgtaccggaa gttctcccac      3840
gccaccacca gacagcacaa gcacgccacc aacatctacg tgctgcacca ggatctggcc      3900
gagcctgcca agaaaatcag cgagaaagtg caccagatct atggcttccc caaagagggc      3960
gccagcagca tcgtgtccaa cctgttcatc cactacctga tgaagaacac ccagcaggtc      4020
gagaacctgg ctgtgctgtg ccacaagctg ctgcagcctg cggcatggt ctggttcacc      4080
accatgctgg gcgaacaggt gctggaactg ctgcacgaga accggatcga actgaacgaa      4140
```

-continued

```
gtgtgggagg cccgggagaa cgaggtggtc aagttcgcca tcaagcggct gttcaaagag    4200
gacatcctgc aggaaaccgg ccaggaaatc ggcgtcctgc tgcccttcag caacggcgac    4260
ttctacaatg agtacctggt caacaccgcc tttctgatca agattttcaa gcaccatggc    4320
tttagcctcg tgcagaagca gagcttcaag gactggatcc ccgagttcca gaacttcagc    4380
aagagcctgt acaagatcct gaccgaggcc gacaagacct ggaccagcct gttcggcttc    4440
atctgcctgc ggaagaacgg gccctga                                        4467
```

<210> SEQ ID NO 33
<211> LENGTH: 1488
<212> TYPE: PRT
<213> ORGANISM: Artificial Sequence
<220> FEATURE:
<223> OTHER INFORMATION: Amino-acid sequence of lambdaN-R341-G4-NP868R

<400> SEQUENCE: 33

```
Met Asp Ala Gln Thr Arg Arg Glu Arg Arg Ala Glu Lys Gln Ala
1               5                   10                  15

Gln Trp Lys Ala Ala Asn Gly Gly Gly Thr Gly Leu Lys Asn Lys
                20                  25                  30

Thr Arg Ala Glu Lys Tyr Gln Thr Tyr Thr Thr Asn Glu Tyr Gln
            35                  40                  45

Ile Val Lys Glu Lys Leu Pro Asp Ile Ile Arg Asp Ala Glu Ile Lys
    50                  55                  60

Ala Ser Glu Val Leu Glu Pro Thr Ile Tyr Glu Lys Arg Ala Ile Met
65                  70                  75                  80

Glu Val Ile Lys Asp Phe Ile Arg Asp His Gln Arg Lys Val Tyr Gly
                85                  90                  95

Gly Thr Ala Leu Asn Glu Ala Leu Lys Gln Val Asn Pro Lys Asp Ala
            100                 105                 110

Ile Tyr Asp Asn Tyr Ser Phe Ser Asp Ile Glu Phe Tyr Ser Pro Thr
        115                 120                 125

Pro Val Gln Asp Leu Val Asp Leu Cys Asn Ile Leu Tyr Arg Lys Gly
    130                 135                 140

Tyr Lys Phe Val Gln Gly Lys Asp Ala Gln His Glu Glu Thr Tyr Ser
145                 150                 155                 160

Ile Phe Val Asn Phe Gln Leu Tyr Cys Asp Ile Thr Tyr Ser Pro Thr
                165                 170                 175

Arg Val Phe Tyr Gly Ile Lys Thr Ile Glu Ile Asp Gly Ile Asn Tyr
            180                 185                 190

Thr Asp Pro His Phe Met Leu Ile Asp Tyr Leu Arg Met Val Asn Gln
        195                 200                 205

Pro Leu Thr Ala Ala Gly Gln Arg Trp Glu Lys Ala Phe Glu Arg Met
    210                 215                 220

Tyr Arg Leu Leu Lys Asp Tyr Pro Ile Glu Asp Phe Asp Lys Arg Leu
225                 230                 235                 240

Asp Ile Pro Glu Pro Pro Glu Glu Ile Gln Ser Tyr Ile Ser Arg Ile
                245                 250                 255

Lys Thr Glu Phe Leu Ser Asp Asn Lys Leu Asn Glu Ser Phe Leu Ile
            260                 265                 270

Ser Gly Ile Glu Ala Tyr Asn Phe Tyr Ile Arg His Ala Ala Ser Ser
        275                 280                 285

Lys Asp Glu Glu Gln Met Ala Arg Thr Asn Arg Asn Val Val Asn Leu
    290                 295                 300
```

-continued

```
Asn Asn Phe Ile Ala Asn Val Pro Phe Ser Glu Leu Ile Ser Val Asn
305                 310                 315                 320

Tyr Arg Glu Asp Val Lys Asn Thr Tyr Asn Phe Leu Arg Met Ile Val
                325                 330                 335

Glu Asp Lys Glu Lys Ile Ser Val Asp Glu Tyr Phe Pro Leu Phe Gln
            340                 345                 350

Phe Thr Gly Tyr Ser Thr Val Ile Lys Tyr Asp Asp His Pro Ile Ile
        355                 360                 365

Arg Ile Tyr Glu Gly Asp Gly Tyr Cys Ile Pro Asn Val Lys Thr Val
    370                 375                 380

Lys Thr Val Glu Asn Asp Asn Gly Thr Lys Thr Lys Tyr Glu Tyr Lys
385                 390                 395                 400

Tyr Val Ser Phe Gln Tyr Val Leu Met Ile Leu Tyr Ile Asn Lys Phe
                405                 410                 415

Arg Ala His Leu Asp Lys Asn Lys Pro Met Tyr Phe Asn Tyr Gly Ile
            420                 425                 430

Ala Ile Ser Asn Leu Val Lys Ala Arg Asn Ile Tyr Leu Asp Gln Thr
        435                 440                 445

Gly Lys Ser Val Leu Asp Asn Thr Val Phe Lys Glu Phe Arg Thr Asn
    450                 455                 460

Cys Thr Gly Asn Thr Ile Ser Phe Thr Arg Met Asn Arg Leu Arg Leu
465                 470                 475                 480

Leu Glu Lys Arg Lys Gln Gly Lys Gln Thr Ser Phe Val Tyr Thr Pro
                485                 490                 495

Glu Asp Phe Phe Lys Lys Asp Leu Glu Thr Gln Ala Lys Leu Asp Pro
            500                 505                 510

Ser Lys Ala Arg Phe Lys Asn Thr Ser Gly Asn Lys Ile Met Val Pro
        515                 520                 525

Lys Tyr Leu Leu Phe Lys Ile Asp Asn Asn Gly Asn Ile Glu Asp Asn
    530                 535                 540

Ile His Ser Glu Glu Ala Glu Ile Ser Glu Lys Glu Glu Thr Ser Gly
545                 550                 555                 560

Gly Ser Ser Ile Ser Thr Asp Lys Ser Phe Glu Glu Ser Pro Asn Ser
                565                 570                 575

Ser Pro Asn Ser Ser Pro Asn Asn Ser Leu Asn Asn Ser Ile Asp Ile
            580                 585                 590

Ser Thr Asn Asn Tyr Asp Asp Arg Ser Glu Asn Ser Leu Asp Ser Leu
        595                 600                 605

Thr Ser Asp Gly Pro Gly Gly Gly Glu Phe Ala Ser Leu Asp Asn
    610                 615                 620

Leu Val Ala Arg Tyr Gln Arg Cys Phe Asn Asp Gln Ser Leu Lys Asn
625                 630                 635                 640

Ser Thr Ile Glu Leu Glu Ile Arg Phe Gln Gln Ile Asn Phe Leu Leu
                645                 650                 655

Phe Lys Thr Val Tyr Glu Ala Leu Val Ala Gln Glu Ile Pro Ser Thr
            660                 665                 670

Ile Ser His Ser Ile Arg Cys Ile Lys Lys Val His His Glu Asn His
        675                 680                 685

Cys Arg Glu Lys Ile Leu Pro Ser Glu Asn Leu Tyr Phe Lys Lys Gln
    690                 695                 700

Pro Leu Met Phe Phe Lys Phe Ser Glu Pro Ala Ser Leu Gly Cys Lys
705                 710                 715                 720

Val Ser Leu Ala Ile Glu Gln Pro Ile Arg Lys Phe Ile Leu Asp Ser
```

-continued

```
                725                 730                 735
Ser Val Leu Val Arg Leu Lys Asn Arg Thr Thr Phe Arg Val Ser Glu
            740                 745                 750
Leu Trp Lys Ile Glu Leu Thr Ile Val Lys Gln Leu Met Gly Ser Glu
            755                 760                 765
Val Ser Ala Lys Leu Ala Ala Phe Lys Thr Leu Leu Phe Asp Thr Pro
            770                 775                 780
Glu Gln Gln Thr Thr Lys Asn Met Met Thr Leu Ile Asn Pro Asp Asp
785                 790                 795                 800
Glu Tyr Leu Tyr Glu Ile Glu Ile Glu Tyr Thr Gly Lys Pro Glu Ser
                805                 810                 815
Leu Thr Ala Ala Asp Val Ile Lys Ile Lys Asn Thr Val Leu Thr Leu
            820                 825                 830
Ile Ser Pro Asn His Leu Met Leu Thr Ala Tyr His Gln Ala Ile Glu
            835                 840                 845
Phe Ile Ala Ser His Ile Leu Ser Ser Glu Ile Leu Leu Ala Arg Ile
            850                 855                 860
Lys Ser Gly Lys Trp Gly Leu Lys Arg Leu Leu Pro Gln Val Lys Ser
865                 870                 875                 880
Met Thr Lys Ala Asp Tyr Met Lys Phe Tyr Pro Pro Val Gly Tyr Tyr
                885                 890                 895
Val Thr Asp Lys Ala Asp Gly Ile Arg Gly Ile Ala Val Ile Gln Asp
                900                 905                 910
Thr Gln Ile Tyr Val Val Ala Asp Gln Leu Tyr Ser Leu Gly Thr Thr
            915                 920                 925
Gly Ile Glu Pro Leu Lys Pro Thr Ile Leu Asp Gly Glu Phe Met Pro
930                 935                 940
Glu Lys Lys Glu Phe Tyr Gly Phe Asp Val Ile Met Tyr Glu Gly Asn
945                 950                 955                 960
Leu Leu Thr Gln Gln Gly Phe Glu Thr Arg Ile Glu Ser Leu Ser Lys
                965                 970                 975
Gly Ile Lys Val Leu Gln Ala Phe Asn Ile Lys Ala Glu Met Lys Pro
            980                 985                 990
Phe Ile Ser Leu Thr Ser Ala Asp Pro Asn Val Leu Leu Lys Asn Phe
            995                1000                1005
Glu Ser Ile Phe Lys Lys Thr Arg Pro Tyr Ser Ile Asp Gly
            1010                1015                1020
Ile Ile Leu Val Glu Pro Gly Asn Ser Tyr Leu Asn Thr Asn Thr
            1025                1030                1035
Phe Lys Trp Lys Pro Thr Trp Asp Asn Thr Leu Asp Phe Leu Val
            1040                1045                1050
Arg Lys Cys Pro Glu Ser Leu Asn Val Pro Glu Tyr Ala Pro Lys
            1055                1060                1065
Lys Gly Phe Ser Leu His Leu Phe Val Gly Ile Ser Gly Glu
            1070                1075                1080
Leu Phe Lys Lys Leu Ala Leu Asn Trp Cys Pro Gly Tyr Thr Lys
            1085                1090                1095
Leu Phe Pro Val Thr Gln Arg Asn Gln Asn Tyr Phe Pro Val Gln
            1100                1105                1110
Phe Gln Pro Ser Asp Phe Pro Leu Ala Phe Leu Tyr Tyr His Pro
            1115                1120                1125
Asp Thr Ser Ser Phe Ser Asn Ile Asp Gly Lys Val Leu Glu Met
            1130                1135                1140
```

Arg Cys Leu Lys Arg Glu Ile Asn Tyr Val Arg Trp Glu Ile Val
        1145                1150                1155

Lys Ile Arg Glu Asp Arg Gln Gln Asp Leu Lys Thr Gly Gly Tyr
    1160                1165                1170

Phe Gly Asn Asp Phe Lys Thr Ala Glu Leu Thr Trp Leu Asn Tyr
    1175                1180                1185

Met Asp Pro Phe Ser Phe Glu Glu Leu Ala Lys Gly Pro Ser Gly
    1190                1195                1200

Met Tyr Phe Ala Gly Ala Lys Thr Gly Ile Tyr Arg Ala Gln Thr
    1205                1210                1215

Ala Leu Ile Ser Phe Ile Lys Gln Glu Ile Ile Gln Lys Ile Ser
    1220                1225                1230

His Gln Ser Trp Val Ile Asp Leu Gly Ile Gly Lys Gly Gln Asp
    1235                1240                1245

Leu Gly Arg Tyr Leu Asp Ala Gly Val Arg His Leu Val Gly Ile
    1250                1255                1260

Asp Lys Asp Gln Thr Ala Leu Ala Glu Leu Val Tyr Arg Lys Phe
    1265                1270                1275

Ser His Ala Thr Thr Arg Gln His Lys His Ala Thr Asn Ile Tyr
    1280                1285                1290

Val Leu His Gln Asp Leu Ala Glu Pro Ala Lys Glu Ile Ser Glu
    1295                1300                1305

Lys Val His Gln Ile Tyr Gly Phe Pro Lys Glu Gly Ala Ser Ser
    1310                1315                1320

Ile Val Ser Asn Leu Phe Ile His Tyr Leu Met Lys Asn Thr Gln
    1325                1330                1335

Gln Val Glu Asn Leu Ala Val Leu Cys His Lys Leu Leu Gln Pro
    1340                1345                1350

Gly Gly Met Val Trp Phe Thr Thr Met Leu Gly Glu Gln Val Leu
    1355                1360                1365

Glu Leu Leu His Glu Asn Arg Ile Glu Leu Asn Glu Val Trp Glu
    1370                1375                1380

Ala Arg Glu Asn Glu Val Val Lys Phe Ala Ile Lys Arg Leu Phe
    1385                1390                1395

Lys Glu Asp Ile Leu Gln Glu Thr Gly Gln Glu Ile Gly Val Leu
    1400                1405                1410

Leu Pro Phe Ser Asn Gly Asp Phe Tyr Asn Glu Tyr Leu Val Asn
    1415                1420                1425

Thr Ala Phe Leu Ile Lys Ile Phe Lys His His Gly Phe Ser Leu
    1430                1435                1440

Val Gln Lys Gln Ser Phe Lys Asp Trp Ile Pro Glu Phe Gln Asn
    1445                1450                1455

Phe Ser Lys Ser Leu Tyr Lys Ile Leu Thr Glu Ala Asp Lys Thr
    1460                1465                1470

Trp Thr Ser Leu Phe Gly Phe Ile Cys Leu Arg Lys Asn Gly Pro
    1475                1480                1485

<210> SEQ ID NO 34
<211> LENGTH: 4467
<212> TYPE: DNA
<213> ORGANISM: Artificial Sequence
<220> FEATURE:
<223> OTHER INFORMATION: Nucleotide sequence of lambdaN-NP868R-G4-R341

<400> SEQUENCE: 34

-continued

```
atggatgctc agaccagacg cagagaacgg cgggcagaga agcaggcaca gtggaaggcc      60
gctaatggcg gtggcggcac cggtgccagc ctggacaacc tggtggccag ataccagcgg     120
tgcttcaacg accagagcct gaagaacagc accatcgagc tggaaatccg gttccagcag     180
atcaacttcc tgctgttcaa gaccgtgtac gaggccctgg tcgcccagga aatccccagc     240
accatcagcc acagcatccg gtgcatcaag aaggtgcacc acgagaacca ctgccgggag     300
aagatcctgc ccagcgagaa cctgtacttc aagaaacagc ccctgatgtt cttcaagttc     360
agcgagcccg ccagcctggg ctgtaaagtg tccctggcca tcgagcagcc catccggaag     420
ttcatcctgg acagcagcgt gctggtccgg ctgaagaacc ggaccacctt ccgggtgtcc     480
gagctgtgga agatcgagct gaccatcgtg aagcagctga tgggcagcga ggtgtcagcc     540
aagctggccg ccttcaagac cctgctgttc gacaccccg agcagcagac caccaagaac      600
atgatgaccc tgatcaaccc cgacgacgag tacctgtacg agatcgagat cgagtacacc     660
ggcaagcctg agagcctgac agccgccgac gtgatcaaga tcaagaacac cgtgctgaca     720
ctgatcagcc ccaaccacct gatgctgacc gcctaccacc aggccatcga gtttatcgcc     780
agccacatcc tgagcagcga gatcctgctg gcccggatca gagcggcaa gtggggcctg      840
aagagactgc tgccccaggt caagtccatg accaaggccg actacatgaa gttctacccc     900
cccgtgggct actacgtgac cgacaaggcc gacggcatcc ggggcattgc cgtgatccag     960
gacacccaga tctacgtggt ggccgaccag ctgtacagcc tgggcaccac cggcatcgag    1020
cccctgaagc ccaccatcct ggacggcgag ttcatgcccg agaagaaaga gttctacggc    1080
tttgacgtga tcatgtacga gggcaacctg ctgacccagc agggcttcga gacacggatc    1140
gagagcctga gcaagggcat caaggtgctg caggccttca acatcaaggc cgagatgaag    1200
cccttcatca gcctgaccte cgccgacccc aacgtgctgc tgaagaattt cgagagcatc    1260
ttcaagaaga aaacccggcc ctacagcatc gacggcatca tcctggtgga gcccggcaac    1320
agctacctga acaccaacac cttcaagtgg aagcccacct gggacaacac cctggacttt    1380
ctggtccgga gtgccccga gtccctgaac gtgcccgagt acgcccccaa gaagggcttc     1440
agcctgcatc tgctgttcgt gggcatcagc ggcgagctgt ttaagaagct ggccctgaac    1500
tggtgccccg gctacaccaa gctgttcccc gtgacccagc ggaaccagaa ctacttcccc    1560
gtgcagttcc agcccagcga cttccccctg gccttcctgt actaccaccc cgacaccagc    1620
agcttcagca catcgatgg caaggtgctg gaaatgcggt gcctgaagcg ggagatcaac     1680
tacgtgcgct gggagatcgt gaagatccgg gaggaccggc agcaggatct gaaaaccggc    1740
ggctacttcg gcaacgactt caagaccgcc gagctgacct ggctgaacta catggacccc    1800
ttcagcttcg aggaactggc caagggacce agcggcatga cttcgctgg cgccaagacc     1860
ggcatctaca gagcccagac cgccctgatc agcttcatca gcaggaaat catccagaag     1920
atcagccacc agagctgggt gatcgacctg ggcatcggca agggccagga cctgggcaga    1980
tacctggacg ccggcgtgag cacctggtc ggcatcgata aggaccagac agccctggcc     2040
gagctggtgt accggaagtt ctcccacgcc accaccagac agcacaagca cgccaccaac    2100
atctacgtgt gcaccaggga tctggccgag cctgccaaag aaatcagcga gaaagtgcac    2160
cagatctatg gcttccccaa agagggcgcc agcagcatcg tgtccaacct gttcatccac    2220
tacctgatga agaacaccca gcaggtcgag aacctggctg tgctgtgcca caagctgctg    2280
cagcctggcg gcatggtctg gttcaccacc atgctgggcg aacaggtgct ggaactgctg    2340
```

```
cacgagaacc ggatcgaact gaacgaagtg tgggaggccc gggagaacga ggtggtcaag    2400
ttcgccatca agcggctgtt caaagaggac atcctgcagg aaaccggcca ggaaatcggc    2460
gtcctgctgc ccttcagcaa cggcgacttc tacaatgagt acctggtcaa caccgccttt    2520
ctgatcaaga ttttcaagca ccatggcttt agcctcgtgc agaagcagag cttcaaggac    2580
tggatccccg agttccagaa cttcagcaag agcctgtaca agatcctgac cgaggccgac    2640
aagacctgga ccagcctgtt cggcttcatc tgcctgcgga gaacgggcc cggcggtggc    2700 ggcgaattcc tcaaaaacaa gaccagggct gagaagtatc agacctacta caccaccaat    2760
gaatatcaga tcgttaaaga aaaactacca gacattataa gagacgcgga aattaaggcg    2820
tctgaagtgc tcgagccaac catctacgag aagcgcgcaa tcatggaagt cattaaggat    2880
ttcattcggg atcatcaaag gaaagtgtat ggcggaacag ccctgaatga ggcattgaaa    2940
caggtgaatc ccaaggatgc catctatgat aactattcct cagcgacat cgagttttat    3000 tcccctaccc ccgtgcagga tctcgtggat ctctgcaaca tcctgtatag aaaagggtat    3060
aagttcgtcc aggggaagga cgctcagcat gaggaaacct attctatctt tgtaaatttc    3120
cagctctact gtgacattac ctattcgcca acccgggtct tttatggtat taaaacgata    3180
gaaattgacg gcattaacta taccgatcct catttcatgc tcatagatta cctccgaatg    3240
gtgaaccagc ccttgactgc cgccggccag cgctgggaga aagcgttcga acggatgtac    3300
aggctgctca aagactatcc cattgaggat tttgacaaga ggctggatat tcctgagcca    3360
cccgaagaaa tccagagtta tatttctcgg attaagaccg agtttctgag cgataacaag    3420
ctgaatgaaa gcttcctcat ctccggcatc gaggcttaca acttctacat cgccatgct    3480 gcctctagca agatgaaga acagatggcc cggacaaacc gcaatgtggt caatcttaat    3540
aactttattg caaatgtccc ctttagcgag ctgatctccg tgaactatcg cgaagatgtc    3600
aagaatacct ataacttcct gcggatgatc gtcgaggata agagaaaat cagtgttgac    3660 gaatatttcc ctctctttca attcactggc tattccactg tcatcaaata cgatgatcac    3720
cccataatta ggatctacga gggcgacggt tattgtattc ctaacgtcaa gaccgttaaa    3780
acggtggaga atgacaacgg aacgaagaca aagtacgagt acaagtacgt atccttccag    3840
tacgtcctca tgattctata tatcaacaaa tttcgtgcgc acttggacaa gaataagcct    3900
atgtatttta actacggtat tgccatatcc aatctggtca agctcgcaa tatatacctg    3960 gaccagaccg ggaaaagcgt ccttgacaac actgtgttta aggagttccg cactaactgt    4020
accggaaata cgatctcttt cacacggatg aacagactga gattactcga gaaagaaag    4080 cagggcaagc agacttcgtt cgtttacacc cctgaagact tctttaagaa ggatctggaa    4140
acccaagcca agcttgaccc gtcgaaagcg agattcaaaa ataccagtgg taacaagatt    4200
atggtgccaa agtacctgct gttcaaaata gataacaacg gaaatattga agataacata    4260
catagcgaag aggcagaaat ctcagagaaa gaagaaactt ccggtggctc ttctatatcc    4320
actgataaat cattcgaaga atcacctaat tcctccccta cagctctcc taacaactcg    4380 ttgaataatt ctattgatat cagtacaaat aattacgacg accgctcgga aacagcctg    4440 gactcactca cgtctgatgg gccctga                                       4467
```

<210> SEQ ID NO 35
<211> LENGTH: 1488
<212> TYPE: PRT
<213> ORGANISM: Artificial Sequence
<220> FEATURE:
<223> OTHER INFORMATION: Amino-acid sequence of lambdaN-NP868R-G4-R341

<400> SEQUENCE: 35

```
Met Asp Ala Gln Thr Arg Arg Glu Arg Arg Ala Glu Lys Gln Ala
1               5                   10                  15

Gln Trp Lys Ala Ala Asn Gly Gly Gly Thr Gly Ala Ser Leu Asp
            20                  25                  30

Asn Leu Val Ala Arg Tyr Gln Arg Cys Phe Asn Asp Gln Ser Leu Lys
        35                  40                  45

Asn Ser Thr Ile Glu Leu Glu Ile Arg Phe Gln Gln Ile Asn Phe Leu
    50                  55                  60

Leu Phe Lys Thr Val Tyr Glu Ala Leu Val Ala Gln Glu Ile Pro Ser
65                  70                  75                  80

Thr Ile Ser His Ser Ile Arg Cys Ile Lys Lys Val His His Glu Asn
                85                  90                  95

His Cys Arg Glu Lys Ile Leu Pro Ser Glu Asn Leu Tyr Phe Lys Lys
            100                 105                 110

Gln Pro Leu Met Phe Phe Lys Phe Ser Glu Pro Ala Ser Leu Gly Cys
        115                 120                 125

Lys Val Ser Leu Ala Ile Glu Gln Pro Ile Arg Lys Phe Ile Leu Asp
130                 135                 140

Ser Ser Val Leu Val Arg Leu Lys Asn Arg Thr Thr Phe Arg Val Ser
145                 150                 155                 160

Glu Leu Trp Lys Ile Glu Leu Thr Ile Val Lys Gln Leu Met Gly Ser
                165                 170                 175

Glu Val Ser Ala Lys Leu Ala Ala Phe Lys Thr Leu Leu Phe Asp Thr
            180                 185                 190

Pro Glu Gln Gln Thr Thr Lys Asn Met Met Thr Leu Ile Asn Pro Asp
        195                 200                 205

Asp Glu Tyr Leu Tyr Glu Ile Glu Ile Glu Tyr Thr Gly Lys Pro Glu
210                 215                 220

Ser Leu Thr Ala Ala Asp Val Ile Lys Ile Lys Asn Thr Val Leu Thr
225                 230                 235                 240

Leu Ile Ser Pro Asn His Leu Met Leu Thr Ala Tyr His Gln Ala Ile
                245                 250                 255

Glu Phe Ile Ala Ser His Ile Leu Ser Ser Glu Ile Leu Leu Ala Arg
            260                 265                 270

Ile Lys Ser Gly Lys Trp Gly Leu Lys Arg Leu Leu Pro Gln Val Lys
        275                 280                 285

Ser Met Thr Lys Ala Asp Tyr Met Lys Phe Tyr Pro Pro Val Gly Tyr
290                 295                 300

Tyr Val Thr Asp Lys Ala Asp Gly Ile Arg Gly Ile Ala Val Ile Gln
305                 310                 315                 320

Asp Thr Gln Ile Tyr Val Val Ala Asp Gln Leu Tyr Ser Leu Gly Thr
                325                 330                 335

Thr Gly Ile Glu Pro Leu Lys Pro Thr Ile Leu Asp Gly Glu Phe Met
            340                 345                 350

Pro Glu Lys Lys Glu Phe Tyr Gly Phe Asp Val Ile Met Tyr Glu Gly
        355                 360                 365

Asn Leu Leu Thr Gln Gln Gly Phe Glu Thr Arg Ile Glu Ser Leu Ser
    370                 375                 380

Lys Gly Ile Lys Val Leu Gln Ala Phe Asn Ile Lys Ala Glu Met Lys
385                 390                 395                 400

Pro Phe Ile Ser Leu Thr Ser Ala Asp Pro Asn Val Leu Leu Lys Asn
```

```
                405                 410                 415
Phe Glu Ser Ile Phe Lys Lys Thr Arg Pro Tyr Ser Ile Asp Gly
            420                 425                 430

Ile Ile Leu Val Glu Pro Gly Asn Ser Tyr Leu Asn Thr Asn Thr Phe
            435                 440                 445

Lys Trp Lys Pro Thr Trp Asp Asn Thr Leu Asp Phe Leu Val Arg Lys
        450                 455                 460

Cys Pro Glu Ser Leu Asn Val Pro Glu Tyr Ala Pro Lys Lys Gly Phe
465                 470                 475                 480

Ser Leu His Leu Leu Phe Val Gly Ile Ser Gly Glu Leu Phe Lys Lys
                485                 490                 495

Leu Ala Leu Asn Trp Cys Pro Gly Tyr Thr Lys Leu Phe Pro Val Thr
            500                 505                 510

Gln Arg Asn Gln Asn Tyr Phe Pro Val Gln Phe Gln Pro Ser Asp Phe
            515                 520                 525

Pro Leu Ala Phe Leu Tyr Tyr His Pro Asp Thr Ser Ser Phe Ser Asn
            530                 535                 540

Ile Asp Gly Lys Val Leu Glu Met Arg Cys Leu Lys Arg Glu Ile Asn
545                 550                 555                 560

Tyr Val Arg Trp Glu Ile Val Lys Ile Arg Glu Asp Arg Gln Gln Asp
                565                 570                 575

Leu Lys Thr Gly Gly Tyr Phe Gly Asn Asp Phe Lys Thr Ala Glu Leu
            580                 585                 590

Thr Trp Leu Asn Tyr Met Asp Pro Phe Ser Phe Glu Glu Leu Ala Lys
            595                 600                 605

Gly Pro Ser Gly Met Tyr Phe Ala Gly Ala Lys Thr Gly Ile Tyr Arg
            610                 615                 620

Ala Gln Thr Ala Leu Ile Ser Phe Ile Lys Gln Glu Ile Ile Gln Lys
625                 630                 635                 640

Ile Ser His Gln Ser Trp Val Ile Asp Leu Gly Ile Gly Lys Gly Gln
                645                 650                 655

Asp Leu Gly Arg Tyr Leu Asp Ala Gly Val Arg His Leu Val Gly Ile
            660                 665                 670

Asp Lys Asp Gln Thr Ala Leu Ala Glu Leu Val Tyr Arg Lys Phe Ser
            675                 680                 685

His Ala Thr Thr Arg Gln His Lys His Ala Thr Asn Ile Tyr Val Leu
            690                 695                 700

His Gln Asp Leu Ala Glu Pro Ala Lys Glu Ile Ser Glu Lys Val His
705                 710                 715                 720

Gln Ile Tyr Gly Phe Pro Lys Glu Gly Ala Ser Ser Ile Val Ser Asn
                725                 730                 735

Leu Phe Ile His Tyr Leu Met Lys Asn Thr Gln Gln Val Glu Asn Leu
            740                 745                 750

Ala Val Leu Cys His Lys Leu Leu Gln Pro Gly Gly Met Val Trp Phe
            755                 760                 765

Thr Thr Met Leu Gly Glu Gln Val Leu Glu Leu His Glu Asn Arg
            770                 775                 780

Ile Glu Leu Asn Glu Val Trp Glu Ala Arg Glu Asn Glu Val Val Lys
785                 790                 795                 800

Phe Ala Ile Lys Arg Leu Phe Lys Glu Asp Ile Leu Gln Glu Thr Gly
                805                 810                 815

Gln Glu Ile Gly Val Leu Leu Pro Phe Ser Asn Gly Asp Phe Tyr Asn
            820                 825                 830
```

```
Glu Tyr Leu Val Asn Thr Ala Phe Leu Ile Lys Ile Phe Lys His His
    835                 840                 845
Gly Phe Ser Leu Val Gln Lys Gln Ser Phe Lys Asp Trp Ile Pro Glu
    850                 855                 860
Phe Gln Asn Phe Ser Lys Ser Leu Tyr Lys Ile Leu Thr Glu Ala Asp
865                 870                 875                 880
Lys Thr Trp Thr Ser Leu Phe Gly Phe Ile Cys Leu Arg Lys Asn Gly
                885                 890                 895
Pro Gly Gly Gly Glu Phe Leu Lys Asn Lys Thr Arg Ala Glu Lys
                900                 905                 910
Tyr Gln Thr Tyr Tyr Thr Asn Glu Tyr Gln Ile Val Lys Glu Lys
                915                 920                 925
Leu Pro Asp Ile Ile Arg Asp Ala Glu Ile Lys Ala Ser Glu Val Leu
    930                 935                 940
Glu Pro Thr Ile Tyr Glu Lys Arg Ala Ile Met Glu Val Ile Lys Asp
945                 950                 955                 960
Phe Ile Arg Asp His Gln Arg Lys Val Tyr Gly Gly Thr Ala Leu Asn
                965                 970                 975
Glu Ala Leu Lys Gln Val Asn Pro Lys Asp Ala Ile Tyr Asp Asn Tyr
                980                 985                 990
Ser Phe Ser Asp Ile Glu Phe Tyr  Ser Pro Thr Pro Val  Gln Asp Leu
                995                 1000                1005
Val Asp  Leu Cys Asn Ile Leu  Tyr Arg Lys Gly Tyr  Lys Phe Val
    1010                1015                1020
Gln Gly  Lys Asp Ala Gln His  Glu Glu Thr Tyr Ser  Ile Phe Val
    1025                1030                1035
Asn Phe  Gln Leu Tyr Cys Asp  Ile Thr Tyr Ser Pro  Thr Arg Val
    1040                1045                1050
Phe Tyr  Gly Ile Lys Thr Ile  Glu Ile Asp Gly Ile  Asn Tyr Thr
    1055                1060                1065
Asp Pro  His Phe Met Leu Ile  Asp Tyr Leu Arg Met  Val Asn Gln
    1070                1075                1080
Pro Leu  Thr Ala Ala Gly Gln  Arg Trp Glu Lys Ala  Phe Glu Arg
    1085                1090                1095
Met Tyr  Arg Leu Leu Lys Asp  Tyr Pro Ile Glu Asp  Phe Asp Lys
    1100                1105                1110
Arg Leu  Asp Ile Pro Glu Pro  Pro Glu Glu Ile Gln  Ser Tyr Ile
    1115                1120                1125
Ser Arg  Ile Lys Thr Glu Phe  Leu Ser Asp Asn Lys  Leu Asn Glu
    1130                1135                1140
Ser Phe  Leu Ile Ser Gly Ile  Glu Ala Tyr Asn Phe  Tyr Ile Arg
    1145                1150                1155
His Ala  Ala Ser Ser Lys Asp  Glu Glu Gln Met Ala  Arg Thr Asn
    1160                1165                1170
Arg Asn  Val Val Asn Leu Asn  Asn Phe Ile Ala Asn  Val Pro Phe
    1175                1180                1185
Ser Glu  Leu Ile Ser Val Asn  Tyr Arg Glu Asp Val  Lys Asn Thr
    1190                1195                1200
Tyr Asn  Phe Leu Arg Met Ile  Val Glu Asp Lys Glu  Lys Ile Ser
    1205                1210                1215
Val Asp  Glu Tyr Phe Pro Leu  Phe Gln Phe Thr Gly  Tyr Ser Thr
    1220                1225                1230
```

Val Ile Lys Tyr Asp Asp His Pro Ile Ile Arg Ile Tyr Glu Gly
1235                1240                1245

Asp Gly Tyr Cys Ile Pro Asn Val Lys Thr Val Lys Thr Val Glu
1250                1255                1260

Asn Asp Asn Gly Thr Lys Thr Lys Tyr Glu Tyr Lys Tyr Val Ser
1265                1270                1275

Phe Gln Tyr Val Leu Met Ile Leu Tyr Ile Asn Lys Phe Arg Ala
1280                1285                1290

His Leu Asp Lys Asn Lys Pro Met Tyr Phe Asn Tyr Gly Ile Ala
1295                1300                1305

Ile Ser Asn Leu Val Lys Ala Arg Asn Ile Tyr Leu Asp Gln Thr
1310                1315                1320

Gly Lys Ser Val Leu Asp Asn Thr Val Phe Lys Glu Phe Arg Thr
1325                1330                1335

Asn Cys Thr Gly Asn Thr Ile Ser Phe Thr Arg Met Asn Arg Leu
1340                1345                1350

Arg Leu Leu Glu Lys Arg Lys Gln Gly Lys Gln Thr Ser Phe Val
1355                1360                1365

Tyr Thr Pro Glu Asp Phe Phe Lys Lys Asp Leu Glu Thr Gln Ala
1370                1375                1380

Lys Leu Asp Pro Ser Lys Ala Arg Phe Lys Asn Thr Ser Gly Asn
1385                1390                1395

Lys Ile Met Val Pro Lys Tyr Leu Leu Phe Lys Ile Asp Asn Asn
1400                1405                1410

Gly Asn Ile Glu Asp Asn Ile His Ser Glu Glu Ala Glu Ile Ser
1415                1420                1425

Glu Lys Glu Glu Thr Ser Gly Gly Ser Ser Ile Ser Thr Asp Lys
1430                1435                1440

Ser Phe Glu Glu Ser Pro Asn Ser Ser Pro Asn Ser Ser Pro Asn
1445                1450                1455

Asn Ser Leu Asn Asn Ser Ile Asp Ile Ser Thr Asn Asn Tyr Asp
1460                1465                1470

Asp Arg Ser Glu Asn Ser Leu Asp Ser Leu Thr Ser Asp Gly Pro
1475                1480                1485

<210> SEQ ID NO 36
<211> LENGTH: 390
<212> TYPE: DNA
<213> ORGANISM: Bacteriophage MS2

<400> SEQUENCE: 36
atggcttcaa acttcacgca gtttgttctg gtcgacaacg gcgggaccgg agacgtgaca     60
gtcgcccctt ctaactttgc taatggagtc gctgaatgga tctccagtaa ttcccggtca    120
caagcctata aggttacatg ctccgtccgc caatccagcg cgcagaatcg taagtacact    180
ataaaggtag aggtaccgaa ggtagcgact cagaccgttg gagggaagaa actgcccgtc    240
gcggggtggc gctcctacct gaacatggag ttgaccatcc cgattttcgc gacaaactct    300
gactgtgaac tgattgtgaa ggccatgcag ggactgctga aggatgggaa ccctattccc    360
agcgccattg cggcaaattc agggatatat                                      390

<210> SEQ ID NO 37
<211> LENGTH: 130
<212> TYPE: PRT
<213> ORGANISM: Bacteriophage MS2

<400> SEQUENCE: 37

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ala Gln Asn Arg Lys Tyr Thr Ile Lys Val Glu
50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr
    130

<210> SEQ ID NO 38
<211> LENGTH: 15
<212> TYPE: DNA
<213> ORGANISM: Bacteriophage lambda

<400> SEQUENCE: 38
gccctgaaga agggc                                                        15

<210> SEQ ID NO 39
<211> LENGTH: 19
<212> TYPE: DNA
<213> ORGANISM: Bacteriophage MS2

<400> SEQUENCE: 39
acatgaggat cacccatgt                                                    19

<210> SEQ ID NO 40
<211> LENGTH: 7125
<212> TYPE: DNA
<213> ORGANISM: Artificial Sequence
<220> FEATURE:
<223> OTHER INFORMATION: Nucleotide sequence of lambdaN-R341-G4-NP868R-
      (G4S)2-K1ERNAP

<400> SEQUENCE: 40
atggatgctc agaccagacg cagagaacgg cgggcagaga agcaggcaca gtggaaggcc       60
gctaatggcg gtggcggcac cggtctcaaa acaagaccaa gggctgagaa gtatcagacc      120
tactacacca ccaatgaata tcagatcgtt aaagaaaaac taccagacat tataagagac      180
gcggaaatta aggcgtctga agtgctcgag ccaaccatct acgagaagcg cgcaatcatg      240
gaagtcatta aggatttcat tcgggatcat caaaggaaag tgtatggcgg aacagccctg      300
aatgaggcat tgaaacaggt gaatcccaag gatgccatct atgataacta ttccttcagc      360
gacatcgagt tttattcccc tacccccgtg caggatctcg tggatctctg caacatcctg      420
tatagaaaag gtataagtt cgtccagggg aagacgctc agcatgagga aacctattct       480
atctttgtaa atttccagct ctactgtgac attaccatt cgccaaccg ggtctttat        540 ggtattaaaa cgatagaaat tgacggcatt aactataccg atcctcattt catgctcata      600

-continued

```
gattacctcc gaatggtgaa ccagcccttg actgccgccg ccagcgctg ggagaaagcg      660 ttcgaacgga tgtacaggct gctcaaagac tatcccattg aggattttga caagaggctg      720
gatattcctg agccacccga agaaatccag agttatattt ctcggattaa gaccgagttt      780
ctgagcgata caagctgaa tgaaagcttc ctcatctccg gcatcgaggc ttacaacttc       840
tacattcgcc atgctgcctc tagcaaagat gaagaacaga tggcccggac aaaccgcaat      900
gtggtcaatc ttaataactt tattgcaaat gtccccttta gcgagctgat ctccgtgaac      960
tatcgcgaag atgtcaagaa tacctataac ttcctgcgga tgatcgtcga ggataaagag     1020
aaaatcagtg ttgacgaata tttccctctc tttcaattca ctggctattc cactgtcatc     1080
aaatacgatg atcaccccat aattaggatc tacgagggcg acggttattg tattcctaac     1140
gtcaagaccg ttaaaacggt ggagaatgac aacggaacga agacaaagta cgagtacaag     1200
tacgtatcct tccagtacgt cctcatgatt ctatatatca acaaatttcg tgcgcacttg     1260
gacaagaata agcctatgta tttaactac ggtattgcca tatccaatct ggtcaaagct     1320
cgcaatatat acctggacca gaccgggaaa agcgtccttg acaacactgt gtttaaggag     1380
ttccgcacta actgtaccgg aaatacgatc tctttcacac ggatgaacag actgagatta     1440
ctcgagaaaa gaaagcaggg caagcagact tcgttcgttt acaccctga agacttcttt      1500 aagaaggatc tggaaaccca agccaagctt gacccgtcga aagcgagatt caaaaatacc     1560
agtggtaaca agattatggt gccaaagtac ctgctgttca aaatagataa caacggaaat     1620
attgaagata acatacatag cgaagaggca gaaatctcag agaaagaaga aacttccggt     1680
ggctcttcta tatccactga taaatcattc gaagaatcac ctaattcctc ccctaacagc     1740
tctcctaaca actcgttgaa taattctatt gatatcagta caaataatta cgacgaccgc     1800
tcggaaaaca gcctggactc actcacgtct gatgggcccg gcggtggcgg cgaattcgcc     1860
agcctggaca acctggtggc cagataccag cggtgcttca cgaccagag cctgaagaac      1920 agcaccatcg agctggaaat ccggttccag cagatcaact tcctgctgtt caagaccgtg     1980
tacgaggccc tggtcgccca ggaaatcccc agcaccatca gccacagcat ccggtgcatc     2040
aagaaggtgc accacgagaa ccactgccgg gagaagatcc tgcccagcga aacctgtac     2100 ttcaagaaac agcccctgat gttcttcaag ttcagcgagc cgccagcct gggctgtaaa      2160 gtgtccctgg ccatcgagca gcccatccgg aagttcatcc tggacagcag cgtgctggtc     2220
cggctgaaga accggaccac cttcggggtg tccgagctgt ggaagatcga gctgaccatc     2280
gtgaagcagc tgatgggcag cgaggtgtca gccaagctgg ccgccttcaa gaccctgctg     2340
ttcgacaccc ccgagcagca gaccaccaag aacatgatga ccctgatcaa ccccgacgac     2400
gagtacctgt acgagatcga gatcgagtac ccggcaagc tgagagcct gacagccgcc      2460 gacgtgatca agatcaagaa caccgtgctg acactgatca gccccaacca cctgatgctg     2520
accgcctacc accaggccat cgagtttatc gccagccaca cctgagcag cgagatcctg     2580 ctggcccgga tcaagagcgg caagtggggc ctgaagagac tgctgcccca ggtcaagtcc     2640
atgaccaagg ccgactacat gaagttctac cccccgtgg gctactacgt gaccgacaag     2700
gccgacggca tccggggcat tgccgtgatc caggacaccc agatctacgt ggtggccgac     2760
cagctgtaca gcctgggcac caccggcatc gagcccctga gcccaccat cctggacggc     2820 gagttcatgc ccgagaagaa agagttctac ggctttgacg tgatcatgta cgagggcaac     2880
ctgctgaccc agcagggctt cgagacacgg atcgagagcc tgagcaaggg catcaaggtg     2940
```

```
ctgcaggcct tcaacatcaa ggccgagatg aagcccttca tcagcctgac ctccgccgac    3000
cccaacgtgc tgctgaagaa tttcgagagc atcttcaaga agaaaacccg gccctacagc    3060
atcgacggca tcatcctggt ggagcccggc aacagctacc tgaacaccaa caccttcaag    3120
tggaagccca cctgggacaa caccctggac tttctggtcc ggaagtgccc cgagtccctg    3180
aacgtgcccg agtacgcccc caagaagggc ttcagcctgc atctgctgtt cgtgggcatc    3240
agcggcgagc tgtttaagaa gctggccctg aactggtgcc ccggctacac caagctgttc    3300
cccgtgaccc agcggaacca gaactacttc cccgtgcagt tccagcccag cgacttcccc    3360
ctggccttcc tgtactacca ccccgacacc agcagcttca gcaacatcga tggcaaggtg    3420
ctggaaatgc ggtgcctgaa gcgggagatc aactacgtgc gctgggagat cgtgaagatc    3480
cgggaggacc ggcagcagga tctgaaaacc ggcggctact tcggcaacga cttcaagacc    3540
gccgagctga cctggctgaa ctacatggac cccttcagct tcgaggaact ggccaaggga    3600
cccagcggca tgtacttcgc tggcgccaag accggcatct acagagccca gaccgccctg    3660
atcagcttca tcaagcagga aatcatccag aagatcagcc accagagctg ggtgatcgac    3720
ctgggcatcg gcaagggcca ggacctgggc agatacctgg acgccggcgt gagacacctg    3780
gtcggcatcg ataaggacca gacagccctg gccgagctgt gtaccggaa gttctcccac    3840 gccaccacca gacagcacaa gcacgccacc aacatctacg tgctgcacca ggatctggcc    3900
gagcctgcca agaaaatcag cgagaaagtg caccagatct atggcttccc caaagagggc    3960
gccagcagca tcgtgtccaa cctgttcatc cactacctga tgaagaacac ccagcaggtc    4020
gagaacctgg ctgtgctgtg ccacaagctg ctgcagcctg cggcatggt ctggttcacc    4080 accatgctgg gcgaacaggt gctggaactg ctgcacgaga accggatcga actgaacgaa    4140
gtgtgggagg cccgggagaa cgaggtggtc aagttcgcca tcaagcggct gttcaaagag    4200
gacatcctgc aggaaaccgg ccaggaaatc ggcgtcctgc tgcccttcag caacggcgac    4260
ttctacaatg agtacctggt caacaccgcc tttctgatca agattttcaa gcaccatggc    4320
tttagcctcg tgcagaagca gagcttcaag gactggatcc ccgagttcca gaacttcagc    4380
aagagcctgt acaagatcct gaccgaggcc gacaagacct ggaccagcct gttcggcttc    4440
atctgcctgc ggaagaacct cgagggagga ggaggatcag gcggaggcgg aagtgtcgag    4500
caggacctgc acgccatcca gctgcagctc aagaggaaa tgttcaacgg cggcatcaga    4560
agattcgagg ccgaccagca gagacagatc gcctctggca cgagagcga caccgcctgg    4620 aatagaaggc tgctgtctga gctgatcgcc cctatggccg aaggcatcca ggcctacaaa    4680
gaggaatacg agggcaagag aggcagagcc cctagagccc tggccttcat caactgtgtg    4740
ggcaatgagg tggccgccta catcaccatg aagatcgtga tggacatgct gaacaccgac    4800
gtgaccctgc aggccattgc catgaacgtg gccgacagaa tcgaggacca ggtccgattc    4860
agcaagctgg aaggacacgc cgccaagtac ttcgagaaag tgaagaagtc cctgaaggcc    4920
agcaagacca gagctacag acacgcccac aacgtggccg tggtggccga aaatctgtg    4980 gccgataggg acgccgactt ctctagatgg gaggcctggc taaggacac cctgctgcag    5040 atcggcatga ccctgctgga aatcctggaa acagcgtgt cttcaacgg ccagcccgtg    5100 ttcctgagaa ccctgaggac aaatggcggc aagcacggcg tgtactacct gcagacatct    5160
gagcacgtgg gcgagtggat caccgccttc aaagaacatg tggcccagct gagccctgcc    5220
tatgcccctt gtgtgatccc tcctagaccc tgggtgtccc ctttcaatgg cggctttcac    5280
accgagaagg tggccagcag aatcagactg gtcaagggca accgggaaca cgtgcggaag    5340
```

```
ctgaccaaga aacagatgcc cgccgtgtac aaggccgtga atgctctgca ggccaccaag    5400
tggcaggtca acaaagaggt gctgcaggtc gtcgaggacg tgatcagact ggatctgggc    5460
tacggcgtgc caagctttaa gcccctgatc gacagagaga acaagcccgc caaccctgtg    5520
cccctggaat tcagcacct gagaggccgc gagctgaaag atgctgac acctgaacag       5580 tggcaggcct ttatcaattg aagggcgag tgcaccaagc tgtacaccgc cgagacaaag     5640
aggggctcta agtctgccgc cacagtgcga atggtcggac aggccagaaa gtacagccag    5700
ttcgacgcca tctacttcgt gtacgccctg gacagccggt ctagagtgta tgcccagagc    5760
agcacactga gcccccagtc taacgatctg gaaaaggccc tgctgagatt caccgagggc    5820
cagagactgg attctgccga agccctgaag tggttcctgg tcaacggcgc caacaactgg    5880
ggctgggaca agaaaacctt cgatgtgcgg accgccaacg tgctggatag cgagttccag    5940
gacatgtgca gagatatcgc cgccgaccct ctgaccttta cccagtgggt caacgccgat    6000
agcccctatg gattcctggc ctggtgcttc gagtacgcca gatacctgga cgccctggat    6060
gagggaaccc aggatcagtt catgacccat ctgcccgtgc accaggatgg ctcttgttct    6120
ggcatccagc actacagcgc catgctgagc gatgccgtgg agccaaaagc cgtgaacctg    6180
aagcctagcg acagccccca ggatatctat ggcgctgtgg cccaggtggt catccagaaa    6240
aactacgcct acatgaacgc cgaggacgcc gagacattca aagcggaag cgtgacactg    6300 acaggcgccg agctgagatc tatggcctct gcctgggaca tgatcggcat cacacggggc    6360
ctgaccaaaa agcctgtgat gacactgccc tacggcagca ccagactgac ctgtagagaa    6420
agcgtgatcg actacatcgt ggacctggaa gagaagagg cccagagagc cattgccgag    6480
ggcagaacag ccaatcctgt gcaccccttc gacaacgacc ggaaggatag cctgacacct    6540
agcgccgcct acaactacat gaccgccctg atctggccca gcatctctga agtggtcaag    6600 gccctatcg tggccatgaa gatgatcaga cagctggcca gattcgccgc caagagaaat    6660
gagggcctgg aatacctct gcccaccggc tttatcctgc agcagaaaat catggccacc    6720
gacatgctgc gggtgtccac atgtctgatg ggcgagatca gatgagcct gcagatcgag    6780 acagacgtgg tggacgagac agccatgatg ggagccgccg ctcctaattt tgtgcacgga    6840
cacgatgcca gccacctgat cctgaccgtg tgcgatctgg tggacaaggg catcactagc    6900
gtggccgtga tccacgatag ctttggaaca cacgccggca gaaccgccga cctgagagat    6960
tctctgcggg aagagatggt caagatgtac cagaaccaca cgccctgca gaacctgctg    7020 gacgtgcacg aagaaagatg gctggtggac accggcatcc aggtgccaga cagggagag    7080 ttcgacctga cgagatcct ggtgtccgac tactgcttcg cctga                    7125
```

<210> SEQ ID NO 41
<211> LENGTH: 2374
<212> TYPE: PRT
<213> ORGANISM: Artificial Sequence
<220> FEATURE:
<223> OTHER INFORMATION: Amino-acid sequence of lambdaN-R341-G4-NP868R-(G4S)2-K1ERNAP

<400> SEQUENCE: 41

Met Asp Ala Gln Thr Arg Arg Arg Glu Arg Arg Ala Glu Lys Gln Ala
1               5                   10                  15

Gln Trp Lys Ala Ala Asn Gly Gly Gly Gly Thr Gly Leu Lys Asn Lys
            20                  25                  30

Thr Arg Ala Glu Lys Tyr Gln Thr Tyr Tyr Thr Thr Asn Glu Tyr Gln

```
            35                  40                  45
Ile Val Lys Glu Lys Leu Pro Asp Ile Ile Arg Asp Ala Glu Ile Lys
 50                  55                  60
Ala Ser Glu Val Leu Glu Pro Thr Ile Tyr Glu Lys Arg Ala Ile Met
 65                  70                  75                  80
Glu Val Ile Lys Asp Phe Ile Arg Asp His Gln Arg Lys Val Tyr Gly
                     85                  90                  95
Gly Thr Ala Leu Asn Glu Ala Leu Lys Gln Val Asn Pro Lys Asp Ala
                    100                 105                 110
Ile Tyr Asp Asn Tyr Ser Phe Ser Asp Ile Glu Phe Tyr Ser Pro Thr
                    115                 120                 125
Pro Val Gln Asp Leu Val Asp Leu Cys Asn Ile Leu Tyr Arg Lys Gly
                    130                 135                 140
Tyr Lys Phe Val Gln Gly Lys Asp Ala Gln His Glu Glu Thr Tyr Ser
145                 150                 155                 160
Ile Phe Val Asn Phe Gln Leu Tyr Cys Asp Ile Thr Tyr Ser Pro Thr
                    165                 170                 175
Arg Val Phe Tyr Gly Ile Lys Thr Ile Glu Ile Asp Gly Ile Asn Tyr
                    180                 185                 190
Thr Asp Pro His Phe Met Leu Ile Asp Tyr Leu Arg Met Val Asn Gln
                    195                 200                 205
Pro Leu Thr Ala Ala Gly Gln Arg Trp Glu Lys Ala Phe Glu Arg Met
                    210                 215                 220
Tyr Arg Leu Leu Lys Asp Tyr Pro Ile Glu Asp Phe Asp Lys Arg Leu
225                 230                 235                 240
Asp Ile Pro Glu Pro Pro Glu Ile Gln Ser Tyr Ile Ser Arg Ile
                    245                 250                 255
Lys Thr Glu Phe Leu Ser Asp Asn Lys Leu Asn Glu Ser Phe Leu Ile
                    260                 265                 270
Ser Gly Ile Glu Ala Tyr Asn Phe Tyr Ile Arg His Ala Ala Ser Ser
                    275                 280                 285
Lys Asp Glu Glu Gln Met Ala Arg Thr Asn Arg Asn Val Val Asn Leu
                    290                 295                 300
Asn Asn Phe Ile Ala Asn Val Pro Phe Ser Glu Leu Ile Ser Val Asn
305                 310                 315                 320
Tyr Arg Glu Asp Val Lys Asn Thr Tyr Asn Phe Leu Arg Met Ile Val
                    325                 330                 335
Glu Asp Lys Glu Lys Ile Ser Val Asp Glu Tyr Phe Pro Leu Phe Gln
                    340                 345                 350
Phe Thr Gly Tyr Ser Thr Val Ile Lys Tyr Asp Asp His Pro Ile Ile
                    355                 360                 365
Arg Ile Tyr Glu Gly Asp Gly Tyr Cys Ile Pro Asn Val Lys Thr Val
                    370                 375                 380
Lys Thr Val Glu Asn Asp Asn Gly Thr Lys Thr Lys Tyr Glu Tyr Lys
385                 390                 395                 400
Tyr Val Ser Phe Gln Tyr Val Leu Met Ile Leu Tyr Ile Asn Lys Phe
                    405                 410                 415
Arg Ala His Leu Asp Lys Asn Lys Pro Met Tyr Phe Asn Tyr Gly Ile
                    420                 425                 430
Ala Ile Ser Asn Leu Val Lys Ala Arg Asn Ile Tyr Leu Asp Gln Thr
                    435                 440                 445
Gly Lys Ser Val Leu Asp Asn Thr Val Phe Lys Glu Phe Arg Thr Asn
                    450                 455                 460
```

```
Cys Thr Gly Asn Thr Ile Ser Phe Thr Arg Met Asn Arg Leu Arg Leu
465                 470                 475                 480

Leu Glu Lys Arg Lys Gln Gly Lys Gln Thr Ser Phe Val Tyr Thr Pro
            485                 490                 495

Glu Asp Phe Phe Lys Lys Asp Leu Glu Thr Gln Ala Lys Leu Asp Pro
                500                 505                 510

Ser Lys Ala Arg Phe Lys Asn Thr Ser Gly Asn Lys Ile Met Val Pro
            515                 520                 525

Lys Tyr Leu Leu Phe Lys Ile Asp Asn Asn Gly Asn Ile Glu Asp Asn
530                 535                 540

Ile His Ser Glu Glu Ala Glu Ile Ser Glu Lys Glu Thr Ser Gly
545                 550                 555                 560

Gly Ser Ser Ile Ser Thr Asp Lys Ser Phe Glu Glu Ser Pro Asn Ser
                565                 570                 575

Ser Pro Asn Ser Ser Pro Asn Asn Ser Leu Asn Asn Ser Ile Asp Ile
            580                 585                 590

Ser Thr Asn Asn Tyr Asp Asp Arg Ser Glu Asn Ser Leu Asp Ser Leu
            595                 600                 605

Thr Ser Asp Gly Pro Gly Gly Gly Gly Glu Phe Ala Ser Leu Asp Asn
610                 615                 620

Leu Val Ala Arg Tyr Gln Arg Cys Phe Asn Asp Gln Ser Leu Lys Asn
625                 630                 635                 640

Ser Thr Ile Glu Leu Glu Ile Arg Phe Gln Gln Ile Asn Phe Leu Leu
            645                 650                 655

Phe Lys Thr Val Tyr Glu Ala Leu Val Ala Gln Glu Ile Pro Ser Thr
            660                 665                 670

Ile Ser His Ser Ile Arg Cys Ile Lys Lys Val His His Glu Asn His
            675                 680                 685

Cys Arg Glu Lys Ile Leu Pro Ser Glu Asn Leu Tyr Phe Lys Lys Gln
690                 695                 700

Pro Leu Met Phe Phe Lys Phe Ser Glu Pro Ala Ser Leu Gly Cys Lys
705                 710                 715                 720

Val Ser Leu Ala Ile Glu Gln Pro Ile Arg Lys Phe Ile Leu Asp Ser
            725                 730                 735

Ser Val Leu Val Arg Leu Lys Asn Arg Thr Thr Phe Arg Val Ser Glu
            740                 745                 750

Leu Trp Lys Ile Glu Leu Thr Ile Val Lys Gln Leu Met Gly Ser Glu
            755                 760                 765

Val Ser Ala Lys Leu Ala Ala Phe Lys Thr Leu Leu Phe Asp Thr Pro
770                 775                 780

Glu Gln Gln Thr Thr Lys Asn Met Met Thr Leu Ile Asn Pro Asp Asp
785                 790                 795                 800

Glu Tyr Leu Tyr Glu Ile Glu Ile Glu Tyr Thr Gly Lys Pro Glu Ser
            805                 810                 815

Leu Thr Ala Ala Asp Val Ile Lys Ile Lys Asn Thr Val Leu Thr Leu
                820                 825                 830

Ile Ser Pro Asn His Leu Met Leu Thr Ala Tyr His Gln Ala Ile Glu
            835                 840                 845

Phe Ile Ala Ser His Ile Leu Ser Ser Glu Ile Leu Leu Ala Arg Ile
            850                 855                 860

Lys Ser Gly Lys Trp Gly Leu Lys Arg Leu Leu Pro Gln Val Lys Ser
865                 870                 875                 880
```

-continued

```
Met Thr Lys Ala Asp Tyr Met Lys Phe Tyr Pro Pro Val Gly Tyr Tyr
                885                 890                 895

Val Thr Asp Lys Ala Asp Gly Ile Arg Gly Ile Ala Val Ile Gln Asp
        900                 905                 910

Thr Gln Ile Tyr Val Val Ala Asp Gln Leu Tyr Ser Leu Gly Thr Thr
        915                 920                 925

Gly Ile Glu Pro Leu Lys Pro Thr Ile Leu Asp Gly Glu Phe Met Pro
930                 935                 940

Glu Lys Lys Glu Phe Tyr Gly Phe Asp Val Ile Met Tyr Glu Gly Asn
945                 950                 955                 960

Leu Leu Thr Gln Gln Gly Phe Glu Thr Arg Ile Glu Ser Leu Ser Lys
                965                 970                 975

Gly Ile Lys Val Leu Gln Ala Phe Asn Ile Lys Ala Glu Met Lys Pro
            980                 985                 990

Phe Ile Ser Leu Thr Ser Ala Asp Pro Asn Val Leu Leu Lys Asn Phe
                995                1000                1005

Glu Ser Ile Phe Lys Lys Thr Arg Pro Tyr Ser Ile Asp Gly
    1010                1015                1020

Ile Ile Leu Val Glu Pro Gly Asn Ser Tyr Leu Asn Thr Asn Thr
    1025                1030                1035

Phe Lys Trp Lys Pro Thr Trp Asp Asn Thr Leu Asp Phe Leu Val
    1040                1045                1050

Arg Lys Cys Pro Glu Ser Leu Asn Val Pro Glu Tyr Ala Pro Lys
    1055                1060                1065

Lys Gly Phe Ser Leu His Leu Phe Val Gly Ile Ser Gly Glu
    1070                1075                1080

Leu Phe Lys Lys Leu Ala Leu Asn Trp Cys Pro Gly Tyr Thr Lys
    1085                1090                1095

Leu Phe Pro Val Thr Gln Arg Asn Gln Asn Tyr Phe Pro Val Gln
    1100                1105                1110

Phe Gln Pro Ser Asp Phe Pro Leu Ala Phe Leu Tyr Tyr His Pro
    1115                1120                1125

Asp Thr Ser Ser Phe Ser Asn Ile Asp Gly Lys Val Leu Glu Met
    1130                1135                1140

Arg Cys Leu Lys Arg Glu Ile Asn Tyr Val Arg Trp Glu Ile Val
    1145                1150                1155

Lys Ile Arg Glu Asp Arg Gln Gln Asp Leu Lys Thr Gly Gly Tyr
    1160                1165                1170

Phe Gly Asn Asp Phe Lys Thr Ala Glu Leu Thr Trp Leu Asn Tyr
    1175                1180                1185

Met Asp Pro Phe Ser Phe Glu Glu Leu Ala Lys Gly Pro Ser Gly
    1190                1195                1200

Met Tyr Phe Ala Gly Ala Lys Thr Gly Ile Tyr Arg Ala Gln Thr
    1205                1210                1215

Ala Leu Ile Ser Phe Ile Lys Gln Glu Ile Ile Gln Lys Ile Ser
    1220                1225                1230

His Gln Ser Trp Val Ile Asp Leu Gly Ile Gly Lys Gly Gln Asp
    1235                1240                1245

Leu Gly Arg Tyr Leu Asp Ala Gly Val Arg His Leu Val Gly Ile
    1250                1255                1260

Asp Lys Asp Gln Thr Ala Leu Ala Glu Leu Val Tyr Arg Lys Phe
    1265                1270                1275

Ser His Ala Thr Thr Arg Gln His Lys His Ala Thr Asn Ile Tyr
```

```
            1280                1285                1290

Val Leu His Gln Asp Leu Ala Glu Pro Ala Lys Glu Ile Ser Glu
            1295                1300                1305

Lys Val His Gln Ile Tyr Gly Phe Pro Lys Glu Gly Ala Ser Ser
            1310                1315                1320

Ile Val Ser Asn Leu Phe Ile His Tyr Leu Met Lys Asn Thr Gln
            1325                1330                1335

Gln Val Glu Asn Leu Ala Val Leu Cys His Lys Leu Leu Gln Pro
            1340                1345                1350

Gly Gly Met Val Trp Phe Thr Thr Met Leu Gly Glu Gln Val Leu
            1355                1360                1365

Glu Leu Leu His Glu Asn Arg Ile Glu Leu Asn Glu Val Trp Glu
            1370                1375                1380

Ala Arg Glu Asn Glu Val Val Lys Phe Ala Ile Lys Arg Leu Phe
            1385                1390                1395

Lys Glu Asp Ile Leu Gln Glu Thr Gly Gln Glu Ile Gly Val Leu
            1400                1405                1410

Leu Pro Phe Ser Asn Gly Asp Phe Tyr Asn Glu Tyr Leu Val Asn
            1415                1420                1425

Thr Ala Phe Leu Ile Lys Ile Phe Lys His His Gly Phe Ser Leu
            1430                1435                1440

Val Gln Lys Gln Ser Phe Lys Asp Trp Ile Pro Glu Phe Gln Asn
            1445                1450                1455

Phe Ser Lys Ser Leu Tyr Lys Ile Leu Thr Glu Ala Asp Lys Thr
            1460                1465                1470

Trp Thr Ser Leu Phe Gly Phe Ile Cys Leu Arg Lys Asn Leu Glu
            1475                1480                1485

Gly Gly Gly Gly Ser Gly Gly Gly Ser Val Glu Gln Asp Leu
            1490                1495                1500

His Ala Ile Gln Leu Gln Leu Glu Glu Glu Met Phe Asn Gly Gly
            1505                1510                1515

Ile Arg Arg Phe Glu Ala Asp Gln Gln Arg Gln Ile Ala Ser Gly
            1520                1525                1530

Asn Glu Ser Asp Thr Ala Trp Asn Arg Arg Leu Leu Ser Glu Leu
            1535                1540                1545

Ile Ala Pro Met Ala Glu Gly Ile Gln Ala Tyr Lys Glu Glu Tyr
            1550                1555                1560

Glu Gly Lys Arg Gly Arg Ala Pro Arg Ala Leu Ala Phe Ile Asn
            1565                1570                1575

Cys Val Gly Asn Glu Val Ala Ala Tyr Ile Thr Met Lys Ile Val
            1580                1585                1590

Met Asp Met Leu Asn Thr Asp Val Thr Leu Gln Ala Ile Ala Met
            1595                1600                1605

Asn Val Ala Asp Arg Ile Glu Asp Gln Val Arg Phe Ser Lys Leu
            1610                1615                1620

Glu Gly His Ala Ala Lys Tyr Phe Glu Lys Val Lys Lys Ser Leu
            1625                1630                1635

Lys Ala Ser Lys Thr Lys Ser Tyr Arg His Ala His Asn Val Ala
            1640                1645                1650

Val Val Ala Glu Lys Ser Val Ala Asp Arg Asp Ala Asp Phe Ser
            1655                1660                1665

Arg Trp Glu Ala Trp Pro Lys Asp Thr Leu Leu Gln Ile Gly Met
            1670                1675                1680
```

-continued

```
Thr Leu Leu Glu Ile Leu Glu Asn Ser Val Phe Phe Asn Gly Gln
    1685            1690                1695

Pro Val Phe Leu Arg Thr Leu Arg Thr Asn Gly Gly Lys His Gly
    1700            1705                1710

Val Tyr Tyr Leu Gln Thr Ser Glu His Val Gly Glu Trp Ile Thr
    1715            1720                1725

Ala Phe Lys Glu His Val Ala Gln Leu Ser Pro Ala Tyr Ala Pro
    1730            1735                1740

Cys Val Ile Pro Pro Arg Pro Trp Val Ser Pro Phe Asn Gly Gly
    1745            1750                1755

Phe His Thr Glu Lys Val Ala Ser Arg Ile Arg Leu Val Lys Gly
    1760            1765                1770

Asn Arg Glu His Val Arg Lys Leu Thr Lys Lys Gln Met Pro Ala
    1775            1780                1785

Val Tyr Lys Ala Val Asn Ala Leu Gln Ala Thr Lys Trp Gln Val
    1790            1795                1800

Asn Lys Glu Val Leu Gln Val Val Glu Asp Val Ile Arg Leu Asp
    1805            1810                1815

Leu Gly Tyr Gly Val Pro Ser Phe Lys Pro Leu Ile Asp Arg Glu
    1820            1825                1830

Asn Lys Pro Ala Asn Pro Val Pro Leu Glu Phe Gln His Leu Arg
    1835            1840                1845

Gly Arg Glu Leu Lys Glu Met Leu Thr Pro Glu Gln Trp Gln Ala
    1850            1855                1860

Phe Ile Asn Trp Lys Gly Glu Cys Thr Lys Leu Tyr Thr Ala Glu
    1865            1870                1875

Thr Lys Arg Gly Ser Lys Ser Ala Ala Thr Val Arg Met Val Gly
    1880            1885                1890

Gln Ala Arg Lys Tyr Ser Gln Phe Asp Ala Ile Tyr Phe Val Tyr
    1895            1900                1905

Ala Leu Asp Ser Arg Ser Arg Val Tyr Ala Gln Ser Ser Thr Leu
    1910            1915                1920

Ser Pro Gln Ser Asn Asp Leu Gly Lys Ala Leu Leu Arg Phe Thr
    1925            1930                1935

Glu Gly Gln Arg Leu Asp Ser Ala Glu Ala Leu Lys Trp Phe Leu
    1940            1945                1950

Val Asn Gly Ala Asn Asn Trp Gly Trp Asp Lys Lys Thr Phe Asp
    1955            1960                1965

Val Arg Thr Ala Asn Val Leu Asp Ser Glu Phe Gln Asp Met Cys
    1970            1975                1980

Arg Asp Ile Ala Ala Asp Pro Leu Thr Phe Thr Gln Trp Val Asn
    1985            1990                1995

Ala Asp Ser Pro Tyr Gly Phe Leu Ala Trp Cys Phe Glu Tyr Ala
    2000            2005                2010

Arg Tyr Leu Asp Ala Leu Asp Glu Gly Thr Gln Asp Gln Phe Met
    2015            2020                2025

Thr His Leu Pro Val His Gln Asp Gly Ser Cys Ser Gly Ile Gln
    2030            2035                2040

His Tyr Ser Ala Met Leu Ser Asp Ala Val Gly Ala Lys Ala Val
    2045            2050                2055

Asn Leu Lys Pro Ser Asp Ser Pro Gln Asp Ile Tyr Gly Ala Val
    2060            2065                2070
```

| | | | | | | | | | |
|---|---|---|---|---|---|---|---|---|---|
| Ala | Gln | Val | Val | Ile | Gln | Lys | Asn | Tyr | Ala | Tyr | Met | Asn | Ala | Glu |
| 2075 | | | | | 2080 | | | | | 2085 | | | | |
| Asp | Ala | Glu | Thr | Phe | Thr | Ser | Gly | Ser | Val | Thr | Leu | Thr | Gly | Ala |
| 2090 | | | | | 2095 | | | | | 2100 | | | | |
| Glu | Leu | Arg | Ser | Met | Ala | Ser | Ala | Trp | Asp | Met | Ile | Gly | Ile | Thr |
| 2105 | | | | | 2110 | | | | | 2115 | | | | |
| Arg | Gly | Leu | Thr | Lys | Lys | Pro | Val | Met | Thr | Leu | Pro | Tyr | Gly | Ser |
| 2120 | | | | | 2125 | | | | | 2130 | | | | |
| Thr | Arg | Leu | Thr | Cys | Arg | Glu | Ser | Val | Ile | Asp | Tyr | Ile | Val | Asp |
| 2135 | | | | | 2140 | | | | | 2145 | | | | |
| Leu | Glu | Glu | Lys | Glu | Ala | Gln | Arg | Ala | Ile | Ala | Glu | Gly | Arg | Thr |
| 2150 | | | | | 2155 | | | | | 2160 | | | | |
| Ala | Asn | Pro | Val | His | Pro | Phe | Asp | Asn | Asp | Arg | Lys | Asp | Ser | Leu |
| 2165 | | | | | 2170 | | | | | 2175 | | | | |
| Thr | Pro | Ser | Ala | Ala | Tyr | Asn | Tyr | Met | Thr | Ala | Leu | Ile | Trp | Pro |
| 2180 | | | | | 2185 | | | | | 2190 | | | | |
| Ser | Ile | Ser | Glu | Val | Val | Lys | Ala | Pro | Ile | Val | Ala | Met | Lys | Met |
| 2195 | | | | | 2200 | | | | | 2205 | | | | |
| Ile | Arg | Gln | Leu | Ala | Arg | Phe | Ala | Ala | Lys | Arg | Asn | Glu | Gly | Leu |
| 2210 | | | | | 2215 | | | | | 2220 | | | | |
| Glu | Tyr | Pro | Leu | Pro | Thr | Gly | Phe | Ile | Leu | Gln | Gln | Lys | Ile | Met |
| 2225 | | | | | 2230 | | | | | 2235 | | | | |
| Ala | Thr | Asp | Met | Leu | Arg | Val | Ser | Thr | Cys | Leu | Met | Gly | Glu | Ile |
| 2240 | | | | | 2245 | | | | | 2250 | | | | |
| Lys | Met | Ser | Leu | Gln | Ile | Glu | Thr | Asp | Val | Val | Asp | Glu | Thr | Ala |
| 2255 | | | | | 2260 | | | | | 2265 | | | | |
| Met | Met | Gly | Ala | Ala | Ala | Pro | Asn | Phe | Val | His | Gly | His | Asp | Ala |
| 2270 | | | | | 2275 | | | | | 2280 | | | | |
| Ser | His | Leu | Ile | Leu | Thr | Val | Cys | Asp | Leu | Val | Asp | Lys | Gly | Ile |
| 2285 | | | | | 2290 | | | | | 2295 | | | | |
| Thr | Ser | Val | Ala | Val | Ile | His | Asp | Ser | Phe | Gly | Thr | His | Ala | Gly |
| 2300 | | | | | 2305 | | | | | 2310 | | | | |
| Arg | Thr | Ala | Asp | Leu | Arg | Asp | Ser | Leu | Arg | Glu | Glu | Met | Val | Lys |
| 2315 | | | | | 2320 | | | | | 2325 | | | | |
| Met | Tyr | Gln | Asn | His | Asn | Ala | Leu | Gln | Asn | Leu | Leu | Asp | Val | His |
| 2330 | | | | | 2335 | | | | | 2340 | | | | |
| Glu | Glu | Arg | Trp | Leu | Val | Asp | Thr | Gly | Ile | Gln | Val | Pro | Glu | Gln |
| 2345 | | | | | 2350 | | | | | 2355 | | | | |
| Gly | Glu | Phe | Asp | Leu | Asn | Glu | Ile | Leu | Val | Ser | Asp | Tyr | Cys | Phe |
| 2360 | | | | | 2365 | | | | | 2370 | | | | |
| Ala | | | | | | | | | | | | | | |

<210> SEQ ID NO 42
<211> LENGTH: 7161
<212> TYPE: DNA
<213> ORGANISM: Artificial Sequence
<220> FEATURE:
<223> OTHER INFORMATION: Nucleotide sequence of lambdaN-R341-G4-NP868R-
      F2A-K1ERNAP

<400> SEQUENCE: 42
atggatgctc agaccagacg cagagaacgg cgggcagaga agcaggcaca gtggaaggcc      60
gctaatggcg gtggcggcac cggtctcaaa acaagaccca gggctgagaa gtatcagacc     120 tactcacca ccaatgaata tcagatcgtt aaagaaaaac taccagacat tataagagac     180

```
gcggaaatta aggcgtctga agtgctcgag ccaaccatct acgagaagcg cgcaatcatg    240
gaagtcatta aggatttcat tcgggatcat caaaggaaag tgtatggcgg aacagccctg    300
aatgaggcat tgaaacaggt gaatcccaag gatgccatct atgataacta ttccttcagc    360
gacatcgagt tttattcccc taccccgtg caggatctcg tggatctctg caacatcctg    420
tatagaaaag ggtataagtt cgtccagggg aaggacgctc agcatgagga aacctattct    480
atctttgtaa atttccagct ctactgtgac attacctatt cgccaacccg ggtcttttat    540
ggtattaaaa cgatagaaat tgacggcatt aactataccg atcctcattt catgctcata    600
gattacctcc gaatggtgaa ccagcccttg actgccgccg ccagcgctg ggagaaagcg    660 ttcgaacgga tgtacaggct gctcaaagac tatcccattg aggattttga caagaggctg    720
gatattcctg agccacccga agaaatccag agttatattt ctcggattaa gaccgagttt    780
ctgagcgata acaagctgaa tgaaagcttc ctcatctccg gcatcgaggc ttacaacttc    840
tacattcgcc atgctgcctc tagcaaagat gaagaacaga tggcccggac aaaccgcaat    900
gtggtcaatc ttaataactt tattgcaaat gtccccttta gcgagctgat ctccgtgaac    960
tatcgcgaag atgtcaagaa tacctataac ttcctgcgga tgatcgtcga ggataaagag   1020
aaaatcagtg ttgacgaata tttccctctc tttcaattca ctggctattc cactgtcatc   1080
aaatacgatg atcaccccat aattaggatc tacgagggcg acggttattg tattcctaac   1140
gtcaagaccg ttaaaacggt ggagaatgac aacggaacga agacaaagta cgagtacaag   1200
tacgtatcct ccagtacgt cctcatgatt ctatatatca acaaatttcg tgcgcacttg   1260
gacaagaata agcctatgta ttttaactac ggtattgcca tatccaatct ggtcaaagct   1320
cgcaatatat acctggacca gaccgggaaa agcgtccttg acaacactgt gtttaaggag   1380
ttccgcacta actgtaccgg aaatacgatc tctttcacac ggatgaacag actgagatta   1440
ctcgagaaaa gaaagcaggg caagcagact tcgttcgttt acaccctga agacttcttt   1500 aagaaggatc tggaaaccca gccaagcttt gacccgtcga aagcgagatt caaaaatacc   1560
agtggtaaca agattatggt gccaaagtac ctgctgttca aaatagataa caacggaaat   1620
attgaagata acatacatag cgaagaggca gaaatctcag agaaagaaga aacttccggt   1680
ggctcttcta tatccactga taaatcattc gaagaatcac ctaattcctc ccctaacagc   1740
tctcctaaca actcgttgaa taattctatt gatatcagta caaataatta cgacgaccgc   1800
tcggaaaaca gcctggactc actcacgtct gatgggcccg gcggtggcgg cgaattcgcc   1860
agcctggaca acctggtggc cagataccag cggtgcttca acgaccagag cctgaagaac   1920
agcaccatcg agctggaaat ccggttccag cagatcaact tcctgctgtt caagaccgtg   1980
tacgaggccc tggtcgccca ggaaatcccc agcaccatca gccacagcat ccggtgcatc   2040
aagaaggtgc accacgagaa ccactgccgg gagaagatcc tgcccagcga aacctgtac    2100 ttcaagaaac agcccctgat gttcttcaag ttcagcgagc ccgccagcct gggctgtaaa   2160
gtgtccctgg ccatcgagca gcccatccgg aagttcatcc tggacagcag cgtgctggtc   2220
cggctgaaga accggaccac cttcggggtg tccgagctgt ggaagatcga gctgaccatc   2280
gtgaagcagc tgatgggcag cgaggtgtca gccaagctgg ccgccttcaa gaccctgctg   2340
ttcgacaccc ccgagcagca gaccaccaag aacatgatga ccctgatcaa ccccgacgac   2400
gagtacctgt acgagatcga gatcgagtac accggcaagc tgagagcct gacagccgcc   2460 gacgtgatca agatcaagaa caccgtgctg acactgatca gccccaacca cctgatgctg   2520
accgcctacc accaggccat cgagtttatc gccagccaca tcctgagcag cgagatcctg   2580
```

```
ctggcccgga tcaagagcgg caagtggggc ctgaagagac tgctgcccca ggtcaagtcc    2640
atgaccaagg ccgactacat gaagttctac cccccgtgg gctactacgt gaccgacaag    2700
gccgacggca tccggggcat tgccgtgatc caggacaccc agatctacgt ggtggccgac    2760
cagctgtaca gcctgggcac caccggcatc gagcccctga gcccaccat cctggacggc    2820
gagttcatgc ccgagaagaa agagttctac ggctttgacg tgatcatgta cgagggcaac    2880
ctgctgaccc agcagggctt cgagacacgg atcgagagcc tgagcaaggg catcaaggtg    2940
ctgcaggcct tcaacatcaa ggccgagatg aagcccttca tcagcctgac ctccgccgac    3000
cccaacgtgc tgctgaagaa tttcgagagc atcttcaaga gaaaacccg gcccttacagc    3060
atcgacggca tcatcctggt ggagcccggc aacagctacc tgaacaccaa caccttcaag    3120
tggaagccca cctgggacaa caccctggac tttctggtcc ggaagtgccc cgagtccctg    3180
aacgtgcccg agtacgcccc caagaagggc ttcagcctgc atctgctgtt cgtgggcatc    3240
agcggcgagc tgtttaagaa gctggccctg aactggtgcc ccggctacac caagctgttc    3300
cccgtgaccc agcggaacca gaactacttc cccgtgcagt ccagcccag cgacttcccc    3360
ctggccttcc tgtactacca ccccgacacc agcagcttca gcaacatcga tggcaaggtg    3420
ctggaaatgc ggtgcctgaa gcgggagatc aactacgtgc gctgggagat cgtgaagatc    3480
cgggaggacc ggcagcagga tctgaaaacc ggcggctact ccggcaacga cttcaagacc    3540
gccgagctga cctggctgaa ctacatggac cccttcagct tcgaggaact ggccaaggga    3600
cccagcggca tgtacttcgc tggcgccaag accggcatct acagagccca gaccgccctg    3660
atcagcttca tcaagcagga aatcatccag aagatcagcc accagagctg ggtgatcgac    3720
ctgggcatcg gcaagggcca ggacctgggc agataacctgg acgccggcgt gagacacctg    3780
gtcggcatcg ataaggacca gacagccctg gccgagctgg tgtaccggaa gttctcccac    3840
gccaccacca gacagcacaa gcacgccacc aacatctacg tgctgcacca ggatctggcc    3900
gagcctgcca aagaaatcag cgagaaagtg caccagatct atggcttccc caagagggc    3960
gccagcagca tcgtgtccaa cctgttcatc cactacctga tgaagaacac ccagcaggtc    4020
gagaacctgg ctgtgctgtg ccacaagctg ctgcagcctg cggcatggt ctggttcacc    4080
accatgctgg cgaacaggt gctggaactg ctgcacgaga accggatcga actgaacgaa    4140
gtgtgggagg cccgggagaa cgaggtggtc aagttcgcca tcaagcggct gttcaaagag    4200
gacatcctgc aggaaaccgg ccaggaaatc ggcgtcctgc tgcccttcag caacggcgac    4260
ttctacaatg agtacctggt caacaccgcc tttctgatca gattttcaa gcaccatggc    4320
tttagcctcg tgcagaagca gagcttcaag gactggatcc ccgagttcca gaacttcagc    4380
aagagcctgt acaagatcct gaccgaggcc gacaagacct ggaccagcct gttcggcttc    4440
atctgcctgc ggaagaaccc gcgggtgaag cagactctga actttgactt gttgaaactt    4500
gcgggtgacg tggaaagcaa cccaggcccc actagtcagg acctgcacgc catccagctg    4560
cagctcgaag aggaaatgtt caacggcggc atcagaagat cgaggccga ccagcagaga    4620
cagatcgcct ctggcaacga gagcgacacc gcctggaata aaggctgct gtctgagctg    4680
atcgcccta tggccgaagg catccaggcc tacaaagagg aatacgaggg caagagaggc    4740
agagccccta gagccctggc cttcatcaac tgtgtgggca atgaggtggc cgcctacatc    4800
accatgaaga tcgtgatgga catgctgaac ccgacgtga ccctgcaggc cattgccatg    4860
aacgtggccg acagaatcga ggaccaggtc cgattcagca agctggaagg acacgccgcc    4920
```

```
aagtacttcg agaaagtgaa gaagtccctg aaggccagca agaccaagag ctacagacac    4980
gcccacaacg tggccgtggt ggccgaaaaa tctgtggccg atagggacgc cgacttctct    5040
agatgggagg cctggcctaa ggacaccctg ctgcagatcg gcatgaccct gctggaaatc    5100
ctggaaaaca gcgtgttctt caacggccag cccgtgttcc tgagaaccct gaggacaaat    5160
ggcggcaagc acggcgtgta ctacctgcag acatctgagc acgtgggcga gtggatcacc    5220
gccttcaaag aacatgtggc ccagctgagc cctgcctatg ccccttgtgt gatccctcct    5280
agaccctggg tgtcccettt caatggcggc tttcacaccg agaaggtggc cagcagaatc    5340
agactggtca agggcaaccg ggaacacgtg cggaagctga ccaagaaaca gatgcccgcc    5400
gtgtacaagg ccgtgaatgc tctgcaggcc accaagtggc aggtcaacaa agaggtgctg    5460
caggtcgtcg aggacgtgat cagactggat ctgggctacg gcgtgccaag ctttaagccc    5520
ctgatcgaca gagagaacaa gcccgccaac cctgtgcccc tggaatttca gcacctgaga    5580
ggccgcgagc tgaaagagat gctgacacct gaacagtggc aggcctttat caattggaag    5640
ggcgagtgca ccaagctgta caccgccgag acaaagaggg gctctaagtc tgccgccaca    5700
gtgcgaatgg tcggacaggc cagaaagtac agccagttcg acgccatcta cttcgtgtac    5760
gccctggaca gccggtctag agtgtatgcc cagagcagca cactgagccc ccagtctaac    5820
gatctgggaa aggccctgct gagattcacc gagggccaga gactggattc tgccgaagcc    5880
ctgaagtggt tcctggtcaa cggcgccaac aactggggct gggacaagaa accttcgat    5940
gtgcggaccg ccaacgtgct ggatagcgag ttccaggaca tgtgcagaga tatcgccgcc    6000
gaccctctga cctttaccca gtgggtcaac gccgatagcc cctatggatt cctggcctgg    6060
tgcttcgagt acgccagata cctggacgcc ctggatgagg aacccagga tcagttcatg    6120
acccatctgc ccgtgcacca ggatggctct tgttctggca tccagcacta cagcgccatg    6180
ctgagcgatg ccgtgggagc caaagccgtg aacctgaagc ctagcgacag ccccaggat    6240
atctatggcg ctgtgcccca ggtggtcatc cagaaaaact acgcctacat gaacgccgag    6300
gacgccgaga cattcacaag cggaagcgtg acactgacag cgccgagct gagatctatg    6360
gcctctgcct gggacatgat cggcatcaca cggggcctga ccaaaaagcc tgtgatgaca    6420
ctgccctacg gcagcaccag actgacctgt agagaaagcg tgatcgacta catcgtggac    6480
ctggaagaga aagaggccca gagagccatt gccgagggca aacagccaa tcctgtgcac    6540
cccttcgaca acgaccggaa ggatagcctg acacctagcg ccgcctacaa ctacatgacc    6600
gccctgatct ggcccagcat ctctgaagtg gtcaaggccc ctatcgtggc catgaagatg    6660
atcagacagc tggccagatt cgccgccaag agaaatgagg gcctggaata ccctctgccc    6720
accggcttta tcctgcagca gaaaatcatg gccaccgaca tgctgcgggt gtccacatgt    6780
ctgatgggcg agatcaagat gagcctgcag atcgagacag acgtggtgga cgagacagcc    6840
atgatgggag ccgccgctcc taattttgtg cacggacacg atgccagcca cctgatcctg    6900
accgtgtgcg atcggtgga caagggcatc actagcgtgg ccgtgatcca cgatagcttt    6960
ggaacacacg ccggcagaac cgccgacctg agagattctc tgcgggaaga gatggtcaag    7020
atgtaccaga accacaacgc cctgcagaac ctgctggacg tgcacgaaga agatggctgt    7080
gtggacaccg gcatccaggt gccagaacag ggagagttcg acctgaacga gatcctggtg    7140
tccgactact gcttcgcctg a                                              7161
```

<210> SEQ ID NO 43
<211> LENGTH: 2386

```
<212> TYPE: PRT
<213> ORGANISM: Artificial Sequence
<220> FEATURE:
<223> OTHER INFORMATION: Amino-acid sequence of lambdaN-R341-G4-NP868R-
      F2A-K1ERNAP

<400> SEQUENCE: 43

Met Asp Ala Gln Thr Arg Arg Glu Arg Ala Glu Lys Gln Ala
1               5                   10                  15

Gln Trp Lys Ala Ala Asn Gly Gly Gly Thr Gly Leu Lys Asn Lys
            20                  25                  30

Thr Arg Ala Glu Lys Tyr Gln Thr Tyr Tyr Thr Asn Glu Tyr Gln
        35                  40                  45

Ile Val Lys Glu Lys Leu Pro Asp Ile Ile Arg Asp Ala Glu Ile Lys
    50                  55                  60

Ala Ser Glu Val Leu Glu Pro Thr Ile Tyr Glu Lys Arg Ala Ile Met
65                  70                  75                  80

Glu Val Ile Lys Asp Phe Ile Arg Asp His Gln Arg Lys Val Tyr Gly
                    85                  90                  95

Gly Thr Ala Leu Asn Glu Ala Leu Lys Gln Val Asn Pro Lys Asp Ala
                100                 105                 110

Ile Tyr Asp Asn Tyr Ser Phe Ser Asp Ile Glu Phe Tyr Ser Pro Thr
                115                 120                 125

Pro Val Gln Asp Leu Val Asp Leu Cys Asn Ile Leu Tyr Arg Lys Gly
130                 135                 140

Tyr Lys Phe Val Gln Gly Lys Asp Ala Gln His Glu Glu Thr Tyr Ser
145                 150                 155                 160

Ile Phe Val Asn Phe Gln Leu Tyr Cys Asp Ile Thr Tyr Ser Pro Thr
                165                 170                 175

Arg Val Phe Tyr Gly Ile Lys Thr Ile Glu Ile Asp Gly Ile Asn Tyr
                180                 185                 190

Thr Asp Pro His Phe Met Leu Ile Asp Tyr Leu Arg Met Val Asn Gln
                195                 200                 205

Pro Leu Thr Ala Ala Gly Gln Arg Trp Glu Lys Ala Phe Glu Arg Met
210                 215                 220

Tyr Arg Leu Leu Lys Asp Tyr Pro Ile Glu Asp Phe Asp Lys Arg Leu
225                 230                 235                 240

Asp Ile Pro Glu Pro Pro Glu Glu Ile Gln Ser Tyr Ile Ser Arg Ile
                245                 250                 255

Lys Thr Glu Phe Leu Ser Asp Asn Lys Leu Asn Glu Ser Phe Leu Ile
                260                 265                 270

Ser Gly Ile Glu Ala Tyr Asn Phe Tyr Ile Arg His Ala Ala Ser Ser
            275                 280                 285

Lys Asp Glu Glu Gln Met Ala Arg Thr Asn Arg Asn Val Val Asn Leu
290                 295                 300

Asn Asn Phe Ile Ala Asn Val Pro Phe Ser Glu Leu Ile Ser Val Asn
305                 310                 315                 320

Tyr Arg Glu Asp Val Lys Asn Thr Tyr Asn Phe Leu Arg Met Ile Val
                325                 330                 335

Glu Asp Lys Glu Lys Ile Ser Val Asp Glu Tyr Phe Pro Leu Phe Gln
                340                 345                 350

Phe Thr Gly Tyr Ser Thr Val Ile Lys Tyr Asp Asp His Pro Ile Ile
            355                 360                 365

Arg Ile Tyr Glu Gly Asp Gly Tyr Cys Ile Pro Asn Val Lys Thr Val
            370                 375                 380
```

```
Lys Thr Val Glu Asn Asp Asn Gly Thr Lys Thr Lys Tyr Glu Tyr Lys
385                 390                 395                 400

Tyr Val Ser Phe Gln Tyr Val Leu Met Ile Leu Tyr Ile Asn Lys Phe
            405                 410                 415

Arg Ala His Leu Asp Lys Asn Lys Pro Met Tyr Phe Asn Tyr Gly Ile
            420                 425                 430

Ala Ile Ser Asn Leu Val Lys Ala Arg Asn Ile Tyr Leu Asp Gln Thr
            435                 440                 445

Gly Lys Ser Val Leu Asp Asn Thr Val Phe Lys Glu Phe Arg Thr Asn
            450                 455                 460

Cys Thr Gly Asn Thr Ile Ser Phe Thr Arg Met Asn Arg Leu Arg Leu
465                 470                 475                 480

Leu Glu Lys Arg Lys Gln Gly Lys Gln Thr Ser Phe Val Tyr Thr Pro
            485                 490                 495

Glu Asp Phe Phe Lys Lys Asp Leu Glu Thr Gln Ala Lys Leu Asp Pro
            500                 505                 510

Ser Lys Ala Arg Phe Lys Asn Thr Ser Gly Asn Lys Ile Met Val Pro
            515                 520                 525

Lys Tyr Leu Leu Phe Lys Ile Asp Asn Asn Gly Asn Ile Glu Asp Asn
530                 535                 540

Ile His Ser Glu Glu Ala Glu Ile Ser Glu Lys Glu Glu Thr Ser Gly
545                 550                 555                 560

Gly Ser Ser Ile Ser Thr Asp Lys Ser Phe Glu Ser Pro Asn Ser
            565                 570                 575

Ser Pro Asn Ser Ser Pro Asn Asn Ser Leu Asn Asn Ser Ile Asp Ile
            580                 585                 590

Ser Thr Asn Asn Tyr Asp Asp Arg Ser Glu Asn Ser Leu Asp Ser Leu
            595                 600                 605

Thr Ser Asp Gly Pro Gly Gly Gly Glu Phe Ala Ser Leu Asp Asn
            610                 615                 620

Leu Val Ala Arg Tyr Gln Arg Cys Phe Asn Asp Gln Ser Leu Lys Asn
625                 630                 635                 640

Ser Thr Ile Glu Leu Glu Ile Arg Phe Gln Gln Ile Asn Phe Leu Leu
            645                 650                 655

Phe Lys Thr Val Tyr Glu Ala Leu Val Ala Gln Glu Ile Pro Ser Thr
            660                 665                 670

Ile Ser His Ser Ile Arg Cys Ile Lys Lys Val His Glu Asn His
            675                 680                 685

Cys Arg Glu Lys Ile Leu Pro Ser Glu Asn Leu Tyr Phe Lys Lys Gln
            690                 695                 700

Pro Leu Met Phe Phe Lys Phe Ser Glu Pro Ala Ser Leu Gly Cys Lys
705                 710                 715                 720

Val Ser Leu Ala Ile Glu Gln Pro Ile Arg Lys Phe Ile Leu Asp Ser
            725                 730                 735

Ser Val Leu Val Arg Leu Lys Asn Arg Thr Thr Phe Arg Val Ser Glu
            740                 745                 750

Leu Trp Lys Ile Glu Leu Thr Ile Val Lys Gln Leu Met Gly Ser Glu
            755                 760                 765

Val Ser Ala Lys Leu Ala Ala Phe Lys Thr Leu Leu Phe Asp Thr Pro
            770                 775                 780

Glu Gln Gln Thr Thr Lys Asn Met Met Thr Leu Ile Asn Pro Asp Asp
785                 790                 795                 800
```

```
Glu Tyr Leu Tyr Glu Ile Glu Ile Glu Tyr Thr Gly Lys Pro Glu Ser
                805                 810                 815

Leu Thr Ala Ala Asp Val Ile Lys Ile Lys Asn Thr Val Leu Thr Leu
            820                 825                 830

Ile Ser Pro Asn His Leu Met Leu Thr Ala Tyr His Gln Ala Ile Glu
            835                 840                 845

Phe Ile Ala Ser His Ile Leu Ser Ser Glu Ile Leu Leu Ala Arg Ile
850                 855                 860

Lys Ser Gly Lys Trp Gly Leu Lys Arg Leu Leu Pro Gln Val Lys Ser
865                 870                 875                 880

Met Thr Lys Ala Asp Tyr Met Lys Phe Tyr Pro Pro Val Gly Tyr Tyr
            885                 890                 895

Val Thr Asp Lys Ala Asp Gly Ile Arg Gly Ile Ala Val Ile Gln Asp
            900                 905                 910

Thr Gln Ile Tyr Val Val Ala Asp Gln Leu Tyr Ser Leu Gly Thr Thr
            915                 920                 925

Gly Ile Glu Pro Leu Lys Pro Thr Ile Leu Asp Gly Glu Phe Met Pro
            930                 935                 940

Glu Lys Lys Glu Phe Tyr Gly Phe Asp Val Ile Met Tyr Glu Gly Asn
945                 950                 955                 960

Leu Leu Thr Gln Gln Gly Phe Glu Thr Arg Ile Glu Ser Leu Ser Lys
            965                 970                 975

Gly Ile Lys Val Leu Gln Ala Phe Asn Ile Lys Ala Glu Met Lys Pro
            980                 985                 990

Phe Ile Ser Leu Thr Ser Ala Asp  Pro Asn Val Leu  Lys Asn Phe
            995                 1000                 1005

Glu Ser  Ile Phe Lys Lys Lys  Thr Arg Pro Tyr Ser  Ile Asp Gly
   1010                 1015                 1020

Ile Ile Leu Val Glu Pro Gly  Asn Ser Tyr Leu Asn  Thr Asn Thr
   1025                 1030                 1035

Phe Lys  Trp Lys Pro Thr Trp  Asp Asn Thr Leu Asp  Phe Leu Val
   1040                 1045                 1050

Arg Lys  Cys Pro Glu Ser Leu  Asn Val Pro Glu Tyr  Ala Pro Lys
   1055                 1060                 1065

Lys Gly  Phe Ser Leu His Leu  Leu Phe Val Gly Ile  Ser Gly Glu
   1070                 1075                 1080

Leu Phe  Lys Lys Leu Ala Leu  Asn Trp Cys Pro Gly  Tyr Thr Lys
   1085                 1090                 1095

Leu Phe  Pro Val Thr Gln Arg  Asn Gln Asn Tyr Phe  Pro Val Gln
   1100                 1105                 1110

Phe Gln  Pro Ser Asp Phe Pro  Leu Ala Phe Leu Tyr  Tyr His Pro
   1115                 1120                 1125

Asp Thr  Ser Ser Phe Ser Asn  Ile Asp Gly Lys Val  Leu Glu Met
   1130                 1135                 1140

Arg Cys  Leu Lys Arg Glu Ile  Asn Tyr Val Arg Trp  Glu Ile Val
   1145                 1150                 1155

Lys Ile  Arg Glu Asp Arg Gln  Gln Asp Leu Lys Thr  Gly Gly Tyr
   1160                 1165                 1170

Phe Gly  Asn Asp Phe Lys Thr  Ala Glu Leu Thr Trp  Leu Asn Tyr
   1175                 1180                 1185

Met Asp  Pro Phe Ser Phe Glu  Glu Leu Ala Lys Gly  Pro Ser Gly
   1190                 1195                 1200

Met Tyr  Phe Ala Gly Ala Lys  Thr Gly Ile Tyr Arg  Ala Gln Thr
```

```
               1205                1210                1215

Ala Leu Ile Ser Phe Ile Lys Gln Glu Ile Ile Gln Lys Ile Ser
               1220                1225                1230

His Gln Ser Trp Val Ile Asp Leu Gly Ile Gly Lys Gly Gln Asp
               1235                1240                1245

Leu Gly Arg Tyr Leu Asp Ala Gly Val Arg His Leu Val Gly Ile
               1250                1255                1260

Asp Lys Asp Gln Thr Ala Leu Ala Glu Leu Val Tyr Arg Lys Phe
               1265                1270                1275

Ser His Ala Thr Thr Arg Gln His Lys His Ala Thr Asn Ile Tyr
               1280                1285                1290

Val Leu His Gln Asp Leu Ala Glu Pro Ala Lys Glu Ile Ser Glu
               1295                1300                1305

Lys Val His Gln Ile Tyr Gly Phe Pro Lys Glu Gly Ala Ser Ser
               1310                1315                1320

Ile Val Ser Asn Leu Phe Ile His Tyr Leu Met Lys Asn Thr Gln
               1325                1330                1335

Gln Val Glu Asn Leu Ala Val Leu Cys His Lys Leu Leu Gln Pro
               1340                1345                1350

Gly Gly Met Val Trp Phe Thr Thr Met Leu Gly Glu Gln Val Leu
               1355                1360                1365

Glu Leu Leu His Glu Asn Arg Ile Glu Leu Asn Glu Val Trp Glu
               1370                1375                1380

Ala Arg Glu Asn Glu Val Val Lys Phe Ala Ile Lys Arg Leu Phe
               1385                1390                1395

Lys Glu Asp Ile Leu Gln Glu Thr Gly Gln Glu Ile Gly Val Leu
               1400                1405                1410

Leu Pro Phe Ser Asn Gly Asp Phe Tyr Asn Glu Tyr Leu Val Asn
               1415                1420                1425

Thr Ala Phe Leu Ile Lys Ile Phe Lys His His Gly Phe Ser Leu
               1430                1435                1440

Val Gln Lys Gln Ser Phe Lys Asp Trp Ile Pro Glu Phe Gln Asn
               1445                1450                1455

Phe Ser Lys Ser Leu Tyr Lys Ile Leu Thr Glu Ala Asp Lys Thr
               1460                1465                1470

Trp Thr Ser Leu Phe Gly Phe Ile Cys Leu Arg Lys Asn Pro Arg
               1475                1480                1485

Val Lys Gln Thr Leu Asn Phe Asp Leu Leu Lys Leu Ala Gly Asp
               1490                1495                1500

Val Glu Ser Asn Pro Gly Pro Thr Ser Gln Asp Leu His Ala Ile
               1505                1510                1515

Gln Leu Gln Leu Glu Glu Glu Met Phe Asn Gly Gly Ile Arg Arg
               1520                1525                1530

Phe Glu Ala Asp Gln Gln Arg Gln Ile Ala Ser Gly Asn Glu Ser
               1535                1540                1545

Asp Thr Ala Trp Asn Arg Arg Leu Leu Ser Glu Leu Ile Ala Pro
               1550                1555                1560

Met Ala Glu Gly Ile Gln Ala Tyr Lys Glu Glu Tyr Glu Gly Lys
               1565                1570                1575

Arg Gly Arg Ala Pro Arg Ala Leu Ala Phe Ile Asn Cys Val Gly
               1580                1585                1590

Asn Glu Val Ala Ala Tyr Ile Thr Met Lys Ile Val Met Asp Met
               1595                1600                1605
```

```
Leu Asn Thr Asp Val Thr Leu Gln Ala Ile Ala Met Asn Val Ala
    1610            1615            1620

Asp Arg Ile Glu Asp Gln Val Arg Phe Ser Lys Leu Glu Gly His
    1625            1630            1635

Ala Ala Lys Tyr Phe Glu Lys Val Lys Lys Ser Leu Lys Ala Ser
    1640            1645            1650

Lys Thr Lys Ser Tyr Arg His Ala His Asn Val Ala Val Val Ala
    1655            1660            1665

Glu Lys Ser Val Ala Asp Arg Asp Ala Asp Phe Ser Arg Trp Glu
    1670            1675            1680

Ala Trp Pro Lys Asp Thr Leu Leu Gln Ile Gly Met Thr Leu Leu
    1685            1690            1695

Glu Ile Leu Glu Asn Ser Val Phe Phe Asn Gly Gln Pro Val Phe
    1700            1705            1710

Leu Arg Thr Leu Arg Thr Asn Gly Gly Lys His Gly Val Tyr Tyr
    1715            1720            1725

Leu Gln Thr Ser Glu His Val Gly Glu Trp Ile Thr Ala Phe Lys
    1730            1735            1740

Glu His Val Ala Gln Leu Ser Pro Ala Tyr Ala Pro Cys Val Ile
    1745            1750            1755

Pro Pro Arg Pro Trp Val Ser Pro Phe Asn Gly Gly Phe His Thr
    1760            1765            1770

Glu Lys Val Ala Ser Arg Ile Arg Leu Val Lys Gly Asn Arg Glu
    1775            1780            1785

His Val Arg Lys Leu Thr Lys Lys Gln Met Pro Ala Val Tyr Lys
    1790            1795            1800

Ala Val Asn Ala Leu Gln Ala Thr Lys Trp Gln Val Asn Lys Glu
    1805            1810            1815

Val Leu Gln Val Val Glu Asp Val Ile Arg Leu Asp Leu Gly Tyr
    1820            1825            1830

Gly Val Pro Ser Phe Lys Pro Leu Ile Asp Arg Glu Asn Lys Pro
    1835            1840            1845

Ala Asn Pro Val Pro Leu Glu Phe Gln His Leu Arg Gly Arg Glu
    1850            1855            1860

Leu Lys Glu Met Leu Thr Pro Glu Gln Trp Gln Ala Phe Ile Asn
    1865            1870            1875

Trp Lys Gly Glu Cys Thr Lys Leu Tyr Thr Ala Glu Thr Lys Arg
    1880            1885            1890

Gly Ser Lys Ser Ala Ala Thr Val Arg Met Val Gly Gln Ala Arg
    1895            1900            1905

Lys Tyr Ser Gln Phe Asp Ala Ile Tyr Phe Val Tyr Ala Leu Asp
    1910            1915            1920

Ser Arg Ser Arg Val Tyr Ala Gln Ser Ser Thr Leu Ser Pro Gln
    1925            1930            1935

Ser Asn Asp Leu Gly Lys Ala Leu Leu Arg Phe Thr Glu Gly Gln
    1940            1945            1950

Arg Leu Asp Ser Ala Glu Ala Leu Lys Trp Phe Leu Val Asn Gly
    1955            1960            1965

Ala Asn Asn Trp Gly Trp Asp Lys Lys Thr Phe Asp Val Arg Thr
    1970            1975            1980

Ala Asn Val Leu Asp Ser Glu Phe Gln Asp Met Cys Arg Asp Ile
    1985            1990            1995
```

```
Ala Ala Asp Pro Leu Thr Phe Thr Gln Trp Val Asn Ala Asp Ser
2000                2005                2010

Pro Tyr Gly Phe Leu Ala Trp Cys Phe Glu Tyr Ala Arg Tyr Leu
2015                2020                2025

Asp Ala Leu Asp Glu Gly Thr Gln Asp Gln Phe Met Thr His Leu
2030                2035                2040

Pro Val His Gln Asp Gly Ser Cys Ser Gly Ile Gln His Tyr Ser
2045                2050                2055

Ala Met Leu Ser Asp Ala Val Gly Ala Lys Ala Val Asn Leu Lys
2060                2065                2070

Pro Ser Asp Ser Pro Gln Asp Ile Tyr Gly Ala Val Ala Gln Val
2075                2080                2085

Val Ile Gln Lys Asn Tyr Ala Tyr Met Asn Ala Glu Asp Ala Glu
2090                2095                2100

Thr Phe Thr Ser Gly Ser Val Thr Leu Thr Gly Ala Glu Leu Arg
2105                2110                2115

Ser Met Ala Ser Ala Trp Asp Met Ile Gly Ile Thr Arg Gly Leu
2120                2125                2130

Thr Lys Lys Pro Val Met Thr Leu Pro Tyr Gly Ser Thr Arg Leu
2135                2140                2145

Thr Cys Arg Glu Ser Val Ile Asp Tyr Ile Val Asp Leu Glu Glu
2150                2155                2160

Lys Glu Ala Gln Arg Ala Ile Ala Glu Gly Arg Thr Ala Asn Pro
2165                2170                2175

Val His Pro Phe Asp Asn Arg Lys Asp Ser Leu Thr Pro Ser
2180                2185                2190

Ala Ala Tyr Asn Tyr Met Thr Ala Leu Ile Trp Pro Ser Ile Ser
2195                2200                2205

Glu Val Val Lys Ala Pro Ile Val Ala Met Lys Met Ile Arg Gln
2210                2215                2220

Leu Ala Arg Phe Ala Ala Lys Arg Asn Glu Gly Leu Glu Tyr Pro
2225                2230                2235

Leu Pro Thr Gly Phe Ile Leu Gln Gln Lys Ile Met Ala Thr Asp
2240                2245                2250

Met Leu Arg Val Ser Thr Cys Leu Met Gly Glu Ile Lys Met Ser
2255                2260                2265

Leu Gln Ile Glu Thr Asp Val Val Asp Glu Thr Ala Met Met Gly
2270                2275                2280

Ala Ala Ala Pro Asn Phe Val His Gly His Asp Ala Ser His Leu
2285                2290                2295

Ile Leu Thr Val Cys Asp Leu Val Asp Lys Gly Ile Thr Ser Val
2300                2305                2310

Ala Val Ile His Asp Ser Phe Gly Thr His Ala Gly Arg Thr Ala
2315                2320                2325

Asp Leu Arg Asp Ser Leu Arg Glu Glu Met Val Lys Met Tyr Gln
2330                2335                2340

Asn His Asn Ala Leu Gln Asn Leu Leu Asp Val His Glu Glu Arg
2345                2350                2355

Trp Leu Val Asp Thr Gly Ile Gln Val Pro Glu Gln Gly Glu Phe
2360                2365                2370

Asp Leu Asn Glu Ile Leu Val Ser Asp Tyr Cys Phe Ala
2375                2380                2385
```

```
<210> SEQ ID NO 44
<211> LENGTH: 7179
<212> TYPE: DNA
<213> ORGANISM: Artificial Sequence
<220> FEATURE:
<223> OTHER INFORMATION: Nucleotide sequence of lambdaN-R341-F2A-NP868R-
      (G4S)2-K1ERNAP

<400> SEQUENCE: 44
atggatgctc agaccagacg cagagaacgg cgggcagaga agcaggcaca gtggaaggcc     60
gctaatggcg gtggcggcac cggtctcaaa aacaagacca gggctgagaa gtatcagacc    120
tactacacca ccaatgaata tcagatcgtt aaagaaaaac taccagacat tataagagac    180
gcggaaatta aggcgtctga agtgctcgag ccaaccatct acgagaagcg cgcaatcatg    240
gaagtcatta aggatttcat tcgggatcat caaaggaaag tgtatggcgg aacagccctg    300
aatgaggcat tgaaacaggt gaatcccaag gatgccatct atgataacta ttccttcagc    360
gacatcgagt tttattcccc tacccccgtg caggatctcg tggatctctg caacatcctg    420
tatagaaaag ggtataagtt cgtccagggg aaggacgctc agcatgagga aacctattct    480
atctttgtaa atttccagct ctactgtgac attacctatt cgccaacccg ggtctttat     540 ggtattaaaa cgatagaaat tgacggcatt aactataccg atcctcattt catgctcata    600
gattacctcc gaatggtgaa ccagcccttg actgccgccg ccagcgctg ggagaaagcg     660 ttcgaacgga tgtacaggct gctcaaagac tatcccattg aggattttga caagaggctg    720
gatattcctg agccacccga agaaatccag agttatattt ctcggattaa gaccgagttt    780
ctgagcgata acaagctgaa tgaaagcttc ctcatctccg gcatcgaggc ttacaacttc    840
tacattcgcc atgctgcctc tagcaaagat gaagaacaga tggcccggac aaaccgcaat    900
gtggtcaatc ttaataactt tattgcaaat gtccccttta gcgagctgat ctccgtgaac    960
tatcgcgaag atgtcaagaa tacctataac ttcctgcgga tgatcgtcga ggataaagag   1020
aaaatcagtg ttgacgaata tttcctctc tttcaattca ctggctattc cactgtcatc   1080
aaatacgatg atcaccccat aattaggatc tacgagggcg acggttattg tattcctaac   1140
gtcaagaccg ttaaaacggt ggagaatgac aacggaacga agacaaagta cgagtacaag   1200
tacgtatcct tccagtacgt cctcatgatt ctatatatca acaaatttcg tgcgcacttg   1260
gacaagaata agcctatgta ttttaactac ggtattgcca tatccaatct ggtcaaagct   1320
cgcaatatat acctggacca gaccgggaaa agcgtccttg acaacactgt gtttaaggag   1380
ttccgcacta actgtaccgg aaatacgatc tctttcacac ggatgaacag actgagatta   1440
ctcgagaaaa gaaagcaggg caagcagact tcgttcgttt acacccctga agacttcttt   1500
aagaaggatc tggaaaccca agccaagctt gacccgtcga agcgagatt caaaaatacc   1560 agtggtaaca agattatggt gccaaagtac ctgctgttca aaatagataa caacggaaat   1620
attgaagata catacatag cgaagaggca gaaatctcag agaaagaaga aacttccggt   1680
ggctcttcta tatccactga taaatcattc gaagaatcac ctaattcctc ccctaacagc   1740
tctcctaaca actcgttgaa taattctatt gatatcagta caaataatta cgacgaccgc   1800
tcggaaaaca gcctggactc actcacgtct gatgggcccg tgaagcagac tctgaacttt   1860
gacttgttga acttgcggg tgacgtggaa agcaacccag ccccgaatt cgccagcctg   1920 gacaacctgg tggccagata ccagcggtgc ttcaacgacc agagcctgaa gaacagcacc   1980
atcgagctgg aaatccggtt ccagcagatc aacttcctgc tgttcaagac cgtgtacgag   2040
gccctggtcg cccaggaaat ccccagcacc atcagccaca gcatccggtg catcaagaag   2100
```

```
gtgcaccacg agaaccactg ccgggagaag atcctgccca gcgagaacct gtacttcaag    2160
aaacagcccc tgatgttctt caagttcagc gagcccgcca gcctgggctg taaagtgtcc    2220
ctggccatcg agcagcccat ccggaagttc atcctggaca gcagcgtgct ggtccggctg    2280
aagaaccgga ccaccttccg ggtgtccgag ctgtggaaga tcgagctgac catcgtgaag    2340
cagctgatgg gcagcgaggt gtcagccaag ctggccgcct tcaagaccct gctgttcgac    2400 accccccgagc agcagaccac caagaacatg atgaccctga tcaaccccga cgacgagtac   2460
ctgtacgaga tcgagatcga gtacaccggc aagcctgaga gcctgacagc cgccgacgtg    2520
atcaagatca agaaccccgt gctgacactg atcagcccca accacctgat gctgaccgcc    2580
taccaccagg ccatcgagtt tatcgccagc acatcctga gcagcgagat cctgctggcc     2640
cggatcaaga gcgcaagtg gggcctgaag agactgctgc cccaggtcaa gtccatgacc     2700
aaggccgact acatgaagtt ctaccccccc gtgggctact acgtgaccga caaggccgac    2760
ggcatccggg gcattgccgt gatccaggac acccagatct acgtggtggc cgaccagctg    2820
tacagcctgg gcaccaccgg catcgagccc ctgaagccca ccatcctgga cggcgagttc    2880
atgcccgaga agaagagtt ctacggcttt gacgtgatca tgtacgaggg caacctgctg     2940
acccagcagg gcttcgagac acggatcgag agcctgagca agggcatcaa ggtgctgcag    3000
gccttcaaca tcaaggccga gatgaagccc ttcatcagcc tgacctccgc cgaccccaac    3060
gtgctgctga agaatttcga gagcatcttc aagaagaaaa cccggcccta cagcatcgac    3120
ggcatcatcc tggtggagcc cggcaacagc tacctgaaca ccaacacctt caagtggaag    3180
cccacctggg acaacaccct ggactttctg gtccggaagt gccccgagtc cctgaacgtg    3240
cccgagtacg cccccaagaa gggcttcagc ctgcatctgc tgttcgtggg catcagcggc    3300 gagctgtttta agaagctggc cctgaactgg tgccccggct acaccaagct gttccccgtg    3360
acccagcgga accagaacta cttccccgtg cagttccagc ccagcgactt ccccctggcc    3420
ttcctgtact accacccccga caccagcagc ttcagcaaca tcgatggcaa ggtgctggaa   3480
atgcggtgcc tgaagcggga gatcaactac gtgcgctggg agatcgtgaa gatccgggag    3540
gaccggcagc aggatctgaa aaccggcggc tacttcggca cgacttcaa gaccgccgag     3600 ctgacctggc tgaactacat ggaccccttc agcttcgagg aactggccaa gggacccagc    3660
ggcatgtact cgctggcgc caagaccggc atctacagag cccagaccgc cctgatcagc     3720
ttcatcaagc aggaaatcat ccagaagatc agccaccaga gctgggtgat cgacctgggc    3780
atcggcaagg ccaggaccct gggcagatac ctggacgccg cgtgagaca cctggtcggc    3840 atcgataagg accagacagc cctggccgag ctggtgtacc ggaagttctc ccacgccacc    3900
accagacagc acaagcacgc caccaacatc tacgtgctgc accaggatct ggccgagcct    3960
gccaaagaaa tcagcgagaa agtgcaccag atctatggct cccccaaaga gggcgccagc    4020
agcatcgtgt ccaacctgtt catccactac ctgatgaaga cacccagca ggtcgagaac    4080 ctggctgtgc tgtgccacaa gctgctgcag cctggcggca tggtctggtt caccaccatg    4140
ctgggcgaac aggtgctgga actgctgcac gagaaccgga tcgaactgaa cgaagtgtgg    4200
gaggcccggg agaacgaggt ggtcaagttc gccatcaagc ggctgttcaa agaggacatc    4260
ctgcaggaaa ccggccagga aatcggcgtc ctgctgccct tcagcaacgg cgacttctac    4320
aatgagtacc tggtcaacac cgccttcctg atcaagattt tcaagcacca tggctttagc    4380
ctcgtgcaga agcagagctt caaggactgg atccccgagt tccagaactt cagcaagagc    4440
```

```
ctgtacaaga tcctgaccga ggccgacaag acctggacca gcctgttcgg cttcatctgc   4500
ctgcggaaga acctcgaggg aggaggagga tcaggcggag gcggaagtgt cgagcaggac   4560
ctgcacgcca tccagctgca gctcgaagag gaaatgttca acggcggcat cagaagattc   4620
gaggccgacc agcagagaca gatcgcctct ggcaacgaga gcgacaccgc ctggaataga   4680
aggctgctgt ctgagctgat cgcccctatg gccgaaggca tccaggccta caaagaggaa   4740
tacgagggca agagaggcag agccctagg gccctggcct tcatcaactg tgtgggcaat   4800
gaggtggccg cctacatcac catgaagatc gtgatggaca tgctgaacac cgacgtgacc   4860
ctgcaggcca ttgccatgaa cgtggccgac agaatcgagg accaggtccg attcagcaag   4920
ctggaaggac acgccgccaa gtacttcgag aaagtgaaga agtccctgaa ggccagcaag   4980
accaagagct acagacacgc ccacaacgtg gccgtggtgg ccgaaaaatc tgtggccgat   5040
agggacgccg acttctctag atgggaggcc tggcctaagg acaccctgct gcagatcggc   5100
atgaccctgc tggaaatcct ggaaaacagc gtgttcttca acggccagcc cgtgttcctg   5160
agaaccctga ggacaaatgg cggcaagcac ggcgtgtact acctgcagac atctgagcac   5220
gtgggcgagt ggatcaccgc cttcaaagaa catgtggccc agctgagccc tgcctatgcc   5280
ccttgtgtga tccctcctag accctgggtg tccccttca atggcggctt tcacaccgag   5340
aaggtggcca gcagaatcag actggtcaag ggcaaccggg aacacgtgcg gaagctgacc   5400
aagaaacaga tgcccgccgt gtacaaggcc gtgaatgctc tgcaggccac caagtggcag   5460
gtcaacaaag aggtgctgca ggtcgtcgag gacgtgatca gactggatct gggctacggc   5520
gtgccaagct ttaagcccct gatcgacaga gagaacaagc cgccaaccc tgtgcccctg   5580 gaatttcagc acctgagagg ccgcgagctg aaagagatgc tgacacctga acagtggcag   5640
gcctttatca attggaaggg cgagtgcacc aagctgtaca ccgccgagac aaagaggggc   5700
tctaagtctg ccgccacagt gcgaatggtc ggacaggcca aaagtacag ccagttcgac   5760 gccatctact tcgtgtacgc cctggacagc cggtctagag tgtatgccca gagcagcaca   5820
ctgagccccc agtctaacga tctgggaaag gccctgctga gattcaccga gggccagaga   5880
ctggattctg ccgaagccct gaagtggttc tggtcaacg cgccaacaa ctggggctgg   5940 gacaagaaaa ccttcgatgt gcggaccgcc aacgtgctgg atagcgagtt ccaggacatg   6000
tgcagagata tcgccgccga ccctctgacc tttacccagt gggtcaacgc cgatagcccc   6060
tatggattcc tggcctggtg cttcgagtac gccagatacc tggacgccct ggatgaggga   6120
acccaggatc agttcatgac ccatctgccc gtgcaccagg atggctcttg ttctggcatc   6180
cagcactaca gcgccatgct gagcgatgcc gtgggagcca agccgtgaa cctgaagcct   6240 agcgacagcc cccaggatat ctatggcgct gtggcccagg tggtcatcca gaaaaactac   6300
gcctacatga acgccgagga cgccgagaca ttcacaagcg gaagcgtgac actgacaggc   6360
gccgagctga gatctatggc ctctgcctgg gacatgatcg gcatcacacg gggcctgacc   6420
aaaaagcctg tgatgacact gccctacggc agcaccagac tgacctgtag agaaagcgtg   6480
atcgactaca tcgtggacct ggaagagaaa gaggcccaga gagccattgc cgagggcaga   6540
acagccaatc ctgtgcaccc cttcgacaac gacggaagg atagcctgac cctagcgcc   6600 gcctacaact acatgaccgc cctgatctgg cccagcatct ctgaagtggt caaggcccct   6660
atcgtggcca tgaagatgat cagacagctg ccagattcg ccgccaagag aaatgagggc   6720
ctggaatacc ctctgcccac cggctttatc ctgcagcaga aaatcatggc caccgacatg   6780 ctgcggggtgt ccacatgtct gatgggcgag atcaagatga gcctgcagat cgagacagac   6840
```

```
gtggtggacg agacagccat gatgggagcc gccgctccta attttgtgca cggacacgat    6900
gccagccacc tgatcctgac cgtgtgcgat ctggtggaca agggcatcac tagcgtggcc    6960
gtgatccacg atagctttgg aacacacgcc ggcagaaccg ccgacctgag agattctctg    7020
cgggaagaga tggtcaagat gtaccagaac cacaacgccc tgcagaacct gctggacgtg    7080
cacgaagaaa gatggctggt ggacaccggc atccaggtgc agaacaggg agagttcgac     7140 ctgaacgaga tcctggtgtc cgactactgc ttcgcctga                            7179
```

<210> SEQ ID NO 45
<211> LENGTH: 2392
<212> TYPE: PRT
<213> ORGANISM: Artificial Sequence
<220> FEATURE:
<223> OTHER INFORMATION: Amino-acid sequence of lambdaN-R341-F2A-NP868R-(G4S)2-K1ERNAP

<400> SEQUENCE: 45

```
Met Asp Ala Gln Thr Arg Arg Glu Arg Arg Ala Glu Lys Gln Ala
1               5                   10                  15

Gln Trp Lys Ala Ala Asn Gly Gly Gly Thr Gly Leu Lys Asn Lys
                20                  25                  30

Thr Arg Ala Glu Lys Tyr Gln Thr Tyr Tyr Thr Thr Asn Glu Tyr Gln
        35                  40                  45

Ile Val Lys Glu Lys Leu Pro Asp Ile Ile Arg Asp Ala Glu Ile Lys
    50                  55                  60

Ala Ser Glu Val Leu Glu Pro Thr Ile Tyr Glu Lys Arg Ala Ile Met
65                  70                  75                  80

Glu Val Ile Lys Asp Phe Ile Arg Asp His Gln Arg Lys Val Tyr Gly
                85                  90                  95

Gly Thr Ala Leu Asn Glu Ala Leu Lys Gln Val Asn Pro Lys Asp Ala
            100                 105                 110

Ile Tyr Asp Asn Tyr Ser Phe Ser Asp Ile Glu Phe Tyr Ser Pro Thr
        115                 120                 125

Pro Val Gln Asp Leu Val Asp Leu Cys Asn Ile Leu Tyr Arg Lys Gly
    130                 135                 140

Tyr Lys Phe Val Gln Gly Lys Asp Ala Gln His Glu Glu Thr Tyr Ser
145                 150                 155                 160

Ile Phe Val Asn Phe Gln Leu Tyr Cys Asp Ile Thr Tyr Ser Pro Thr
                165                 170                 175

Arg Val Phe Tyr Gly Ile Lys Thr Ile Glu Ile Asp Gly Ile Asn Tyr
            180                 185                 190

Thr Asp Pro His Phe Met Leu Ile Asp Tyr Leu Arg Met Val Asn Gln
        195                 200                 205

Pro Leu Thr Ala Ala Gly Gln Arg Trp Glu Lys Ala Phe Glu Arg Met
    210                 215                 220

Tyr Arg Leu Leu Lys Asp Tyr Pro Ile Glu Asp Phe Asp Lys Arg Leu
225                 230                 235                 240

Asp Ile Pro Glu Pro Glu Glu Ile Gln Ser Tyr Ile Ser Arg Ile
                245                 250                 255

Lys Thr Glu Phe Leu Ser Asp Asn Lys Leu Asn Glu Ser Phe Leu Ile
            260                 265                 270

Ser Gly Ile Glu Ala Tyr Asn Phe Tyr Ile Arg His Ala Ala Ser Ser
        275                 280                 285

Lys Asp Glu Glu Gln Met Ala Arg Thr Asn Arg Asn Val Val Asn Leu
```

```
            290                 295                 300
Asn Asn Phe Ile Ala Asn Val Pro Phe Ser Glu Leu Ile Ser Val Asn
305                 310                 315                 320

Tyr Arg Glu Asp Val Lys Asn Thr Tyr Asn Phe Leu Arg Met Ile Val
                325                 330                 335

Glu Asp Lys Glu Lys Ile Ser Val Asp Glu Tyr Phe Pro Leu Phe Gln
            340                 345                 350

Phe Thr Gly Tyr Ser Thr Val Ile Lys Tyr Asp Asp His Pro Ile Ile
            355                 360                 365

Arg Ile Tyr Glu Gly Asp Gly Tyr Cys Ile Pro Asn Val Lys Thr Val
        370                 375                 380

Lys Thr Val Glu Asn Asp Asn Gly Thr Lys Thr Lys Tyr Glu Tyr Lys
385                 390                 395                 400

Tyr Val Ser Phe Gln Tyr Val Leu Met Ile Leu Tyr Ile Asn Lys Phe
                405                 410                 415

Arg Ala His Leu Asp Lys Asn Lys Pro Met Tyr Phe Asn Tyr Gly Ile
            420                 425                 430

Ala Ile Ser Asn Leu Val Lys Ala Arg Asn Ile Tyr Leu Asp Gln Thr
        435                 440                 445

Gly Lys Ser Val Leu Asp Asn Thr Val Phe Lys Glu Phe Arg Thr Asn
    450                 455                 460

Cys Thr Gly Asn Thr Ile Ser Phe Thr Arg Met Asn Arg Leu Arg Leu
465                 470                 475                 480

Leu Glu Lys Arg Lys Gln Gly Lys Gln Thr Ser Phe Val Tyr Thr Pro
                485                 490                 495

Glu Asp Phe Phe Lys Lys Asp Leu Glu Thr Gln Ala Lys Leu Asp Pro
            500                 505                 510

Ser Lys Ala Arg Phe Lys Asn Thr Ser Gly Asn Lys Ile Met Val Pro
        515                 520                 525

Lys Tyr Leu Leu Phe Lys Ile Asp Asn Asn Gly Asn Ile Glu Asp Asn
530                 535                 540

Ile His Ser Glu Glu Ala Glu Ile Ser Glu Lys Glu Glu Thr Ser Gly
545                 550                 555                 560

Gly Ser Ser Ile Ser Thr Asp Lys Ser Phe Glu Ser Pro Asn Ser
                565                 570                 575

Ser Pro Asn Ser Ser Pro Asn Asn Ser Leu Asn Ser Ile Asp Ile
            580                 585                 590

Ser Thr Asn Asn Tyr Asp Asp Arg Ser Glu Asn Ser Leu Asp Ser Leu
        595                 600                 605

Thr Ser Asp Gly Pro Val Lys Gln Thr Leu Asn Phe Asp Leu Leu Lys
    610                 615                 620

Leu Ala Gly Asp Val Glu Ser Asn Pro Gly Pro Glu Phe Ala Ser Leu
625                 630                 635                 640

Asp Asn Leu Val Ala Arg Tyr Gln Arg Cys Phe Asn Asp Gln Ser Leu
                645                 650                 655

Lys Asn Ser Thr Ile Glu Leu Glu Ile Arg Phe Gln Gln Ile Asn Phe
            660                 665                 670

Leu Leu Phe Lys Thr Val Tyr Glu Ala Leu Val Ala Gln Glu Ile Pro
        675                 680                 685

Ser Thr Ile Ser His Ser Ile Arg Cys Ile Lys Lys Val His His Glu
    690                 695                 700

Asn His Cys Arg Glu Lys Ile Leu Pro Ser Glu Asn Leu Tyr Phe Lys
705                 710                 715                 720
```

```
Lys Gln Pro Leu Met Phe Phe Lys Phe Ser Glu Pro Ala Ser Leu Gly
            725                 730                 735

Cys Lys Val Ser Leu Ala Ile Glu Gln Pro Ile Arg Lys Phe Ile Leu
            740                 745                 750

Asp Ser Ser Val Leu Val Arg Leu Lys Asn Arg Thr Thr Phe Arg Val
            755                 760                 765

Ser Glu Leu Trp Lys Ile Glu Leu Thr Ile Val Lys Gln Leu Met Gly
            770                 775                 780

Ser Glu Val Ser Ala Lys Leu Ala Ala Phe Lys Thr Leu Leu Phe Asp
785                 790                 795                 800

Thr Pro Glu Gln Gln Thr Thr Lys Asn Met Met Thr Leu Ile Asn Pro
            805                 810                 815

Asp Asp Glu Tyr Leu Tyr Glu Ile Glu Ile Glu Tyr Thr Gly Lys Pro
            820                 825                 830

Glu Ser Leu Thr Ala Ala Asp Val Ile Lys Ile Lys Asn Thr Val Leu
            835                 840                 845

Thr Leu Ile Ser Pro Asn His Leu Met Leu Thr Ala Tyr His Gln Ala
            850                 855                 860

Ile Glu Phe Ile Ala Ser His Ile Leu Ser Ser Glu Ile Leu Leu Ala
865                 870                 875                 880

Arg Ile Lys Ser Gly Lys Trp Gly Leu Lys Arg Leu Leu Pro Gln Val
            885                 890                 895

Lys Ser Met Thr Lys Ala Asp Tyr Met Lys Phe Tyr Pro Pro Val Gly
            900                 905                 910

Tyr Tyr Val Thr Asp Lys Ala Asp Gly Ile Arg Gly Ile Ala Val Ile
            915                 920                 925

Gln Asp Thr Gln Ile Tyr Val Val Ala Asp Gln Leu Tyr Ser Leu Gly
            930                 935                 940

Thr Thr Gly Ile Glu Pro Leu Lys Pro Thr Ile Leu Asp Gly Glu Phe
945                 950                 955                 960

Met Pro Glu Lys Lys Glu Phe Tyr Gly Phe Asp Val Ile Met Tyr Glu
            965                 970                 975

Gly Asn Leu Leu Thr Gln Gln Gly Phe Glu Thr Arg Ile Glu Ser Leu
            980                 985                 990

Ser Lys Gly Ile Lys Val Leu Gln Ala Phe Asn Ile Lys Ala Glu Met
            995                 1000                1005

Lys Pro Phe Ile Ser Leu Thr Ser Ala Asp Pro Asn Val Leu Leu
            1010            1015            1020

Lys Asn Phe Glu Ser Ile Phe Lys Lys Lys Thr Arg Pro Tyr Ser
            1025            1030            1035

Ile Asp Gly Ile Ile Leu Val Glu Pro Gly Asn Ser Tyr Leu Asn
            1040            1045            1050

Thr Asn Thr Phe Lys Trp Lys Pro Thr Trp Asp Asn Thr Leu Asp
            1055            1060            1065

Phe Leu Val Arg Lys Cys Pro Glu Ser Leu Asn Val Pro Glu Tyr
            1070            1075            1080

Ala Pro Lys Lys Gly Phe Ser Leu His Leu Leu Phe Val Gly Ile
            1085            1090            1095

Ser Gly Glu Leu Phe Lys Lys Leu Ala Leu Asn Trp Cys Pro Gly
            1100            1105            1110

Tyr Thr Lys Leu Phe Pro Val Thr Gln Arg Asn Gln Asn Tyr Phe
            1115            1120            1125
```

```
Pro Val Gln Phe Gln Pro Ser Asp Phe Pro Leu Ala Phe Leu Tyr
1130                1135                1140

Tyr His Pro Asp Thr Ser Ser Phe Ser Asn Ile Asp Gly Lys Val
1145                1150                1155

Leu Glu Met Arg Cys Leu Lys Arg Glu Ile Asn Tyr Val Arg Trp
1160                1165                1170

Glu Ile Val Lys Ile Arg Glu Arg Gln Gln Asp Leu Lys Thr
1175                1180                1185

Gly Gly Tyr Phe Gly Asn Asp Phe Lys Thr Ala Glu Leu Thr Trp
1190                1195                1200

Leu Asn Tyr Met Asp Pro Phe Ser Phe Glu Glu Leu Ala Lys Gly
1205                1210                1215

Pro Ser Gly Met Tyr Phe Ala Gly Ala Lys Thr Gly Ile Tyr Arg
1220                1225                1230

Ala Gln Thr Ala Leu Ile Ser Phe Ile Lys Gln Glu Ile Ile Gln
1235                1240                1245

Lys Ile Ser His Gln Ser Trp Val Ile Asp Leu Gly Ile Gly Lys
1250                1255                1260

Gly Gln Asp Leu Gly Arg Tyr Leu Asp Ala Gly Val Arg His Leu
1265                1270                1275

Val Gly Ile Asp Lys Asp Gln Thr Ala Leu Ala Glu Leu Val Tyr
1280                1285                1290

Arg Lys Phe Ser His Ala Thr Thr Arg Gln His Lys His Ala Thr
1295                1300                1305

Asn Ile Tyr Val Leu His Gln Asp Leu Ala Glu Pro Ala Lys Glu
1310                1315                1320

Ile Ser Glu Lys Val His Gln Ile Tyr Gly Phe Pro Lys Glu Gly
1325                1330                1335

Ala Ser Ser Ile Val Ser Asn Leu Phe Ile His Tyr Leu Met Lys
1340                1345                1350

Asn Thr Gln Gln Val Glu Asn Leu Ala Val Leu Cys His Lys Leu
1355                1360                1365

Leu Gln Pro Gly Gly Met Val Trp Phe Thr Thr Met Leu Gly Glu
1370                1375                1380

Gln Val Leu Glu Leu Leu His Glu Asn Arg Ile Glu Leu Asn Glu
1385                1390                1395

Val Trp Glu Ala Arg Glu Asn Glu Val Val Lys Phe Ala Ile Lys
1400                1405                1410

Arg Leu Phe Lys Glu Asp Ile Leu Gln Glu Thr Gly Gln Glu Ile
1415                1420                1425

Gly Val Leu Leu Pro Phe Ser Asn Gly Asp Phe Tyr Asn Glu Tyr
1430                1435                1440

Leu Val Asn Thr Ala Phe Leu Ile Lys Ile Phe Lys His His Gly
1445                1450                1455

Phe Ser Leu Val Gln Lys Gln Ser Phe Lys Asp Trp Ile Pro Glu
1460                1465                1470

Phe Gln Asn Phe Ser Lys Ser Leu Tyr Lys Ile Leu Thr Glu Ala
1475                1480                1485

Asp Lys Thr Trp Thr Ser Leu Phe Gly Phe Ile Cys Leu Arg Lys
1490                1495                1500

Asn Leu Glu Gly Gly Gly Gly Ser Gly Gly Gly Gly Ser Val Glu
1505                1510                1515

Gln Asp Leu His Ala Ile Gln Leu Gln Leu Glu Glu Glu Met Phe
```

-continued

```
            1520                1525                1530
Asn Gly Gly Ile Arg Arg Phe Glu Ala Asp Gln Gln Arg Gln Ile
            1535                1540                1545
Ala Ser Gly Asn Glu Ser Asp Thr Ala Trp Asn Arg Arg Leu Leu
            1550                1555                1560
Ser Glu Leu Ile Ala Pro Met Ala Glu Gly Ile Gln Ala Tyr Lys
            1565                1570                1575
Glu Glu Tyr Glu Gly Lys Arg Gly Arg Ala Pro Arg Ala Leu Ala
            1580                1585                1590
Phe Ile Asn Cys Val Gly Asn Glu Val Ala Ala Tyr Ile Thr Met
            1595                1600                1605
Lys Ile Val Met Asp Met Leu Asn Thr Asp Val Thr Leu Gln Ala
            1610                1615                1620
Ile Ala Met Asn Val Ala Asp Arg Ile Glu Asp Gln Val Arg Phe
            1625                1630                1635
Ser Lys Leu Glu Gly His Ala Ala Lys Tyr Phe Glu Lys Val Lys
            1640                1645                1650
Lys Ser Leu Lys Ala Ser Lys Thr Lys Ser Tyr Arg His Ala His
            1655                1660                1665
Asn Val Ala Val Ala Glu Lys Ser Val Ala Asp Arg Asp Ala
            1670                1675                1680
Asp Phe Ser Arg Trp Glu Ala Trp Pro Lys Asp Thr Leu Leu Gln
            1685                1690                1695
Ile Gly Met Thr Leu Leu Glu Ile Leu Glu Asn Ser Val Phe Phe
            1700                1705                1710
Asn Gly Gln Pro Val Phe Leu Arg Thr Leu Arg Thr Asn Gly Gly
            1715                1720                1725
Lys His Gly Val Tyr Tyr Leu Gln Thr Ser Glu His Val Gly Glu
            1730                1735                1740
Trp Ile Thr Ala Phe Lys Glu His Val Ala Gln Leu Ser Pro Ala
            1745                1750                1755
Tyr Ala Pro Cys Val Ile Pro Pro Arg Pro Trp Val Ser Pro Phe
            1760                1765                1770
Asn Gly Gly Phe His Thr Glu Lys Val Ala Ser Arg Ile Arg Leu
            1775                1780                1785
Val Lys Gly Asn Arg Glu His Val Arg Lys Leu Thr Lys Lys Gln
            1790                1795                1800
Met Pro Ala Val Tyr Lys Ala Val Asn Ala Leu Gln Ala Thr Lys
            1805                1810                1815
Trp Gln Val Asn Lys Glu Val Leu Gln Val Val Glu Asp Val Ile
            1820                1825                1830
Arg Leu Asp Leu Gly Tyr Gly Val Pro Ser Phe Lys Pro Leu Ile
            1835                1840                1845
Asp Arg Glu Asn Lys Pro Ala Asn Pro Val Pro Leu Glu Phe Gln
            1850                1855                1860
His Leu Arg Gly Arg Glu Leu Lys Glu Met Leu Thr Pro Glu Gln
            1865                1870                1875
Trp Gln Ala Phe Ile Asn Trp Lys Gly Glu Cys Thr Lys Leu Tyr
            1880                1885                1890
Thr Ala Glu Thr Lys Arg Gly Ser Lys Ser Ala Ala Thr Val Arg
            1895                1900                1905
Met Val Gly Gln Ala Arg Lys Tyr Ser Gln Phe Asp Ala Ile Tyr
            1910                1915                1920
```

-continued

Phe Val Tyr Ala Leu Asp Ser Arg Ser Arg Val Tyr Ala Gln Ser
1925                1930                1935

Ser Thr Leu Ser Pro Gln Ser Asn Asp Leu Gly Lys Ala Leu Leu
1940                1945                1950

Arg Phe Thr Glu Gly Gln Arg Leu Asp Ser Ala Glu Ala Leu Lys
1955                1960                1965

Trp Phe Leu Val Asn Gly Ala Asn Asn Trp Gly Trp Asp Lys Lys
1970                1975                1980

Thr Phe Asp Val Arg Thr Ala Asn Val Leu Asp Ser Glu Phe Gln
1985                1990                1995

Asp Met Cys Arg Asp Ile Ala Ala Asp Pro Leu Thr Phe Thr Gln
2000                2005                2010

Trp Val Asn Ala Asp Ser Pro Tyr Gly Phe Leu Ala Trp Cys Phe
2015                2020                2025

Glu Tyr Ala Arg Tyr Leu Asp Ala Leu Asp Glu Gly Thr Gln Asp
2030                2035                2040

Gln Phe Met Thr His Leu Pro Val His Gln Asp Gly Ser Cys Ser
2045                2050                2055

Gly Ile Gln His Tyr Ser Ala Met Leu Ser Asp Ala Val Gly Ala
2060                2065                2070

Lys Ala Val Asn Leu Lys Pro Ser Asp Ser Pro Gln Asp Ile Tyr
2075                2080                2085

Gly Ala Val Ala Gln Val Val Ile Gln Lys Asn Tyr Ala Tyr Met
2090                2095                2100

Asn Ala Glu Asp Ala Glu Thr Phe Thr Ser Gly Ser Val Thr Leu
2105                2110                2115

Thr Gly Ala Glu Leu Arg Ser Met Ala Ser Ala Trp Asp Met Ile
2120                2125                2130

Gly Ile Thr Arg Gly Leu Thr Lys Lys Pro Val Met Thr Leu Pro
2135                2140                2145

Tyr Gly Ser Thr Arg Leu Thr Cys Arg Glu Ser Val Ile Asp Tyr
2150                2155                2160

Ile Val Asp Leu Glu Glu Lys Glu Ala Gln Arg Ala Ile Ala Glu
2165                2170                2175

Gly Arg Thr Ala Asn Pro Val His Pro Phe Asp Asn Asp Arg Lys
2180                2185                2190

Asp Ser Leu Thr Pro Ser Ala Ala Tyr Asn Tyr Met Thr Ala Leu
2195                2200                2205

Ile Trp Pro Ser Ile Ser Glu Val Val Lys Ala Pro Ile Val Ala
2210                2215                2220

Met Lys Met Ile Arg Gln Leu Ala Arg Phe Ala Ala Lys Arg Asn
2225                2230                2235

Glu Gly Leu Glu Tyr Pro Leu Pro Thr Gly Phe Ile Leu Gln Gln
2240                2245                2250

Lys Ile Met Ala Thr Asp Met Leu Arg Val Ser Thr Cys Leu Met
2255                2260                2265

Gly Glu Ile Lys Met Ser Leu Gln Ile Glu Thr Asp Val Val Asp
2270                2275                2280

Glu Thr Ala Met Met Gly Ala Ala Ala Pro Asn Phe Val His Gly
2285                2290                2295

His Asp Ala Ser His Leu Ile Leu Thr Val Cys Asp Leu Val Asp
2300                2305                2310

-continued

| Lys | Gly | Ile | Thr | Ser | Val | Ala | Val | Ile | His | Asp | Ser | Phe | Gly | Thr |
| --- | --- | --- | --- | --- | --- | --- | --- | --- | --- | --- | --- | --- | --- | --- |
| | 2315 | | | | 2320 | | | | | 2325 | | | | |

| His | Ala | Gly | Arg | Thr | Ala | Asp | Leu | Arg | Asp | Ser | Leu | Arg | Glu | Glu |
| --- | --- | --- | --- | --- | --- | --- | --- | --- | --- | --- | --- | --- | --- | --- |
| | 2330 | | | | 2335 | | | | | 2340 | | | | |

| Met | Val | Lys | Met | Tyr | Gln | Asn | His | Asn | Ala | Leu | Gln | Asn | Leu | Leu |
| --- | --- | --- | --- | --- | --- | --- | --- | --- | --- | --- | --- | --- | --- | --- |
| | 2345 | | | | 2350 | | | | | 2355 | | | | |

| Asp | Val | His | Glu | Glu | Arg | Trp | Leu | Val | Asp | Thr | Gly | Ile | Gln | Val |
| --- | --- | --- | --- | --- | --- | --- | --- | --- | --- | --- | --- | --- | --- | --- |
| | 2360 | | | | 2365 | | | | | 2370 | | | | |

| Pro | Glu | Gln | Gly | Glu | Phe | Asp | Leu | Asn | Glu | Ile | Leu | Val | Ser | Asp |
| --- | --- | --- | --- | --- | --- | --- | --- | --- | --- | --- | --- | --- | --- | --- |
| | 2375 | | | | 2380 | | | | | 2385 | | | | |

| Tyr | Cys | Phe | Ala |
| --- | --- | --- | --- |
| | 2390 | | |

<210> SEQ ID NO 46
<211> LENGTH: 7170
<212> TYPE: DNA
<213> ORGANISM: Artificial Sequence
<220> FEATURE:
<223> OTHER INFORMATION: Nucleotide sequence of lambdaN-R341-T2A-NP868R-(G4S)2-K1ERNAP

<400> SEQUENCE: 46

```
atggatgctc agaccagacg cagagaacgg cgggcagaga agcaggcaca gtggaaggcc      60
gctaatggcg gtggcggcac cggtctcaaa acaagacca gggctgagaa gtatcagacc      120
tactacacca ccaatgaata tcagatcgtt aaagaaaaac taccagacat tataagagac    180
gcggaaatta aggcgtctga agtgctcgag ccaaccatct acgagaagcg cgcaatcatg    240
gaagtcatta aggatttcat tcgggatcat caaaggaaag tgtatggcgg aacagccctg    300
aatgaggcat tgaaacaggt gaatcccaag gatgccatct atgataacta ttccttcagc    360
gacatcgagt tttattcccc taccccgtg caggatctcg tggatctctg caacatcctg    420
tatagaaaag ggtataagtt cgtccagggg aaggacgctc agcatgagga aacctattct    480
atctttgtaa atttccagct ctactgtgac attacctatt cgccaacccg ggtctttat    540
ggtattaaaa cgatagaaat tgacggcatt aactataccg atcctcattt catgctcata    600
gattacctcc gaatggtgaa ccagcccttg actgccgccg ccagcgctg ggagaaagcg     660
ttcgaacgga tgtacaggct gctcaaagac tatcccattg aggattttga caagaggctg   720
gatattcctg agccacccga agaaatccag agttatattt ctcggattaa gaccgagttt    780
ctgagcgata caagctgaa tgaaagcttc ctcatctccg gcatcgaggc ttacaacttc    840
tacattcgcc atgctgcctc tagcaaagat gaagaacaga tggcccggac aaaccgcaat    900
gtggtcaatc ttaataactt tattgcaaat gtcccctttta gcgagctgat ctccgtgaac   960
tatcgcgaag atgtcaagaa tacctataac ttcctgcgga tgatcgtcga ggataaagag  1020
aaaatcagtg ttgacgaata tttccctctc tttcaattca ctggctattc cactgtcatc  1080
aaatacgatg atcacccat aattaggatc tacgagggcg acggttattg tattcctaac   1140
gtcaagaccg ttaaaacggt ggagaatgac aacggaacga agacaaagta cgagtacaag  1200
tacgtatcct tccagtacgt cctcatgatt ctatatatca acaaatttcg tgcgcacttg  1260
gacaagaata agcctatgta ttttaactac ggtattgcca tatccaatct ggtcaaagct  1320
cgcaatatat acctggacca gaccgggaaa agcgtccttg acaacactgt gtttaaggag  1380
ttccgcacta actgtaccgg aaaatacgatc tctttcacac ggatgaacag actgagatta  1440
ctcgagaaaa gaaagcaggg caagcagact tcgttcgttt acaccctga agacttcttt  1500
```

-continued

```
aagaaggatc tggaaaccca agccaagctt gacccgtcga aagcgagatt caaaaatacc  1560
agtggtaaca agattatggt gccaaagtac ctgctgttca aaatagataa caacggaaat  1620
attgaagata acatacatag cgaagaggca gaaatctcag agaaagaaga aacttccggt  1680
ggctcttcta tatccactga taaatcattc gaagaatcac ctaattcctc ccctaacagc  1740
tctcctaaca actcgttgaa taattctatt gatatcagta caaataatta cgacgaccgc  1800
tcggaaaaca gcctggactc actcacgtct gatgggcccg caaccaactt ttctctgctg  1860
aagcaggcag gggacgttga ggagaaccct ggtcccgaat cgccagcct ggacaacctg  1920 gtggccagat accagcggtg cttcaacgac cagagcctga gaacagcac catcgagctg  1980 gaaatccggt tccagcagat caacttcctg ctgttcaaga ccgtgtacga ggccctggtc  2040
gcccaggaaa tccccagcac catcagccac agcatccggt gcatcaagaa ggtgcaccac  2100
gagaaccact gccgggagaa gatcctgccc agcgagaacc tgtacttcaa gaaacagccc  2160
ctgatgttct tcaagttcag cgagcccgcc agcctgggct gtaaagtgtc cctggccatc  2220
gagcagccca tccggaagtt catcctggac agcagcgtgc tggtccggct gaagaaccgg  2280
accaccttcc gggtgtccga gctgtggaag atcgagctga ccatcgtgaa gcagctgatg  2340
ggcagcgagg tgtcagccaa gctggccgcc ttcaagaccc tgctgttcga cacccccgag  2400
cagcagacca ccaagaacat gatgacccctg atcaaccccg acgacgagta cctgtacgag  2460
atcgagatcg agtacaccgg caagcctgag agcctgacag ccgccgacgt gatcaagatc  2520
aagaacaccg tgctgacact gatcagcccc aaccacctga tgctgaccgc ctaccaccag  2580
gccatcgagt ttatcgccag ccacatcctg agcagcgaga tcctgctggc ccggatcaag  2640
agcggcaagt ggggcctgaa gagactgctg ccccaggtca agtccatgac caaggccgac  2700
tacatgaagt tctacccccc cgtgggctac tacgtgaccg acaaggccga cggcatccgg  2760
ggcattgccg tgatccagga cacccagatc tacgtggtgg ccgaccagct gtacagcctg  2820
ggcaccaccg gcatcgagcc cctgaagccc accatcctgg acggcgagtt catgcccgag  2880
aagaaagagt tctacggctt tgacgtgatc atgtacgagg gcaacctgct gacccagcag  2940
ggcttcgaga cacggatcga gagcctgagc aagggcatca aggtgctgca ggccttcaac  3000
atcaaggccg agatgaagcc cttcatcagc ctgacctccg ccgaccccaa cgtgctgctg  3060
aagaatttcg agagcatctt caagaagaaa cccggccct acagcatcga cggcatcatc  3120
ctggtggagc ccggcaacag ctacctgaac accaacacct tcaagtggaa gcccacctgg  3180
gacaacaccc tggactttct ggtccggaag tgccccgagt ccctgaacgt gcccgagtac  3240
gcccccaaga agggcttcag cctgcatctg ctgttcgtgg gcatcagcgg cgagctgttt  3300
aagaagctgg ccctgaactg gtgccccggc tacaccaagc tgttccccgt gacccagcgg  3360
aaccagaact acttccccgt gcagttccag cccagcgact ccccctggc cttcctgtac  3420 taccaccccg acaccagcag cttcagcaac atcgatggca aggtgctgga aatgcggtgc  3480
ctgaagcggg agatcaacta cgtgcgctgg gagatcgtga agatccggga ggaccggcag  3540
caggatctga aaccggcgg ctacttcggc aacgacttca gaccgccga gctgacctgg  3600 ctgaactaca tggaccccctt cagcttcgag gaactggcca agggaccag cggcatgtac  3660 ttcgctggcg ccaagaccgg catctacaga gcccagaccg ccctgatcag cttcatcaag  3720
caggaaatca tccagaagat cagccaccag agctgggtga tcgacctggg catcggcaag  3780
ggccaggacc tgggcagata cctggacgcc ggcgtgagac acctggtcgg catcgataag  3840
gaccagacag ccctggccga gctggtgtac cggaagttct cccacgccac caccagacag  3900
```

```
cacaagcacg ccaccaacat ctacgtgctg caccaggatc tggccgagcc tgccaaagaa    3960
atcagcgaga aagtgcacca gatctatggc ttccccaaag agggcgccag cagcatcgtg    4020
tccaacctgt tcatccacta cctgatgaag aacacccagc aggtcgagaa cctggctgtg    4080
ctgtgccaca agctgctgca gcctggcggc atggtctggt tcaccaccat gctgggcgaa    4140
caggtgctgg aactgctgca cgagaaccgg atcgaactga cgaagtgtgg gaggcccgg    4200 gagaacgagg tggtcaagtt cgccatcaag cggctgttca agaggacat cctgcaggaa    4260 accggccagg aaatcggcgt cctgctgccc ttcagcaacg gcgacttcta caatgagtac    4320
ctggtcaaca ccgcctttct gatcaagatt ttcaagcacc atggctttag cctcgtgcag    4380
aagcagagct tcaaggactg gatccccgag ttccagaact cagcaagag cctgtacaag    4440 atcctgaccg aggccgacaa gacctggacc agcctgttcg gcttcatctg cctgcggaag    4500
aacctcgagg gaggaggagg atcaggcgga ggcggaagtg tcgagcagga cctgcacgcc    4560
atccagctgc agctcgaaga ggaaatgttc aacggcggca tcagaagatt cgaggccgac    4620
cagcagagac agatcgcctc tggcaacgag agcgacaccg cctggaatag aaggctgctg    4680
tctgagctga tcgcccctat ggccgaaggc atccaggcct acaaagagga atacgagggc    4740
aagagaggca gagcccctag agccctggcc ttcatcaact gtgtgggcaa tgaggtggcc    4800
gcctacatca ccatgaagat cgtgatggac atgctgaaca ccgacgtgac cctgcaggcc    4860
attgccatga acgtggccga cagaatcgag gaccaggtcc gattcagcaa gctggaagga    4920
cacgccgcca agtacttcga gaaagtgaag aagtccctga aggccagcaa gaccaagagc    4980
tacagacacg cccacaacgt ggccgtggtg gccgaaaaat ctgtggccga tagggacgcc    5040
gacttctcta gatgggaggc ctggcctaag gacaccctgc tgcagatcgg catgaccctg    5100
ctggaaatcc tggaaaacag cgtgttcttc aacggccagc ccgtgttcct gagaacccgt    5160
aggacaaatg gcggcaagca cggcgtgtac tacctgcaga catctgagca cgtgggcgag    5220
tggatcaccg ccttcaaaga acatgtggcc cagctgagcc ctgcctatgc cccttgtgtg    5280
atccctccta gacccggggt gtccccttc aatggcggct tcacaccga gaaggtggcc    5340 agcagaatca gactggtcaa gggcaaccgg gaacacgtgc ggaagctgac caagaaacag    5400
atgcccgccg tgtacaaggc cgtgaatgct ctgcaggcca ccaagtggca ggtcaacaaa    5460
gaggtgctgc aggtcgtcga ggacgtgatc agactggatc tgggctacgg cgtgccaagc    5520
tttaagcccc tgatcgacag agagaacaag cccgccaacc tgtgcccct ggaatttcag    5580 cacctgagag gccgcgagct gaaagagatg ctgacacctg aacagtggca ggcctttatc    5640
aattggaagg gcgagtgcac caagctgtac accgccgaga caaagagggg ctctaagtct    5700
gccgccacag tgcgaatggt cggacaggcc agaaagtaca gccagttcga cgccatctac    5760
ttcgtgtacg ccctggacag ccggtctaga gtgtatgccc agagcagcac actgagcccc    5820
cagtctaacg atctgggaaa ggccctgctg agattcaccg agggcagag actggattct    5880 gccgaagccc tgaagtggtt cctggtcaac ggcgccaaca actgggctg ggacaagaaa    5940 accttcgatg tgcggaccgc caacgtgctg gatagcgagt ccaggacat gtgcagagat    6000 atcgccgcca ccctctgac cttaccccag tgggtcaacg ccgatagccc ctatggattc    6060
ctggcctggt gcttcgagta cgccagatac ctggacgccc tggatgaggg aacccaggat    6120
cagttcatga cccatctgcc cgtgcaccag atggctctt gttctggcat ccagcactac    6180
agcgccatgc tgagcgatgc cgtgggagcc aaagccgtga acctgaagcc tagcgacagc    6240
```

```
cccccaggata tctatggcgc tgtggcccag gtggtcatcc agaaaaacta cgcctacatg    6300
aacgccgagg acgccgagac attcacaagc ggaagcgtga cactgacagg cgccgagctg    6360
agatctatgg cctctgcctg gacatgatc ggcatcacac ggggcctgac caaaaagcct    6420
gtgatgacac tgccctacgg cagcaccaga ctgacctgta gagaaagcgt gatcgactac    6480
atcgtggacc tggaagagaa agaggcccag agagccattg ccgagggcag aacagccaat    6540
cctgtgcacc ccttcgacaa cgaccggaag gatagcctga cacctagcgc cgcctacaac    6600
tacatgaccg ccctgatctg gcccagcatc tctgaagtgg tcaaggcccc tatcgtggcc    6660
atgaagatga tcagacagct ggccagattc gccgccaaga gaatgagggg cctggaatac    6720
cctctgccca ccggctttat cctgcagcag aaaatcatgg ccaccgacat gctgcgggtg    6780
tccacatgtc tgatgggcga gatcaagatg agcctgcaga tcgagacaga cgtggtggac    6840
gagacagcca tgatgggagc cgccgctcct aattttgtgc acggacacga tgccagccac    6900
ctgatcctga ccgtgtgcga tctggtggac aagggcatca ctagcgtggc cgtgatccac    6960
gatagctttg gaacacacgc cggcagaacc gccgacctga gagattctct gcgggaagag    7020
atggtcaaga tgtaccagaa ccacaacgcc ctgcagaacc tgctggacgt gcacgaagaa    7080
agatggctgg tggacaccgg catccaggtg ccagaacagg gagagttcga cctgaacgag    7140
atcctggtgt ccgactactg cttcgcctga                                     7170
```

<210> SEQ ID NO 47
<211> LENGTH: 2389
<212> TYPE: PRT
<213> ORGANISM: Artificial Sequence
<220> FEATURE:
<223> OTHER INFORMATION: Amino-acid sequence of lambdaN-R341-T2A-NP868R-(G4S)2-K1ERNAP

<400> SEQUENCE: 47

```
Met Asp Ala Gln Thr Arg Arg Arg Glu Arg Arg Ala Glu Lys Gln Ala
1               5                   10                  15

Gln Trp Lys Ala Ala Asn Gly Gly Gly Thr Gly Leu Lys Asn Lys
            20                  25                  30

Thr Arg Ala Glu Lys Tyr Gln Thr Tyr Thr Thr Asn Glu Tyr Gln
        35                  40                  45

Ile Val Lys Glu Lys Leu Pro Asp Ile Arg Asp Ala Glu Ile Lys
    50                  55                  60

Ala Ser Glu Val Leu Glu Pro Thr Ile Tyr Glu Lys Arg Ala Ile Met
65                  70                  75                  80

Glu Val Ile Lys Asp Phe Ile Arg Asp His Gln Arg Lys Val Tyr Gly
                85                  90                  95

Gly Thr Ala Leu Asn Glu Ala Leu Lys Gln Val Asn Pro Lys Asp Ala
            100                 105                 110

Ile Tyr Asp Asn Tyr Ser Phe Ser Asp Ile Glu Phe Tyr Ser Pro Thr
        115                 120                 125

Pro Val Gln Asp Leu Val Asp Leu Cys Asn Ile Leu Tyr Arg Lys Gly
    130                 135                 140

Tyr Lys Phe Val Gln Gly Lys Asp Ala Gln His Glu Glu Thr Tyr Ser
145                 150                 155                 160

Ile Phe Val Asn Phe Gln Leu Tyr Cys Asp Ile Thr Tyr Ser Pro Thr
                165                 170                 175

Arg Val Phe Tyr Gly Ile Lys Thr Ile Glu Ile Asp Gly Ile Asn Tyr
            180                 185                 190
```

```
Thr Asp Pro His Phe Met Leu Ile Asp Tyr Leu Arg Met Val Asn Gln
            195                 200                 205

Pro Leu Thr Ala Ala Gly Gln Arg Trp Glu Lys Ala Phe Glu Arg Met
    210                 215                 220

Tyr Arg Leu Leu Lys Asp Tyr Pro Ile Glu Asp Phe Asp Lys Arg Leu
225                 230                 235                 240

Asp Ile Pro Glu Pro Pro Glu Ile Gln Ser Tyr Ile Ser Arg Ile
                245                 250                 255

Lys Thr Glu Phe Leu Ser Asp Asn Lys Leu Asn Glu Ser Phe Leu Ile
                260                 265                 270

Ser Gly Ile Glu Ala Tyr Asn Phe Tyr Ile Arg His Ala Ala Ser Ser
            275                 280                 285

Lys Asp Glu Glu Gln Met Ala Arg Thr Asn Arg Asn Val Val Asn Leu
    290                 295                 300

Asn Asn Phe Ile Ala Asn Val Pro Phe Ser Glu Leu Ile Ser Val Asn
305                 310                 315                 320

Tyr Arg Glu Asp Val Lys Asn Thr Tyr Asn Phe Leu Arg Met Ile Val
                325                 330                 335

Glu Asp Lys Glu Lys Ile Ser Val Asp Glu Tyr Phe Pro Leu Phe Gln
            340                 345                 350

Phe Thr Gly Tyr Ser Thr Val Ile Lys Tyr Asp Asp His Pro Ile Ile
    355                 360                 365

Arg Ile Tyr Glu Gly Asp Gly Tyr Cys Ile Pro Asn Val Lys Thr Val
    370                 375                 380

Lys Thr Val Glu Asn Asp Asn Gly Thr Lys Thr Lys Tyr Glu Tyr Lys
385                 390                 395                 400

Tyr Val Ser Phe Gln Tyr Val Leu Met Ile Leu Tyr Ile Asn Lys Phe
                405                 410                 415

Arg Ala His Leu Asp Lys Asn Lys Pro Met Tyr Phe Asn Tyr Gly Ile
            420                 425                 430

Ala Ile Ser Asn Leu Val Lys Ala Arg Asn Ile Tyr Leu Asp Gln Thr
    435                 440                 445

Gly Lys Ser Val Leu Asp Asn Thr Val Phe Lys Glu Phe Arg Thr Asn
    450                 455                 460

Cys Thr Gly Asn Thr Ile Ser Phe Thr Arg Met Asn Arg Leu Arg Leu
465                 470                 475                 480

Leu Glu Lys Arg Lys Gln Gly Lys Gln Thr Ser Phe Val Tyr Thr Pro
                485                 490                 495

Glu Asp Phe Phe Lys Lys Asp Leu Glu Thr Gln Ala Lys Leu Asp Pro
            500                 505                 510

Ser Lys Ala Arg Phe Lys Asn Thr Ser Gly Asn Lys Ile Met Val Pro
    515                 520                 525

Lys Tyr Leu Leu Phe Lys Ile Asp Asn Asn Gly Asn Ile Glu Asp Asn
530                 535                 540

Ile His Ser Glu Glu Ala Glu Ile Ser Glu Lys Glu Thr Ser Gly
545                 550                 555                 560

Gly Ser Ser Ile Ser Thr Asp Lys Ser Phe Glu Glu Ser Pro Asn Ser
            565                 570                 575

Ser Pro Asn Ser Ser Pro Asn Asn Ser Leu Asn Asn Ser Ile Asp Ile
    580                 585                 590

Ser Thr Asn Asn Tyr Asp Asp Arg Ser Glu Asn Ser Leu Asp Ser Leu
    595                 600                 605

Thr Ser Asp Gly Pro Ala Thr Asn Phe Ser Leu Leu Lys Gln Ala Gly
```

```
                610                 615                 620
Asp Val Glu Glu Asn Pro Gly Pro Glu Phe Ala Ser Leu Asp Asn Leu
625                 630                 635                 640

Val Ala Arg Tyr Gln Arg Cys Phe Asn Asp Gln Ser Leu Lys Asn Ser
                645                 650                 655

Thr Ile Glu Leu Glu Ile Arg Phe Gln Gln Ile Asn Phe Leu Leu Phe
                660                 665                 670

Lys Thr Val Tyr Glu Ala Leu Val Ala Gln Glu Ile Pro Ser Thr Ile
                675                 680                 685

Ser His Ser Ile Arg Cys Ile Lys Lys Val His His Glu Asn His Cys
                690                 695                 700

Arg Glu Lys Ile Leu Pro Ser Glu Asn Leu Tyr Phe Lys Lys Gln Pro
705                 710                 715                 720

Leu Met Phe Phe Lys Phe Ser Glu Pro Ala Ser Leu Gly Cys Lys Val
                725                 730                 735

Ser Leu Ala Ile Glu Gln Pro Ile Arg Lys Phe Ile Leu Asp Ser Ser
                740                 745                 750

Val Leu Val Arg Leu Lys Asn Arg Thr Thr Phe Arg Val Ser Glu Leu
                755                 760                 765

Trp Lys Ile Glu Leu Thr Ile Val Lys Gln Leu Met Gly Ser Glu Val
                770                 775                 780

Ser Ala Lys Leu Ala Ala Phe Lys Thr Leu Leu Phe Asp Thr Pro Glu
785                 790                 795                 800

Gln Gln Thr Thr Lys Asn Met Met Thr Leu Ile Asn Pro Asp Asp Glu
                805                 810                 815

Tyr Leu Tyr Glu Ile Glu Ile Glu Tyr Thr Gly Lys Pro Glu Ser Leu
                820                 825                 830

Thr Ala Ala Asp Val Ile Lys Ile Lys Asn Thr Val Leu Thr Leu Ile
                835                 840                 845

Ser Pro Asn His Leu Met Leu Thr Ala Tyr His Gln Ala Ile Glu Phe
                850                 855                 860

Ile Ala Ser His Ile Leu Ser Ser Glu Ile Leu Leu Ala Arg Ile Lys
865                 870                 875                 880

Ser Gly Lys Trp Gly Leu Lys Arg Leu Leu Pro Gln Val Lys Ser Met
                885                 890                 895

Thr Lys Ala Asp Tyr Met Lys Phe Tyr Pro Pro Val Gly Tyr Tyr Val
                900                 905                 910

Thr Asp Lys Ala Asp Gly Ile Arg Gly Ile Ala Val Ile Gln Asp Thr
                915                 920                 925

Gln Ile Tyr Val Val Ala Asp Gln Leu Tyr Ser Leu Gly Thr Thr Gly
930                 935                 940

Ile Glu Pro Leu Lys Pro Thr Ile Leu Asp Gly Glu Phe Met Pro Glu
945                 950                 955                 960

Lys Lys Glu Phe Tyr Gly Phe Asp Val Ile Met Tyr Glu Gly Asn Leu
                965                 970                 975

Leu Thr Gln Gln Gly Phe Glu Thr Arg Ile Glu Ser Leu Ser Lys Gly
                980                 985                 990

Ile Lys Val Leu Gln Ala Phe Asn Ile Lys Ala Glu Met Lys Pro Phe
                995                 1000                1005

Ile Ser Leu Thr Ser Ala Asp Pro Asn Val Leu Leu Lys Asn Phe
                1010                1015                1020

Glu Ser Ile Phe Lys Lys Lys Thr Arg Pro Tyr Ser Ile Asp Gly
                1025                1030                1035
```

-continued

```
Ile Ile Leu Val Glu Pro Gly Asn Ser Tyr Leu Asn Thr Asn Thr
    1040            1045                1050

Phe Lys Trp Lys Pro Thr Trp Asp Asn Thr Leu Asp Phe Leu Val
    1055            1060                1065

Arg Lys Cys Pro Glu Ser Leu Asn Val Pro Glu Tyr Ala Pro Lys
    1070            1075                1080

Lys Gly Phe Ser Leu His Leu Leu Phe Val Gly Ile Ser Gly Glu
    1085            1090                1095

Leu Phe Lys Lys Leu Ala Leu Asn Trp Cys Pro Gly Tyr Thr Lys
    1100            1105                1110

Leu Phe Pro Val Thr Gln Arg Asn Gln Asn Tyr Phe Pro Val Gln
    1115            1120                1125

Phe Gln Pro Ser Asp Phe Pro Leu Ala Phe Leu Tyr Tyr His Pro
    1130            1135                1140

Asp Thr Ser Ser Phe Ser Asn Ile Asp Gly Lys Val Leu Glu Met
    1145            1150                1155

Arg Cys Leu Lys Arg Glu Ile Asn Tyr Val Arg Trp Glu Ile Val
    1160            1165                1170

Lys Ile Arg Glu Asp Arg Gln Gln Asp Leu Lys Thr Gly Gly Tyr
    1175            1180                1185

Phe Gly Asn Asp Phe Lys Thr Ala Glu Leu Thr Trp Leu Asn Tyr
    1190            1195                1200

Met Asp Pro Phe Ser Phe Glu Glu Leu Ala Lys Gly Pro Ser Gly
    1205            1210                1215

Met Tyr Phe Ala Gly Ala Lys Thr Gly Ile Tyr Arg Ala Gln Thr
    1220            1225                1230

Ala Leu Ile Ser Phe Ile Lys Gln Glu Ile Ile Gln Lys Ile Ser
    1235            1240                1245

His Gln Ser Trp Val Ile Asp Leu Gly Ile Gly Lys Gly Gln Asp
    1250            1255                1260

Leu Gly Arg Tyr Leu Asp Ala Gly Val Arg His Leu Val Gly Ile
    1265            1270                1275

Asp Lys Asp Gln Thr Ala Leu Ala Glu Leu Val Tyr Arg Lys Phe
    1280            1285                1290

Ser His Ala Thr Thr Arg Gln His Lys His Ala Thr Asn Ile Tyr
    1295            1300                1305

Val Leu His Gln Asp Leu Ala Glu Pro Ala Lys Glu Ile Ser Glu
    1310            1315                1320

Lys Val His Gln Ile Tyr Gly Phe Pro Lys Glu Gly Ala Ser Ser
    1325            1330                1335

Ile Val Ser Asn Leu Phe Ile His Tyr Leu Met Lys Asn Thr Gln
    1340            1345                1350

Gln Val Glu Asn Leu Ala Val Leu Cys His Lys Leu Leu Gln Pro
    1355            1360                1365

Gly Gly Met Val Trp Phe Thr Thr Met Leu Gly Glu Gln Val Leu
    1370            1375                1380

Glu Leu Leu His Glu Asn Arg Ile Glu Leu Asn Glu Val Trp Glu
    1385            1390                1395

Ala Arg Glu Asn Glu Val Val Lys Phe Ala Ile Lys Arg Leu Phe
    1400            1405                1410

Lys Glu Asp Ile Leu Gln Glu Thr Gly Gln Glu Ile Gly Val Leu
    1415            1420                1425
```

-continued

```
Leu Pro Phe Ser Asn Gly Asp Phe Tyr Asn Glu Tyr Leu Val Asn
1430                1435                1440

Thr Ala Phe Leu Ile Lys Ile Phe Lys His His Gly Phe Ser Leu
1445                1450                1455

Val Gln Lys Gln Ser Phe Lys Asp Trp Ile Pro Glu Phe Gln Asn
1460                1465                1470

Phe Ser Lys Ser Leu Tyr Lys Ile Leu Thr Glu Ala Asp Lys Thr
1475                1480                1485

Trp Thr Ser Leu Phe Gly Phe Ile Cys Leu Arg Lys Asn Leu Glu
1490                1495                1500

Gly Gly Gly Gly Ser Gly Gly Gly Ser Val Glu Gln Asp Leu
1505                1510                1515

His Ala Ile Gln Leu Gln Leu Glu Glu Glu Met Phe Asn Gly Gly
1520                1525                1530

Ile Arg Arg Phe Glu Ala Asp Gln Gln Arg Gln Ile Ala Ser Gly
1535                1540                1545

Asn Glu Ser Asp Thr Ala Trp Asn Arg Arg Leu Leu Ser Glu Leu
1550                1555                1560

Ile Ala Pro Met Ala Glu Gly Ile Gln Ala Tyr Lys Glu Glu Tyr
1565                1570                1575

Glu Gly Lys Arg Gly Arg Ala Pro Arg Ala Leu Ala Phe Ile Asn
1580                1585                1590

Cys Val Gly Asn Glu Val Ala Ala Tyr Ile Thr Met Lys Ile Val
1595                1600                1605

Met Asp Met Leu Asn Thr Asp Val Thr Leu Gln Ala Ile Ala Met
1610                1615                1620

Asn Val Ala Asp Arg Ile Glu Asp Gln Val Arg Phe Ser Lys Leu
1625                1630                1635

Glu Gly His Ala Ala Lys Tyr Phe Glu Lys Val Lys Lys Ser Leu
1640                1645                1650

Lys Ala Ser Lys Thr Lys Ser Tyr Arg His Ala His Asn Val Ala
1655                1660                1665

Val Val Ala Glu Lys Ser Val Ala Asp Arg Asp Ala Asp Phe Ser
1670                1675                1680

Arg Trp Glu Ala Trp Pro Lys Asp Thr Leu Leu Gln Ile Gly Met
1685                1690                1695

Thr Leu Leu Glu Ile Leu Glu Asn Ser Val Phe Phe Asn Gly Gln
1700                1705                1710

Pro Val Phe Leu Arg Thr Leu Arg Thr Asn Gly Gly Lys His Gly
1715                1720                1725

Val Tyr Tyr Leu Gln Thr Ser Glu His Val Gly Glu Trp Ile Thr
1730                1735                1740

Ala Phe Lys Glu His Val Ala Gln Leu Ser Pro Ala Tyr Ala Pro
1745                1750                1755

Cys Val Ile Pro Pro Arg Pro Trp Val Ser Pro Phe Asn Gly Gly
1760                1765                1770

Phe His Thr Glu Lys Val Ala Ser Arg Ile Arg Leu Val Lys Gly
1775                1780                1785

Asn Arg Glu His Val Arg Lys Leu Thr Lys Lys Gln Met Pro Ala
1790                1795                1800

Val Tyr Lys Ala Val Asn Ala Leu Gln Ala Thr Lys Trp Gln Val
1805                1810                1815

Asn Lys Glu Val Leu Gln Val Val Glu Asp Val Ile Arg Leu Asp
```

```
              1820                1825                1830
Leu Gly Tyr Gly Val Pro Ser Phe Lys Pro Leu Ile Asp Arg Glu
     1835                1840                1845

Asn Lys Pro Ala Asn Pro Val Pro Leu Glu Phe Gln His Leu Arg
     1850                1855                1860

Gly Arg Glu Leu Lys Glu Met Leu Thr Pro Glu Gln Trp Gln Ala
     1865                1870                1875

Phe Ile Asn Trp Lys Gly Glu Cys Thr Lys Leu Tyr Thr Ala Glu
     1880                1885                1890

Thr Lys Arg Gly Ser Lys Ser Ala Ala Thr Val Arg Met Val Gly
     1895                1900                1905

Gln Ala Arg Lys Tyr Ser Gln Phe Asp Ala Ile Tyr Phe Val Tyr
     1910                1915                1920

Ala Leu Asp Ser Arg Ser Arg Val Tyr Ala Gln Ser Ser Thr Leu
     1925                1930                1935

Ser Pro Gln Ser Asn Asp Leu Gly Lys Ala Leu Leu Arg Phe Thr
     1940                1945                1950

Glu Gly Gln Arg Leu Asp Ser Ala Glu Ala Leu Lys Trp Phe Leu
     1955                1960                1965

Val Asn Gly Ala Asn Asn Trp Gly Trp Asp Lys Lys Thr Phe Asp
     1970                1975                1980

Val Arg Thr Ala Asn Val Leu Asp Ser Glu Phe Gln Asp Met Cys
     1985                1990                1995

Arg Asp Ile Ala Ala Asp Pro Leu Thr Phe Thr Gln Trp Val Asn
     2000                2005                2010

Ala Asp Ser Pro Tyr Gly Phe Leu Ala Trp Cys Phe Glu Tyr Ala
     2015                2020                2025

Arg Tyr Leu Asp Ala Leu Asp Glu Gly Thr Gln Asp Gln Phe Met
     2030                2035                2040

Thr His Leu Pro Val His Gln Asp Gly Ser Cys Ser Gly Ile Gln
     2045                2050                2055

His Tyr Ser Ala Met Leu Ser Asp Ala Val Gly Ala Lys Ala Val
     2060                2065                2070

Asn Leu Lys Pro Ser Asp Ser Pro Gln Asp Ile Tyr Gly Ala Val
     2075                2080                2085

Ala Gln Val Val Ile Gln Lys Asn Tyr Ala Tyr Met Asn Ala Glu
     2090                2095                2100

Asp Ala Glu Thr Phe Thr Ser Gly Ser Val Thr Leu Thr Gly Ala
     2105                2110                2115

Glu Leu Arg Ser Met Ala Ser Ala Trp Asp Met Ile Gly Ile Thr
     2120                2125                2130

Arg Gly Leu Thr Lys Lys Pro Val Met Thr Leu Pro Tyr Gly Ser
     2135                2140                2145

Thr Arg Leu Thr Cys Arg Glu Ser Val Ile Asp Tyr Ile Val Asp
     2150                2155                2160

Leu Glu Glu Lys Glu Ala Gln Arg Ala Ile Ala Glu Gly Arg Thr
     2165                2170                2175

Ala Asn Pro Val His Pro Phe Asp Asn Asp Arg Lys Asp Ser Leu
     2180                2185                2190

Thr Pro Ser Ala Ala Tyr Asn Tyr Met Thr Ala Leu Ile Trp Pro
     2195                2200                2205

Ser Ile Ser Glu Val Val Lys Ala Pro Ile Val Ala Met Lys Met
     2210                2215                2220
```

```
Ile Arg Gln Leu Ala Arg Phe Ala Ala Lys Arg Asn Glu Gly Leu
    2225                2230                2235

Glu Tyr Pro Leu Pro Thr Gly Phe Ile Leu Gln Gln Lys Ile Met
    2240                2245                2250

Ala Thr Asp Met Leu Arg Val Ser Thr Cys Leu Met Gly Glu Ile
    2255                2260                2265

Lys Met Ser Leu Gln Ile Glu Thr Asp Val Val Asp Glu Thr Ala
    2270                2275                2280

Met Met Gly Ala Ala Ala Pro Asn Phe Val His Gly His Asp Ala
    2285                2290                2295

Ser His Leu Ile Leu Thr Val Cys Asp Leu Val Asp Lys Gly Ile
    2300                2305                2310

Thr Ser Val Ala Val Ile His Asp Ser Phe Gly Thr His Ala Gly
    2315                2320                2325

Arg Thr Ala Asp Leu Arg Asp Ser Leu Arg Glu Glu Met Val Lys
    2330                2335                2340

Met Tyr Gln Asn His Asn Ala Leu Gln Asn Leu Leu Asp Val His
    2345                2350                2355

Glu Glu Arg Trp Leu Val Asp Thr Gly Ile Gln Val Pro Glu Gln
    2360                2365                2370

Gly Glu Phe Asp Leu Asn Glu Ile Leu Val Ser Asp Tyr Cys Phe
    2375                2380                2385

Ala
```

<210> SEQ ID NO 48
<211> LENGTH: 15
<212> TYPE: PRT
<213> ORGANISM: Artificial Sequence
<220> FEATURE:
<223> OTHER INFORMATION: Peptide linker

<400> SEQUENCE: 48

```
Gly Gly Gly Gly Ile Ala Pro Ser Met Val Gly Gly Gly Gly Ser
1               5                   10                  15
```

<210> SEQ ID NO 49
<211> LENGTH: 21
<212> TYPE: PRT
<213> ORGANISM: Artificial Sequence
<220> FEATURE:
<223> OTHER INFORMATION: Peptide linker

<400> SEQUENCE: 49

```
Ser Pro Asn Gly Ala Ser Asn Ser Gly Ser Ala Pro Asp Thr Ser Ser
1               5                   10                  15

Ala Pro Gly Ser Gln
            20
```

<210> SEQ ID NO 50
<211> LENGTH: 15
<212> TYPE: PRT
<213> ORGANISM: Artificial Sequence
<220> FEATURE:
<223> OTHER INFORMATION: Peptide linker

<400> SEQUENCE: 50

```
Glu Gly Lys Ser Ser Gly Ser Gly Ser Glu Ser Lys Ser Thr Glu
1               5                   10                  15
```

```
<210> SEQ ID NO 51
<211> LENGTH: 14
<212> TYPE: PRT
<213> ORGANISM: Artificial Sequence
<220> FEATURE:
<223> OTHER INFORMATION: Peptide linker

<400> SEQUENCE: 51

Glu Gly Lys Ser Ser Gly Ser Gly Ser Glu Ser Lys Glu Phe
1               5                   10

<210> SEQ ID NO 52
<211> LENGTH: 19
<212> TYPE: PRT
<213> ORGANISM: Artificial Sequence
<220> FEATURE:
<223> OTHER INFORMATION: peptide linker

<400> SEQUENCE: 52

Gly Gly Gly Ser Gly Gly Gly Ser Gly Gly Thr Gly Gly Ser
1               5                   10                  15

Gly Gly Gly

<210> SEQ ID NO 53
<211> LENGTH: 14
<212> TYPE: PRT
<213> ORGANISM: Artificial Sequence
<220> FEATURE:
<223> OTHER INFORMATION: Peptide linker

<400> SEQUENCE: 53

Gly Ser Thr Ser Gly Ser Gly Lys Ser Ser Glu Gly Lys Gly
1               5                   10

<210> SEQ ID NO 54
<211> LENGTH: 18
<212> TYPE: PRT
<213> ORGANISM: Artificial Sequence
<220> FEATURE:
<223> OTHER INFORMATION: Peptide linker

<400> SEQUENCE: 54

Tyr Pro Arg Ser Ile Tyr Ile Arg Arg Arg His Pro Ser Pro Ser Leu
1               5                   10                  15

Thr Thr

<210> SEQ ID NO 55
<211> LENGTH: 15
<212> TYPE: PRT
<213> ORGANISM: Artificial Sequence
<220> FEATURE:
<223> OTHER INFORMATION: peptide linker

<400> SEQUENCE: 55

Gly Ser Thr Ser Gly Ser Gly Lys Pro Gly Ser Gly Glu Gly Ser
1               5                   10                  15

<210> SEQ ID NO 56
<211> LENGTH: 25
<212> TYPE: PRT
<213> ORGANISM: Artificial Sequence
<220> FEATURE:
<223> OTHER INFORMATION: Peptide linker

<400> SEQUENCE: 56

Ser Ser Ala Asp Asp Ala Lys Lys Asp Ala Ala Lys Lys Asp Asp Ala
```

```
                1               5                  10                 15
Lys Lys Asp Asp Ala Lys Lys Asp Ala
                20                 25

<210> SEQ ID NO 57
<211> LENGTH: 26
<212> TYPE: PRT
<213> ORGANISM: Artificial Sequence
<220> FEATURE:
<223> OTHER INFORMATION: Peptide linker
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 57

Gly Ser Ala Asp Asp Ala Xaa Xaa Asp Ala Ala Xaa Lys Asp Ala
1               5                  10                 15
Lys Lys Asp Asp Ala Lys Lys Asp Gly Ser
                20                 25

<210> SEQ ID NO 58
<211> LENGTH: 25
<212> TYPE: PRT
<213> ORGANISM: Artificial Sequence
<220> FEATURE:
<223> OTHER INFORMATION: Peptide linker

<400> SEQUENCE: 58

Leu Ser Ala Asp Asp Ala Lys Lys Asp Ala Ala Lys Lys Asp Ala
1               5                  10                 15
Lys Lys Asp Asp Ala Lys Lys Asp Leu
                20                 25

<210> SEQ ID NO 59
<211> LENGTH: 17
<212> TYPE: PRT
<213> ORGANISM: Artificial Sequence
<220> FEATURE:
<223> OTHER INFORMATION: Peptide linker

<400> SEQUENCE: 59

Ala Glu Ala Ala Ala Lys Glu Ala Ala Ala Lys Glu Ala Ala Ala Lys
1               5                  10                 15
Ala

<210> SEQ ID NO 60
<211> LENGTH: 34
<212> TYPE: PRT
<213> ORGANISM: Artificial Sequence
<220> FEATURE:
<223> OTHER INFORMATION: Peptide linker

<400> SEQUENCE: 60

Gly Ser Thr Ser Gly Ser Gly Lys Pro Gly Ser Gly Glu Gly Ser Thr
1               5                  10                 15
Gly Ala Gly Gly Ala Gly Ser Thr Ser Gly Ser Gly Lys Pro Ser Gly
                20                 25                 30
Glu Gly
```

```
<210> SEQ ID NO 61
<211> LENGTH: 16
<212> TYPE: PRT
<213> ORGANISM: Artificial Sequence
<220> FEATURE:
<223> OTHER INFORMATION: Peptide linker

<400> SEQUENCE: 61

Leu Ser Leu Glu Val Ala Glu Glu Ile Ala Arg Leu Glu Ala Glu Val
1               5                   10                  15

<210> SEQ ID NO 62
<211> LENGTH: 13
<212> TYPE: PRT
<213> ORGANISM: Artificial Sequence
<220> FEATURE:
<223> OTHER INFORMATION: Peptide linker

<400> SEQUENCE: 62

Gly Thr Pro Thr Pro Thr Pro Thr Pro Thr Gly Glu Phe
1               5                   10

<210> SEQ ID NO 63
<211> LENGTH: 18
<212> TYPE: PRT
<213> ORGANISM: Artificial Sequence
<220> FEATURE:
<223> OTHER INFORMATION: Peptide linker

<400> SEQUENCE: 63

Gly Ser Thr Ser Gly Ser Gly Lys Pro Gly Ser Gly Glu Gly Ser Thr
1               5                   10                  15

Lys Gly

<210> SEQ ID NO 64
<211> LENGTH: 9
<212> TYPE: PRT
<213> ORGANISM: Artificial Sequence
<220> FEATURE:
<223> OTHER INFORMATION: Peptide linker

<400> SEQUENCE: 64

Gly Ser His Ser Gly Ser Gly Lys Pro
1               5
```